United States Patent
Brondyk et al.

(10) Patent No.: US 11,498,953 B2
(45) Date of Patent: Nov. 15, 2022

(54) COMPOSITIONS FOR INCREASING HALF-LIFE OF A THERAPEUTIC AGENT IN FELINES AND METHODS OF USE

(71) Applicant: Invetx, Inc., Boston, MA (US)

(72) Inventors: William Brondyk, Mansfield, MA (US); Brett Chevalier, Melrose, MA (US); Juergen Horn, Marblehead, MA (US); Madhusudan Natarajan, Waban, MA (US)

(73) Assignee: Invetx, Inc., Boston, MA (US)

( * ) Notice: Subject to any disclaimer, the term of this patent is extended or adjusted under 35 U.S.C. 154(b) by 0 days.

(21) Appl. No.: 17/355,839

(22) Filed: Jun. 23, 2021

(65) Prior Publication Data

US 2022/0009994 A1 Jan. 13, 2022

Related U.S. Application Data

(60) Provisional application No. 63/143,720, filed on Jan. 29, 2021, provisional application No. 63/050,535, filed on Jul. 10, 2020.

(51) Int. Cl.
*C07K 14/705* (2006.01)
*A61K 38/00* (2006.01)

(52) U.S. Cl.
CPC ........ *C07K 14/70503* (2013.01); *A61K 38/00* (2013.01); *C07K 2317/52* (2013.01)

(58) Field of Classification Search
CPC .......... C07K 14/70503; C07K 2317/52; A61K 38/00
See application file for complete search history.

(56) References Cited

U.S. PATENT DOCUMENTS

| | | | |
|---|---|---|---|
| 4,399,216 A | 8/1983 | Axel et al. | |
| 4,439,196 A | 3/1984 | Higuchi | |
| 4,447,224 A | 5/1984 | DeCant et al. | |
| 4,447,233 A | 5/1984 | Mayfield | |
| 4,487,603 A | 12/1984 | Harris | |
| 4,634,665 A | 1/1987 | Axel et al. | |
| 5,179,017 A | 1/1993 | Axel et al. | |
| 5,292,658 A | 3/1994 | Cormier et al. | |
| 5,418,155 A | 5/1995 | Cormier et al. | |
| 5,683,888 A | 11/1997 | Campbell | |
| 5,741,668 A | 4/1998 | Ward et al. | |
| 5,777,079 A | 7/1998 | Tsien et al. | |
| 5,804,387 A | 9/1998 | Cormack et al. | |
| 5,874,304 A | 2/1999 | Zolotukhin et al. | |
| 5,876,995 A | 3/1999 | Bryan | |
| 5,925,558 A | 7/1999 | Tsien et al. | |
| 8,790,651 B2 | 7/2014 | Bammert et al. | |
| 10,982,002 B2 | 4/2021 | Steiniger et al. | |
| 2006/0067930 A1 | 3/2006 | Adams et al. | |
| 2007/0148164 A1 | 6/2007 | Farrington et al. | |
| 2008/0181887 A1 | 7/2008 | Dall-Acqua et al. | |
| 2013/0129727 A1 | 5/2013 | Zhang et al. | |
| 2018/0009869 A1 | 1/2018 | Lu et al. | |
| 2020/0216536 A1 | 7/2020 | Brondyk et al. | |
| 2020/0362034 A1 | 11/2020 | Zhan et al. | |
| 2020/0362035 A1 | 11/2020 | Brondyk et al. | |
| 2021/0347854 A1 | 11/2021 | Brondyk et al. | |
| 2021/0388053 A1 | 12/2021 | Zhan et al. | |
| 2022/0048981 A1 | 2/2022 | Nakao et al. | |
| 2022/0064263 A1 | 3/2022 | Zhan et al. | |

FOREIGN PATENT DOCUMENTS

| | | |
|---|---|---|
| EP | 3668536 | 6/2020 |
| EP | 3866842 | 8/2021 |
| EP | 3892632 | 10/2021 |
| EP | 3902564 | 11/2021 |
| WO | WO 92/15673 | 9/1992 |
| WO | WO 95/07463 | 3/1995 |
| WO | WO 98/14605 | 4/1998 |
| WO | WO 98/26277 | 6/1998 |
| WO | WO 99/49019 | 9/1999 |
| WO | WO 2010/110838 | 9/2010 |
| WO | WO 2010/117448 | 10/2010 |
| WO | WO 2017/186928 | 11/2017 |
| WO | WO 2018/073185 | 4/2018 |
| WO | WO 2019/035010 | 2/2019 |
| WO | WO 2020/056393 | 3/2020 |
| WO | WO 2020/082048 | 4/2020 |
| WO | WO 2020/116560 | 6/2020 |
| WO | WO 2020/142625 | 7/2020 |
| WO | WO 2021/165417 | 8/2021 |
| WO | WO 2021/212081 | 10/2021 |
| WO | WO 2021/212084 | 10/2021 |

OTHER PUBLICATIONS

International Search Report and Written Opinion in International Appln. No. PCT/US2021/038714, dated Oct. 29, 2021, 19 pages.
Abdiche et al., "The neonatal Fc receptor (FcRn) binds independently to both sites of the IgG homodimer with identical affinity," mAbs, Mar. 2015, 7(2):331-343, 14 pages.
Beniaminovitz et al., "Prevention of rejection in cardiac transplantation by blockade of the interleukin-2 receptor with a monoclonal antibody," New Engl. J. Med., Mar. 2000, 342(9):613-619.
Bergeron et al., "Comparative functional characterization of canine IgG subclasses," Veterinary Immunology and Immunopathology, 2014, 157(1-2):31-41.
Better et al., "*Escherichia coli* secretion of an active chimeric antibody fragment," Science, May 1998, 240(4855):1041-1043.
Booth et al., "Extending human IgG half-life using structure-guided design," MAbs, Oct. 2018, 10(7):1098-1110.
Borrok et al., "pH-dependent binding engineering reveals an FcRn affinity threshold that governs IgG recycling," J. Biol. Chem., Feb. 2015, 290(7):4282-4290, 10 pages.

(Continued)

*Primary Examiner* — Ruixiang Li
(74) *Attorney, Agent, or Firm* — Clark & Elbing LLP

(57) ABSTRACT

Provided are compositions for increasing the half-life of a polypeptide or polypeptides in a feline and methods of their use. The compositions involve variant feline IgG Fc regions.

21 Claims, 105 Drawing Sheets

Specification includes a Sequence Listing.

(56) References Cited

OTHER PUBLICATIONS

Chalfie et al., "Green fluorescent protein as a marker for gene expression," Science, Feb. 1994, 263(5148):802-805.
Dall'Acqua et al., "Increasing the affinity of a human IgG1 for the neonatal Fc receptor: biological consequences," J. Immunol., Nov. 2002, 169(9):5171-5180, 11 pages.
Deng et al., "Pharmacokinetics of humanized monoclonal anti-tumor necrosis factor-{alpha} antibody and its neonatal Fc receptor variants in mice and cynomolgus monkeys," Drug Metab. Dispos., Apr. 2010, 38(4):600-605.
Dong et al., "Quantitative Prediction of Human Pharmacokinetics for Monoclonal Antibodies," Clin Pharmacokinet, Feb. 2011, 50(2):131-142.
Gearing et al., "A fully caninised anti-NGF monoclonal antibody for pain relief in dogs," BMC Veterinary Research, Nov. 2013, 9:226, 12 pages.
Gearing et al., "In Vitro and In Vivo Characterization of a Fully Felinized Therapeutic Anti-Nerve Growth Factor Monoclonal Antibody for the Treatment of Pain in Cats," J Vet Intern Med, Jun. 2016, 30(4):1129-1137.
GenBank Accession No. AAL35301.1, "immunoglobulin gamma heavy chain A [*Canis lupus familiaris*]," Nov. 26, 2001, 2 pages.
GenBank Accession No. AAL35302.1, "immunoglobulin gamma heavy chain B [*Canis lupus familiaris*]," dated Nov. 26, 2001, 2 pages.
GenBank Accession No. AAL35303.1, "immunoglobulin gamma heavy chainC [*Canis lupus familiaris*]," Nov. 26, 2001, 2 pages.
GenBank Accession No. AAL35304.1, "immunoglobulin gamma heavy chain D [*Canis lupus familiaris*]," Nov. 26, 2001, 2 pages.
GenBank Accession No. ABY55569.1, "immunoglobulin lambda light chain variable region, partial [*Canis lupus familiaris*]," Jul. 26, 2016, 2 pages.
GenBank Accession No. ABY57289.1, "immunoglobulin kappa light chain variable region, partial [*Canis lupus familiaris*]," Jul. 26, 2016, 1 page.
GenBank Accession No. AF198257.1, "Felis catus immunoglobulin kappa light chain mRNA, complete cds," Nov. 21, 1999, 2 pages.
GenBank Accession No. AY829266.1, "Felis catus beta-2 microglobulin mRNA, complete cds," Dec. 13, 2004, 1 page.
GenBank Accession No. BAA32229.1, "IgG1 heavy chain, partial [*Felis catus*]," Jul. 25, 2016, 2 pages.
GenBank Accession No. BAA32230.1, "IgG1 heavy chain, partial [*Felis catus*]," Jul. 25, 2016, 2 pages.
GenBank Accession No. E07339.1, "DNA sequence of C lambda gene in the constant region of feline antibody gene," Nov. 4, 2005, 1 page.
GenBank Accession No. KF773786.1, "Felis catus FcRn mRNA, partial cds," Mar. 28, 2014, 2 pages.
GenBank Accession No. KF811175.1, "Felis catus immunoglobulin G2 heavy chain consant region mRNA, partial cds," Mar. 28, 2014.
GenBank Accession No. U55762, "Cloning vector pEGFP-N1, complete sequence, enhanced green fluorescent protein (egfp) and neomycin phosphotransferase genes, complete cds," Aug. 22, 2003, 3 pages.
Ghosh et al., "Natalizumab for active Crohn's disease," New Engl. J. Med., Jan. 2003, 348(1):24-32.
Heim et al., "Engineering green fluorescent protein for improved brightness, longer wavelengths and fluorescence resonance energy transfer," Curr. Biol., Feb. 1996, 6(2):178-182.
Hinton et al., "Engineered human IgG antibodies with longer serum half-lives in primates," J. Biol. Chem., Feb. 2004, 279(8):6213-6216, 5 pages.
Hogrefe et al., "Creating randomized amino acid libraries with the QuikChange Multi Site-Directed Mutagenesis Kit," Biotechniques., Nov. 2002, 33(5):1158-1165.
Ichiki et al., "Regulation of the expression of human C epsilon germline transcript. Identification of a novel IL-4 responsive element," J. Immunol., Jun. 1993, 150(12):5408-5417.

Kanai et al., "Identification of two allelic IgG1 Ch coding regions (Cγl) of cat," Vet. Immunol. Immunopathol., Jan. 2000, 73(1):53-62.
Kaufman et al., "Amplification and expression of sequences cotransfected with a modular dihydrofolate reductase complementary dna gene," Mol. Biol., Aug. 1982, 159(4):601-621.
Lei et al., "Characterization of the Erwinia carotovora pelB gene and its product pectate lyase," J. Bacteriol., Sep. 1987, 169(9):4379-4383.
Lipsky et al., "Infliximab and methotrexate in the treatment of rheumatoid arthritis. Anti-Tumor Necrosis Factor Trial in Rheumatoid Arthritis with Concomitant Therapy Study Group," New Engl. J. Med., Nov. 2000, 343(22):1594-1602.
Milgrom et al., "Treatment of allergic asthma with monoclonal anti-IgE antibody. rhuMAb-E25 Study Group," New Engl. J. Med., Dec. 1999, 341(26):1966-1973.
Mizushima et al., "pEF-BOS, a powerful mammalian expression vector," Nucleic Acids Res., Sep. 1990, 18(17):5322.
Monnet et al., "Combined glyco- and protein-Fc engineering simultaneously enhance cytotoxicity and half-life of a therapeutic antibody," Mabs, Mar. 2014, 6(2):422-436, 16 pages.
Morrison et al., "Combinatorial alanine-scanning," Curr. Opin. Chem. Biol., Jun. 2001, 5(3):302-307.
Mulligan et al., "Synthesis of rabbit beta-globin in cultured monkey kidney cells following infection with a SV40 beta-globin recombinant genome," Nature, Jan. 1979, 277(5692):108-114.
Nolan et al., "Fluorescence-activated cell analysis and sorting of viable mammalian cells based on beta-D-galactosidase activity after transduction of *Escherichia coli* lacZ," Proc. Natl. Acad. Sci. U.S.A., Apr. 1988, 85(8):2603-2607.
Petkova et al., "Enhanced half-life of genetically engineered human IgG1 antibodies in a humanized FcRn mouse model: potential application in humorally mediated autoimmune disease," Int. Immunol., Dec. 2006, 18(12):1759-1769.
Powers et al., "Expression of single-chain Fv-Fc fusions in Pichia pastoris," J Immunol Methods., May 2001, 251(1-2):123-135.
Robbie et al., "A novel investigational Fc-modified humanized monoclonal antibody, motavizumab-YTE, has an extended half-life in healthy adults," Antimicrob. Agents Chemother., Dec. 2013, 57(12):6147-6153.
Shields et al., "High resolution mapping of the binding site on human IgG1 for Fc gamma RI, Fc gamma RII, Fc gamma RIII, and FcRn and design of IgG1 variants with improved binding to the Fc gamma R," J. Biol. Chem., Mar. 2001, 276(9):6591-6604, 15 pages.
Slamon et al., "Use of chemotherapy plus a monoclonal antibody against HER2 for metastatic breast cancer that overexpresses HER2," New Engl. J. Med., Mar. 2001, 344(11):783-792.
Stauber et al., "Development and applications of enhanced green fluorescent protein mutants," Biotechniques, Mar. 1998, 24(3):462-471.
Strietzel et al., "In Vitro functional characterization of feline IgGs," Vet. Immunol. Immunopathol., Apr. 2014, 158(3-4):214-223.
Tang et al., "Cloning and characterization of cDNAs encoding four different canine immunoglobulin gamma chains," Vet. Immunol. Immunopathol., Aug. 2001, 80(3-4):259-270.
Urlaub et al., "Isolation of Chinese hamster cell mutants deficient in dihydrofolate reductase activity," Proc. Natl. Acad. Sci. USA, Jul. 1980, 77(7):4216-4220.
US Third-Party Submission in United States U.S. Appl. No. 16/733,105, mailed May 28, 2021, 19 pages.
US Third-Party Submission in United States U.S. Appl. No. 16/861,077, mailed May 25, 2021, 19 pages.
Ward et al., "Binding activities of a repertoire of single immunoglobulin variable domains secreted from *Escherichia coli*," Nature, Oct. 1989, 341(6242):544-546.
Yeung et al., "Engineering human IgG1 affinity to human neonatal Fc receptor: impact of affinity improvement on pharmacokinetics in primates," J. Immunol., Jun. 2009, 182(12):7663-7671, 10 pages.
Zalevsky et al., "Enhanced antibody half-life improves in vivo activity," Nat. Biotechnol., Feb. 2010, 28(2):457-159.
Zhang et al., "PKSolver: An add-in program for pharmacokinetic and pharmacodynamic data analysis in Microsoft Excel," Comput. Methods Programs Biomed., Sep. 2010, 99(3):306-314.

(56) References Cited

OTHER PUBLICATIONS imgt.org [online], "IMGT Scientific chart," 2016, retrieved from URL <http://www.imgt.org/IMGTScientificChart/Numbering/Hu_IGHGnber.html>, 7 pages.

US Third-Party Submission in U.S. Appl. No. 16/733,105, mailed Jul. 22, 2021, 14 pages.

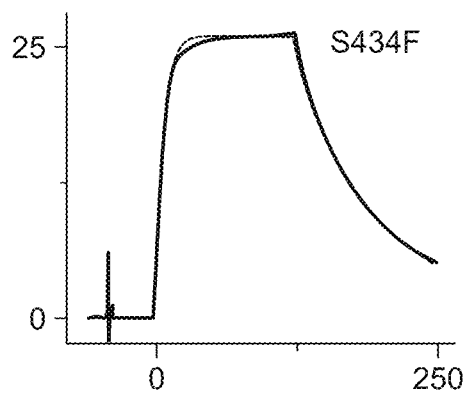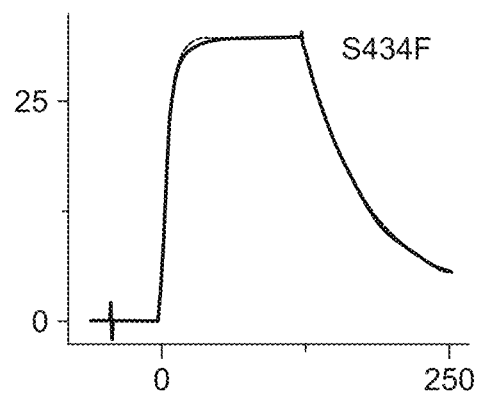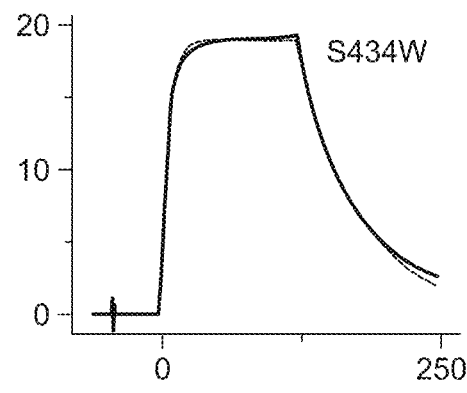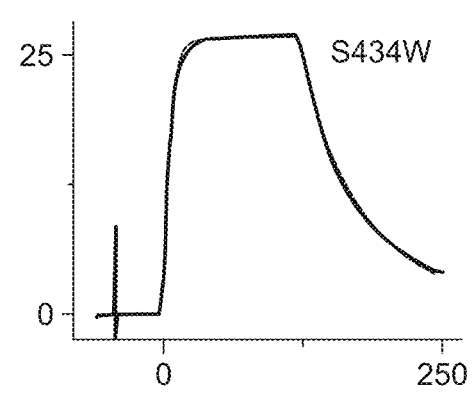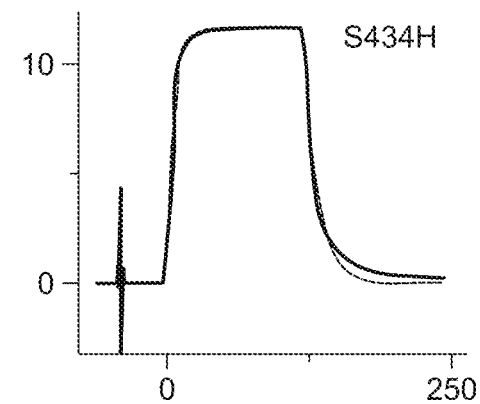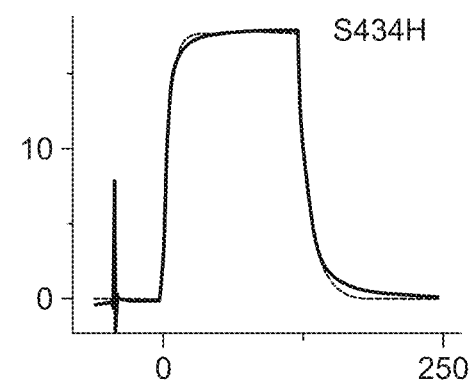
FIG. 1 (Continued)

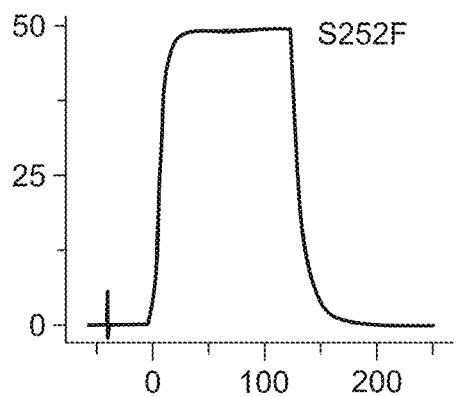
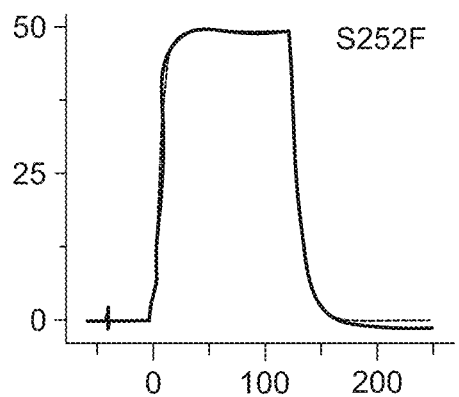
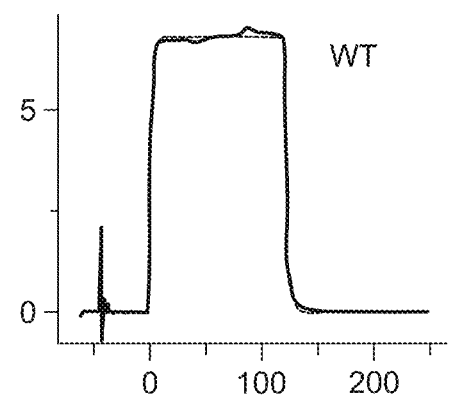
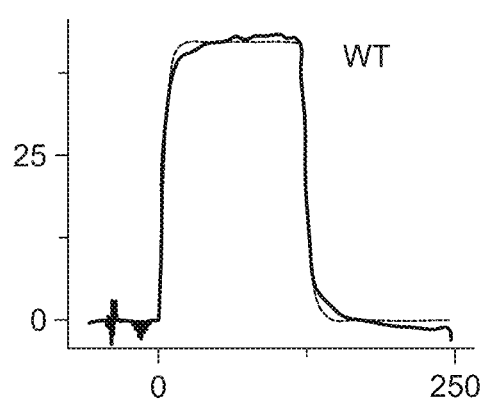
FIG. 2 (Continued)

FIG. 3

```
                        1                                                           60
Feline IgG1a   (1)   ASTTAPSVFPLAPSCGTTSGATVALACLVLGYFPEPVTVSWNSGALTSGVHTFPAVLQAS
Feline IgG1b   (1)   ASTTAPSVFPLAPSCGTTSGATVALACLVLGYFPEPVTVSWNSGALTSGVHTFPAVLQAS
Feline IgG2    (1)   ASTTASSVFPLAPSCGTTSGATVALACLVLGYFPEPVTVSWNSGALTSGVHTFPSVLQAS
                        61                                                          120
Feline IgG1a   (61)  GLYSLSSMVTVPSSRWLSDTFTCNVAHPPSNTKVDKTVAKTDHPPGPKPCDPKCPPPEM
Feline IgG1b   (61)  GLYSLSSMVTVPSSRWLSDTFTCNVAHPPSNTKVDKTVAKTDHPPGPKCDCPKCPPPEM
Feline IgG2    (61)  GLYSLSSMVTVPSSRWLSDTFTCNVAHRPSSTKVDKTYPKTASTIESKTGEGPKCPVFEI
                        121                                                         180
Feline IgG1a   (121) PGPSIFIFPPKPKDTLSISRTPEVTCLVVDLGPDDSDVQITWFVDNTQVITAKTSPREE
Feline IgG1b   (121) PGPSIFIFPPKPKDTLSISRTPEVTCLVVDLGPDDSDVQITWFVDNTQVITAKTSPREE
Feline IgG2    (121) PGAPSVFIFPPKPKDTLSISRTPEVTCLVVDLGPDDSNVQITWFVDNTEMHTAKTRPREE
                        181                                                         240
Feline IgG1a   (181) QFNSTYRVVSVLPILHQDWLKGKEFKCKVNSKSLPSPIERTISKAKGQPHEPQVYVLPPA
Feline IgG1b   (181) QFNSTYRVVSVLPILHQDWLKGKEFKCKVNSKSLPSPIERTISKDKGQPHEPQVYVLPPA
Feline IgG2    (181) QFNSTYRVVSVLPILHQDWLKGKEFKCKVNSKSLPSAMERTISKAKGQPHEPQVYVLPPT
                        241                                                         300
Feline IgG1a   (241) QEELSRNKVSVTCLIKSFHPPDIAVEWEITGQPEPENNYRTTPPQLDSDGTYFVYSKLSV
Feline IgG1b   (241) QEELSRNKVSVTCLIESFYPSDIAVEWEITGQPEPENNYRTTPPQLDSDGTYFFYSRLSV
Feline IgG2    (241) QEELSENKVSVTCLIKGFHPPDIAVEWEITGQPEPENNYQTTPPQLDSDGTYFLYSRLSV
                        301                    335
Feline IgG1a   (301) DRSRWQRGNTYTCSVSHEALHSHHTQKSLTQSPGK
Feline IgG1b   (301) DRSRWQRGNTYTCSVSHEALHSHHTQKSLTQSPGK
Feline IgG2    (301) DRSRWQRGNTYTCSVSHEALHSHHTQKSLTQSPGK
```

FIG. 4

```
                    240                      260                         280                          300
Feline IgG1a Fc  IFIFPPKPKD TLSISRTPEV ICLVVDLGPD DSDVQITWFV DNTQVYTAKT SPREEQFNST YRVVSVLPIL
Human  IgG1  Fc  VFLFPPKPKD TLMISRTPEV TCVVVDVSHE DPEVKFNWYV DGVEVHNAKT KPREEQYNST YRVVSVLTVL 310                      330                         350                          370
Feline IgG1a Fc  HQDWLKGKEF KCKVNSKSLP SPIERTISKA KGQPHEPQVY VLPPAQEELS RNKVSVTCLI KSFHPPDIAV
Human  IgG1  Fc  HQDWLNGKEY KCKVSNKALP APIEKTISKA KGQPREPQVY TLPPSREEMT KNQVSLTCLV KGFYPSDIAV 380    389a          400                            420                430
                           389b
                           389c
                           389d
Feline IgG1a Fc  EWEITGQPEP ENNYRTTPPQLD SDGTYFVYSK LSVDRSHWQR GNTYTCSVSH EALHSHHT
Human  IgG1  Fc  EWESNGQPEN NYKTTPPVLD SDGSFFLYSK LTVDKSRWQQ GNVFSCSVMH EALHNHYT
```

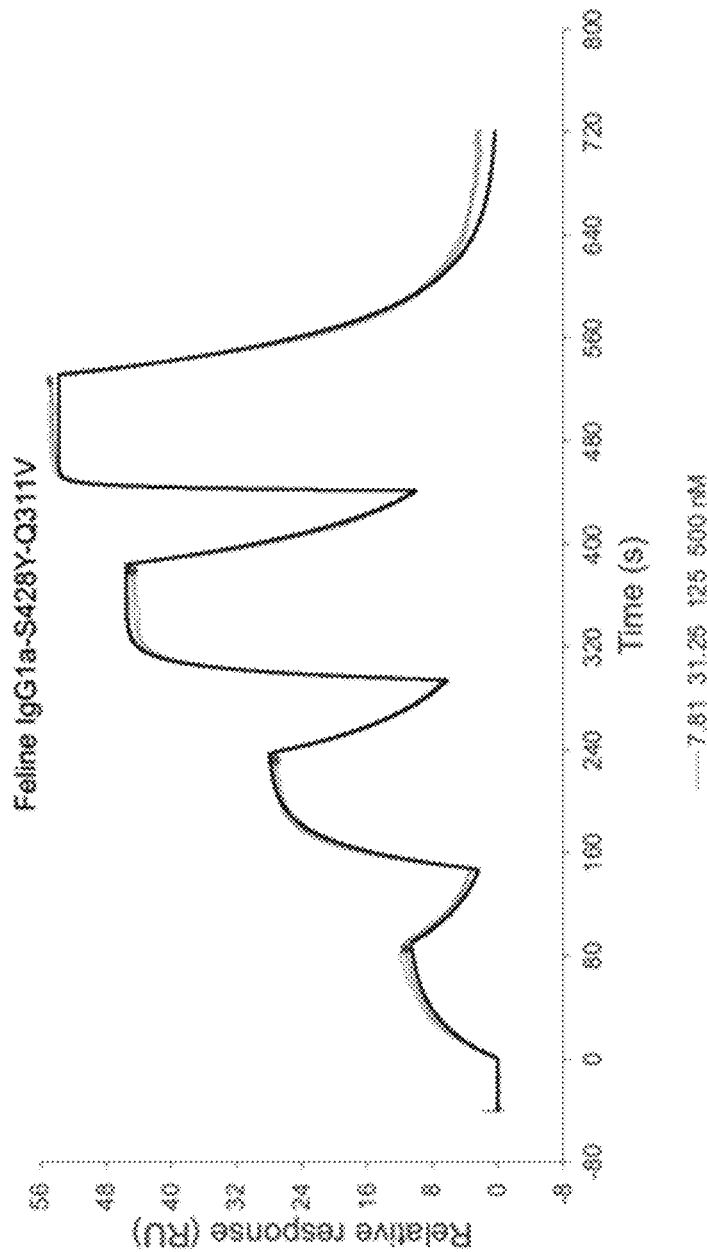

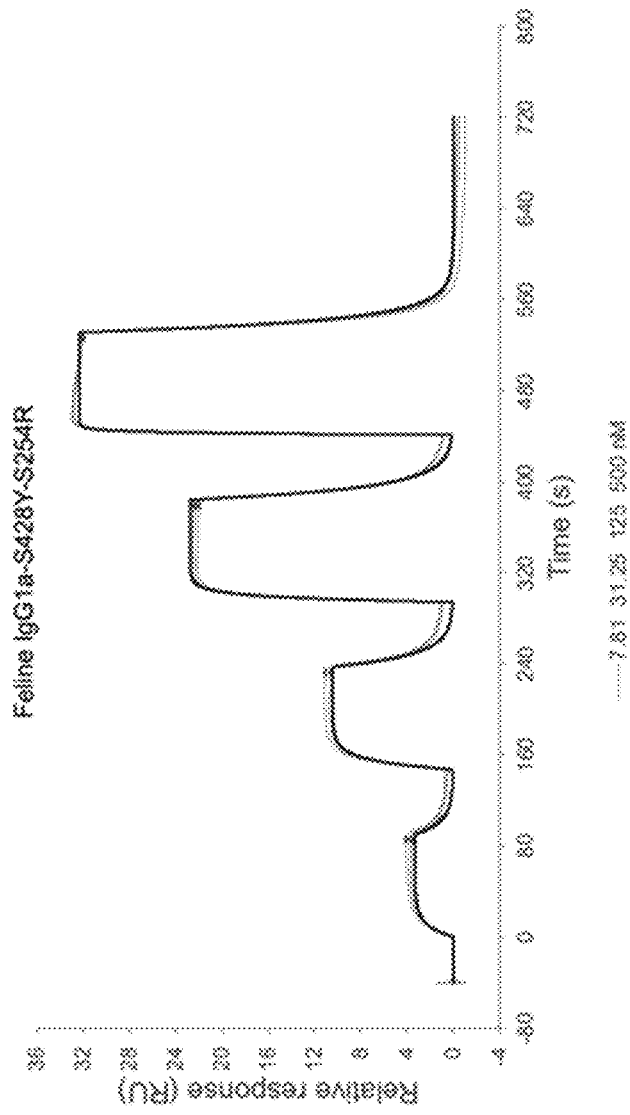

US 11,498,953 B2

COMPOSITIONS FOR INCREASING HALF-LIFE OF A THERAPEUTIC AGENT IN FELINES AND METHODS OF USE

CROSS REFERENCE TO RELATED APPLICATIONS

This application claims priority to U.S. Provisional Application No. 63/050,535, filed Jul. 10, 2020, and to U.S. Provisional Application No. 63/143,720, filed Jan. 29, 2021, the contents of each of which are incorporated by reference in their entireties.

SEQUENCE LISTING

The instant application contains a Sequence Listing which has been submitted electronically in ASCII format and is hereby incorporated by reference in its entirety. Said ASCII copy, created on Jun. 23, 2021, is named "Sequence_Listing.txt" and is 25 KB in size.

FIELD

This disclosure relates generally to polypeptides (e.g., fusion polypeptides such as polypeptide-Fc region fusions; or binding molecules such as antibodies or ligand-binding portions of receptor-Fc fusions) that have increased half-life in felines compared to their wild type counterparts.

BACKGROUND

The Fc region of antibodies plays a number of functional roles, including, but not limited to, protecting the antibody from degradation through the lysosomal pathway and mediating antibody effector functions. With the increasing use of feline antibodies as therapeutic agents, there has been an enhanced focus on not just selecting an optimal Fab, but also combining it with an appropriate Fc for desired half-life and effector functions.

There is little guidance in the art relating to increasing half-life of polypeptide therapeutics (e.g., antibodies) for use in cats. This disclosure remedies that failing by providing Fc region variants that improve the serum persistence of polypeptides (e.g., antibodies) in felines.

SUMMARY

Provided herein are feline Fc (e.g., feline IgG Fc region variant) or feline FcRn binding fragments thereof that are useful in therapeutic polypeptides. This disclosure features polypeptides that have increased binding to feline FcRn than control polypeptides (e.g., the wild type counterpart IgG feline Fc regions). In some instances, these polypeptides have increased binding to feline FcRn than control polypeptides at pH 5.5, pH 6.0 and/or pH 6.5. In some instances, these polypeptides can, e.g., bind to feline FcRn at a higher level at acidic pH (e.g., pH 5.5, pH 6.0 or pH 6.5) than at a neutral pH (e.g., pH 7.0, 7.1, 7.2, 7.3, 7.4, or 7.5). In some instances, these polypeptides bind to feline FcRn at a higher level at pH 5.5 and/or 6.0 than at pH 7.4. This disclosure relates, in part, to polypeptides that have increased half-life in felines than their wild type counterparts. For example, provided are binding molecules (e.g., antibodies or ligand-binding portions of receptors) with increased half-life relative to versions of these binding molecules not attached to the Fc regions or feline FcRn binding regions thereof disclosed herein. Also provided are enzyme-Fc region fusions, ligand-Fc region fusions, nanobody-Fc fusions, and peptide-Fc region fusions, wherein the fusions have increased half-life compared with their wild type counterparts. The Fc regions, in addition to having a substitution or substitutions (relative to the wild type feline Fc region) that increase half-life may also include other substitutions that, e.g., increase effector function, decrease effector function, increase binding to Protein A and/or decrease heterogeneity of the polypeptide (e.g., by removing one or more post-translational modifications in the Fc region). The feline Fc region sequences can be from any feline antibody. In some instances, the feline Fc region sequences are from a feline IgG (e.g., IgG1a, IgG1b, IgG2).

The disclosure features a recombinant protein comprising (1) a binding domain, or a fragment thereof, that specifically binds to a ligand, or an epitope of a protein, wherein the binding domain is attached to (2) a domain comprising an Fc region (CH2+CH3 region) or a feline FcRn binding region thereof, as disclosed herein. In some instances, the binding domain comprises (i) the six complementarity determining regions (CDRs), for example, of a feline or human/humanized antibody; (ii) a nanobody; (iii) a soluble receptor-binding domain that binds a ligand, or a ligand-binding fragment thereof and (iv) an extracellular domain of a feline receptor protein.

The disclosure also provides a composition comprising: (1) a first polypeptide comprising a first Fc region (e.g., a CH2 region, a CH3 region, a CH2+CH3 region) comprising a feline IgG Fc region variant described herein; and (2) a second polypeptide comprising a second Fc region comprising a feline IgG Fc region variant described herein. The first and second polypeptide can be associated through the first and second Fc regions. In some instances, the amino acid sequences of the first and second Fc regions are the same. In other instances, the amino acid sequences of the first and second Fc regions are different (e.g., by 1, 2, 3, 4, 5, 6, 7, 8, 9, 10, 11, 12, 13, 14, 15, 16, 17, 18, 19, 20, 21, 22, 23, 24, or 25 amino acids). In some instances, the Fc region variant is a variant of a feline IgG1a antibody Fc region. In some instances, the Fc region variant is a variant of a feline IgG1b antibody Fc region. In some instances, the Fc region variant is a variant of a feline IgG2 antibody Fc region.

Also disclosed is a fusion molecule comprising a feline IgG Fc region variant disclosed herein and a polypeptide. In some instances, the feline IgG Fc region variant is covalently attached to the polypeptide (e.g., through a hinge region or a linker). In some instances, the polypeptide is a ligand binding domain of a feline receptor protein, an extracellular domain of a feline receptor protein, or an antigen-binding domain. In some instances, the polypeptide is selected from the ligand binding domain or extracellular domain of feline IL-13Rα1, or IL-13Rα2, feline EPO, feline CTLA4, feline LFA3, feline VEGFR1/VEGFR3, feline IL-1R, feline GLP-1 receptor agonist, and feline Thrombopoietin binding peptide. In some instances, the polypeptide is an scFv, a nanobody, or single domain antibody. In some instances, the IgG Fc region variant is a variant of a feline IgG1a antibody Fc region. In some instances, the IgG Fc region variant is a variant of a feline IgG1b antibody Fc region. In some instances, the IgG Fc region variant is a variant of a feline IgG2 antibody Fc region.

In some aspects, the disclosure provides a polypeptide comprising a feline IgG Fc region variant, or a feline FcRn-binding region thereof, wherein the polypeptide comprises an amino acid substitution at at least one position selected from the group consisting of:

(i) a position that corresponds to amino acid position 252 of a wild type feline IgG, wherein the amino acid substitution is S252W;
(ii) a position that corresponds to amino acid position 254 of a wild type feline IgG, wherein the amino acid substitution is selected from the group consisting of S254R and S254K;
(iii) a position that corresponds to amino acid position 309 of a wild type feline IgG, wherein the amino acid substitution is L309V or L309Y;
(iv) a position that corresponds to amino acid position 311 of a wild type feline IgG, wherein the amino acid substitution is selected from the group consisting of Q311R, Q311V, Q311L and Q311K;
(v) a position that corresponds to amino acid position 428 of a wild type feline IgG, wherein the amino acid substitution is selected from the group consisting of S428M, S428Y, S428H and S428R; and
(vi) one or more positions that correspond to amino acid positions selected from the group consisting of 262, 286, 289, 290, 293, 301, 312, 326, 334, 347, 355, 377, 380, 383, 389c, 392, 426 and 437 of a wild type feline IgG;
wherein the amino acid positions are based on EU numbering, and wherein the polypeptide has increased binding affinity to feline FcRn when compared to an Fc domain of the wild type feline IgG.

In some embodiments, the polypeptide comprises the amino acid substitution at a position that corresponds to amino acid position 252 of a wild type feline IgG. In some embodiments, the amino acid substitution at position 252 of the wild type feline IgG is S252W.

In some embodiments, the polypeptide comprises the amino acid substitution at a position that corresponds to amino acid position 254 of a wild type feline IgG. In some embodiments, the amino acid substitution at position 254 of the wild type feline IgG is S254R. In some embodiments, the amino acid substitution at position 254 of the wild type feline IgG is S254K.

In some embodiments, the polypeptide comprises the amino acid substitution at a position that corresponds to amino acid position 309 of a wild type feline IgG. In some embodiments, the amino acid substitution at position 309 of the wild type feline IgG is L309V. In some embodiments, the amino acid substitution at position 309 of the wild type feline IgG is L309Y.

In some embodiments, the polypeptide comprises the amino acid substitution at a position that corresponds to amino acid position 311 of a wild type feline IgG. In some embodiments, the amino acid substitution at position 311 of the wild type feline IgG is Q311R. In some embodiments, the amino acid substitution at position 311 of the wild type feline IgG is Q311V. In some embodiments, the amino acid substitution at position 311 of the wild type feline IgG is Q311K. In some embodiments, the amino acid substitution at position 311 of the wild type feline IgG is Q311L.

In some embodiments, the polypeptide comprises the amino acid substitution at a position that corresponds to amino acid position 428 of a wild type feline IgG. In some embodiments, the amino acid substitution at position 428 of the wild type feline IgG is S428M.

In some embodiments, the polypeptide comprises at least the amino acid substitution S428Y. In some embodiments, the amino acid substitution at position 428 of the wild type feline IgG is S428Y. In some embodiments, the amino acid substitution at position 428 of the wild type feline IgG is S428R. In some embodiments, the amino acid substitution at position 428 of the wild type feline IgG is S428H.

In another embodiment, the polypeptide comprises an amino acid substitution at one or more positions that correspond to amino acid positions selected from the group consisting of 262, 286, 289, 290, 293, 301, 312, 326, 334, 347, 355, 377, 380, 383, 389c, 392, 426 and 437 of a wild type feline IgG. In some embodiments, the amino acid substitution is selected from the group consisting of L262Q, L262E, T286E, T286D, T289K, S290V, S290Y, E293D, E293H, E293K, R301L, D312T, K326D, R334D, Q347L, Q355L, I377V, I377Y, E380D, E380V, E380T, I383L, N389c-R, R392E, S426L, S426H and T437L, and conservative amino acid substitutions of any of the foregoing. In some embodiments, the amino acid substitution is selected from the group consisting of L262Q, L262E, T286E, T286D, T289K, S290V, S290Y, E293D, E293H, E293K, R301L, D312T, K326D, R334D, Q347L, Q355L, I377V, I377Y, E380D, E380V, E380T, I383L, N389c-R, R392E, S426L, S426H and T437L.

In another aspect, the disclosure provides a polypeptide comprising a feline IgG Fc region variant, or a feline FcRn-binding region thereof, wherein the polypeptide comprises two or more amino acid substitutions, wherein the two or more amino acid substitutions are selected from the group consisting of:
(i) an amino acid substitution at a position that corresponds to amino acid position 252 of a wild type feline IgG, wherein the amino acid substitution is selected from the group consisting of S252W, S252Y, S252F and S252R;
(ii) an amino acid substitution at a position that corresponds to amino acid position 254 of a wild type feline IgG, wherein the amino acid substitution is selected from the group consisting of S254R and S254K;
(iii) an amino acid substitution at a position that corresponds to amino acid position 309 of a wild type feline IgG, wherein the amino acid substitution is selected from the group consisting of L309V, L309Y and L309E;
(iv) an amino acid substitution at a position that corresponds to amino acid position 311 of a wild type feline IgG, wherein the amino acid substitution is selected from the group consisting of Q311R, Q311V, Q311L and Q311K;
(v) an amino acid substitution at a position that corresponds to amino acid position 428 of a wild type feline IgG, wherein the amino acid substitution is selected from the group consisting of S428L, S428M, S428Y, S428H and S428R;
(vi) an amino acid substitution at one or more positions that correspond to amino acid positions selected from the group consisting of 262, 286, 289, 290, 293, 301, 312, 326, 334, 347, 355, 377, 380, 383, 389c, 392, 426 and 437 of a wild type feline IgG; and
(vii) an amino acid substitution at a position that corresponds to amino acid position 434 of a wild type feline IgG, wherein the amino acid substitution is selected from the group consisting of S434F, S434W, S434H, S434R, and S434Y;
wherein the amino acid positions are based on EU numbering, wherein the two or more amino acid substitutions are at different positions, and wherein the polypeptide has increased binding affinity to feline FcRn when compared to (a) an Fc domain of the wild type feline IgG, and (b) a polypeptide comprising only one of the two or more amino acid substitutions.

In some embodiments, the two or more amino acid substitutions comprise an amino acid substitution at a position that corresponds to amino acid position 286 of a wild type feline IgG. In some embodiments, the amino acid substitution is selected from the group consisting of T286E and T286D.

In some embodiments, the two or more amino acid substitutions comprise an amino acid substitution at a position that corresponds to amino acid position 289 of a wild type feline IgG. In some embodiments, the amino acid substitution is selected from the group consisting of T289K and T289H.

In some embodiments, the two or more amino acid substitutions comprise an amino acid substitution at a position that corresponds to amino acid position 301 of a wild type feline IgG. In some embodiments the amino acid substitution is R301L.

In some embodiments, the two or more amino acid substitutions comprise an amino acid substitution at a position that corresponds to amino acid position 334 of a wild type feline IgG. In some embodiments, the amino acid substitution is R334D.

In some embodiments, the two or more amino acid substitutions comprise an amino acid substitution at a position that corresponds to amino acid position 426 of a wild type feline IgG. In some embodiments, the amino acid substitution is selected from the group consisting of S426L and S426H.

In some embodiments, the two or more amino acid substitutions comprise an amino acid substitution at a position that corresponds to amino acid position 437 of a wild type feline IgG. In some embodiments, the amino acid substitution is T437L.

In some embodiments, the two or more amino acid substitutions are selected from the group consisting of:
(i) S252Y in combination with Q311R and/or Q311L;
(ii) S434Y in combination with one or more of S254R, S254K, L262E, T286D, T286E, T289K, E293D, E293K, L309V, L309E, K326D and Q347L;
(iii) S434F in combination with E380D;
(iv) S428L in combination with one or more of S252R, T286E, Q311V, Q311K, D312T, I377V, I383L, and N389cR;
(v) S428L, E380D and S434R;
(vi) S428L, E380T and S434R;
(vii) S252R in combination with L262Q;
(viii) T260E, L309E and Q355L;
(ix) S290V in combination with R344D;
(x) R301L, E380V and T437L;
(xi) T286E in combination with S428H;
(xii) R334D in combination with one or more of S428R, T437L and R301L;
(xiii) S426L in combination with T289H and/or S428H;
(xiv) S428Y in combination with one or more of Q311V, S254R, L309V, T286E, and E380T; and
(xv) S428H in combination with T289H.

In some embodiments, the polypeptide comprises an amino acid sequence that is at least 80% identical to an amino acid sequence selected from the group consisting of SEQ ID NOs: 1 to 3.

In some embodiments, the wild type feline IgG is a feline IgG1a comprising an Fc domain having an amino acid sequence that is at least 80% (e.g., at least 85%, 90%, 92%, 94%, 95%, 96%, 97%, 98%, or 99%) identical to SEQ ID NO: 1, a feline IgG1b comprising an Fc domain having an amino acid sequence that is at least 80% (e.g., at least 85%, 90%, 92%, 94%, 95%, 96%, 97%, 98%, or 99%) identical to SEQ ID NO: 2, or a feline IgG2 comprising an Fc domain having an amino acid sequence that is at least 80% (e.g., at least 85%, 90%, 92%, 94%, 95%, 96%, 97%, 98%, or 99%) identical to SEQ ID NO: 3.

In other embodiments, the wild type feline IgG is a feline IgG1a comprising an Fc domain having an amino acid sequence of SEQ ID NO: 1. In other embodiments, the wild type feline IgG is a feline IgG1b comprising an Fc domain having an amino acid sequence of SEQ ID NO: 2. In other embodiments, the wild type feline IgG is a feline IgG2 comprising an Fc domain having an amino acid sequence of SEQ ID NO: 3.

In some embodiments, the polypeptide further comprises a binding domain. In some embodiments, the binding domain comprises (i) six complementarity determining regions (CDRs) of an immunoglobulin molecule, (ii) a ligand binding domain of a feline receptor protein, (iii) a nanobody, or (iv) an extracellular domain of a feline receptor protein. In some embodiments, the binding domain specifically binds to an antigen selected from the group consisting of NGF, TrKA, ADAMTS, IL-1, IL-2, IL-4, IL-4R, Angiotensin type 1 (AT1) receptor, Angiotensin type 2 (AT2) receptor, IL-5, IL-12, IL-13, IL-31, IL-33, CD3, CD20, CD47, CD52, and complement system complex.

In some embodiments, the polypeptide further comprises a protein selected from the group consisting of EPO, CTLA4, LFA3, VEGFR1/VEGFR3, IL-1R, IL-4R, GLP-1 receptor agonist, and Thrombopoietin binding peptide.

In some embodiments, the polypeptide binds to a feline FcRn at a higher level at an acidic pH than at a neutral pH. In some embodiments, the polypeptide binds to a feline FcRn at a higher level at pH 5.5 than at pH 7.4. In some embodiments, the polypeptide binds to a feline FcRn at a higher level at pH 6.0 than at pH 7.4.

In some embodiments, the polypeptide has: (1) increased half-life in a cat than a control polypeptide or control polypeptides, wherein the control polypeptide or control polypeptides are identical to the polypeptide or polypeptides except for having the corresponding wild type feline IgG Fc region in place of the IgG Fc region variant; and/or (2) increased binding to feline FcRn than the control polypeptides; and wherein the amino acid positions are based on EU numbering.

In some aspects, the disclosure provides a pharmaceutical composition comprising (i) the polypeptide described herein, and (ii) a pharmaceutically acceptable excipient.

In some aspects, the disclosure provides a nucleic acid or nucleic acids encoding the polypeptide described herein.

In some aspects, the disclosure provides an expression vector or expression vectors comprising the nucleic acid or nucleic acids described herein.

In some aspects, the disclosure provides a host cell comprising the nucleic acid or nucleic acids described herein or the expression vector or expression vectors described herein.

In some aspects, the disclosure provides a method of making a polypeptide or polypeptides, the method comprising:
(a) providing a nucleic acid or nucleic acids described herein;
(b) expressing the nucleic acid or nucleic acids in a host cell culture, thereby producing the polypeptide; and
(c) collecting the polypeptide produced in (b) from the host cell culture.

In some embodiments, the method further comprises formulating the polypeptide as a pharmaceutical formulation.

In some aspects, the disclosure provides a method of treating a feline disease or disorder in a cat in need thereof, the method comprising administering an effective amount of a composition comprising the pharmaceutical composition described herein to the cat.

In some aspects, the disclosure provides a method of preventing a feline disease or disorder in a cat in need thereof, the method comprising administering an effective amount of a composition comprising the pharmaceutical composition described herein to the cat.

In some embodiments, the disease or disorder is an allergic disease, a chronic pain, an acute pain, an inflammatory disease, an autoimmune disease, an endocrine disease, a gastrointestinal disease, a cardiovascular disease, a renal disease, a fertility related disorder, an infectious disease or a cancer.

In some embodiments, the disease or disorder is atopic dermatitis, allergic dermatitis, osteoarthritic pain, arthritis, anemia, or obesity.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description and from the claims.

BRIEF DESCRIPTION OF DRAWINGS

FIG. 3 shows the alignment of the amino acid sequences of the wild-type feline IgG1a Fc region (SEQ ID NO:1) and the wild-type feline IgG1b Fc region (SEQ ID NO:2) with the putative wild-type feline IgG2 Fc region (SEQ ID NO:3). The hinge region lies between the triangles. Arrows indicate the cysteine residues in the hinge region likely involved in disulfide bridges between the two heavy chains (from Strietzel et al., 2014, *Vet. Immunol. Immunopathol.*, 158:214-223).

FIG. 4 shows the alignment of the amino acid sequences of the wild-type feline IgG1a Fc (SEQ ID NO: 1) and the human IgG1 Fc region, based on EU numbering. The 55 amino acid positions used in the generation of the phage library described in Example 2 are highlighted and underlined.

FIGS. 49A-49L depict Biacore sensorgrams showing the binding of wild-type feline IgG1a and feline IgG1a variants. The lighter lines on each figure represents the measured data and the darker line represents the fitted curve. Y-axis: Resonance Units (RU); X-axis: time (seconds).

DETAILED DESCRIPTION

Figure 1:
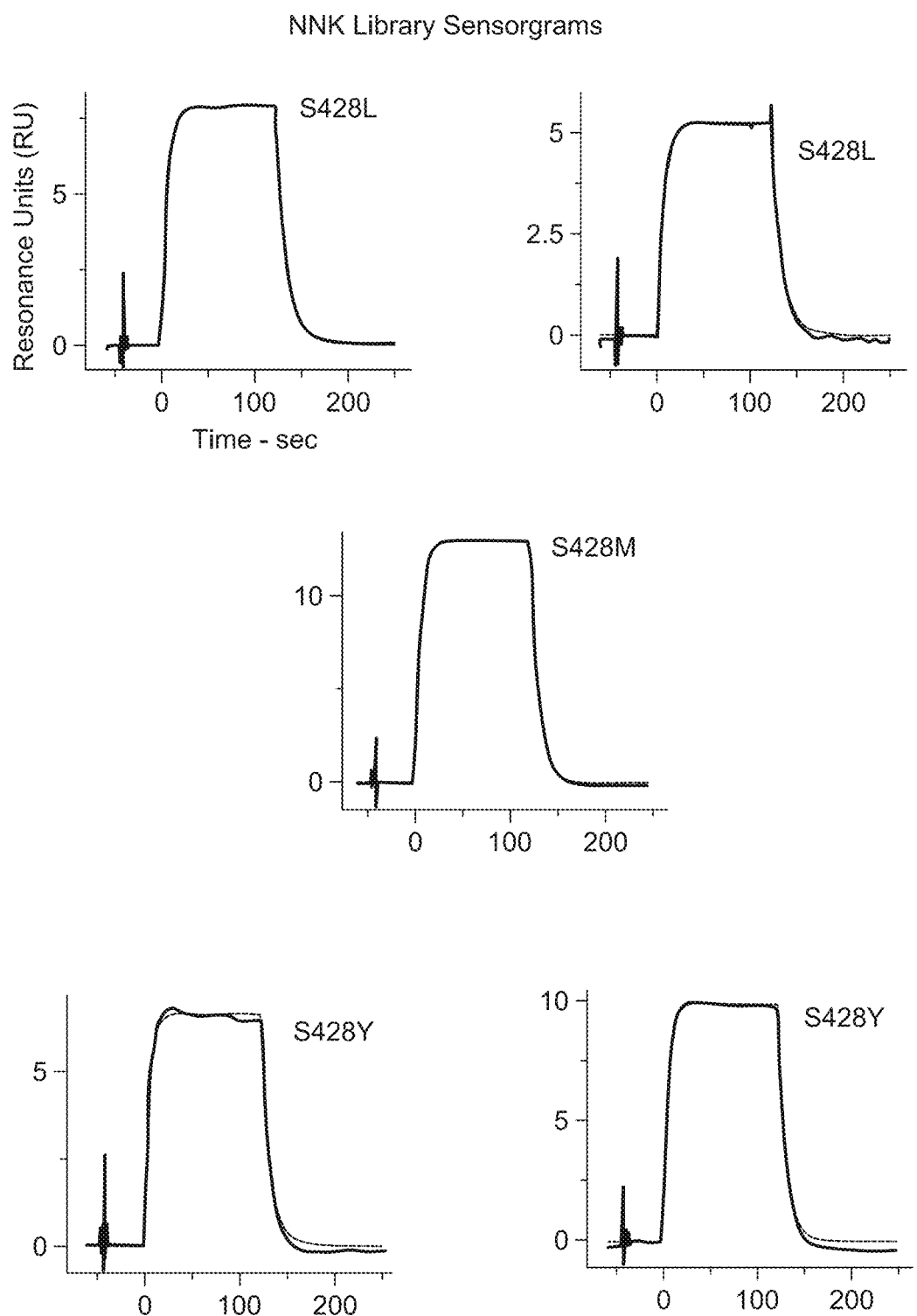
FIG. 1 depicts Biacore sensorgrams for the S428L, S428M, S428Y, S434F, S434W and S434H feline IgG1a Fc variants from the NNK libraries. The lighter line on each figure represents the measured data and the darker line represents the fitted curve using a 1:1 interaction model. Y-axis: Resonance Units (RU); X-axis: time (seconds).

With the increasing use of polypeptide (e.g., antibodies, ligand-binding domains of receptors, enzymes, ligands, peptides) as therapeutics for the prevention and treatment of a wide variety of feline diseases, it is important to develop polypeptides with extended half-life, especially for the prevention or treatment of chronic diseases in which a polypeptide must be administered repetitively.

Accordingly, this disclosure features feline immunoglobulin Fc regions or feline FcRn-binding regions thereof comprising mutations that enhance the half-life of a polypeptide or polypeptides comprising these sequences. Also disclosed are polypeptides comprising these domains and methods of their use. These peptides can be used for various therapeutic and diagnostic purposes.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated. All numerical designations, e.g., pH, temperature, time, concentration, and molecular weight, including ranges, are approximations which are varied (+) or (−) by increments of 1.0 or 0.1, as appropriate, or alternatively by a variation of +/−15%, or alternatively 10%, or alternatively 5%, or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

The term "about," as used herein when referring to a measurable value such as an amount or concentration and the like, is meant to encompass variations of 20%, 10%, 5%, 1%, 0.5%, or even 0.1% of the specified amount.

Feline Antibodies

Cats typically have three IgG heavy chains referred to as IgG1a, IgG1b and IgG2. These heavy chains represent three different subclasses of cat IgG. The amino acid and DNA sequences for these heavy chains are available from Strietzel et al., 2014, *Vet. Immunol. Immunopathol.*, 158:214-223 and the GENBANK database. For example, the amino acid sequence of feline IgG1a heavy chain has GENBANK accession number BAA32229.1, feline IgG1b heavy chain has GENBANK accession number BAA32230.1, and feline IgG2 heavy chain has GENBANK accession number KF811175.1. Feline antibodies also include two types of light chains: kappa and lambda. The DNA and amino acid sequence of these light chains can also be obtained from GENBANK database. For example, the feline kappa light chain amino acid sequence has accession number AF198257.1 and the feline lambda light chain has accession number E07339.1.

CH2 Region of a Feline Fc Region:

The CH2 region of a feline antibody comprises or consists of amino acids 231 to 340 (according to EU numbering) of a feline IgG antibody. It is to be understood that the CH2 region may include one to six (e.g., 1, 2, 3, 4, 5, 6) additional amino acids or deletions at their N and/or C-terminus.

The amino acid sequence of the CH2 region of feline IgG1a is provided below:

(SEQ ID NO: 4)
PPEMLGGPSIFIFPPKPKDTLSISRTPEVTCLVVDLGPDDSDVQITWFVDN

TQVYTAKTSPREEQFNSTYRVVSVLPILHQDWLKGKEFKCKVNSKSLPSPI

ERTISKAK

The amino acid sequence of the CH2 domain of feline IgG1b is provided below:

(SEQ ID NO: 5)
PPEMLGGPSIFIFPPKPKDTLSISRTPEVTCLVVDLGPDDSDVQITWFVDN

TQVYTAKTSPREEQFNSTYRVVSVLPILHQDWLKGKEFKCKVNSKSLPSPI

ERTISKDK

The amino acid sequence of the CH2 domain of feline IgG2 is provided below:

(SEQ ID NO: 6)
VPEIPGAPSVFIFPPKPKDTLSISRTPEVTCLVVDLGPDDSNVQITWFVDN

TEMHTAKTRPREEQFNSTYRVVSVLPILHQDWLKGKEFKCKVNSKSLPSAM

ERTISKAK

CH3 Region of a Feline Fc Region:

The CH3 region of a feline antibody comprises or consists of amino acids 341 to 447 (according to EU numbering) of a feline IgG antibody. It is to be understood that the CH3 region may include one to six (e.g., 1, 2, 3, 4, 5, 6) additional amino acids or deletions at their N and/or C-terminus.

The amino acid sequence of the CH3 domain of feline IgG1a is provided below:

(SEQ ID NO: 7)
GQPHEPQVYVLPPAQEELSRNKVSVTCLIKSFHPPDIAVEWEITGQPEPEN

NYRTTPPQLDSDGTYFVYSKLSVDRSHWQRGNTYTCSVSHEALHSHHTQKS

LTQSPGK

The amino acid sequence of the CH3 domain of feline IgG1b is provided below:

(SEQ ID NO: 8)
GQPHEPQVYVLPPAQEELSRNKVSVTCLIEGFYPSDIAVEWEITGQPEPEN

NYRTTPPQLDSDGTYFLYSRLSVDRSRWQRGNTYTCSVSHEALHSHHTQKS

LTQSPGK

The amino acid sequence of the CH3 domain of feline IgG2 is provided below:

(SEQ ID NO: 9)
GQPHEPQVYVLPPTQEELSENKVSVTCLIKGFHPPDIAVEWEITGQPEPEN

NYQTTPPQLDSDGTYFLYSRLSVDRSHWQRGNTYTCSVSHEALHSHHTQKS

LTQSPGK

Fc Region of a Feline Fc Region:

The Fc region of a feline IgG antibody comprises or consists of amino acids 231 to 447 (according to EU numbering) of the feline IgG antibody.

The amino acid sequence of the Fc domain of feline IgG1a is provided below:

(SEQ ID NO: 1)
PPEMLGGPSIFIFPPKPKDTLSISRTPEVTCLVVDLGPDDSDVQITWFVDN

TQVYTAKTSPREEQFNSTYRVVSVLPILHQDWLKGKEFKCKVNSKSLPSPI

ERTISKAKGQPHEPQVYVLPPAQEELSRNKVSVTCLIKSFHPPDIAVEWEI

TGQPEPENNYRTTPPQLDSDGTYFVYSKLSVDRSHWQRGNTYTCSVSHEAL

HSHHTQKSLTQSPGK

The amino acid sequence of the Fc domain of feline IgG1b is provided below:

(SEQ ID NO: 2)
PPEMLGGPSIFIFPPKPKDTLSISRTPEVTCLVVDLGPDDSDVQITWFVDN

TQVYTAKTSPREEQFNSTYRVVSVLPILHQDWLKGKEFKCKVNSKSLPSPI

ERTISKDKGQPHEPQVYVLPPAQEELSRNKVSVTCLIEGFYPSDIAVEWEI

TGQPEPENNYRTTPPQLDSDGTYFLYSRLSVDRSRWQRGNTYTCSVSHEAL

HSHHTQKSLTQSPGK

The amino acid sequence of the Fc domain of feline IgG2 is provided below:

(SEQ ID NO: 3)
VPEIPGAPSVFIFPPKPKDTLSISRTPEVTCLVVDLGPDDSNVQITWFVDN

TEMHTAKTRPREEQFNSTYRVVSVLPILHQDWLKGKEFKCKVNSKSLPSAM

ERTISKAKGQPHEPQVYVLPPTQEELSENKVSVTCLIKGFHPPDIAVEWEI

TGQPEPENNYQTTPPQLDSDGTYFLYSRLSVDRSHWQRGNTYTCSVSHEAL

HSHHTQKSLTQSPGK

Table 1 below compares the amino acid sequences of the CH2 and CH3 domains of human IgG1, feline IgG1a, feline IgG1b, and feline IgG2, based on EU numbering:

TABLE 1

| EU number | human IgG1 | feline IgG1a | feline IgG1b | feline IgG2 |
|---|---|---|---|---|
| CH2 Domain | | | | |
| 231 | A | P | P | V |
| 232 | P | P | P | P |
| 233 | E | E | E | E |
| 234 | L | M | M | I |
| 235 | L | L | L | P |
| 236 | G | G | G | G |
| 237 | G | G | G | A |
| 238 | P | P | P | P |
| 239 | S | S | S | S |
| 240 | V | I | I | V |
| 241 | F | F | F | F |
| 242 | L | I | I | I |
| 243 | F | F | F | F |
| 244 | P | P | P | P |
| 245 | P | P | P | P |
| 246 | K | K | K | K |
| 247 | P | P | P | P |
| 248 | K | K | K | K |
| 249 | D | D | D | D |
| 250 | T | T | T | T |
| 251 | L | L | L | L |
| 252 | M | S | S | S |
| 253 | I | I | I | I |
| 254 | S | S | S | S |
| 255 | R | R | R | R |
| 256 | T | T | T | T |
| 257 | P | P | P | P |
| 258 | E | E | E | E |
| 259 | V | V | V | V |
| 260 | T | T | T | T |
| 261 | C | C | C | C |
| 262 | V | L | L | L |
| 263 | V | V | V | V |
| 264 | V | V | V | V |
| 265 | D | D | D | D |
| 266 | V | L | L | L |
| 267 | S | G | G | G |
| 268 | H | P | P | P |
| 269 | E | D | D | D |
| 270 | D | D | D | D |
| 271 | P | S | S | S |
| 272 | E | D | D | N |
| 273 | V | V | V | V |
| 274 | K | Q | Q | Q |
| 275 | F | I | I | I |
| 276 | N | T | T | T |
| 277 | W | W | W | W |
| 278 | Y | F | F | F |
| 279 | V | V | V | V |
| 280 | D | D | D | D |
| 281 | G | N | N | N |
| 282 | V | T | T | T |
| 283 | E | Q | Q | E |
| 284 | V | V | V | M |
| 285 | H | Y | Y | H |
| 286 | N | T | T | T |
| 287 | A | A | A | A |
| 288 | K | K | K | K |
| 289 | T | T | T | T |
| 290 | K | S | S | R |
| 291 | P | P | P | P |
| 292 | R | R | R | R |
| 293 | E | E | E | E |
| 294 | E | E | E | E |
| 295 | Q | Q | Q | Q |
| 296 | Y | F | F | F |
| 297 | N | N | N | N |
| 298 | S | S | S | S |
| 299 | T | T | T | T |
| 300 | Y | Y | Y | Y |
| 301 | R | R | R | R |
| 302 | V | V | V | V |
| 303 | V | V | V | V |
| 304 | S | S | S | S |
| 305 | V | V | V | V |
| 306 | L | L | L | L |
| 307 | T | P | P | P |
| 308 | V | I | I | I |
| 309 | L | L | L | L |
| 310 | H | H | H | H |
| 311 | Q | Q | Q | Q |
| 312 | D | D | D | D |
| 313 | W | W | W | W |
| 314 | L | L | L | L |
| 315 | N | K | K | K |
| 316 | G | G | G | G |
| 317 | K | K | K | K |
| 318 | E | E | E | E |
| 319 | Y | F | F | F |
| 320 | K | K | K | K |
| 321 | C | C | C | C |
| 322 | K | K | K | K |
| 323 | V | V | V | V |
| 324 | S | N | N | N |
| 325 | N | S | S | S |
| 326 | K | K | K | K |
| 327 | A | S | S | S |
| 328 | L | L | L | L |
| 329 | P | P | P | P |
| 330 | A | S | S | S |
| 331 | P | P | P | A |
| 332 | I | I | I | M |
| 333 | E | E | E | E |
| 334 | K | R | R | R |
| 335 | T | T | T | T |
| 336 | I | I | I | I |
| 337 | S | S | S | S |
| 338 | K | K | K | K |
| 339 | A | A | D | A |
| 340 | K | K | K | K |
| CH3 Domain | | | | |
| 341 | G | G | G | G |
| 342 | Q | Q | Q | Q |
| 343 | P | P | P | P |
| 344 | R | H | H | H |
| 345 | E | E | E | E |
| 346 | P | P | P | P |
| 347 | Q | Q | Q | Q |
| 348 | V | V | V | V |
| 349 | Y | Y | Y | Y |
| 350 | T | V | V | V |
| 351 | L | L | L | L |
| 352 | P | P | P | P |
| 353 | P | P | P | P |
| 354 | S | A | A | T |
| 355 | R | Q | Q | Q |
| 356 | D | E | E | E |
| 357 | E | E | E | E |
| 358 | L | L | L | L |
| 359 | T | S | S | S |
| 360 | K | R | R | E |

TABLE 1-continued

| EU number | human IgG1 | feline IgG1a | feline IgG1b | feline IgG2 |
|---|---|---|---|---|
| 361 | N | N | N | N |
| 362 | Q | K | K | K |
| 363 | V | V | V | V |
| 364 | S | S | S | S |
| 365 | L | V | V | V |
| 366 | T | T | T | T |
| 367 | C | C | C | C |
| 368 | L | L | L | L |
| 369 | V | I | I | I |
| 370 | K | K | E | K |
| 371 | G | S | G | G |
| 372 | F | F | F | F |
| 373 | Y | H | Y | H |
| 374 | P | P | P | P |
| 375 | S | P | S | P |
| 376 | D | D | D | D |
| 377 | I | I | I | I |
| 378 | A | A | A | A |
| 379 | V | V | V | V |
| 380 | E | E | E | E |
| 381 | W | W | W | W |
| 382 | E | E | E | E |
| 383 | S | I | I | I |
| 384 | N | T | T | T |
| 385 | G | G | G | G |
| 386 | Q | Q | Q | Q |
| 387 | P | P | P | P |
| 388 | E | E | E | E |
| 389a | N | P | P | P |
| 389b |   | E | E | E |
| 389c |   | N | N | N |
| 390 | N | N | N | N |
| 391 | Y | Y | Y | Y |
| 392 | K | R | R | Q |
| 393 | T | T | T | T |
| 394 | T | T | T | T |
| 395 | P | P | P | P |
| 396 | P | P | P | P |
| 397 | V | Q | Q | Q |
| 398 | L | L | L | L |
| 399 | D | D | D | D |
| 400 | S | S | S | S |
| 401 | D | D | D | D |
| 402 | G | G | G | G |
| 403 | S | T | T | T |
| 404 | F | Y | Y | Y |
| 405 | F | F | F | F |
| 406 | L | V | L | L |
| 407 | Y | Y | Y | Y |
| 408 | S | S | S | S |
| 409 | K | K | R | R |
| 410 | L | L | L | L |
| 411 | T | S | S | S |
| 412 | V | V | V | V |
| 413 | D | D | D | D |
| 414 | K | R | R | R |
| 415 | S | S | S | S |
| 416 | R | H | R | H |
| 417 | W | W | W | W |
| 418 | Q | Q | Q | Q |
| 419 | Q | R | R | R |
| 420 | G | G | G | G |
| 421 | N | N | N | N |
| 422 | V | T | T | T |
| 423 | F | Y | Y | Y |
| 424 | S | T | T | T |
| 425 | C | C | C | C |
| 426 | S | S | S | S |
| 427 | V | V | V | V |
| 428 | M | S | S | S |
| 429 | H | H | H | H |
| 430 | E | E | E | E |
| 431 | A | A | A | A |
| 432 | L | L | L | L |
| 433 | H | H | H | H |
| 434 | N | S | S | S |
| 435 | H | H | H | H |
| 436 | Y | H | H | H |
| 437 | T | T | T | T |
| 438 | Q | Q | Q | Q |
| 439 | K | K | K | K |
| 440 | S | S | S | S |
| 441 | L | L | L | L |
| 442 | S | T | T | T |
| 443 | L | Q | Q | Q |
| 444 | S | S | S | S |
| 445 | P | P | P | P |
| 446 | G | G | G | G |
| 447 | K | K | K | K |

Substitutions in Feline IgG Fc that Improve Half-Life

Increased serum persistence is a beneficial property for therapeutic polypeptides. This disclosure features substitutions in wild type feline IgG1a, IgG1b and IgG2 Fc regions that enhance the half-life of a polypeptide or polypeptides comprising these Fc regions in a cat relative to a control polypeptide or control polypeptides, wherein the control polypeptide or control polypeptides are identical to the polypeptide or polypeptides except for having the corresponding wild type feline IgG Fc region in place of the IgG Fc region variant. The substitutions to increase half-life may be made in one or more of a feline CH2 region, a feline CH3 region, or in the context of a feline Fc (e.g., a CH2+CH3) region.

The present disclosure provides a polypeptide comprising a feline IgG Fc region variant, or a feline FcRn-binding region thereof, wherein the polypeptide comprises an amino acid substitution at at least one position selected from the group consisting of:
  (i) a position that corresponds to amino acid position 252 of a wild type feline IgG, wherein the amino acid substitution is S252W;
  (ii) a position that corresponds to amino acid position 254 of a wild type feline IgG, wherein the amino acid substitution is selected from the group consisting of S254R and S254K;
  (iii) a position that corresponds to amino acid position 309 of a wild type feline IgG, wherein the amino acid substitution is L309V or L309Y;
  (iv) a position that corresponds to amino acid position 311 of a wild type feline IgG, wherein the amino acid substitution is selected from the group consisting of Q311R, Q311V, Q311L and Q311K;
  (v) a position that corresponds to amino acid position 428 of a wild type feline IgG, wherein the amino acid substitution is selected from the group consisting of S428M, S428Y, S428H and S428R; and
  (vi) one or more positions that correspond to amino acid positions selected from the group consisting of 262, 286, 289, 290, 293, 301, 312, 326, 334, 347, 355, 377, 380, 383, 389c, 392, 426 and 437 of a wild type feline IgG; wherein the amino acid positions are based on EU numbering, and wherein the polypeptide has increased binding affinity to feline FcRn when compared to an Fc domain of the wild type feline IgG.

In some embodiments, the polypeptide has increased binding affinity to feline FcRn at a pH of about 5.0 to about 6.5 (e.g., about 5.5 or about 6.0) when compared to an Fc domain of the wild type feline IgG.

In some embodiments, the polypeptide comprises the amino acid substitution at a position that corresponds to amino acid position 252 of a wild type feline IgG. In some embodiments, the amino acid substitution at position 252 of the wild type feline IgG is S252W.

In some embodiments, the polypeptide comprises the amino acid substitution at a position that corresponds to amino acid position 254 of a wild type feline IgG. In some embodiments, the amino acid substitution at position 254 of the wild type feline IgG is S254R. In some embodiments, the amino acid substitution at position 254 of the wild type feline IgG is S254K.

In some embodiments, the polypeptide comprises amino acid substitution L309V or L309Y.

In some embodiments, the polypeptide comprises the amino acid substitution at a position that corresponds to amino acid position 311 of a wild type feline IgG. In some embodiments, the amino acid substitution at position 311 of the wild type feline IgG is Q311R. In some embodiments, the amino acid substitution at position 311 of the wild type feline IgG is Q311V. In some embodiments, the amino acid substitution at position 311 of the wild type feline IgG is Q311K. In some embodiments, the amino acid substitution at position 311 of the wild type feline IgG is Q311L.

In some embodiments, the polypeptide comprises the amino acid substitution at a position that corresponds to amino acid position 428 of a wild type feline IgG. In some embodiments, the amino acid substitution at position 428 of the wild type feline IgG is S428M.

In some embodiments, the polypeptide comprises at least the amino acid substitution S428Y. In some embodiments, the amino acid substitution at position 428 of the wild type feline IgG is S428Y. In some embodiments, the amino acid substitution at position 428 of the wild type feline IgG is S428R. In some embodiments, the amino acid substitution at position 428 of the wild type feline IgG is S428H.

In another embodiment, the polypeptide comprises an amino acid substitution at one or more positions that correspond to amino acid positions selected from the group consisting of 262, 286, 289, 290, 293, 301, 312, 326, 334, 347, 355, 377, 380, 383, 389c, 392, 426 and 437 of a wild type feline IgG. In some embodiments, the amino acid substitution is selected from the group consisting of L262Q, L262E, T286E, T286D, T289K, S290V, S290Y, E293D, E293H, E293K, R301L, D312T, K326D, R334D, Q347L, Q355L, I377V, I377Y, E380D, E380V, E380T, I383L, N389c-R, R392E, S426L, S426H and T437L, and conservative amino acid substitutions of any of foregoing. In some embodiments, the amino acid substitution is selected from the group consisting of L262Q, L262E, T286E, T286D, T289K, S290V, S290Y, E293D, E293H, E293K, R301L, D312T, K326D, R334D, Q347L, Q355L, I377V, I377Y, E380D, E380V, E380T, I383L, N389c-R, R392E, S426L, S426H and T437L.

In another aspect, the disclosure provides a polypeptide comprising a feline IgG Fc region variant, or a feline FcRn-binding region thereof, wherein the polypeptide comprises two or more amino acid substitutions, wherein the two or more amino acid substitutions are selected from the group consisting of:
(i) an amino acid substitution at a position that corresponds to amino acid position 252 of a wild type feline IgG, wherein the amino acid substitution is selected from the group consisting of S252W, S252Y, S252F and S252R;
(ii) an amino acid substitution at a position that corresponds to amino acid position 254 of a wild type feline IgG, wherein the amino acid substitution is selected from the group consisting of S254R and S254K;
(iii) an amino acid substitution at a position that corresponds to amino acid position 309 of a wild type feline IgG, wherein the amino acid substitution is selected from the group consisting of L309V, L309Y and L309E;
(iv) an amino acid substitution at a position that corresponds to amino acid position 311 of a wild type feline IgG, wherein the amino acid substitution is selected from the group consisting of Q311R, Q311V, Q311L and Q311K;
(v) an amino acid substitution at a position that corresponds to amino acid position 428 of a wild type feline IgG, wherein the amino acid substitution is selected from the group consisting of S428L, S428M, S428Y, S428H and S428R;
(vi) an amino acid substitution at one or more positions that correspond to amino acid positions selected from the group consisting of 262, 286, 289, 290, 293, 301, 312, 326, 334, 347, 355, 377, 380, 383, 389c, 392, 426 and 437 of a wild type feline IgG; and
(vii) an amino acid substitution at a position that corresponds to amino acid position 434 of a wild type feline IgG, wherein the amino acid substitution is selected from the group consisting of S434F, S434W, S434H, S434R, and S434Y;
wherein the amino acid positions are based on EU numbering, wherein the two or more amino acid substitutions are at different positions, and wherein the polypeptide has increased binding affinity to feline FcRn when compared to (a) an Fc domain of the wild type feline IgG, and (b) a polypeptide comprising only one of the two or more amino acid substitutions.

In some embodiments, the two or more amino acid substitutions comprise an amino acid substitution at a position that corresponds to amino acid position 286 of a wild type feline IgG, wherein the amino acid substitution is selected from the group consisting of T286E and T286D.

In some embodiments, the two or more amino acid substitutions comprise an amino acid substitution at a position that corresponds to amino acid position 289 of a wild type feline IgG, wherein the amino acid substitution is selected from the group consisting of T289K and T289H.

In some embodiments, the two or more amino acid substitutions comprise an amino acid substitution at a position that corresponds to amino acid position 301 of a wild type feline IgG, wherein the amino acid substitution is R301L.

In some embodiments, the two or more amino acid substitutions comprise an amino acid substitution at a position that corresponds to amino acid position 334 of a wild type feline IgG, wherein the amino acid substitution is R334D.

In some embodiments, the two or more amino acid substitutions comprise an amino acid substitution at a position that corresponds to amino acid position 426 of a wild type feline IgG, wherein the amino acid substitution is selected from the group consisting of S426L and S426H.

In some embodiments, the two or more amino acid substitutions comprise an amino acid substitution at a position that corresponds to amino acid position 437 of a wild type feline IgG, wherein the amino acid substitution is T437L.

In some embodiments, the two or more amino acid substitutions are selected from the group consisting of:
(i) S252Y in combination with Q311R and/or Q311L;
(ii) S434Y in combination with one or more of S254R, S254K, L262E, T286D, T286E, T289K, E293D, E293K, L309V, L309E, K326D and Q347L;
(iii) S434F and E380D;

(iv) S428L in combination with one or more of S252R, T286E, Q311V, Q311K, D312T, I377V, I383L, N389cR;
(v) S428L, E380D and S434R;
(vi) S428L, E380T and S434R;
(vii) S252R in combination with L262Q;
(viii) T260E, L309E and Q355L;
(ix) S290V and R344D; and
(x) R301L, E380V and T437L.

In some embodiments, the polypeptide comprises an amino acid sequence that is at least 80% (e.g., at least 85%, 90%, 92%, 94%, 95%, 96%, 97%, 98%, or 99%) identical to an amino acid sequence selected from the group consisting of SEQ ID NOs: 1 to 3.

In some instances, this disclosure provides a feline IgG CH2 region variant comprising an amino acid sequence that is at least 75%, at least 80%, at least 85%, at least 90%, at least 95%, at least 96%, at least 97%, at least 98% or at least 99% identical to the amino acid sequence set forth in any one of SEQ ID NOs.:4 to 6. Also provided are feline IgG CH2 region variants comprising an amino acid sequence that varies from any one of SEQ ID NOs.:4 to 6 by 1 to 15 (e.g., 1, 2, 3, 4, 5, 6, 7, 8, 9, 10, 11, 12, 13, 14, or 15) amino acids.

In other instances, this disclosure features a feline IgG CH3 region variant comprising an amino acid sequence that is at least 75%, at least 80%, at least 85%, at least 90%, at least 95%, at least 96%, at least 97% or at least 98% or at least 99%, identical to the amino acid sequence set forth in any one of SEQ ID NOs.:7 to 9. Also featured are feline IgG CH3 region variants comprising an amino acid sequence that varies from any one of SEQ ID NOs.:7 to 9 by 1 to 15 (e.g., 1, 2, 3, 4, 5, 6, 7, 8, 9, 10, 11, 12, 13, 14, or 15) amino acids.

In certain instances, this disclosure features a feline IgG Fc region variant comprising an amino acid sequence that is at least 75%, at least 80%, at least 85%, at least 90%, at least 95%, at least 96%, at least 97%, at least 98% or at least 99% identical to the amino acid sequence set forth in any one of SEQ ID NOs.:1 to 3. Also disclosed are feline IgG Fc region variants comprising an amino acid sequence that varies from any one of SEQ ID NOs.:1 to 3 by 1 to 20 (e.g., 1, 2, 3, 4, 5, 6, 7, 8, 9, 10, 11, 12, 13, 14, 15, 16, 17, 18, 19, or 20) amino acids.

In some embodiments, provided are a polypeptide or polypeptides comprising a feline IgG Fc CH2 region variant, the CH2 region variant comprising an amino acid sequence that is at least 75%, at least 80%, at least 85%, at least 90%, at least 95%, at least 96%, at least 97%, at least 98% or at least 99%, identical to the amino acid sequence set forth in any one of SEQ ID NOs.:4 to 6.

In some embodiments, featured are a polypeptide or polypeptides comprising a feline IgG Fc CH3 region variant, the CH3 region variant comprising an amino acid sequence that is at least 75%, at least 80%, at least 85%, at least 90%, at least 95%, at least 96%, at least 97%, at least 98% or at least 99% identical to the amino acid sequence set forth in any one of SEQ ID NOs.:7 to 9.

In some embodiments, featured are a polypeptide or polypeptides comprising a feline IgG Fc region variant, the Fc region variant comprising an amino acid sequence that is at least 75%, at least 80%, at least 85%, at least 90%, at least 95%, at least 96%, at least 97%, at least 98% or at least 99% identical to the amino acid sequence set forth in any one of SEQ ID NOs.:1 to 3.

As noted elsewhere, the polypeptide, in some embodiments, further comprises at least one additional amino acid substitution in a region corresponding to amino acid positions 250-256, amino acid positions 285-288; amino acid positions 307-315; amino acid positions 376-380, amino acid positions 383 to 392; or amino acid positions 428-437 of the wild type feline IgG, wherein the amino acid positions are based on EU numbering, and wherein the polypeptide has increased binding to feline FcRn compared to an Fc domain of the wild type feline IgG.

In some embodiments, the polypeptide comprises at least one (e.g., 1, 2, 3, 4, 5, 6, 7, 8, 9, 10, 11, 12, 13, 14, 15, 16, 17, 18, 19, or 20) additional amino acid substitution selected from those disclosed in Table 2, below.

TABLE 2

List of amino acid substitutions (Groups 1 and 2) that increase binding of the feline IgG1a Fc variant to feline FcRN.

| Position by EU numbering | Wild-type feline IgG1a Fc | Feline IgG1a Fc variant amino acid substitutions (Group 1) | Alternative feline IgG1a Fc variant amino acid substitutions (Group 2) |
| --- | --- | --- | --- |
| 252 | S | W | FYMRV |
| 254 | S | RK | WYHLFVM |
| 262 | L | QE | |
| 286 | T | ED | |
| 289 | T | K | |
| 290 | S | VY | |
| 293 | E | DKH | |
| 301 | R | L | |
| 309 | L | VY | E |
| 311 | Q | RVKL | AYF |
| 312 | D | T | |
| 326 | K | D | |
| 334 | R | D | |
| 347 | Q | L | |
| 355 | Q | L | |
| 377 | I | VY | |
| 380 | E | DVT | |
| 383 | I | L | |
| 389c | N | R | |
| 392 | R | E | |
| 426 | S | LH | |
| 428 | S | RMYH | WL |
| 434 | S | RYFWH | A |
| 437 | T | L | |

The amino acid substitutions may be made on one or both chains of a CH2 domain, a CH3 domain, or an Fc domain. In some instances, the substitutions on both chains of a CH2 domain, a CH3 domain, or an Fc domain are identical. In some instances, the substitutions on both chains of a CH2 domain, a CH3 domain, or an Fc domain are not identical. In some instances, the Fc region includes one or more additional substitutions that increase or decrease effector function and/or improve product heterogeneity.

Other Substitutions that can be Combined with the Half-Life Enhancing Substitutions The development of a therapeutic polypeptide/protein (e.g., a monoclonal antibody) is a complex process that entails coordination of a complex set of activities to generate the desired polypeptide/protein. These include optimization of the specificity, affinity, functional activity, expression level in engineered cell lines, long-term stability, elimination or enhancement of effector functions and development of commercially viable manufacturing and purification methods. This disclosure encompasses any additional substitution that facilitates any one or more of the above goals.

In some embodiments, the substitutions are introduced to reduce effector function of the feline Fc region. Such substitutions will be familiar to persons skilled in the art and may be at one or more (e.g., 1, 2, 3, 4, 5, 6, or 7) positions of the feline IgG. Illustrative examples include WO 2019/035010 A1.

In some embodiments, substitutions are introduced to a wild type feline IgG Fc region to enhance binding to Protein A so as to facilitate purification by protein A chromatography. Such substitutions will be familiar to persons skilled in the art and may be at one or more (e.g., 1, 2, 3, 4, 5, 6, or 7) positions of the feline IgG. Illustrative examples include WO 2019/035010 A1.

In some embodiments, additional amino acid substitutions can be made to alter binding affinity to FcRn as compared to a parent polypeptide or a wild-type polypeptide (e.g., to increase or reduce binding affinity with FcRn).

In some embodiments, the polypeptide comprises a hinge region of a feline antibody. In some embodiments, modifications can be made to the hinge region of the feline antibody to increase half-life.

Polypeptides Comprising the Feline IgG Fc Variants

The disclosure encompasses any polypeptide that may benefit from having an increased half-life in a cat. To increase half-life these polypeptides are designed to include an Fc region variant (e.g., a CH2 region, a CH3 region, a CH2+CH3 region) disclosed above.

Exemplary polypeptides include, but are not limited to, whole antibodies, scFvs, nanobodies, ligand-binding portions of a receptor, cytokines, growth factors, enzymes, and peptides. For example, a CH3 domain variant disclosed above may be attached to an scFv nanobody, ligand-binding portion of a receptor (e.g., the ligand-binding portion of feline IL-13Rα1 or IL-13Rα2), a cytokine, a growth factor, an enzyme, or a peptide. As used herein, the terms "nanobody", "VHH", "VHH antibody fragment" and "single domain antibody" are used interchangeably herein to denote the variable domain of the single heavy chain of antibodies of the type of those found in Camelidae, which are typically found in nature to lack light chains. Suitable nanobodies will be familiar to persons skilled in the art, illustrated examples of which include nanobodies of camels, dromedaries, llamas and alpacas. Alternatively, an Fc region variant disclosed above may be attached to these polypeptides. In another embodiment, a feline or felinized antibody is modified to include an Fc region variant disclosed herein.

In some embodiments, the polypeptides of this disclosure include an antibody hinge region. The hinge region may be placed between the antigen or ligand-binding domain of the polypeptide and the Fc region variant. In some instances, the hinge region is attached to the C-terminus of a cytokine, a growth factor, an enzyme, or a peptide and the hinge region is attached to the N-terminus of the Fc region variant. Exemplary hinge region sequences are provided below.

```
IgG1a:
                                       (SEQ ID NO: 10)
KTDHPPGPKPCDCPKCP;

IgG1b:
                                       (SEQ ID NO: 11)
KTDHPPGPKPCDCPKCP;

IgG2:
                                       (SEQ ID NO: 12)
KTASTIESKTGEGPKCP;
```

The hinge region, if used, in a recombinant protein of this disclosure may include zero to six (i.e., 0, 1, 2, 3, 4, 5, or 6) amino acid substitutions relative to an amino acid sequence set forth in any one of SEQ ID NOs.:10-12. In some instances, the hinge region used in a recombinant protein of this disclosure is at least 80%, at least 85%, at least 90%, at least 95%, at least 96%, at least 97%, at least 98%, at least 99%, or 100% identical to an amino acid sequence set forth in any one of SEQ ID NOs:10-12.

The polypeptide or polypeptides of this disclosure may comprise a binding domain. The binding domain can specifically bind to a protein, subunit, domain, motif, and/or epitope of a selected target described herein. In some embodiments, the polypeptide or polypeptides (e.g., fusion polypeptide) can comprise a protein, wherein the protein is a therapeutic protein described herein. In some embodiments, the target (e.g., for the target of the binding domain) or the therapeutic protein (e.g., for the fusion polypeptide) is selected from the group consisting of: 17-IA, 4-1BB, 4Dc, 6-keto-PGF1a, 8-iso-PGF2a, 8-oxo-dG, A1 Adenosine Receptor, A33, ACE, ACE-2, Activin, Activin A, Activin AB, Activin B, Activin C, Activin RIA, Activin RIA ALK-2, Activin RIB ALK-4, Activin RIIA, Activin RIIB, ADAM, ADAM10, ADAM12, ADAM15, ADAM17/TACE, ADAMS, ADAM9, ADAMTS, ADAMTS4, ADAMTS5, Addressins, aFGF, ALCAM, ALK, ALK-1, ALK-7, alpha-1-antitrypsin, alpha-V/beta-1 antagonist, ANG, Ang, APAF-1, APE, APJ, APP, APRIL, AR, IgE, Angiotensin type 1 (AT1) receptor, Angiotensin type 2 (AT2) receptor, ARC, ART, Artemin, anti-Id, ASPARTIC, Atrial natriuretic factor, av/b3 integrin, Axl, b2M, B7-1, B7-2, B7-H, B-lymphocyte Stimulator (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 Osteogenin, BMP-4 BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMPs, b-NGF, BOK, Bombesin, Bone-derived neurotrophic factor, BPDE, BPDE-DNA, BTC, complement factor 3 (C3), C3a, C4, C5, C5a, C10, CA125, CAD-8, Calcitonin, cAMP, carcinoembryonic antigen (CEA), carcinoma-associated antigen, Cathepsin A, Cathepsin B, Cathepsin C/DPPI, Cathepsin D, Cathepsin E, Cathepsin H, Cathepsin L, Cathepsin O, Cathepsin S, Cathepsin V, Cathepsin X/Z/P, CBL, CC1, CCK2, CCL, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL6, CCL7, CCL8, CCL9/10, CCR, CCR1, CCR10, CCR10, CCR2, CCR3, CCR4, CCR5, CCR6, CCR7, CCR8, CCR9, CD1, CD2, CD3, CD3E, CD4, CD5, CD6, CD7, CD8, CD10, CD11a, CD11b, CD11c, CD13, CD14, CD15, CD16, CD18, CD19, CD20, CD21, CD22, CD23, CD25, CD27L, CD28, CD29, CD30, CD30L, CD32, CD33 (p67 proteins), CD34, CD38, CD40, CD40L, CD44, CD45, CD46, CD47, CD49a, CD52, CD54, CD55, CD56, CD61, CD64, CD66e, CD74, CD80 (B7-1), CD89, CD95, CD123, CD137, CD138, CD140a, CD146, CD147, CD148, CD152, CD164, CEACAM5, CFTR, cGMP, CINC, *Clostridium botulinum* toxin, *Clostridium perfringens* toxin, CKb8-1, CLC, CMV, CMV UL, CNTF, CNTN-1, COX, C-Ret, CRG-2, CT-1, CTACK, CTGF, CTLA-4, CX3CL1, CX3CR1, CXCL, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCR5, CXCR6, cytokeratin tumor-associated antigen, DAN, DCC, DcR3, DC-SIGN, Decay accelerating factor, des(1-3)-IGF-I (brain IGF-1), Dhh, digoxin, DNAM-1, Dnase, Dpp, DPPIV/CD26, Dtk, ECAD, EDA, EDA-A1, EDA-A2, EDAR, EGF, EGFR (ErbB-1), EMA, EMMPRIN, ENA, endothelin receptor, Enkephalinase, eNOS, Eot, eotaxinl, EpCAM, Ephrin B2/EphB4, EPO, ERCC, E-selectin, ET-1, Factor IIa, Factor VII, Factor VIIIc, Factor IX, fibroblast activation protein (FAP), Fas, FcR1, FEN-1, Ferritin, FGF, FGF-19, FGF-2, FGF3, FGF-8, FGFR, FGFR-3, Fibrin, FL, FLIP, Flt-3, Flt-4, Follicle stimulating hormone, Fractalkine, FZD1, FZD2, FZD3, FZD4, FZD5, FZD6, FZD7, FZD8, FZD9, FZD10, G250, Gas 6, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (Myostatin), GDF-9, GDF-15 (MIC-1), GDNF, GDNF, GFAP, GFRa-1, GFR-alpha1, GFR-alpha2, GFR-alpha3, GITR, GLP1, GLP2, Glucagon, Glut 4, glycoprotein IIb/IIIa (GP IIb/IIIa), GM-CSF, gp130, gp72, GRO, GnRH, Growth hormone releasing factor, Hapten (NP-cap or NIP-cap), HB-EGF, HCC, HCMV gB envelope glycoprotein, HCMV) gH envelope glycoprotein, HCMV UL, Hemopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, High molecular weight melanoma-associated antigen (HMW-MAA), HIV gp120, HIV IIIB gp120 V3 loop, HLA, HLA-DR, HM1.24, HMFG PEM, HRG, Hrk, cardiac myosin, cytomegalovirus (CMV), growth hormone (GH), HVEM, 1-309, IAP, ICAM, ICAM-1, ICAM-3, ICE, ICOS, IFNg, Ig, IgA receptor, IgE, IGF, IGF binding proteins, IGF-1R, IGFBP, IGF-I, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-17, IL-18, IL-18R, IL-21, IL-22, IL-23, IL-25, IL-31, IL-33, interleukin receptor (e.g., IL-1R, IL-2R, IL-4R, IL-5R, IL-6R, IL-8R, IL-9R, IL-10R, IL-12R, IL-13R, IL-15R, IL-17R, IL-18R, IL-21R, IL-22R, IL-23R, IL-25R, IL-31R, IL-33R), interferon (INF)-alpha, INF-beta, INF-gamma, Inhibin, iNOS, Insulin A-chain, Insulin B-chain, Insulin-like growth factor 1, integrin alpha2, integrin alpha3, integrin alpha4, integrin alpha4/beta1, integrin alpha4/beta7, integrin alpha5 (alphaV), integrin alpha5/beta1, integrin alpha5/beta3, integrin alpha6, integrin beta1, integrin beta2, interferon gamma, IP-10, I-TAC, JE, Kallikrein 2, Kallikrein 5, Kallikrein 6, Kallikrein 11, Kallikrein 12, Kallikrein 14, Kallikrein 15, Kallikrein L1, Kallikrein L2, Kallikrein L3, Kallikrein L4, KC, KDR, Keratinocyte Growth Factor (KGF), laminin 5, LAMP, LAP, LAP (TGF-1), Latent TGF-1, Latent TGF-1 bp1, LBP, LDGF, LECT2, Lefty, Lewis-Y antigen, Lewis-Y related antigen, LFA-1, LFA-3, Lfo, LIF, LIGHT, lipoproteins, LIX, LKN, Lptn, L-Selectin, LT-a, LT-b, LTB4, LTBP-1, Lung surfactant, Luteinizing hormone, Lymphotoxin Beta Receptor, Mac-1, MAdCAM, MAG, MAP2, MARC, MCAM, MCAM, MCK-2, MCP, M-CSF, MDC, Mer, METALLOPROTEASES, MGDF receptor, MGMT, MHC(HLA-DR), MIF, MIG, MIP, MIP-1-alpha, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, MPIF, Mpo, MSK, MSP, mucin (Muc1), MUC18, Muellerian-inhibitin substance, Mug, MuSK, NAIP, NAP, NAV 1.7, NCAD, N-Cadherin, NCA 90, NCAM, NCAM, Neprilysin, Neurotrophin-3, -4, or -6, Neurturin, Neuronal growth factor (NGF), NGFR, NGF-beta, nNOS, NO, NOS, Npn, NRG-3, NT, NTN, OB, OGG1, OPG, OPN, OSM, OX40L, OX40R, p150, p95, PADPr, Parathyroid hormone, PARC, PARP, PBR, PBSF, PCAD, P-Cadherin, PCNA, PD1, PDL1, PDGF, PDGF, PDK-1, PECAM, PEM, PF4, PGE, PGF, PGI2, PGJ2, PIN, PLA2, placental alkaline phosphatase (PLAP), P1GF, PLP, PP14, Proinsulin, Prorelaxin, Protein C, PS, PSA, PSCA, prostate specific membrane antigen (PSMA), PTEN, PTHrp, Ptk, PTN, R51, RANK, RANKL, RANTES, RANTES, Relaxin A-chain, Relaxin B-chain, renin, respiratory syncytial virus (RSV) F, RSV Fgp, Ret, Rheumatoid factors, RLIP76, RPA2, RSK, S100, SCF/KL, SDF-1, SERINE, Serum albumin, sFRP-3, Shh, SIGIRR, SK-1, SLAM, SLPI, SMAC, SMDF, SMOH, SOD, SPARC, Stat, STEAP, STEAP-II, TACE, TACI, TAG-72 (tumor-associated glycoprotein-72), TARC, TCA-3, T-cell receptors (e.g., T-cell receptor alpha/beta), TdT, TECK, TEM1, TEM5, TEM7, TEM8, TERT, testicular PLAP-like alkaline phosphatase, TfR, TGF, TGF-alpha, TGF-beta, TGF-beta Pan Specific, TGF-beta R1 (ALK-5), TGF-beta R11, TGF-beta RIIb, TGF-beta RIII, TGF-beta1, TGF-beta2, TGF-beta3, TGF-beta4, TGF-beta5, Thrombin, Thymus Ck-1, Thyroid stimulating hormone, Tie, TIMP, TIQ, Tissue Factor, TMEFF2, Tmpo, TMPRSS2, TNF, TNF-alpha, TNF-alpha beta, TNF-beta2, TNFc, TNF-RI, TNF-RII, TNFRSF10A (TRAIL R1Apo-2, DR4), TNFRSF10B (TRAIL R2DR5, KILLER, TRICK-2A, TRICK-B), TNFRSF10C (TRAIL R3DcR1, LIT, TRID), TNFRSF10D (TRAIL R4 DcR2, TRUNDD), TNFRSF11A (RANK ODF R, TRANCE R), TNFRSF11B (OPG OCIF, TR1), TNFRSF12 (TWEAK R FN14), TNFRSF13B (TACI), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITR AITR), TNFRSF19 (TROY TAJ, TRADE), TNFRSF19L (RELT), TNFRSF1A (TNF R1CD120a, p55-60), TNFRSFlB (TNF RII CD120b, p75-80), TNFRSF26 (TNFRH3), TNFRSF3 (LTbR TNF RIII, TNFC R), TNFRSF4 (OX40 ACT35, TXGP1 R), TNFRSF5 (CD40 p50), TNFRSF6 (Fas Apo-1, APT1, CD95), TNFRSF6B (DcR3M68, TR6), TNFRSF7 (CD27), TNFRSF8 (CD30), TNFRSF9 (4-1BB CD137, ILA), TNFRSF21 (DR6), TNFRSF22 (DCTRAIL R2 TNFRH2), TNFRST23 (DCTRAIL R1TNFRH1), TNFRSF25 (DR3Apo-3, LARD, TR-3, TRAMP, WSL-1), TNFSF10 (TRAIL Apo-2 Ligand, TL2), TNFSF11 (TRANCE/RANK Ligand ODF, OPG Ligand), TNFSF12 (TWEAK Apo-3 Ligand, DR3Ligand), TNFSF13 (APRIL TALL2), TNFSF13B (BAFF BLYS, TALL1, THANK, TNFSF20), TNFSF14 (LIGHT HVEM Ligand, LTg), TNFSF15 (TL1A/VEGI), TNFSF18 (GITR Ligand AITR Ligand, TL6), TNFSF1A (TNF-a Conectin, DIF, TNFSF2), TNFSFlB (TNF-b LTa, TNFSF1), TNFSF3 (LTb TNFC, p33), TNFSF4 (OX40 Ligand gp34, TXGP1), TNFSF5 (CD40 Ligand CD154, gp39, HIGM1, IMD3, TRAP), TNFSF6 (Fas Ligand Apo-1 Ligand, APT1 Ligand), TNFSF7 (CD27 Ligand CD70), TNFSF8 (CD30 Ligand CD153), TNFSF9 (4-1BB Ligand CD137 Ligand), TP-1, t-PA, Tpo, TRAIL, TRAIL R, TRAIL-R1, TRAIL-R2, TRANCE, transferring receptor, TRF, Trk (e.g., TrkA), TROP-2, TSG, TSLP, tumor-associated antigen CA 125, tumor-associated antigen expressing Lewis Y related carbohydrate, TWEAK, TXB2, Ung, UPAR, uPAR-1, Urokinase, VCAM, VCAM-1, VECAD, VE-Cadherin, VE-cadherin-2, VEFGR-1 (fit-1), VEGF, VEGFR, VEGFR-3 (flt-4), VEGI, VIM, Viral antigens, VLA, VLA-1, VLA-4, VNR integrin, von Willebrands factor, WIF-1, WNT1, WNT2, WNT2n/13, WNT3, WNT3A, WNT4, WNT5A, WNT5B, WNT6, WNT7A, WNT7B, WNT8A, WNT8B, WNT9A, WNT9A, WNT9B, WNT10A, WNT10B, WNT11, WNT16, XCL1, XCL2, XCR1, XCR1, XEDAR, XIAP, XPD, and receptors for hormones and growth factor.

In some embodiments, the binding domain specifically binds to one or more therapeutic targets or antigens in feline, such as, but are not limited to, ACE, ACE-2, Activin, Activin A, Activin AB, Activin B, Activin C, Activin RIA, Activin RIA ALK-2, Activin RIB ALK-4, Activin RIIA, Activin RIIB, ADAM, ADAM10, ADAM12, ADAM15, ADAM17/TACE, ADAMS, ADAM9, ADAMTS, ADAMTS4, ADAMTS5, ANG, Ang, Angiotensin type 1 (AT1) receptor, Angiotensin type 2 (AT2) receptor, Atrial natriuretic factor, av/b3 integrin, b-ECGF, CD19, CD20, CD30, CD34, CD40, CD40L, CD47, COX, CTLA-4, EGFR (ErbB-1), EPO, Follicle stimulating hormone, GDF-8 (Myostatin), GLP1, GLP2, GnRH, Growth hormone releasing factor, IgE, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-17, IL-18, IL-18R, IL-21, IL-22, IL-23, IL-25, IL-31, IL-33, interleukin receptor (e.g., IL-1R, IL-2R, IL-4R, IL-5R, IL-6R, IL-8R, IL-9R, IL-10R, IL-12R, IL-13R, IL-15R, IL-17R, IL-18R, IL-21R, IL-22R, IL-23R, IL-25R, IL-31R, IL-33R), LAP (TGF-1), Latent TGF-1, Latent TGF-1 bp1, LFA-1, Neuronal growth factor (NGF), NGFR, NGF-beta, OX40L, OX40R, PD1, PDL1, TGF, TGF-alpha, TGF-beta, TGF-beta Pan Specific, TGF-beta R1 (ALK-5), TGF-beta R11, TGF-beta RIIb, TGF-beta RIII, TGF-beta1, TGF-beta2, TGF-beta3, TGF-beta4, TGF-beta5, TNF, TNF-alpha, TNF-alpha beta, TNF-beta2, TNFc, TNF-RI, TNF-RII, TNFRSF16 (NGFR p75NTR), TNFRSF9 (4-1BB CD137, ILA), VEFGR-1 (fit-1), VEGF, VEGFR, and VEGFR-3 (flt-4).

In some embodiments, the polypeptide or polypeptides can comprise a protein, wherein the protein is a therapeutic protein, e.g., EPO, CTLA4, LFA3, VEGFR1/VEGFR3, IL-1R, IL-4R, GLP-1 receptor agonist, or Thrombopoietin binding peptide. In some embodiments, the therapeutic protein is ACE, ACE-2, Activin, Activin A, Activin AB, Activin B, Activin C, Activin RIA, Activin RIA ALK-2, Activin RIB ALK-4, Activin RIIA, Activin RIIB, ADAM, ADAM10, ADAM12, ADAM15, ADAM17/TACE, ADAMS, ADAM9, ADAMTS, ADAMTS4, ADAMTS5, ANG, Ang, Angiotensin type 1 (AT1) receptor, Angiotensin type 2 (AT2) receptor, Atrial natriuretic factor, av/b3 integrin, b-ECGF, CD19, CD20, CD30, CD34, CD40, CD40L, CD47, COX, CTLA-4, EGFR (ErbB-1), EPO, Follicle stimulating hormone, GDF-8 (Myostatin), GLP1, GLP2, GnRH, Growth hormone releasing factor, IgE, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-17, IL-18, IL-18R, IL-21, IL-22, IL-23, IL-25, IL-31, IL-33, interleukin receptor (e.g., IL-1R, IL-2R, IL-4R, IL-5R, IL-6R, IL-8R, IL-9R, IL-10R, IL-12R, IL-13R, IL-15R, IL-17R, IL-18R, IL-21R, IL-22R, IL-23R, IL-25R, IL-31R, IL-33R), LAP (TGF-1), Latent TGF-1, Latent TGF-1 bp1, LFA-1, Neuronal growth factor (NGF), NGFR, NGF-beta, OX40L, OX40R, PD1, PDL1, TGF, TGF-alpha, TGF-beta, TGF-beta Pan Specific, TGF-beta R1 (ALK-5), TGF-beta R11, TGF-beta RIIb, TGF-beta RIII, TGF-beta1, TGF-beta2, TGF-beta3, TGF-beta4, TGF-beta5, TNF, TNF-alpha, TNF-alpha beta, TNF-beta2, TNFc, TNF-RI, TNF-RII, TNFRSF16 (NGFR p75NTR), TNFRSF9 (4-1BB CD137, ILA), VEFGR-1 (fit-1), VEGF, VEGFR, or VEGFR-3 (flt-4).

Pharmaceutical Compositions

To prepare pharmaceutical or sterile compositions of a polypeptide or polypeptides described herein, the polypeptide or polypeptides can be admixed with a pharmaceutically acceptable carrier or excipient. (See, e.g., Remington's Pharmaceutical Sciences and U.S. Pharmacopeia: National Formulary, Mack Publishing Company, Easton, Pa. (1984)).

Formulations of therapeutic and diagnostic agents may be prepared by mixing with acceptable carriers, excipients, or stabilizers in the form of, e.g., lyophilized powders, slurries, aqueous solutions or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.). In one embodiment, the polypeptide or polypeptides of the present invention are diluted to an appropriate concentration in a sodium acetate solution pH 5-6, and NaCl or sucrose is added for tonicity. Additional agents, such as polysorbate 20 or polysorbate 80, may be added to enhance stability.

Toxicity and therapeutic efficacy of the polypeptide compositions, administered alone or in combination with another agent, can be determined by standard pharmaceutical procedures in cell cultures or experimental animals, e.g., for determining the LDso (the dose lethal to 50% of the population) and the EDso (the dose therapeutically effective in 50% of the population). The dose ratio between toxic and therapeutic effects is the therapeutic index (LDso/EDso). In particular aspects, a polypeptide or polypeptides exhibiting high therapeutic indices are desirable. The data obtained from these cell culture assays and animal studies can be used in formulating a range of dosage for use in felines. The dosage of such compounds lies preferably within a range of circulating concentrations that include the EDso with little or no toxicity. The dosage may vary within this range depending upon the dosage form employed and the route of administration.

The mode of administration can vary. Suitable routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial. In some embodiments, the polypeptide or polypeptides can be administered by an invasive route such as by injection. In further embodiments, the polypeptide or polypeptides is administered intravenously, subcutaneously, intramuscularly, intraarterially, intratumorally, or by inhalation, aerosol delivery.

The pharmaceutical compositions disclosed herein may also be administered by infusion. Examples of well-known implants and modules form administering pharmaceutical compositions include: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art.

Alternatively, one may administer the polypeptide or polypeptides in a local rather than systemic manner, for example, via injection of the antibody directly into an arthritic joint or pathogen-induced lesion characterized by immunopathology, often in a depot or sustained release formulation. Furthermore, one may administer the polypeptide or polypeptides in a targeted drug delivery system, for example, in a liposome coated with a tissue-specific antibody, targeting, for example, arthritic joint or pathogen-induced lesion characterized by immunopathology. The liposomes will be targeted to and taken up selectively by the afflicted tissue.

The administration regimen depends on several factors, including, without limitation, the age, weight, and physical condition of the feline being treated, the serum or tissue turnover rate of the therapeutic antibody, the level of symptoms, the immunogenicity of the therapeutic polypeptide or polypeptides, and the accessibility of the target cells in the biological matrix. In some implementations, the administration regimen delivers sufficient therapeutic polypeptide or polypeptides to effect improvement in the target disease state, while simultaneously minimizing undesired side effects. Accordingly, the amount of biologic delivered depends in part on the particular therapeutic polypeptide or polypeptides and the severity of the condition being treated. Guidance in selecting appropriate doses of therapeutic antibodies is available (see, e.g., Wawrzynczak Antibody Therapy, Bios Scientific Pub. Ltd, Oxfordshire, U K (1996); Milgrom et al. New Engl. J. Med. 341:1966-1973 (1999); Slamon et al. New Engl. J. Med. 344:783-792 (2001); Beniaminovitz et al. New Engl. J. Med. 342:613-619 (2000); Ghosh et al. New Engl. J. Med. 348:24-32 (2003); Lipsky et al. New Engl. J. Med. 343:1594-1602 (2000)).

Determination of the appropriate dose of the polypeptide or polypeptides is made by one skilled in the art, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Nucleic Acids, Vectors, Host Cells, and Methods of Making

The disclosure also encompasses nucleic acid or nucleic acids encoding the polypeptide or polypeptides described herein, a vector or vectors comprising the nucleic acid or nucleic acids, and host cells comprising the nucleic acid or nucleic acids or the vector or vectors.

The polypeptide or polypeptides described herein may be produced in bacterial or eukaryotic cells. Some polypeptides, e.g., Fab's, can be produced in bacterial cells, e.g., *E. coli* cells. Polypeptides can also be produced in eukaryotic cells such as transformed cell lines (e.g., CHO, 293E, COS, 293T, Hela). In addition, polypeptides (e.g., scFv's) can be expressed in a yeast cell such as *Pichia* (see, e.g., Powers et al., *J Immunol Methods.* 251:123-35 (2001)), *Hansenula*, or *Saccharomyces*. To produce the antibody of interest, a polynucleotide or polynucleotides encoding the polypeptide or polypeptides is/are constructed, introduced into an expression vector or expression vectors, and then expressed in suitable host cells. To improve expression, the nucleotide sequences of the genes can be recoded without changing (or minimally changing—e.g., removal of a C-terminal residue of the heavy or light chain) the amino acid sequence. The areas for potential recoding include those associated with translation initiation, codon usage, and possible unintended mRNA splicing. Polynucleotides encoding an Fc region variant described herein would be readily envisioned by the ordinarily skilled artisan.

Standard molecular biology techniques can be used to prepare the recombinant expression vector(s), transfect the host cells, select for transformants, culture the host cells, and recover the polypeptide (e.g., antibody).

If the polypeptide or polypeptides is to be expressed in bacterial cells (e.g., *E. coli*), the expression vector should have characteristics that permit amplification of the vector in the bacterial cells. Additionally, when *E. coli* such as JM109, DH55a, HB101, or XL1-Blue is used as a host, the vector must have a promoter, for example, a lacZ promoter (Ward et al., 341:544-546 (1989), araB promoter (Better et al., *Science,* 240:1041-1043 (1988)), or T7 promoter that can allow efficient expression in *E. coli*. Examples of such vectors include, for example, M13-series vectors, pUC-series vectors, pBR322, pBluescript, pCR-Script, pGEX-5X-1 (Pharmacia), "QIAexpress system" (QIAGEN), pEGFP, and pET (when this expression vector is used, the host is preferably BL21 expressing T7 RNA polymerase). The expression vector may contain a signal sequence for antibody secretion. For production into the periplasm of *E. coli*, the pelB signal sequence (Lei et al., *J. Bacteriol.,* 169:4379 (1987)) may be used as the signal sequence for antibody secretion. For bacterial expression, calcium chloride methods or electroporation methods may be used to introduce the expression vector into the bacterial cell.

If the polypeptide or polypeptides is to be expressed in animal cells such as CHO, COS, and NIH3T3 cells, the expression vector includes a promoter necessary for expression in these cells, for example, an SV40 promoter (Mulligan et al., *Nature,* 277:108 (1979)) (e.g., early simian virus 40 promoter), MMLV-LTR promoter, EFla promoter (Mizushima et al., *Nucleic Acids Res.,* 18:5322 (1990)), or CMV promoter (e.g., human cytomegalovirus immediate early promoter). In addition to the nucleic acid sequence encoding the Fc region variant, the recombinant expression vectors may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399, 216, 4,634,665 and 5,179,017). For example, typically the selectable marker gene confers resistance to drugs, such as G418, hygromycin, or methotrexate, on a host cell into which the vector has been introduced. Examples of vectors with selectable markers include pMAM, pDR2, pBK-RSV, pBK-CMV, pOPRSV, and pOP13.

In some embodiments, the polypeptide or polypeptides are produced in mammalian cells. Exemplary mammalian host cells for expressing polypeptide or polypeptides include Chinese Hamster Ovary (CHO cells) (including dhfr– CHO cells, described in Urlaub and Chasin (1980) Proc. Natl. Acad. Sci. USA 77:4216-4220, used with a DHFR selectable marker, e.g., as described in Kaufman and Sharp (1982) Mol. Biol. 159:601 621), human embryonic kidney 293 cells (e.g., 293, 293E, 293T), COS cells, NIH3T3 cells, lymphocytic cell lines, e.g., NSO myeloma cells and SP2 cells, and a cell from a transgenic animal, e.g., a transgenic mammal. For example, the cell is a mammary epithelial cell.

In an exemplary system for antibody expression, a recombinant expression vector encoding both the antibody heavy chain and the antibody light chain of the antibody is introduced into dhfr– CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and the antibody is recovered from the culture medium.

Methods of Treatment

The polypeptide or polypeptides disclosed herein can be used to treat or prevent any disease or disorder in a cat in need thereof. This invention is particularly helpful in the treatment of chronic conditions where repeated dosing is required. Because of the increased half-life of the protein therapeutic, less frequent dosing and/or reduced dose levels may be possible.

In some embodiments, the disease, disorder, condition or symptoms being treated or prevented is an allergic disease, a chronic pain, an acute pain, an inflammatory disease, an autoimmune disease, an endocrine disease, a gastrointestinal disease, a skeletal/musculoskeletal disease, a cardiovascular disease, a neurological disease, a renal disease, a metabolic disease, a immunological disease, a genetic/inherited disease, a fertility related disorder, an infectious disease or a cancer. In certain embodiments, the disease or disorder being treated or prevented is atopic dermatitis, allergic dermatitis, food allergy, osteoarthritic pain, perioperative pain, dental pain, cancer pain, arthritis, anemia, obesity, or diabetes.

Antibodies may not only be used to treat or prevent disease but also to modulate normal biological function, for example, to manage fertility or behavior.

Diagnosis

The polypeptide or polypeptides disclosed herein can also be used for various diagnostic purposes, for example, to determine whether a cat has any particular disease or disorder. In some embodiments, the polypeptide or polypeptides may comprise a binding domain. The binding domain can specifically bind to a protein, subunit, domain, motif, and/or epitope as described herein (e.g., a maker for cancer cells). In some embodiments the polypeptide or polypeptides further comprises a labeling group. In general, label groups fall into a variety of classes, depending on the assay in which they are to be detected: a) isotopic labels, which may be radioactive or heavy isotopes; b) magnetic labels (e.g., magnetic particles); c) redox active moieties; d) optical dyes; enzymatic groups (e.g. horseradish peroxidase, β-galactosidase, luciferase, alkaline phosphatase); e) biotinylated groups; and f) predetermined polypeptide epitopes recognized by a secondary reporter (e.g., leucine zipper pair sequences, binding sites for secondary antibodies, metal binding domains, epitope tags, etc.). In some embodiments, the labelling group is coupled to the antibody via spacer arms of various lengths to reduce potential steric hindrance. Various methods for labelling proteins are known in the art and may be used in performing the present invention.

In some embodiments, the labeling group is a probe, a dye (e.g., a fluorescent dye), or a radioactive isotope (e.g., $^{3}$H, $^{14}$C, $^{22}$Na, $^{36}$Cl, $^{35}$S, $^{33}$P, or $^{125}$I)

Specific labels can also include optical dyes, including, but not limited to, chromophores, phosphors and fluorophores, with the latter being specific in many instances. Fluorophores can be either "small molecule" fluores, or proteinaceous fluores.

The fluorescent label can be any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, *Lucifer* Yellow, Cascade BlueJ, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE) (Molecular Probes, Eugene, Oreg.), FITC, Rhodamine, and Texas Red (Pierce, Rockford, Ill.), Cy5, Cy5.5, Cy7 (Amersham Life Science, Pittsburgh, Pa.). Suitable optical dyes, including fluorophores, are described in Molecular Probes Handbook by Richard P. Haugland, which is incorporated by reference in its entirety.

Suitable proteinaceous fluorescent labels also include, but are not limited to, green fluorescent protein, including a *Renilla*, *Ptilosarcus*, or *Aequorea* species of GFP (Chalfie et al., 1994, Science 263:802-805), EGFP (Clontech Laboratories, Inc., Genbank Accession Number U55762), blue fluorescent protein (BFP, Quantum Biotechnologies, Inc. 1801 de Maisonneuve Blvd. West, 8th Floor, Montreal, Quebec, Canada H3H1J9; Stauber, 1998, Biotechniques 24:462-471; Heim et al., 1996, Curr. Biol. 6:178-182), enhanced yellow fluorescent protein (EYFP, Clontech Laboratories, Inc.), luciferase (Ichiki et al., 1993, J. Immunol. 150:5408-5417), β galactosidase (Nolan et al., 1988, Proc. Natl. Acad. Sci. U.S.A. 85:2603-2607) and *Renilla* (WO92/15673, WO95/07463, WO98/14605, WO98/26277, WO99/49019, U.S. Pat. Nos. 5,292,658, 5,418,155, 5,683,888, 5,741,668, 5,777,079, 5,804,387, 5,874,304, 5,876,995, 5,925,558). All of the above-cited references in this paragraph are expressly incorporated herein by reference in the entirety.

Assays

FcγRI and FcγRIII Binding:

Binding to FcγRI and FcγRIII is a measure of the ability of an antibody to mediate ADCC. In order to assess this property for an antibody an assay to measure binding of the antibody to FcγRI and FcγRIII can be conducted using methods known in the art.

C1q Binding:

Binding to the first component of complement, C1q, is a measure of the ability of an antibody to mediate complement-dependent cytotoxicity (CDC). In order to assess this property for an antibody, an assay to measure binding of the antibody to C1q can be conducted using methods known in the art.

Half-Life:

Methods of measuring half-life of an antibody are well known in the art. See, e.g., Booth et al., *MAbs*, 10(7):1098-1110 (2018). As an example, the half-life of an antibody (e.g. a feline antibody) can be measured by injection of the antibody into an animal model (e.g. a cat model) and measuring levels of the antibody in the serum over a certain period of time. Exemplary animal models include non-human primate models and transgenic mouse models. The transgenic mouse models (e.g. Tg32 or Tg276 transgenic mice) can be null for mouse FcRn alpha chain and express the human FcRn alpha transgene (e.g. under the control of a constitutive promoter). The human FcRn alpha chain can pair in vivo with the mouse β2-microglobulin protein forming a functional chimeric FcRn heterodimer.

EXAMPLES

Example 1: Generation of NNK Saturation Mutagenesis Libraries at Selected Positions and Analysis of Individual Variants The wild-type (wt) sequence of the CH2 and CH3 domains of feline IgG1a (SEQ ID NO: 1) was synthesized and used as template for the NNK mutagenesis. The NNK saturation mutagenesis method is an effective strategy to generate all 20 possible amino acids at a desired position (Hogrefe et al., *Biotechniques*. 33: 1158-1165 [2002]). Individual NNK libraries at positions 252, 428 and 434 (EU numbering) were generated. NNK (N=A/C/G/T, K=G/T) primers at the specified position were used with the QuikChange Site-Directed Mutagenesis Kit (Agilent). The PCR-product was subcloned into the GenScript FASEBA plasmid, transformed into E. coli and sequenced verified for the presence of the variant. Downstream of the CH3 domain is the SASA (single-domain antibody against serum albumin) tag (Zhang, J.; Wu, S.; Liu, J. Methods and systems for increasing protein stability. Patent application no: US 2013/0129727 A1) which has pM affinity for albumin. The SASA antibody enables the capture of the Fc to the sensor chip surface described below. The PelB (pectate lyase B) signal peptide is at the N-terminus to facilitate secretion of the Fc into the medium. The expression of CH2-CH3 protein was regulated by the Lac promoter. The supernatants from conditioned medium were analyzed for binding to feline FcRn (GenBank KF773786 [IgG receptor FcRn large subunit p51] and European Nucleotide Archive AY829266.1 [feline beta-2-microglobulin]) at pH 6.0 for variants using surface plasmon resonance (SPR).

The supernatants from ninety individual transformants from each library were assayed for binding to feline FcRn at pH 6.0 using the Biacore method, as described below.

Figure 2:
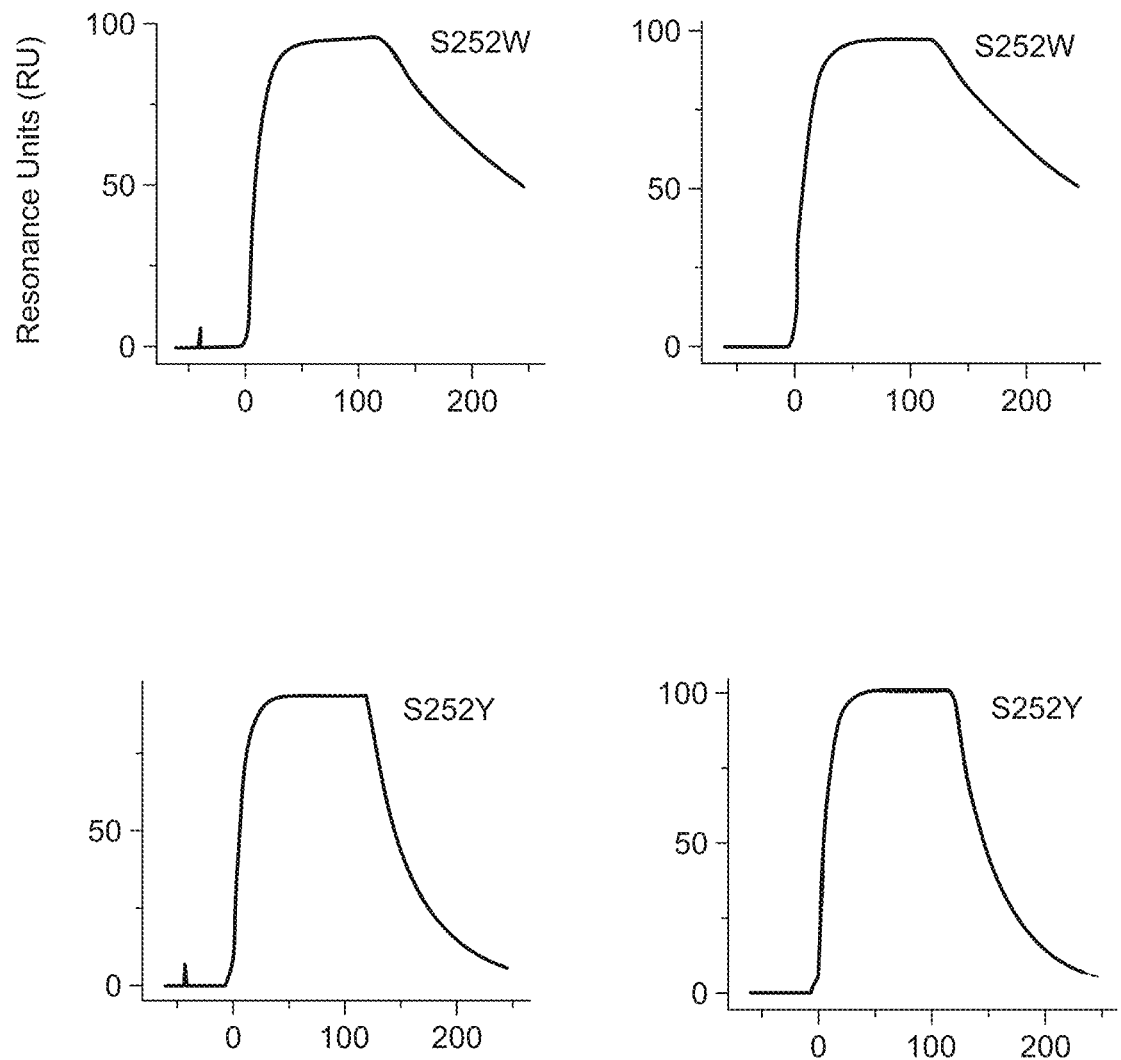
FIG. 2 depicts Biacore sensorgrams for the S252W, S252Y and S252F feline IgG1a Fc variants from the NNK libraries. Also depicted are Biacore sensorgrams for the wild-type (WT). The lighter line on each figure represents the measured data and the darker line represents the fitted curve using a 1:1 interaction model. Y-axis: Resonance Units (RU); X-axis: time (seconds).
Figure 5A:
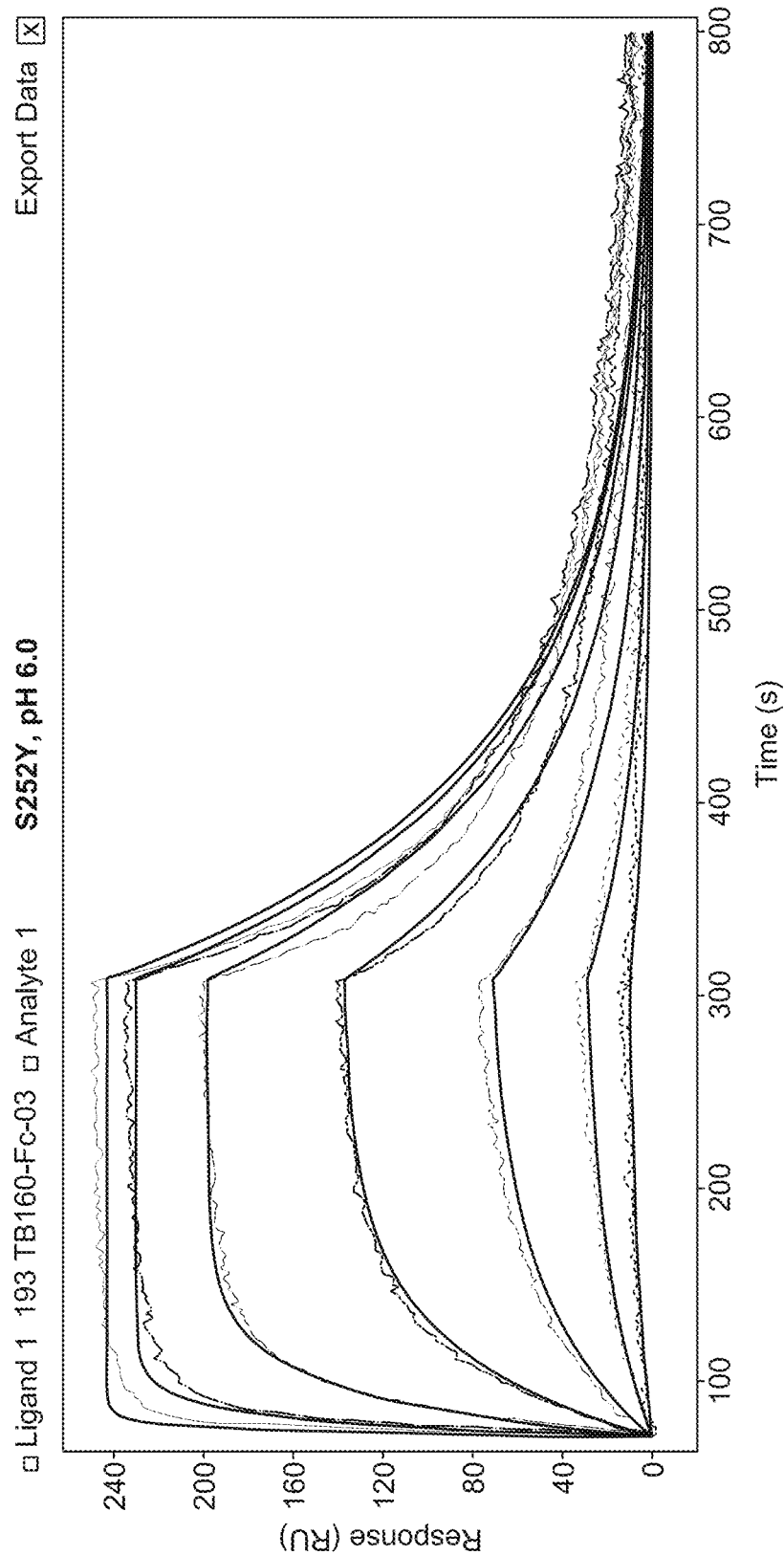
FIGS. 5A and 5B depict Carterra LSA sensorgrams for the S252Y feline IgG1a Fc variant from the phage display library and its interaction with feline FcRN at pH6.0 and pH7.4. The irregular lines represent the measured data and the smooth lines are the fitted curves using a 1:1 interaction model. Y-axis: Resonance Units (RU); X-axis: time (seconds).
Figure 5B:
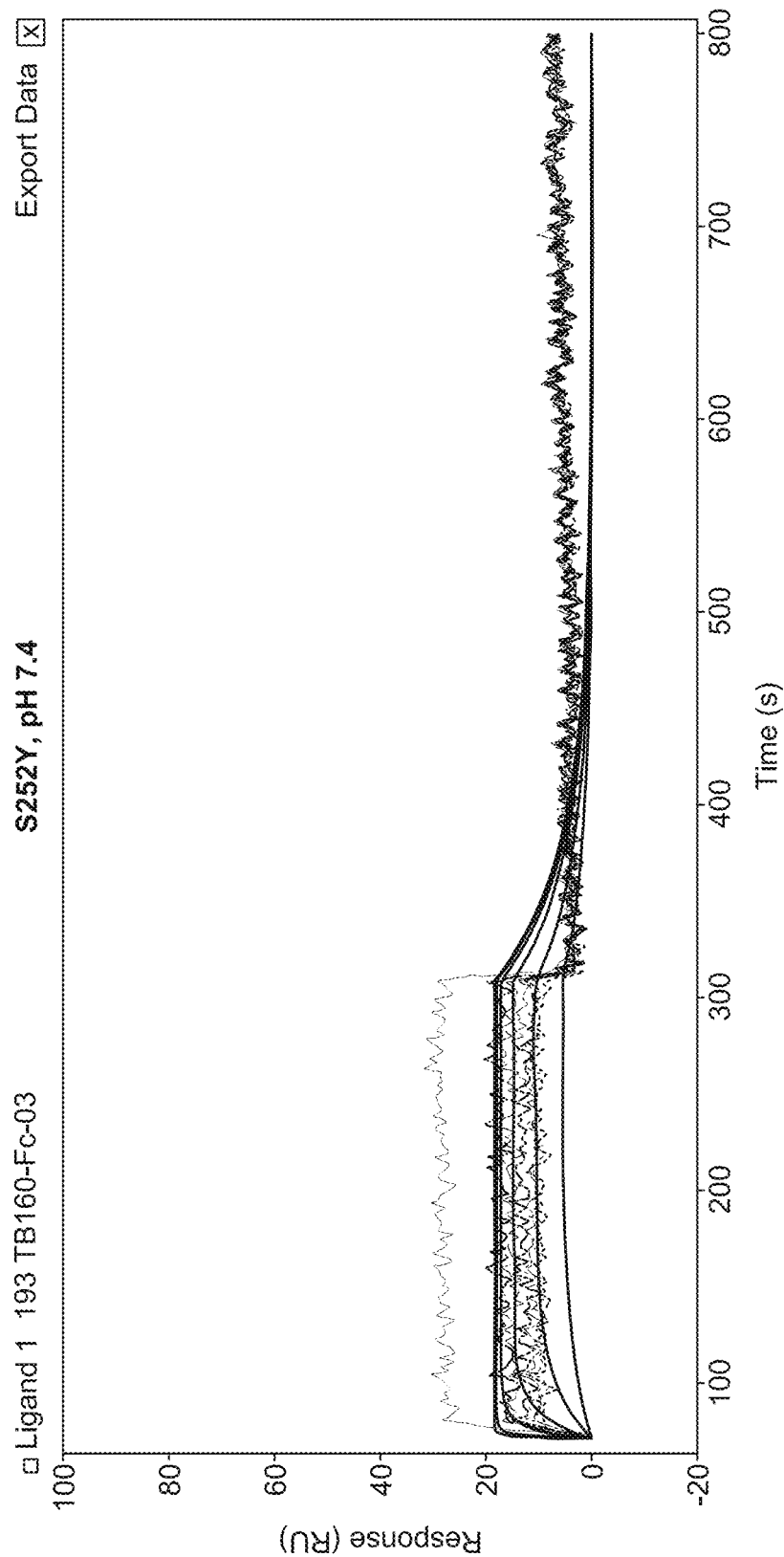
Figure 6A:
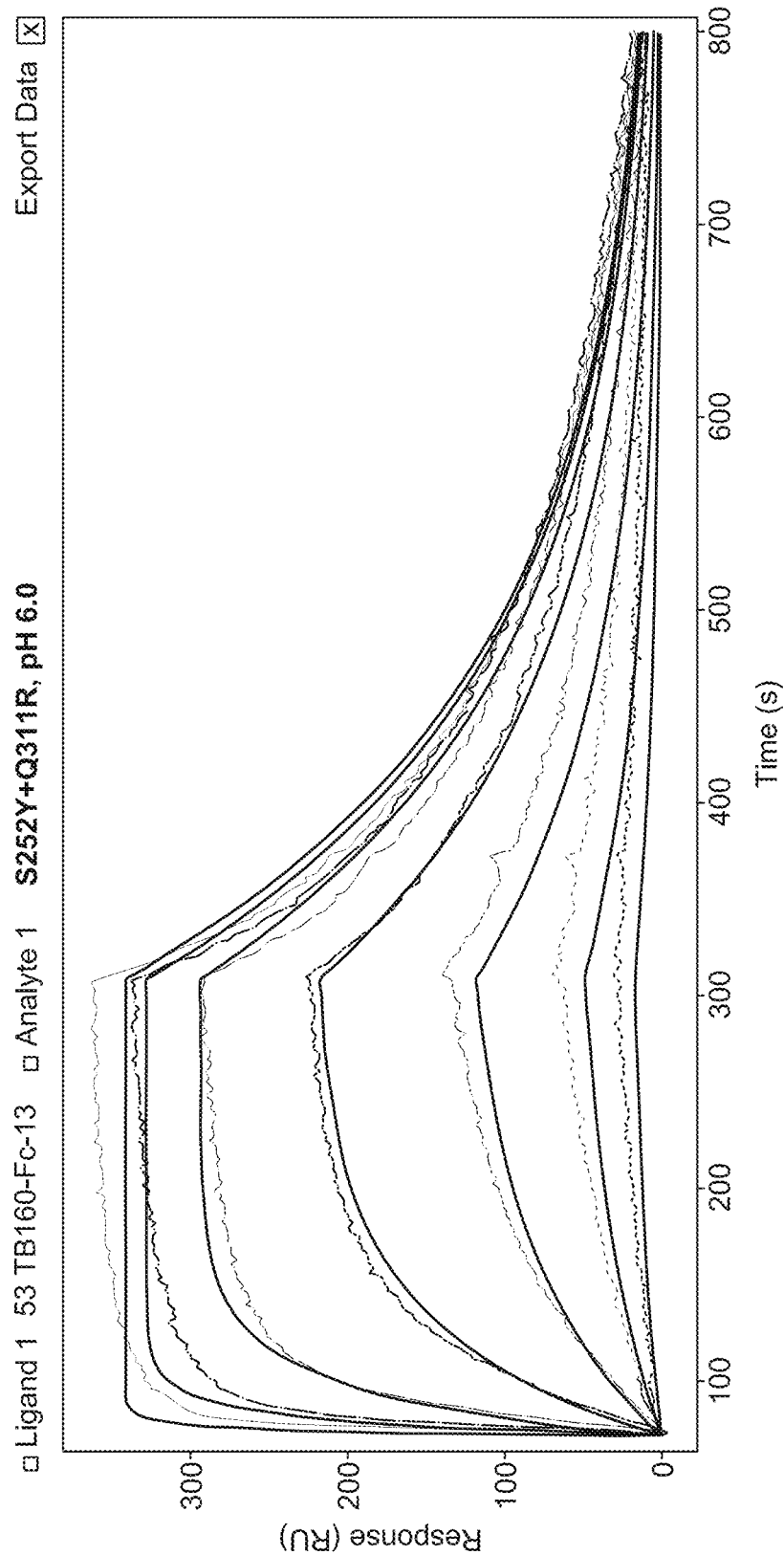
FIGS. 6A and 6B depict Carterra LSA sensorgrams for the S252Y+Q311R feline IgG1a Fc variant from the phage display library and its interaction with feline FcRN at pH6.0 and pH7.4. The irregular lines represent the measured data and the smooth lines are the fitted curves using a 1:1 interaction model. Y-axis: Resonance Units (RU); X-axis: time (seconds).
Figure 6B:
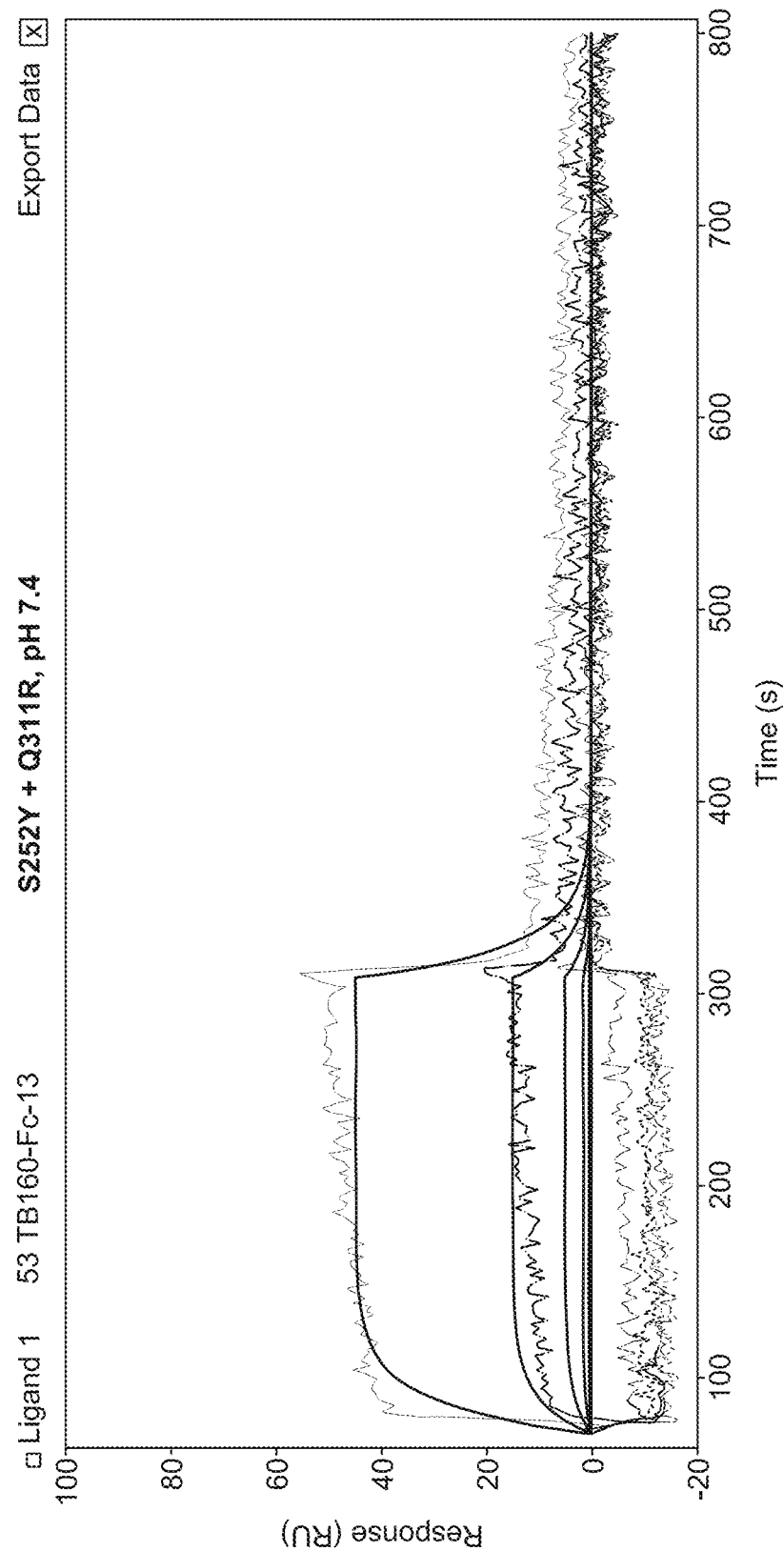
Figure 7A:
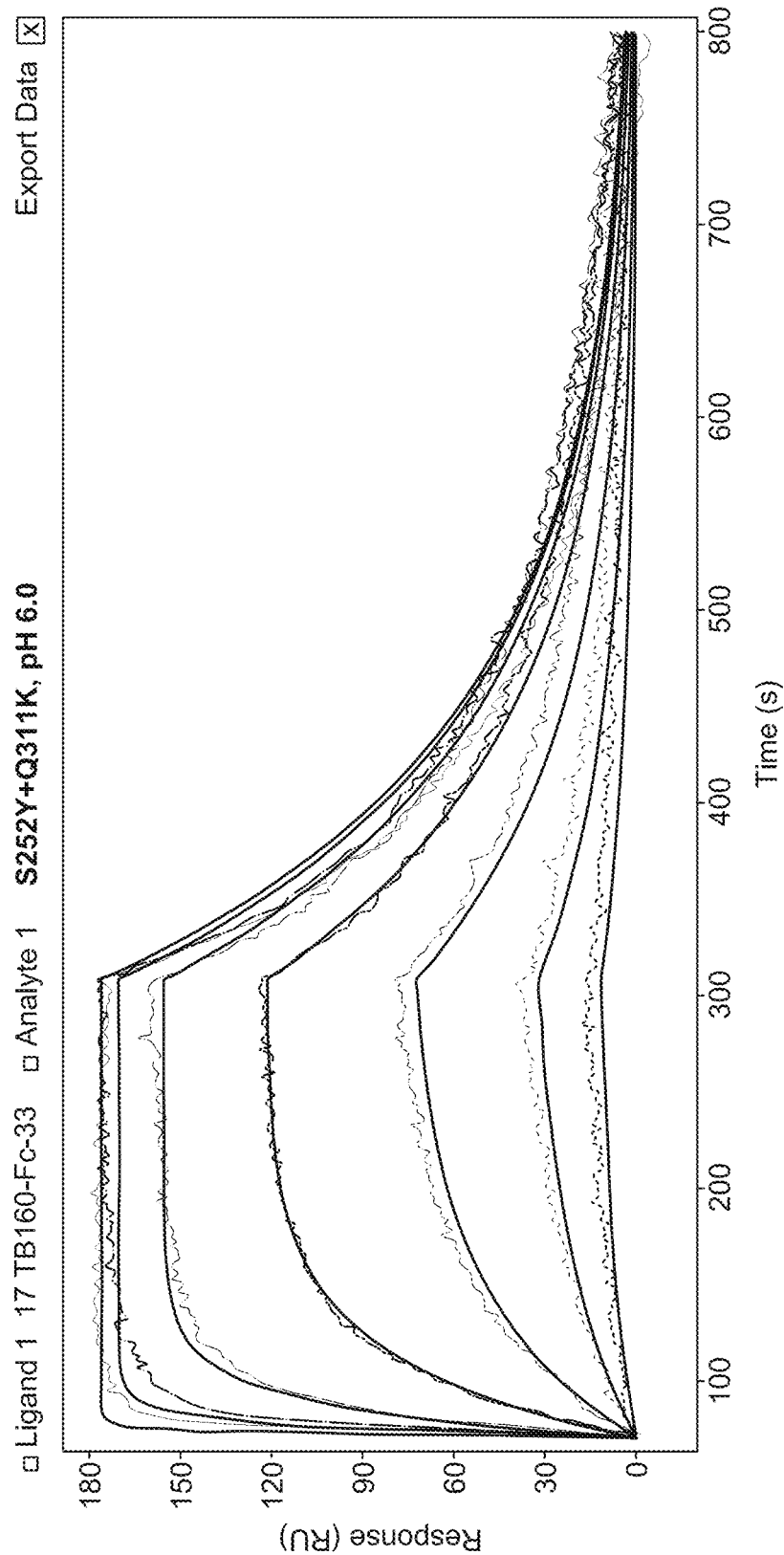
FIGS. 7A and 7B depict Carterra LSA sensorgrams for the S252Y+Q311K feline IgG1a Fc variant from the phage display library and its interaction with feline FcRN at pH6.0 and pH7.4. The irregular lines represent the measured data and the smooth lines are the fitted curves using a 1:1 interaction model. Y-axis: Resonance Units (RU); X-axis: time (seconds).
Figure 7B:
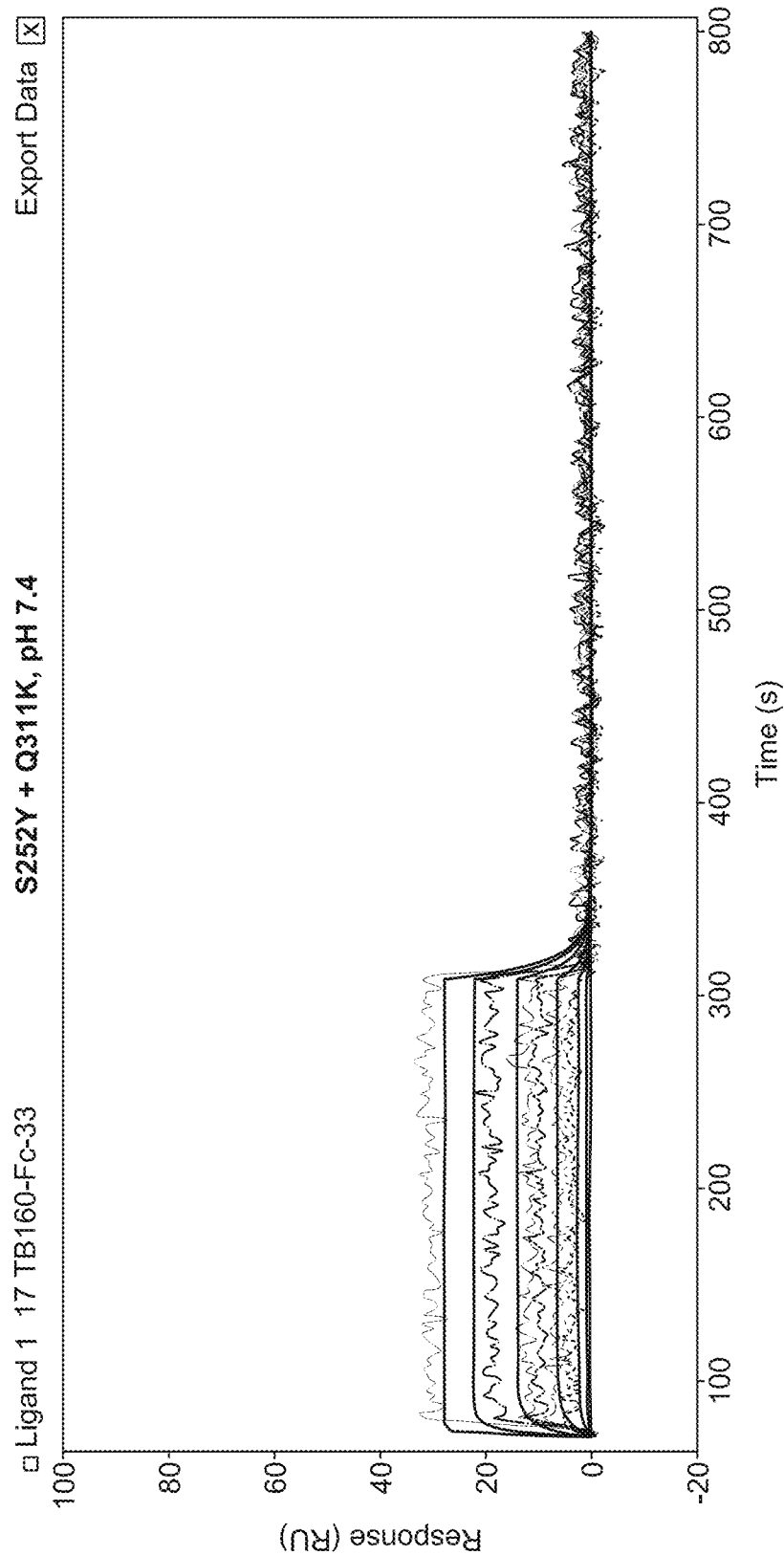
Figure 8A:
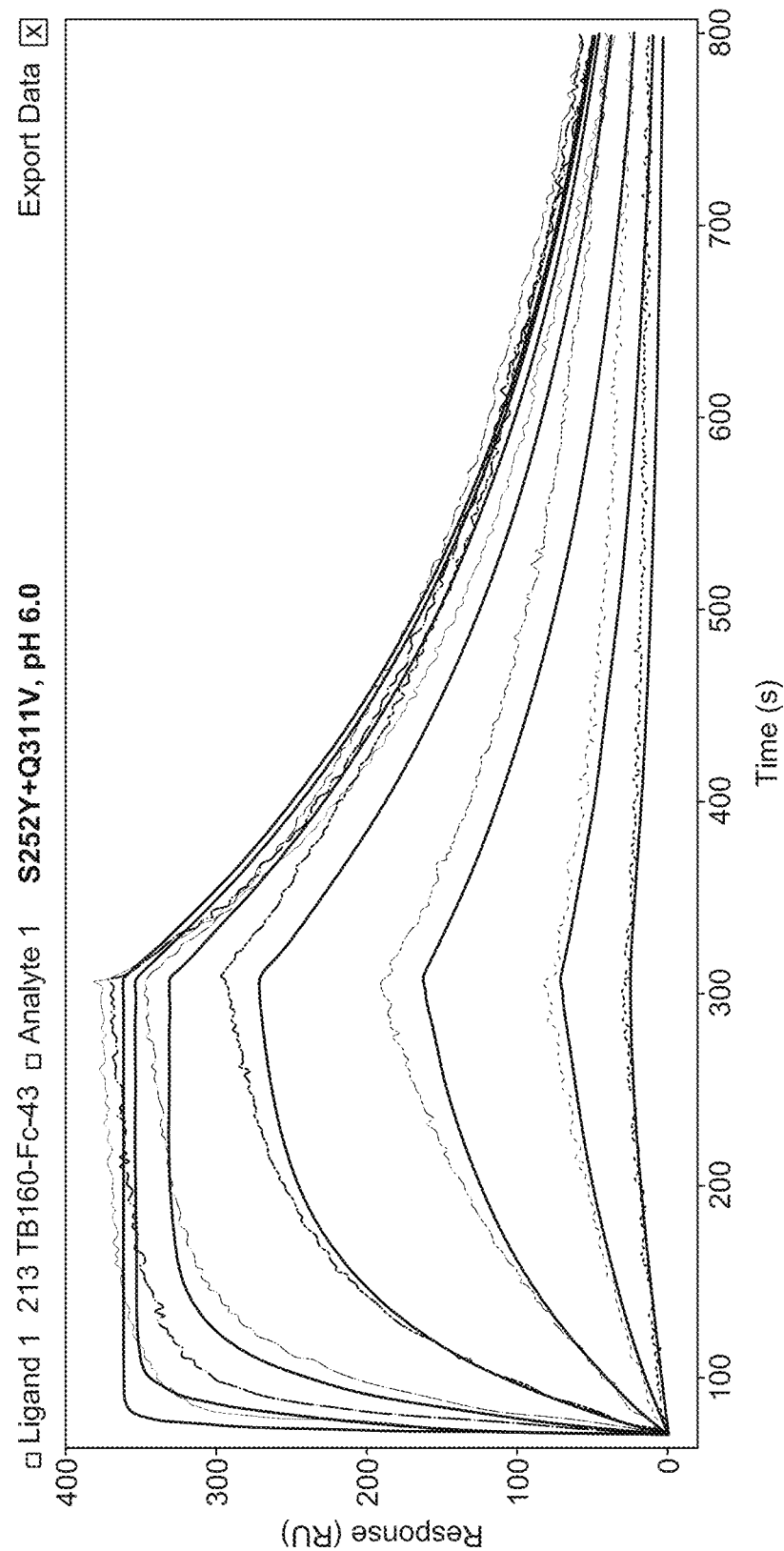
FIGS. 8A and 8B depict Carterra LSA sensorgrams for the S252Y+Q311V feline IgG1a Fc variant from the phage display library and its interaction with feline FcRN at pH6.0 and pH7.4. The irregular lines represent the measured data and the smooth lines are the fitted curves using a 1:1 interaction model. Y-axis: Resonance Units (RU); X-axis: time (seconds).
Figure 8B:
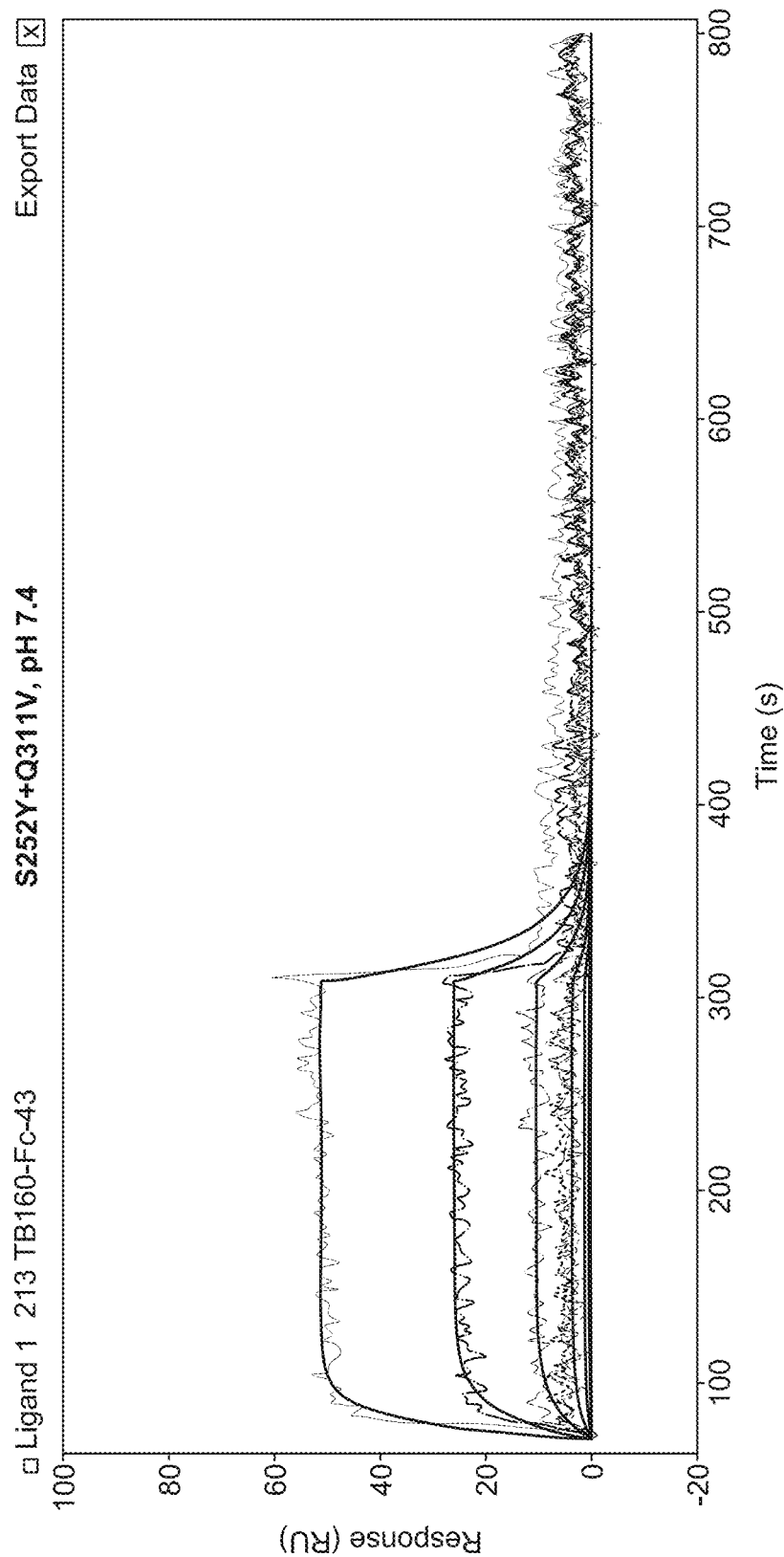
Figure 9A:
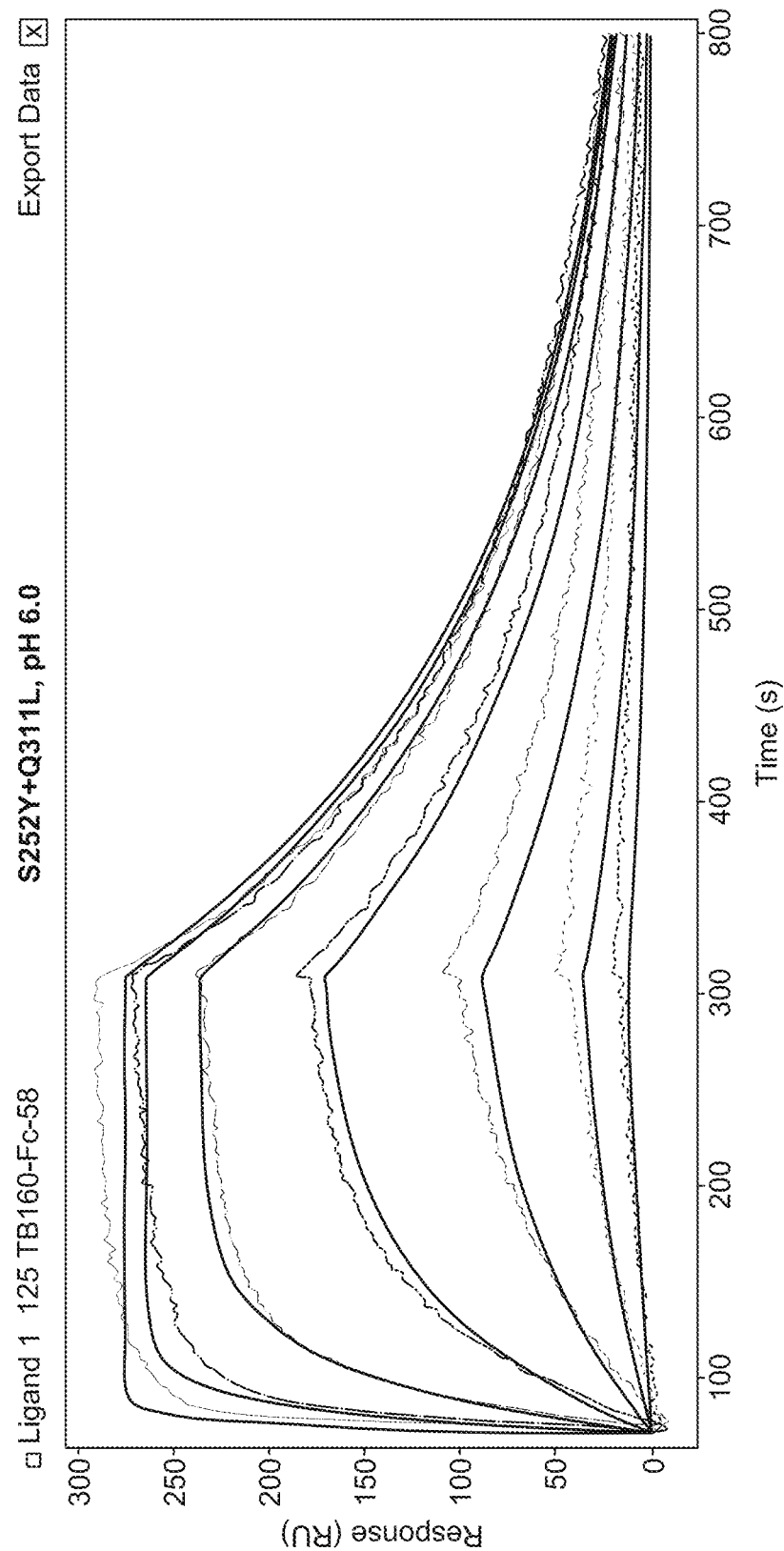
FIGS. 9A and 9B depict Carterra LSA sensorgrams for the S252Y+Q311L feline IgG1a Fc variant from the phage display library and its interaction with feline FcRN at pH6.0 and pH7.4. The irregular lines represent the measured data and the smooth lines are the fitted curves using a 1:1 interaction model. Y-axis: Resonance Units (RU); X-axis: time (seconds).
Figure 9B:
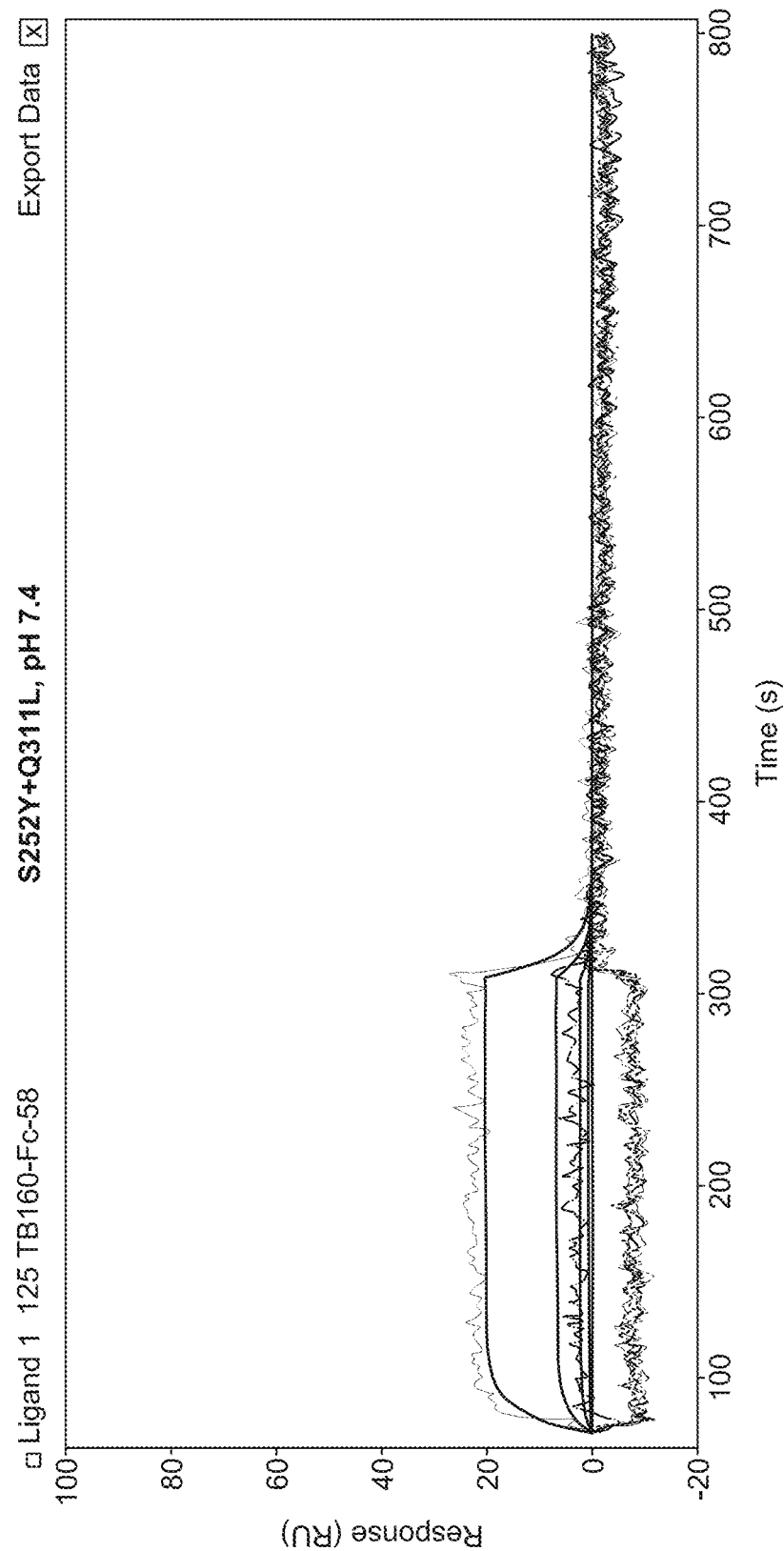
Figure 10A:
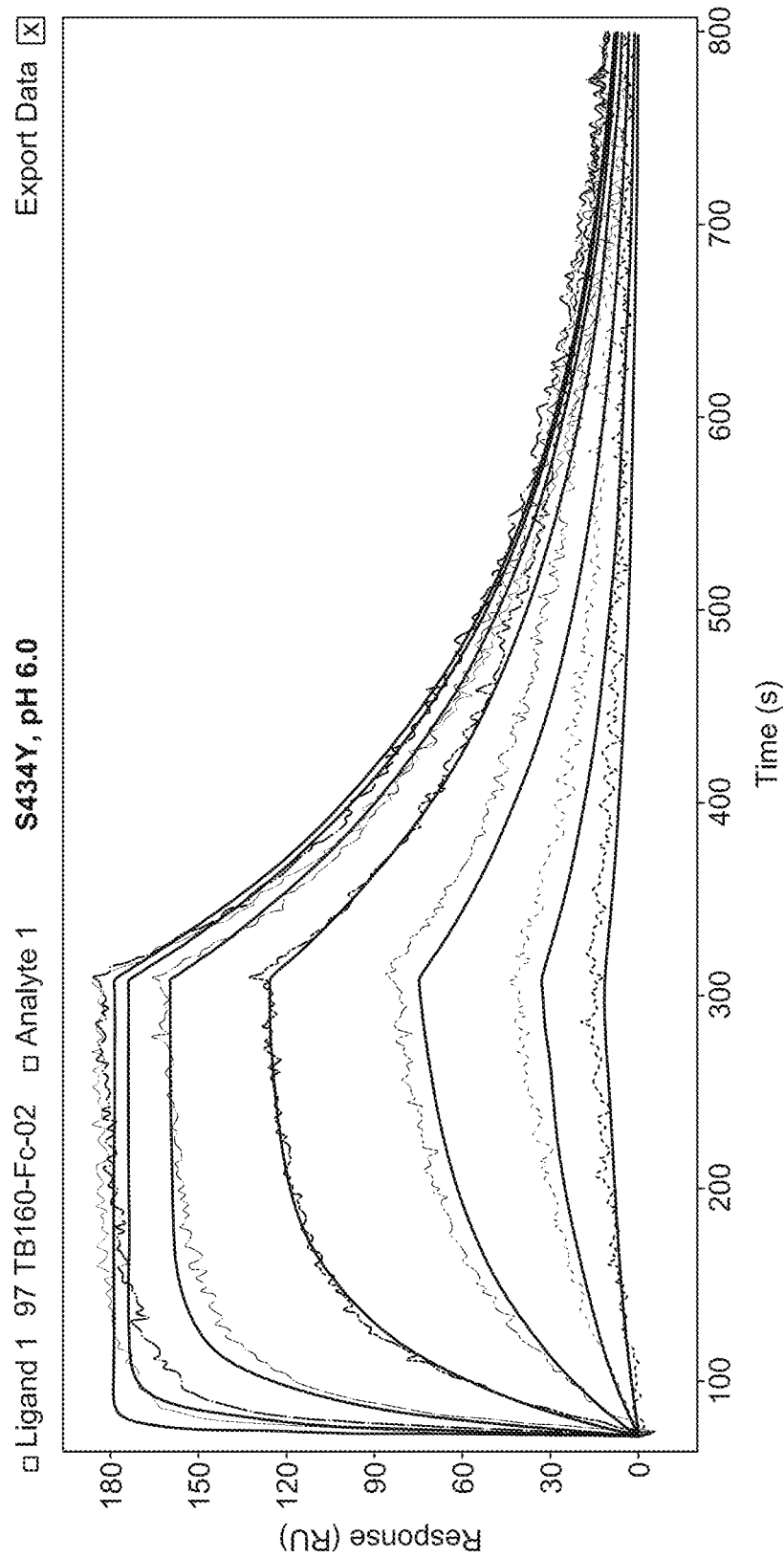
FIGS. 10A and 10B depict Carterra LSA sensorgrams for the S434Y feline IgG1a Fc variant from the phage display library and its interaction with feline FcRN at pH6.0 and pH7.4. The irregular lines represent the measured data and the smooth lines are the fitted curves using a 1:1 interaction model. Y-axis: Resonance Units (RU); X-axis: time (seconds).
Figure 10B:
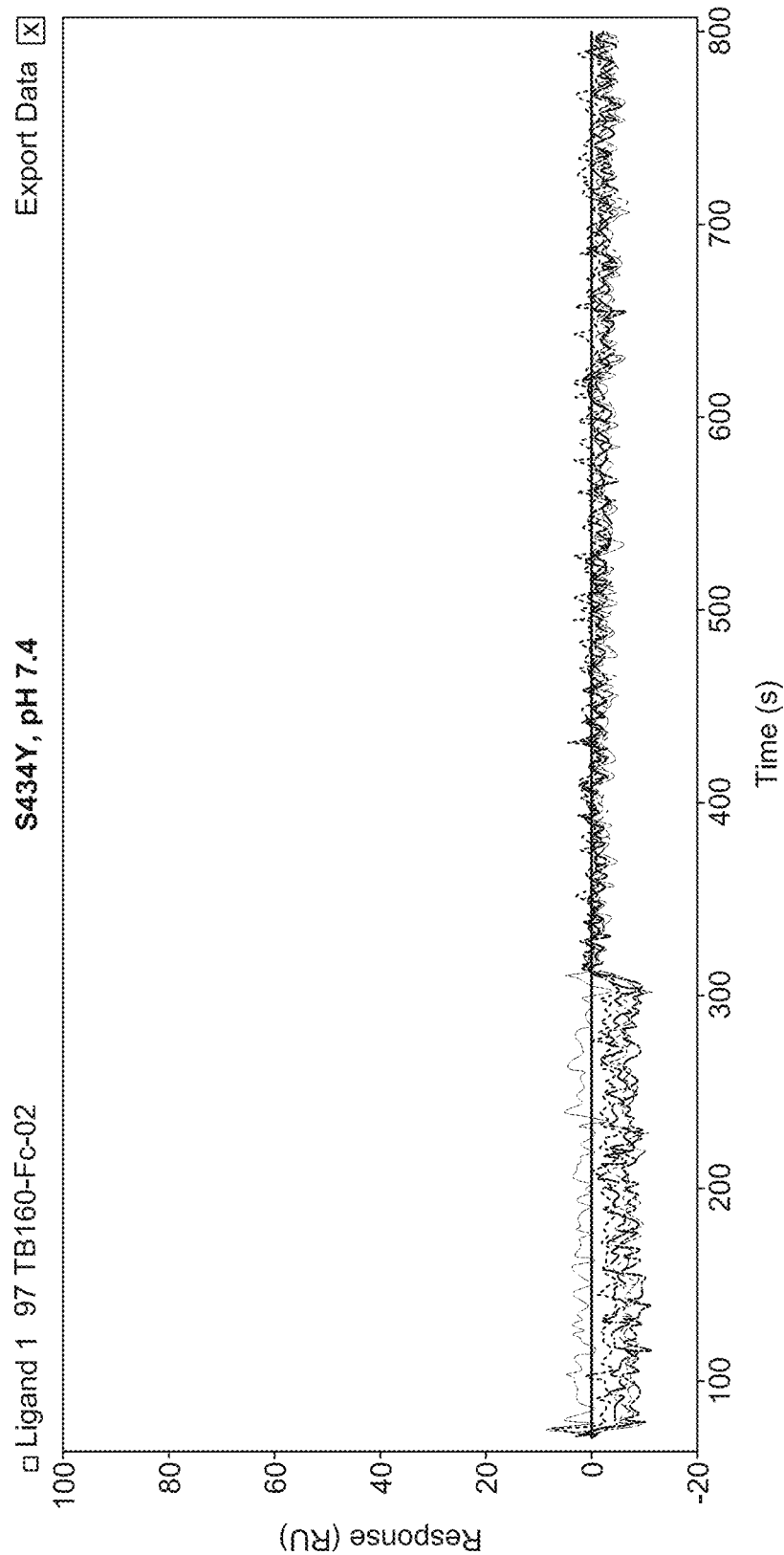
Figure 11A:
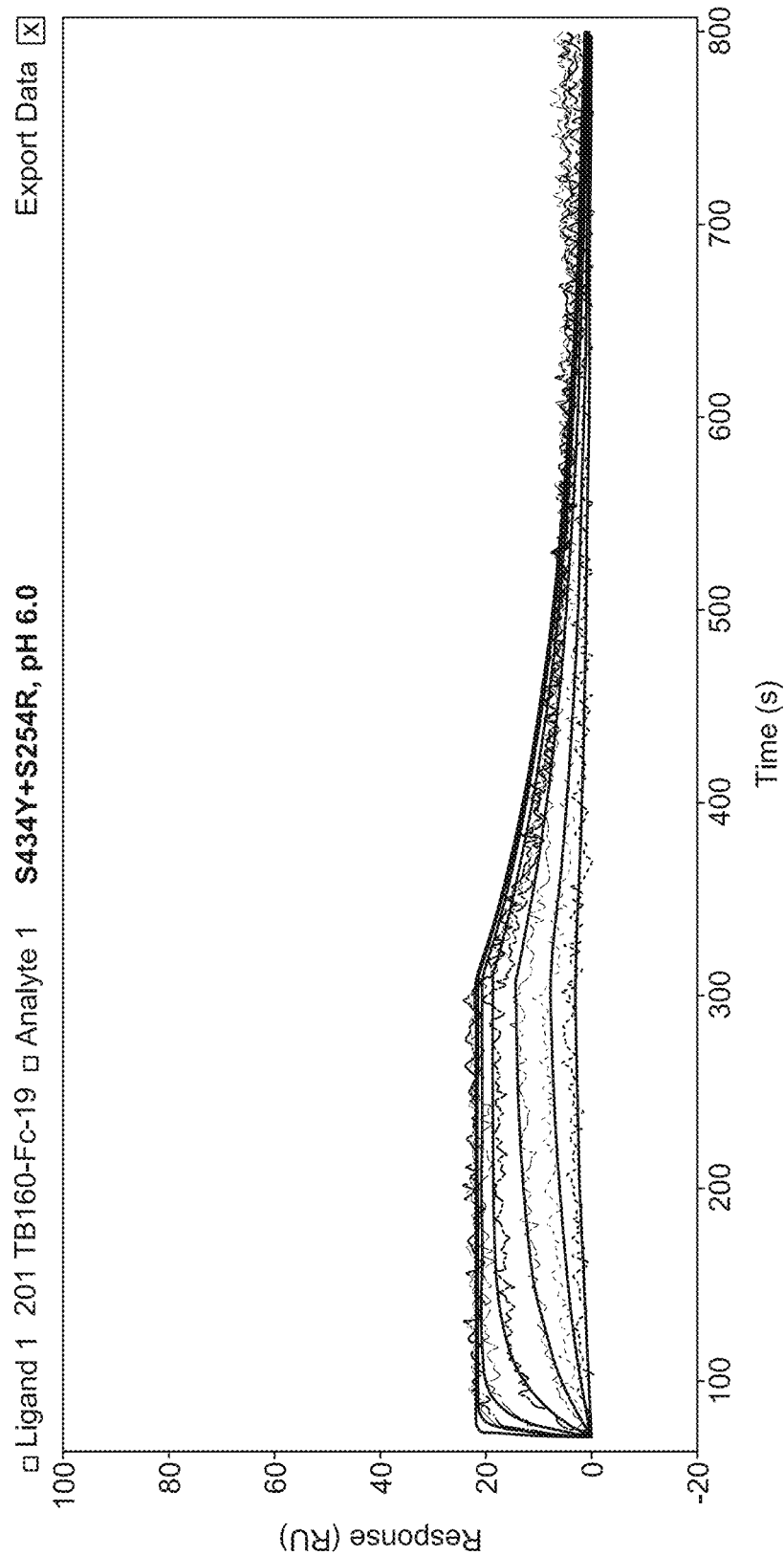
FIGS. 11A and 11B depict Carterra LSA sensorgrams for the S434Y+S254R feline IgG1a Fc variant from the phage display library and its interaction with feline FcRN at pH6.0 and pH7.4. The irregular lines represent the measured data and the smooth lines are the fitted curves using a 1:1 interaction model. Y-axis: Resonance Units (RU); X-axis: time (seconds).
Figure 11B:
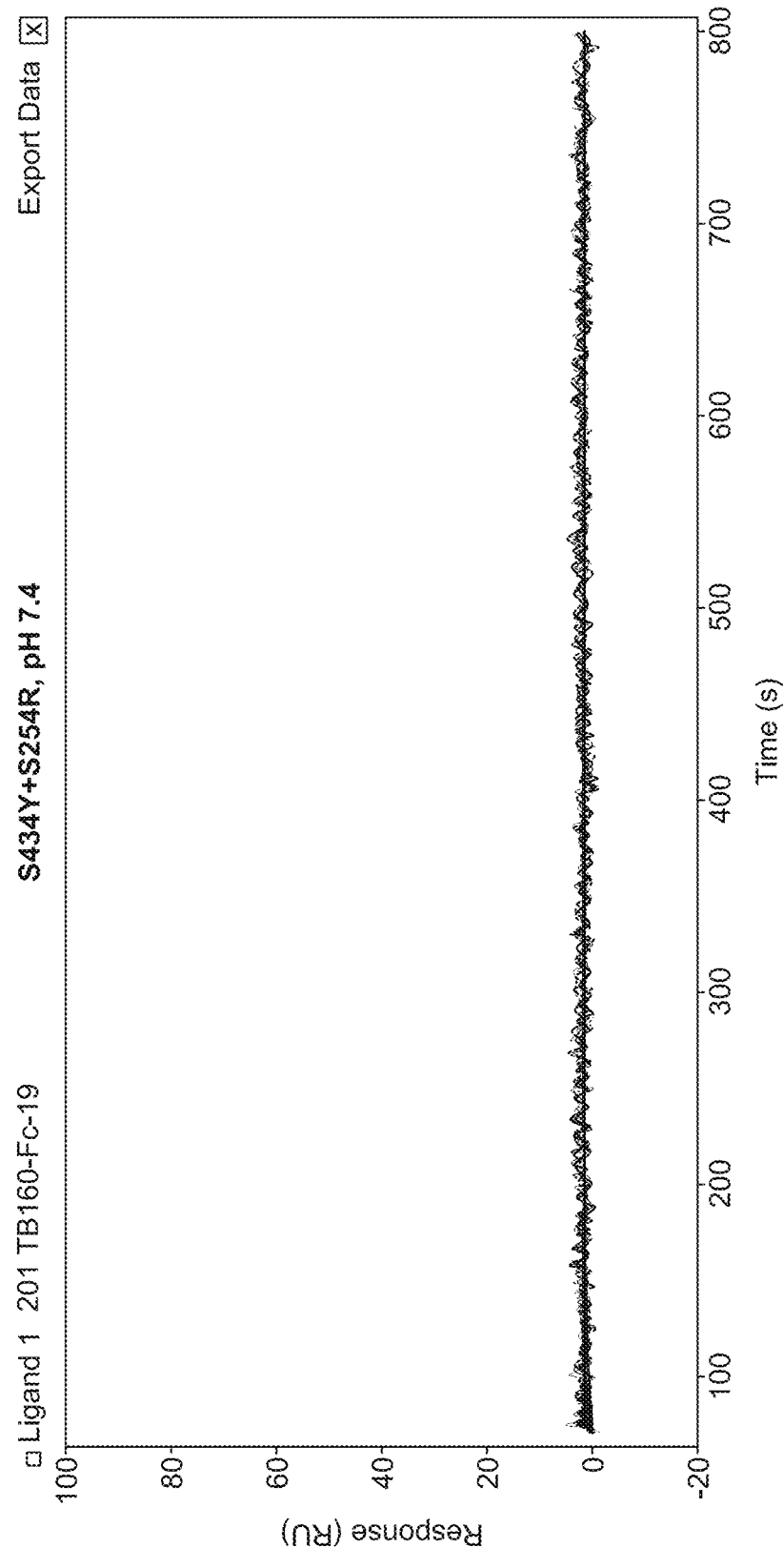
Figure 12A:
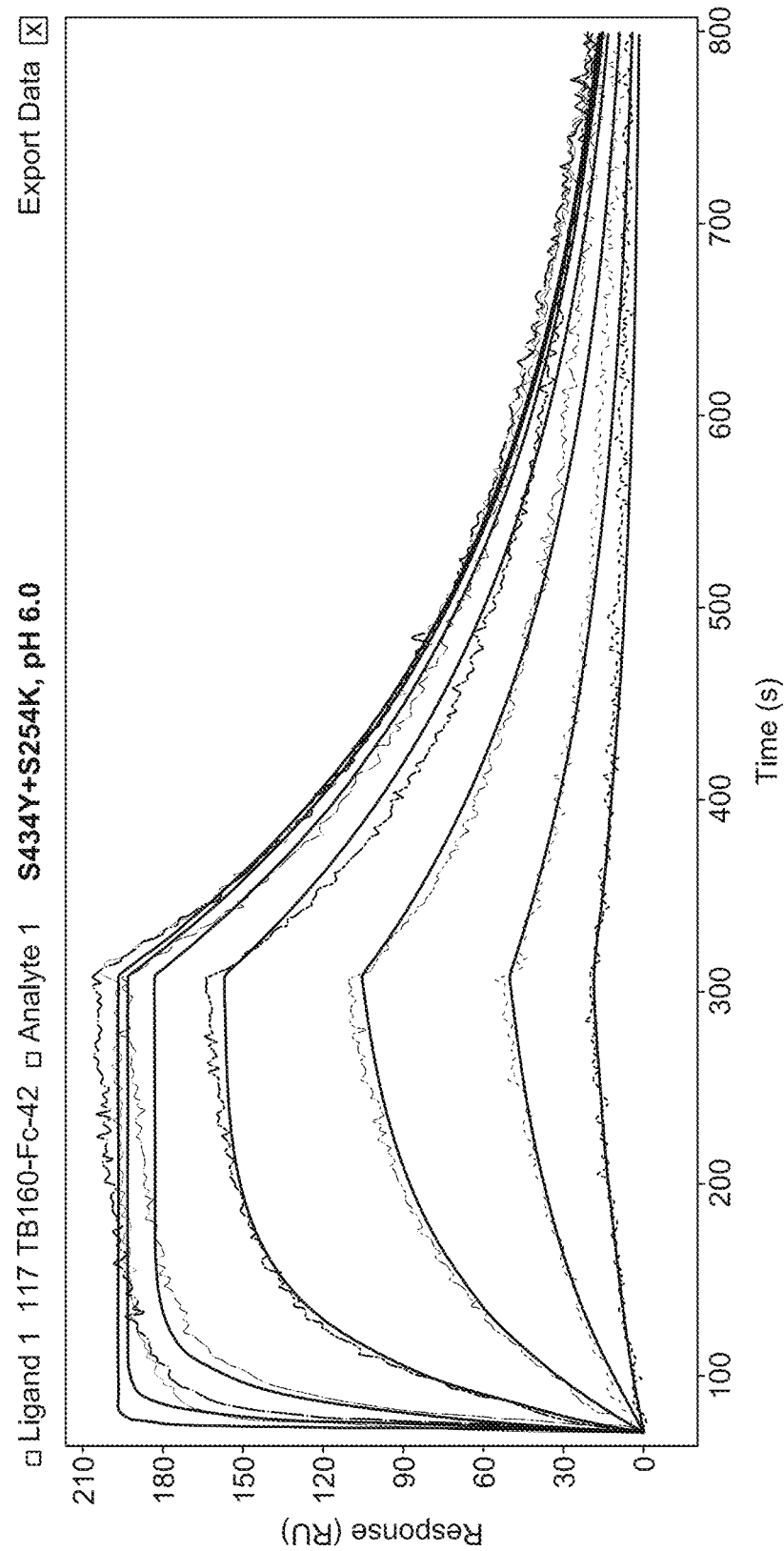
FIGS. 12A and 12B depict Carterra LSA sensorgrams for the S434Y+S254K feline IgG1a Fc variant from the phage display library and its interaction with feline FcRN at pH6.0 and pH7.4. The irregular lines represent the measured data and the smooth lines are the fitted curves using a 1:1 interaction model. Y-axis: Resonance Units (RU); X-axis: time (seconds).
Figure 12B:
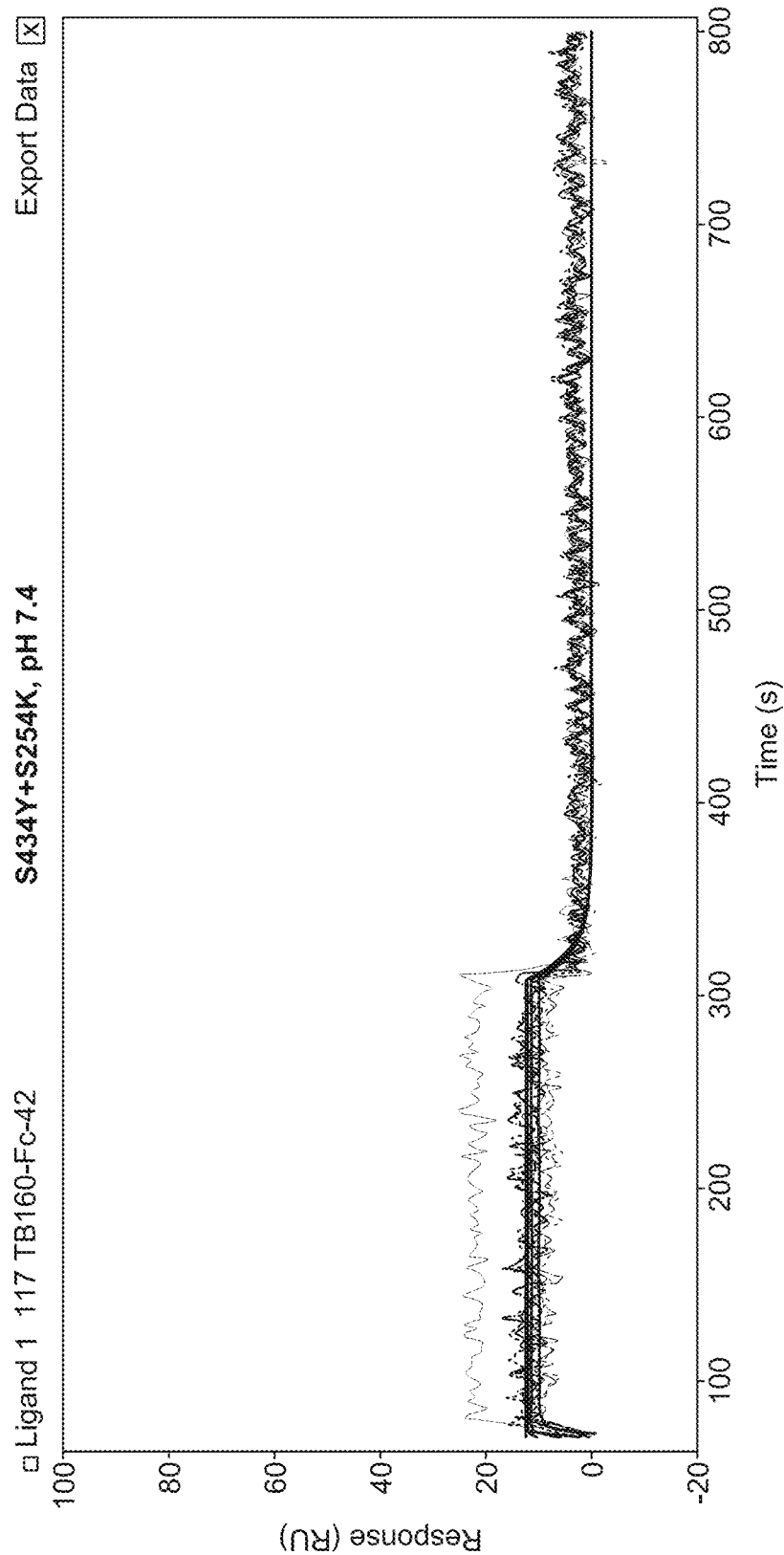
Figure 13A:
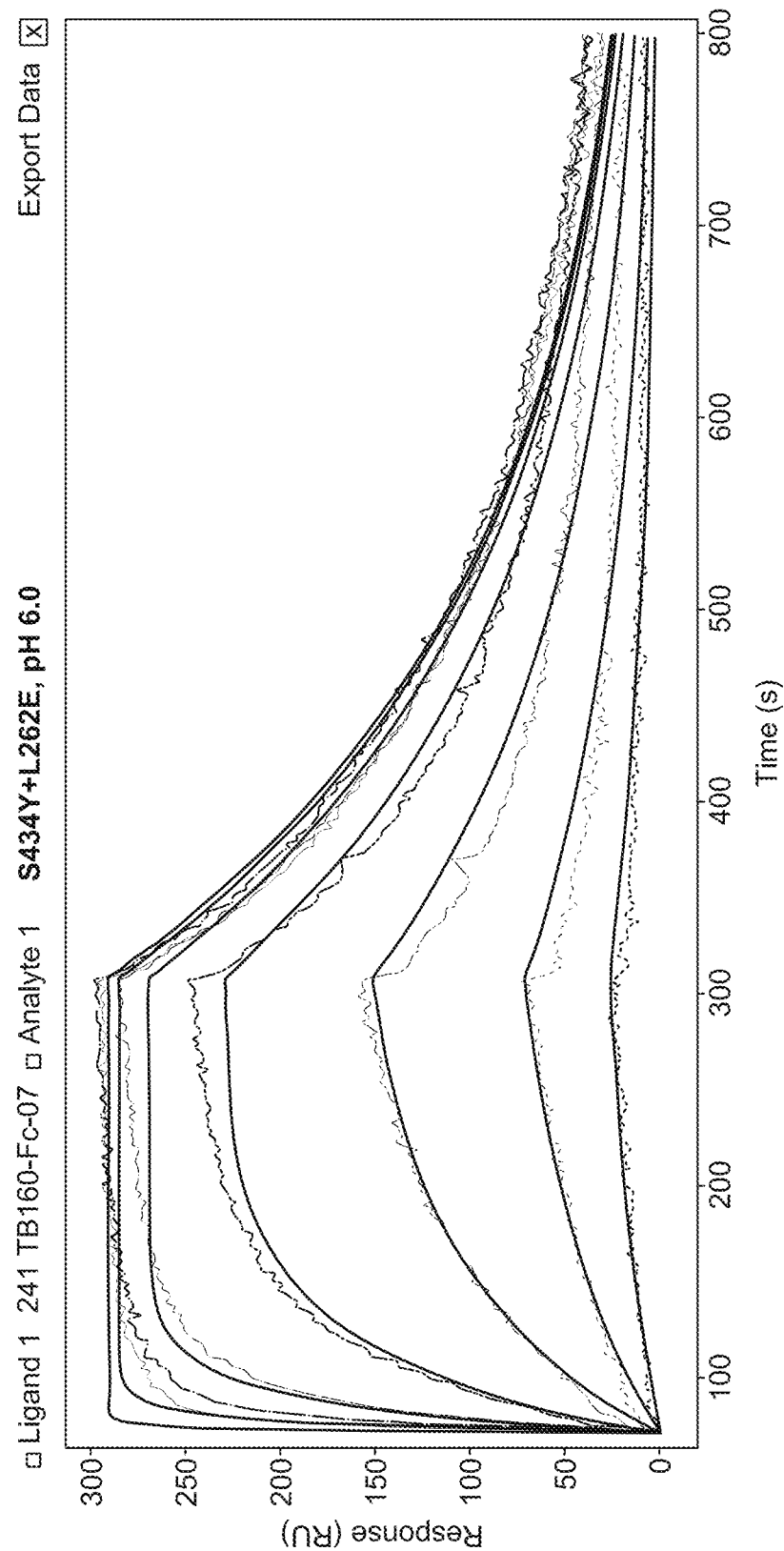
FIGS. 13A and 13B depict Carterra LSA sensorgrams for the S434Y+L262E feline IgG1a Fc variant from the phage display library and its interaction with feline FcRN at pH6.0 and pH7.4. The irregular lines represent the measured data and the smooth lines are the fitted curves using a 1:1 interaction model. Y-axis: Resonance Units (RU); X-axis: time (seconds).
Figure 13B:
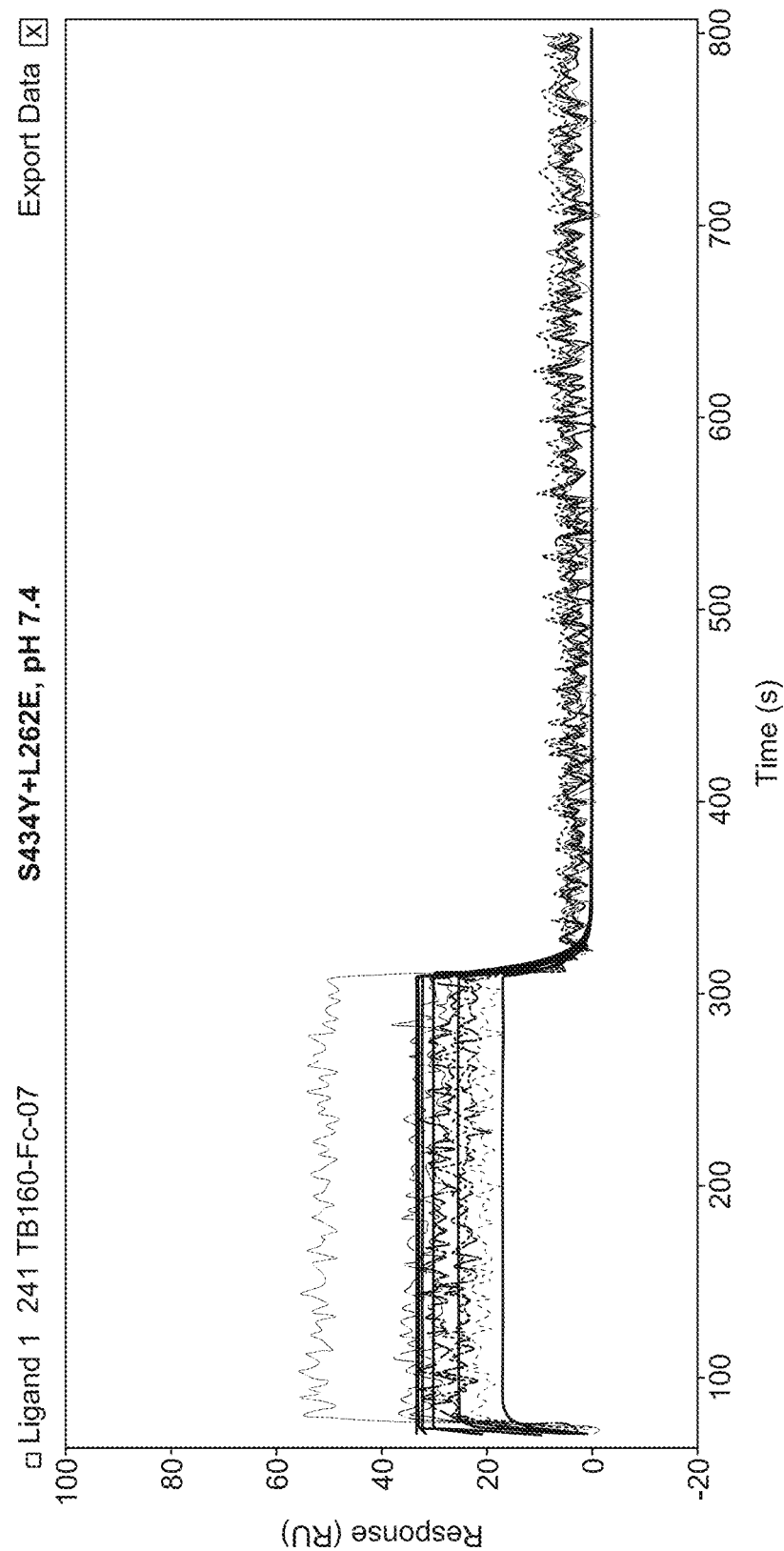
Figure 14A:
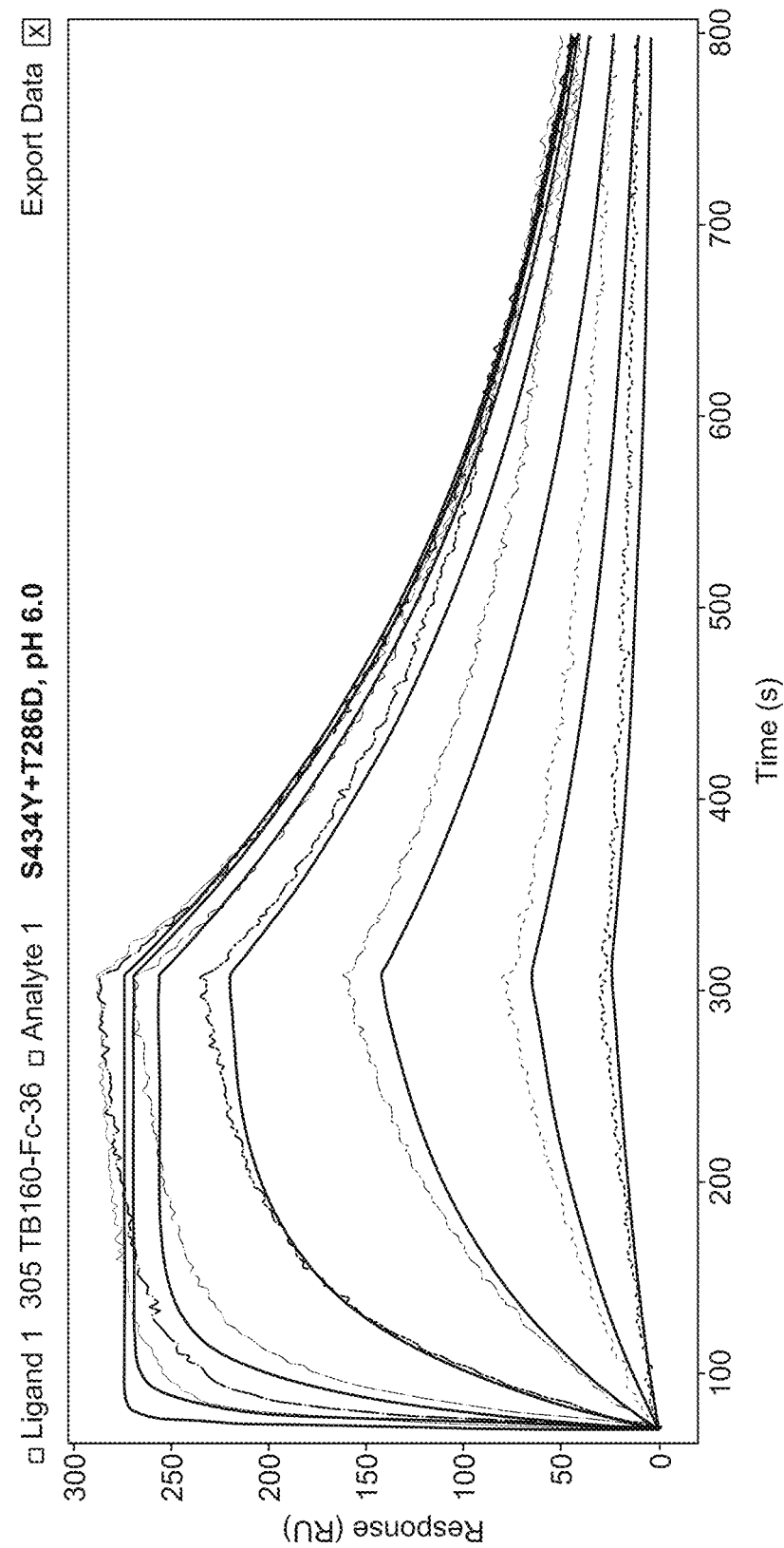
FIGS. 14A and 14B depict Carterra LSA sensorgrams for the S434Y+T286D feline IgG1a Fc variant from the phage display library and its interaction with feline FcRN at pH6.0 and pH7.4. The irregular lines represent the measured data and the smooth lines are the fitted curves using a 1:1 interaction model. Y-axis: Resonance Units (RU); X-axis: time (seconds).
Figure 14B:
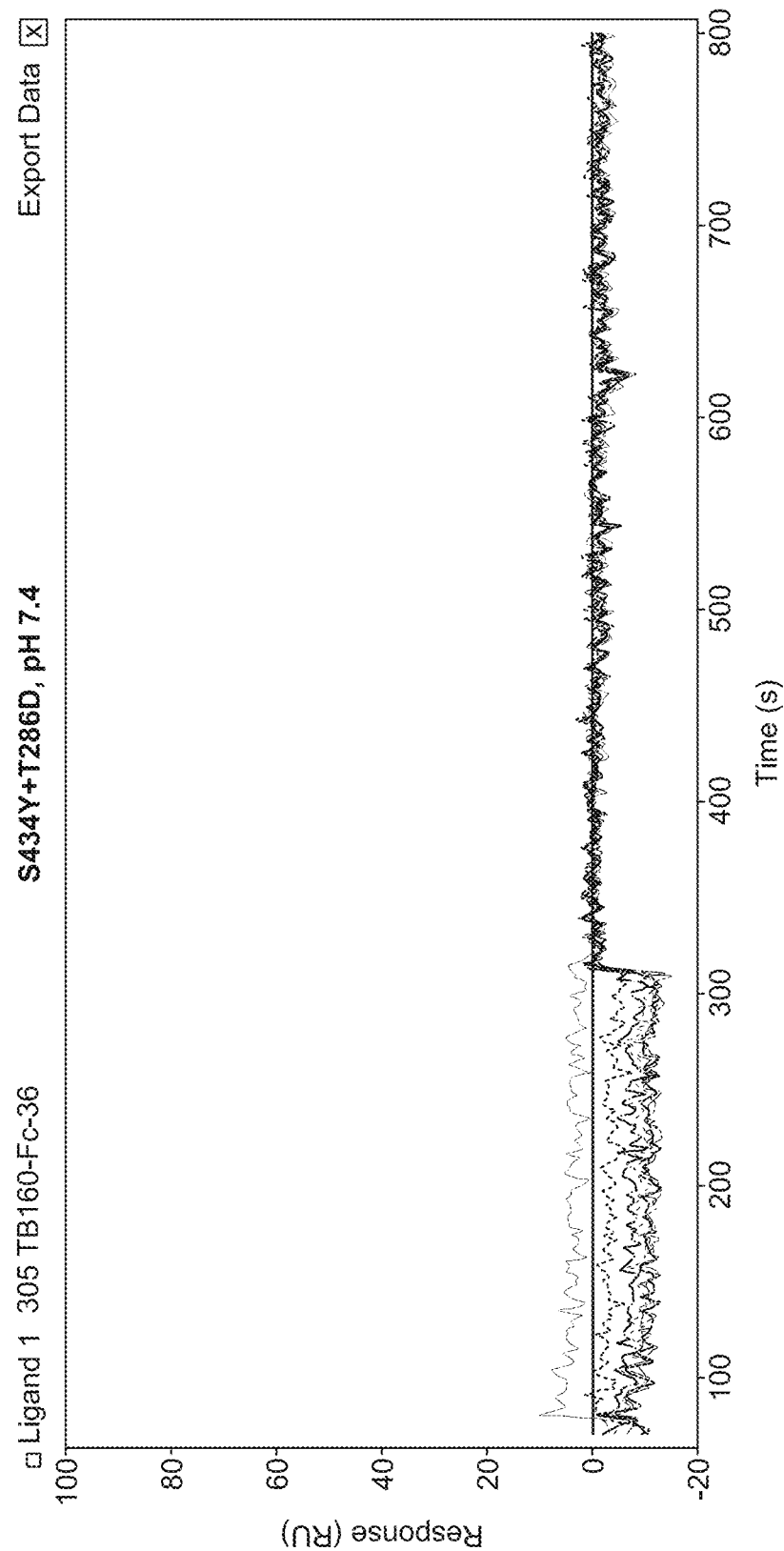
Figure 15A:
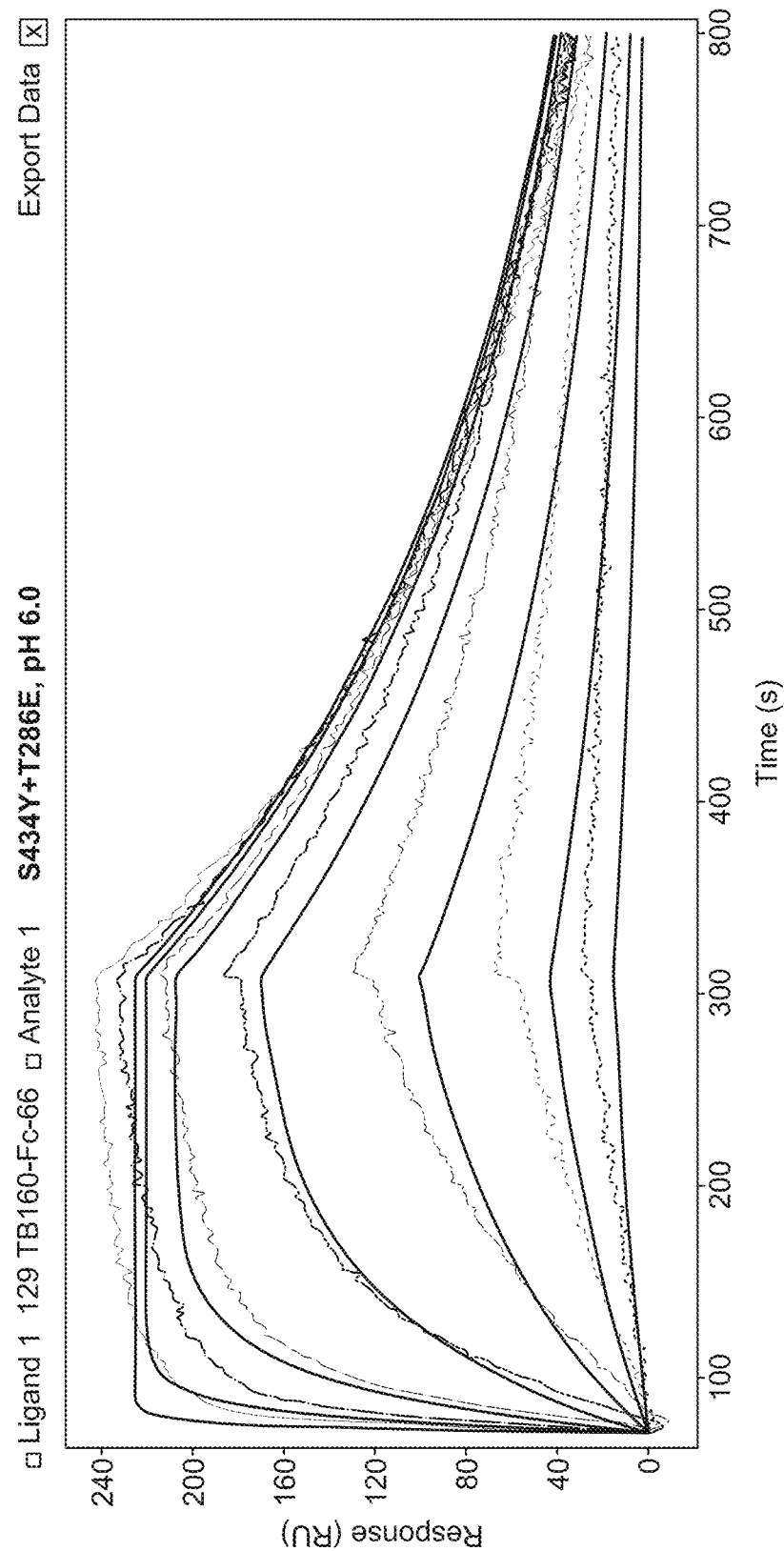
FIGS. 15A and 15B depict Carterra LSA sensorgrams for the S434Y+T286E feline IgG1a Fc variant from the phage display library and its interaction with feline FcRN at pH6.0 and pH7.4. The irregular lines represent the measured data and the smooth lines are the fitted curves using a 1:1 interaction model. Y-axis: Resonance Units (RU); X-axis: time (seconds).
Figure 15B:
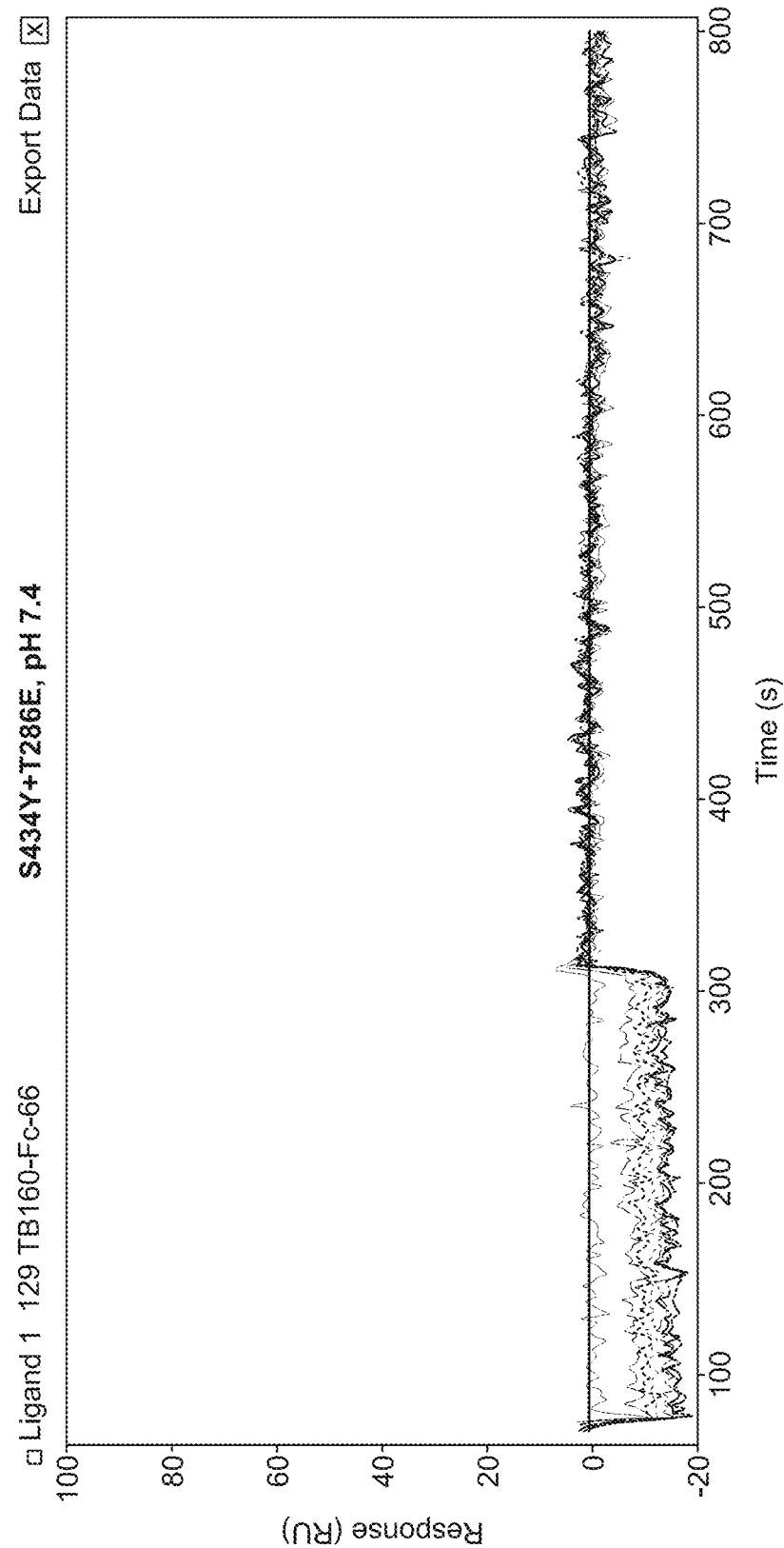
Figure 16A:
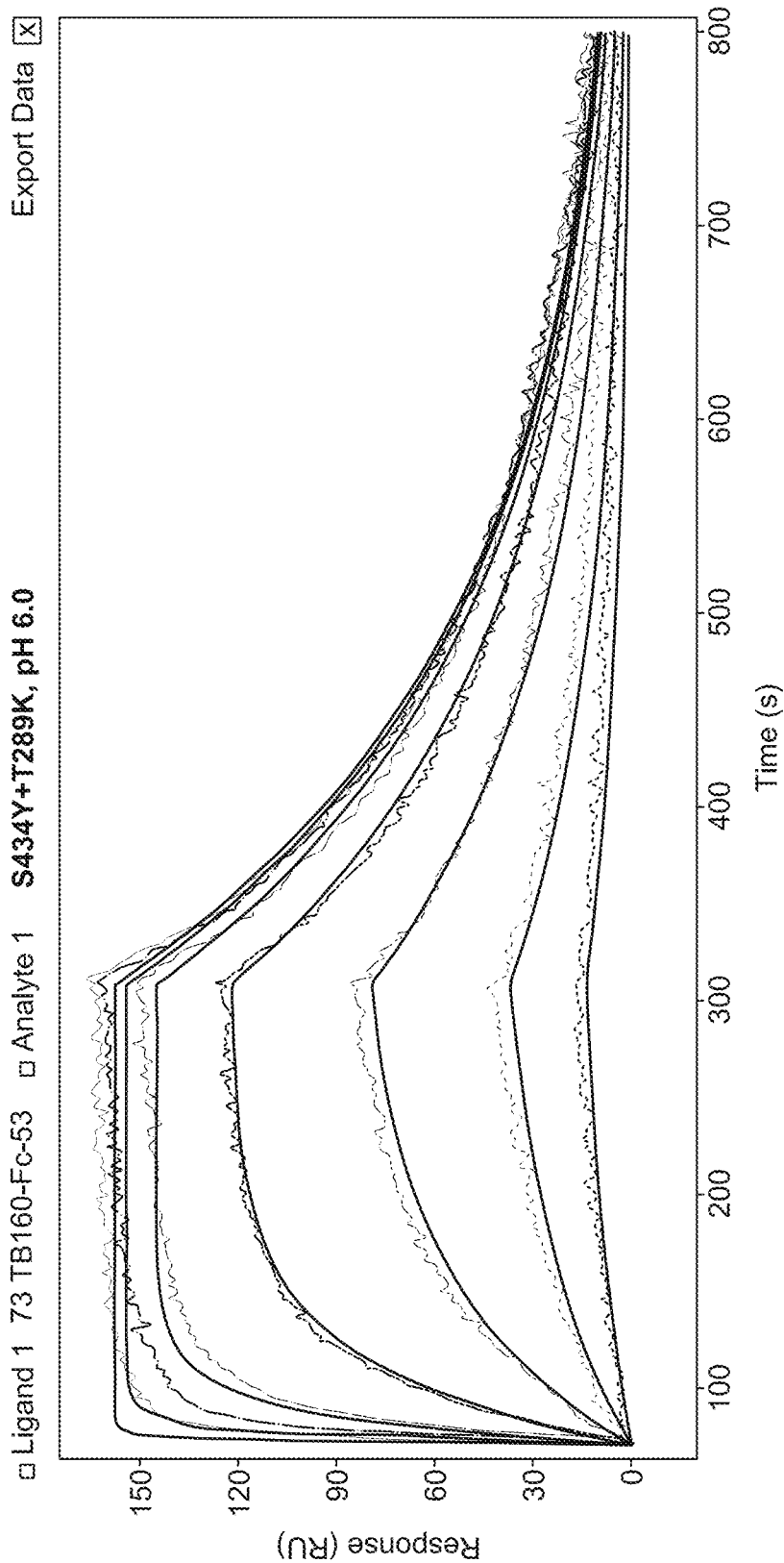
FIGS. 16A and 16B depict Carterra LSA sensorgrams for the S434Y+T289K feline IgG1a Fc variant from the phage display library and its interaction with feline FcRN at pH6.0 and pH7.4. The irregular lines represent the measured data and the smooth lines are the fitted curves using a 1:1 interaction model. Y-axis: Resonance Units (RU); X-axis: time (seconds).
Figure 16B:
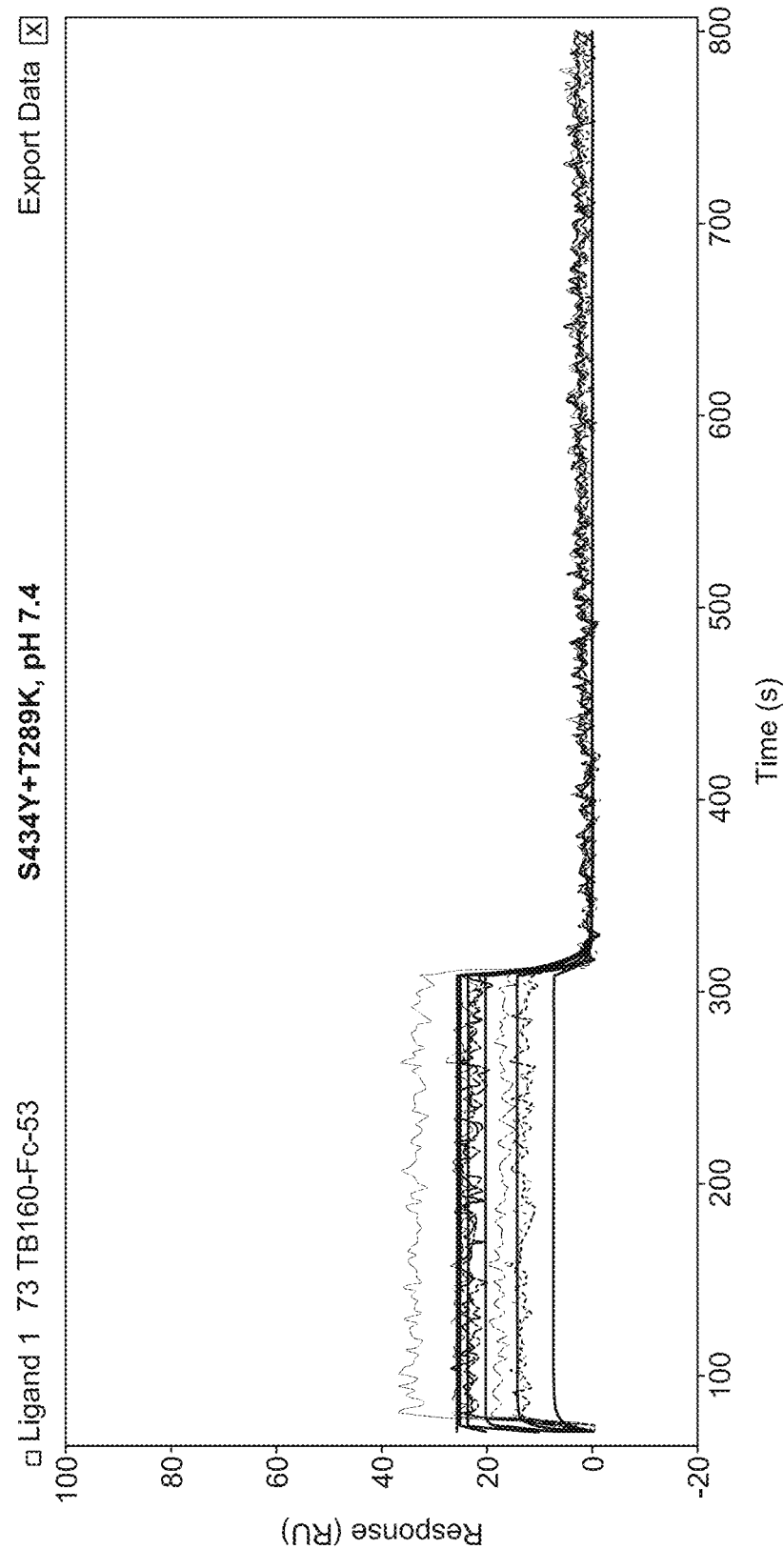
Figure 17A:
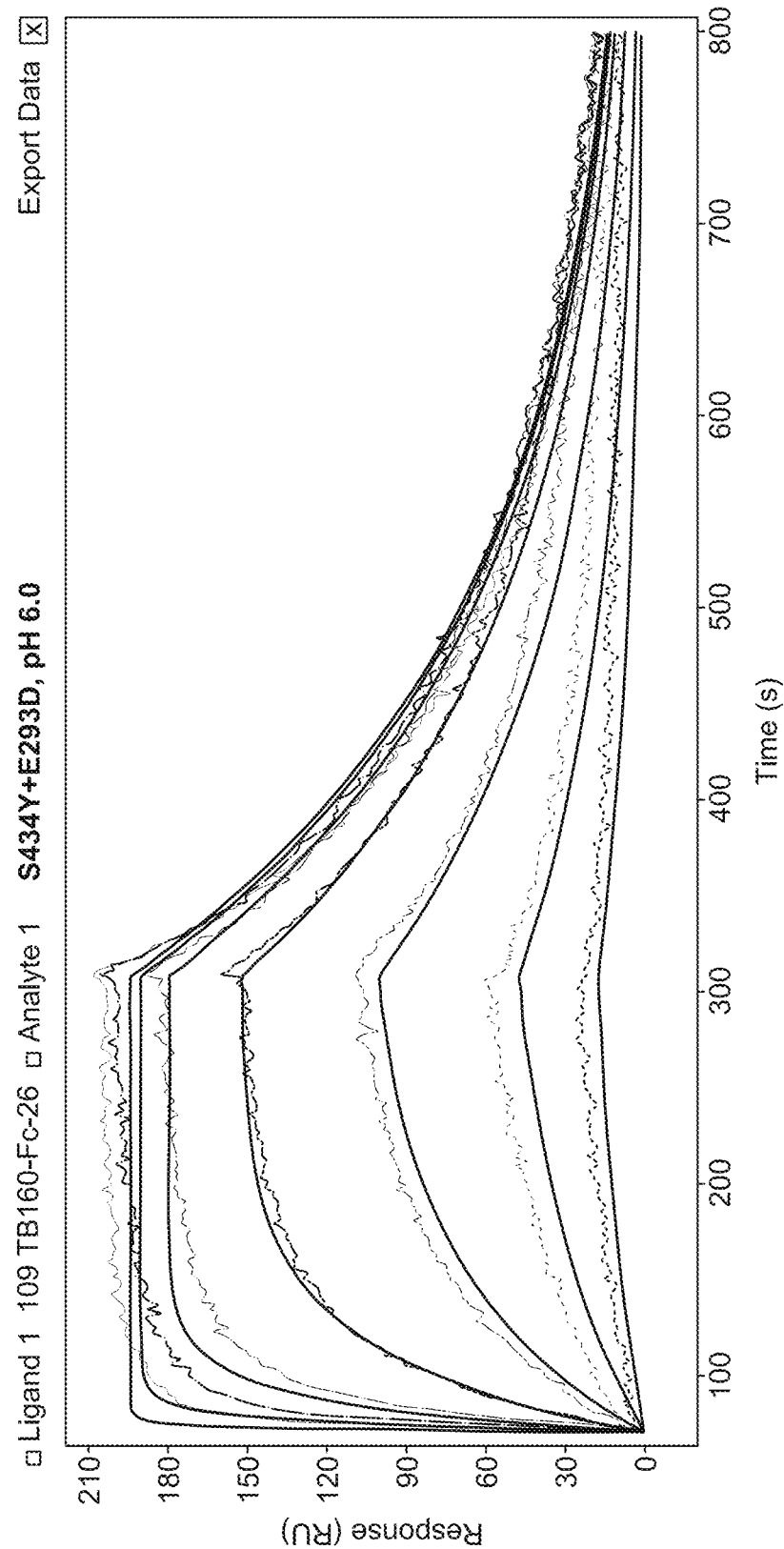
FIGS. 17A and 17B depict Carterra LSA sensorgrams for the S434Y+E293D feline IgG1a Fc variant from the phage display library and its interaction with feline FcRN at pH6.0 and pH7.4. The irregular lines represent the measured data and the smooth lines are the fitted curves using a 1:1 interaction model. Y-axis: Resonance Units (RU); X-axis: time (seconds).
Figure 17B:
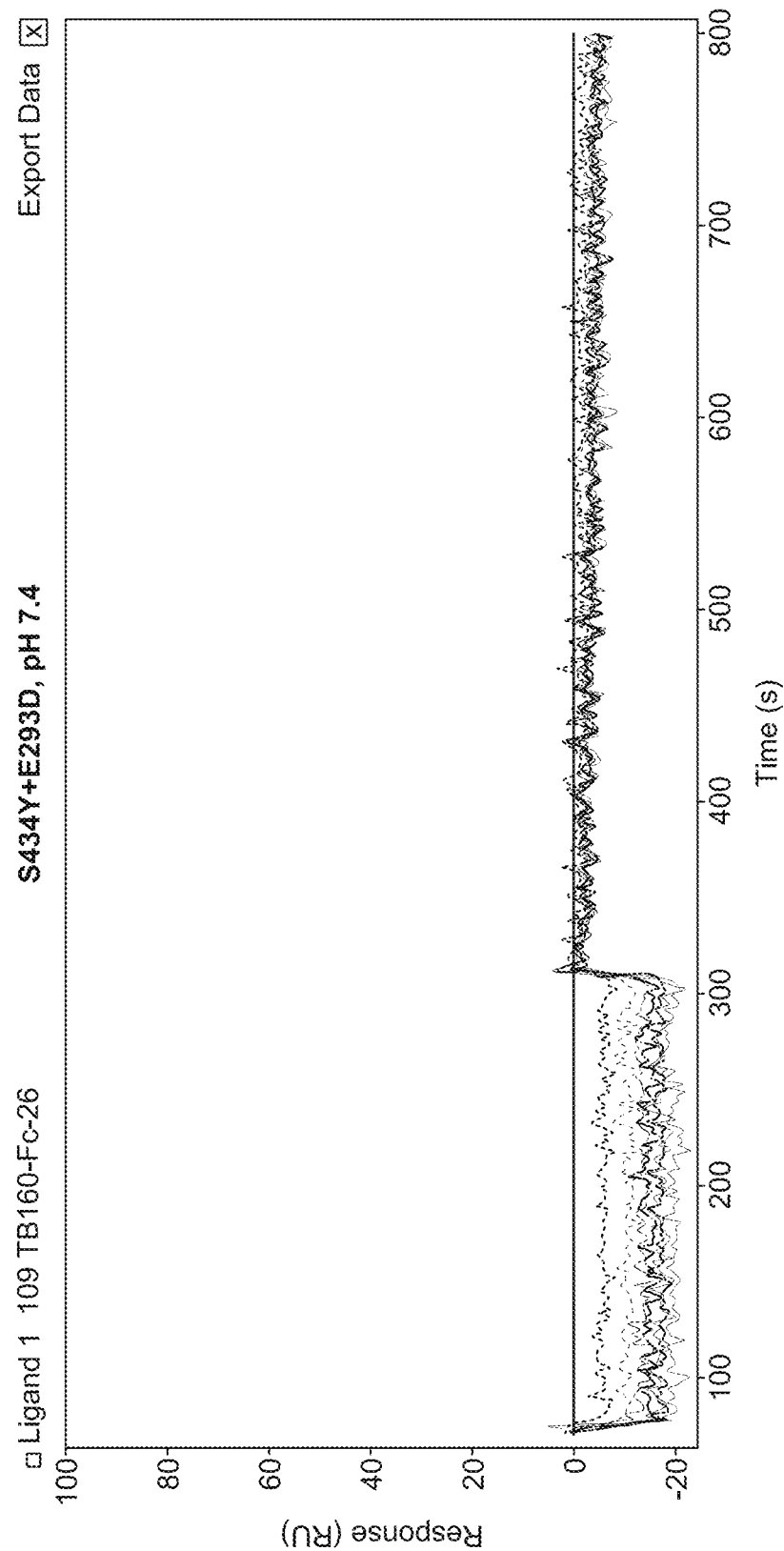
Figure 18A:
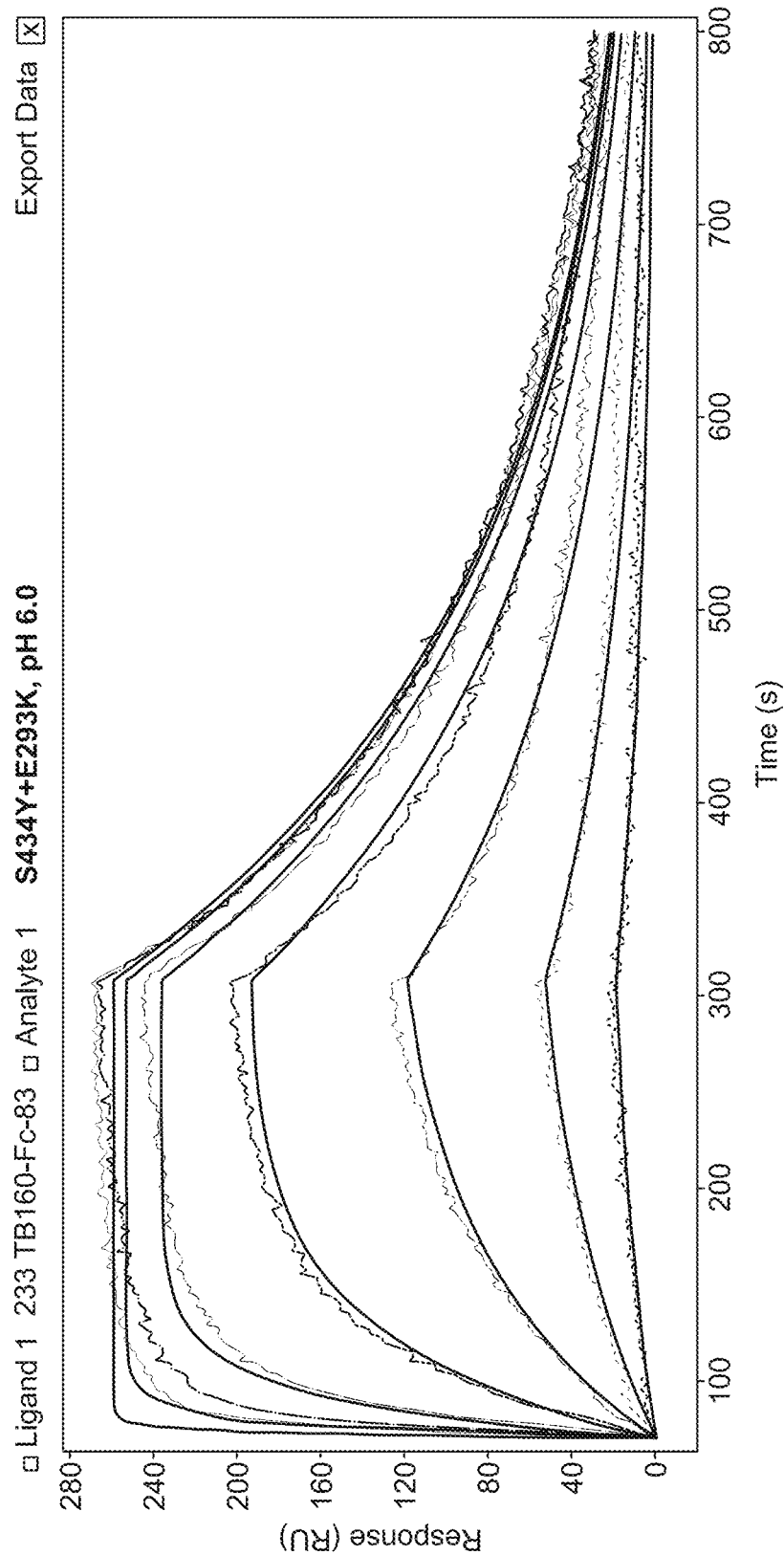
FIGS. 18A and 18B depict Carterra LSA sensorgrams for the S434Y+E293K feline IgG1a Fc variant from the phage display library and its interaction with feline FcRN at pH6.0 and pH7.4. The irregular lines represent the measured data and the smooth lines are the fitted curves using a 1:1 interaction model. Y-axis: Resonance Units (RU); X-axis: time (seconds).
Figure 18B:
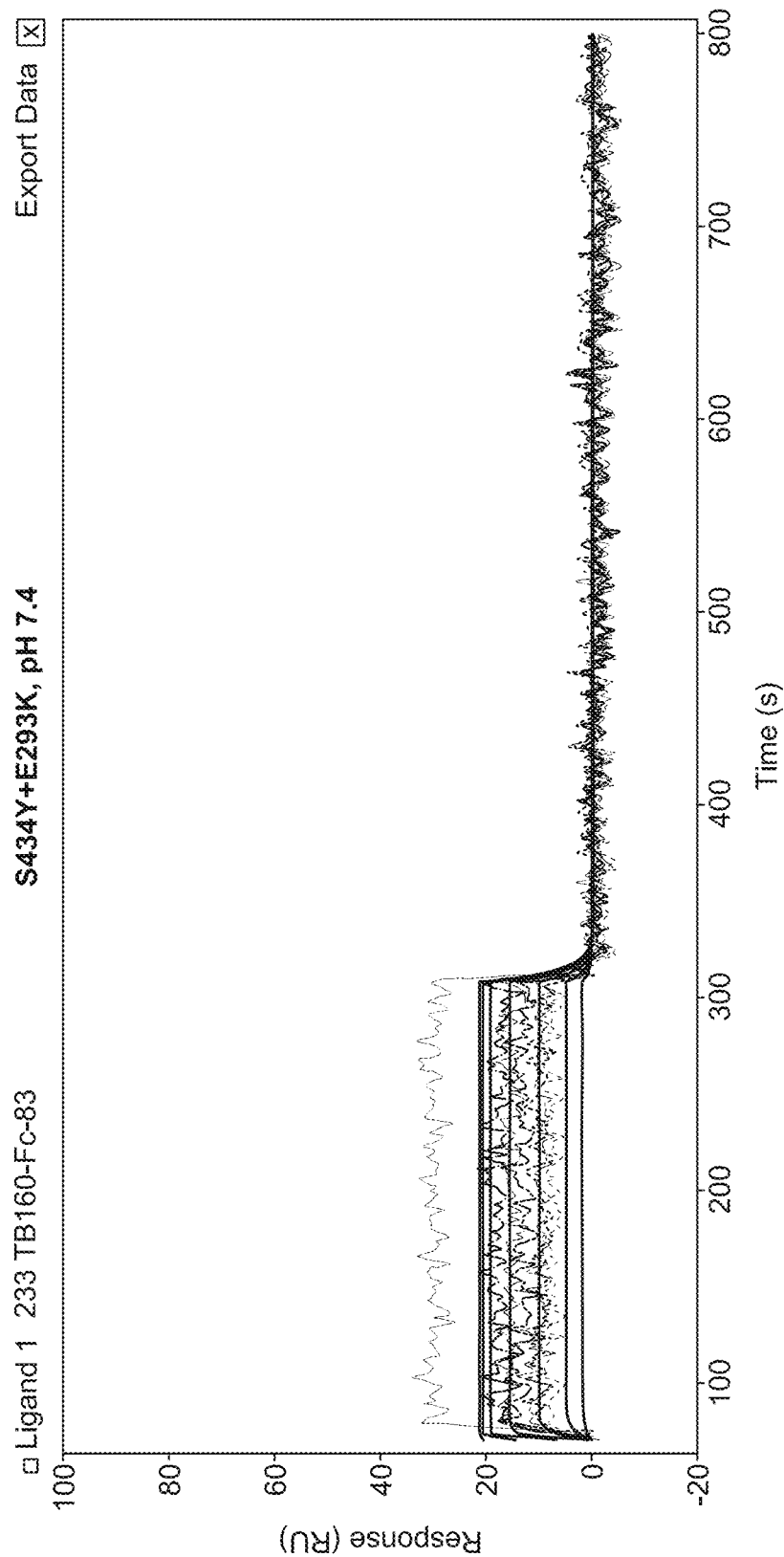
Figure 19A:
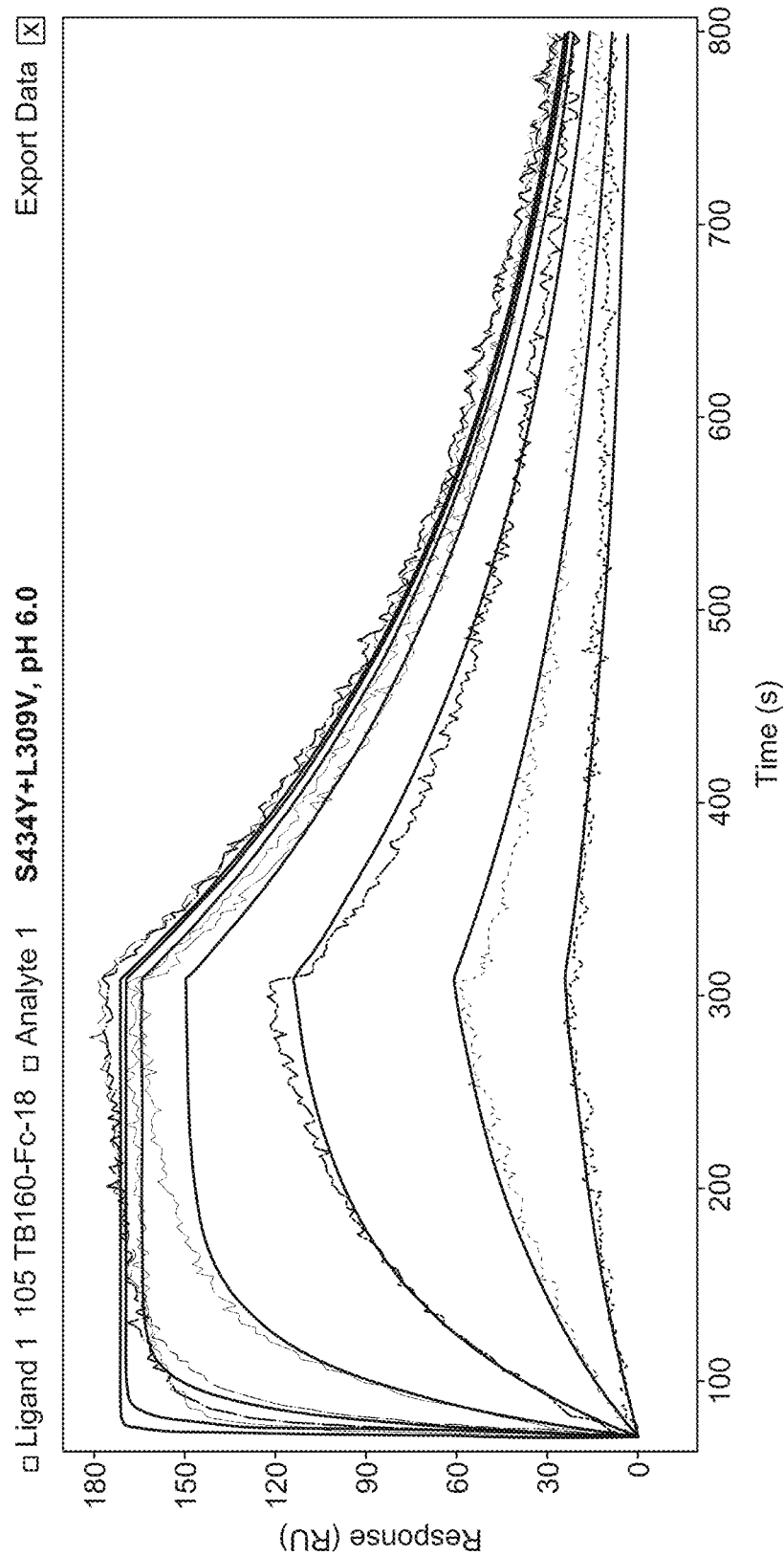
FIGS. 19A and 19B depict Carterra LSA sensorgrams for the S434Y+L309V feline IgG1a Fc variant from the phage display library and its interaction with feline FcRN at pH6.0 and pH7.4. The irregular lines represent the measured data and the smooth lines are the fitted curves using a 1:1 interaction model. Y-axis: Resonance Units (RU); X-axis: time (seconds).
Figure 19B:
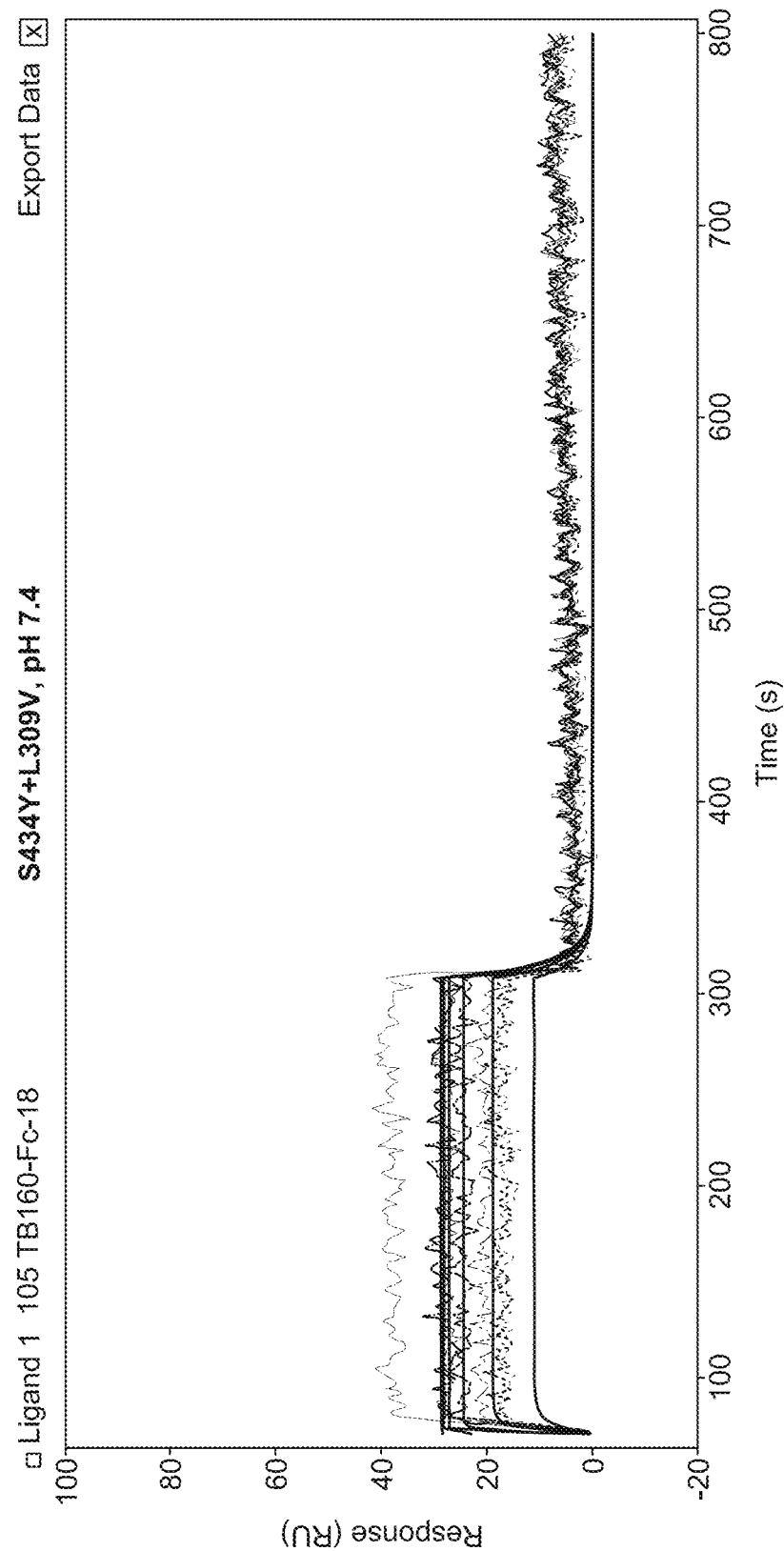
Figure 20A:
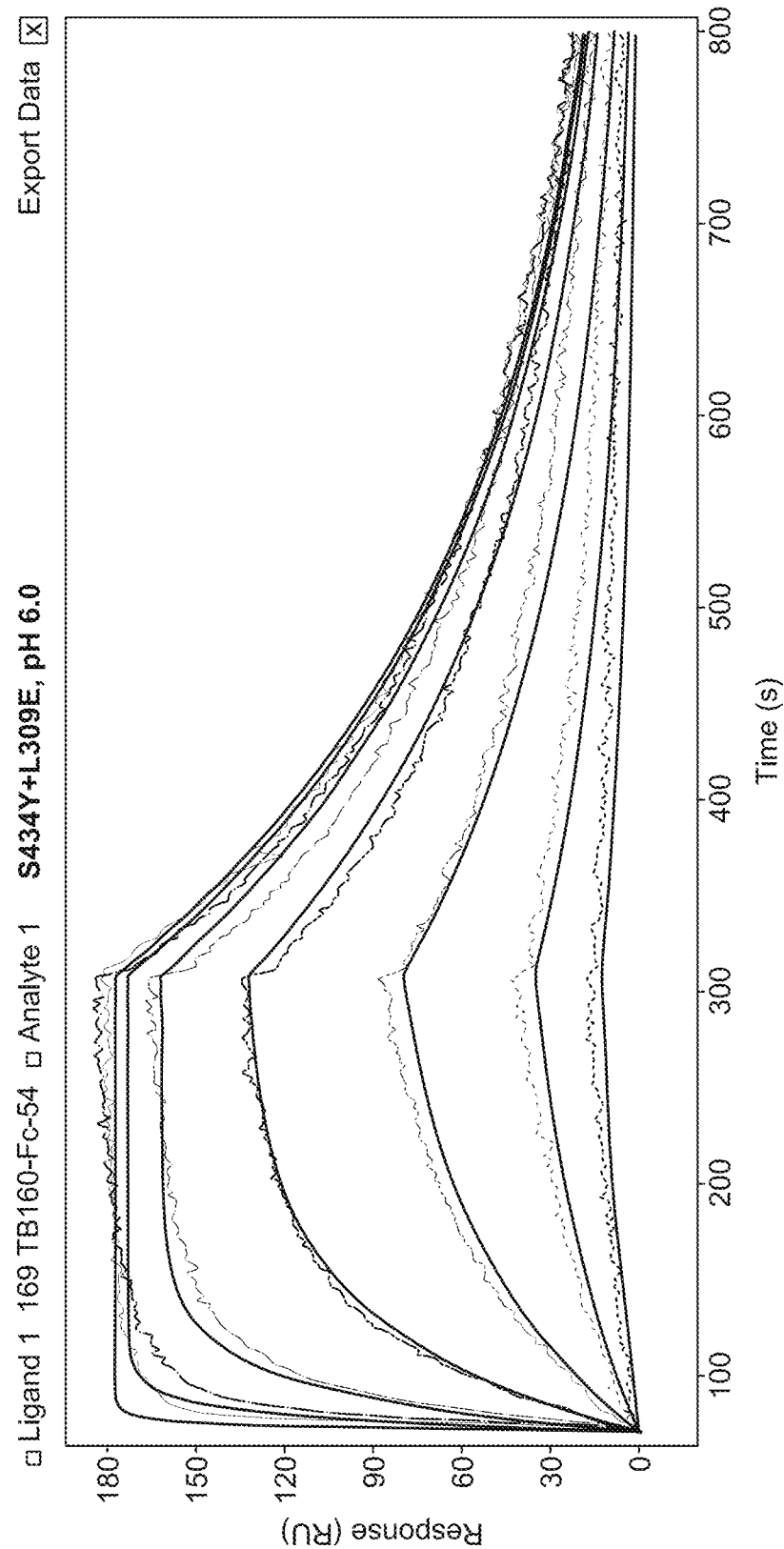
FIGS. 20A and 20B depict Carterra LSA sensorgrams for the S434Y+L309E feline IgG1a Fc variant from the phage display library and its interaction with feline FcRN at pH6.0 and pH7.4. The irregular lines represent the measured data and the smooth lines are the fitted curves using a 1:1 interaction model. Y-axis: Resonance Units (RU); X-axis: time (seconds).
Figure 20B:
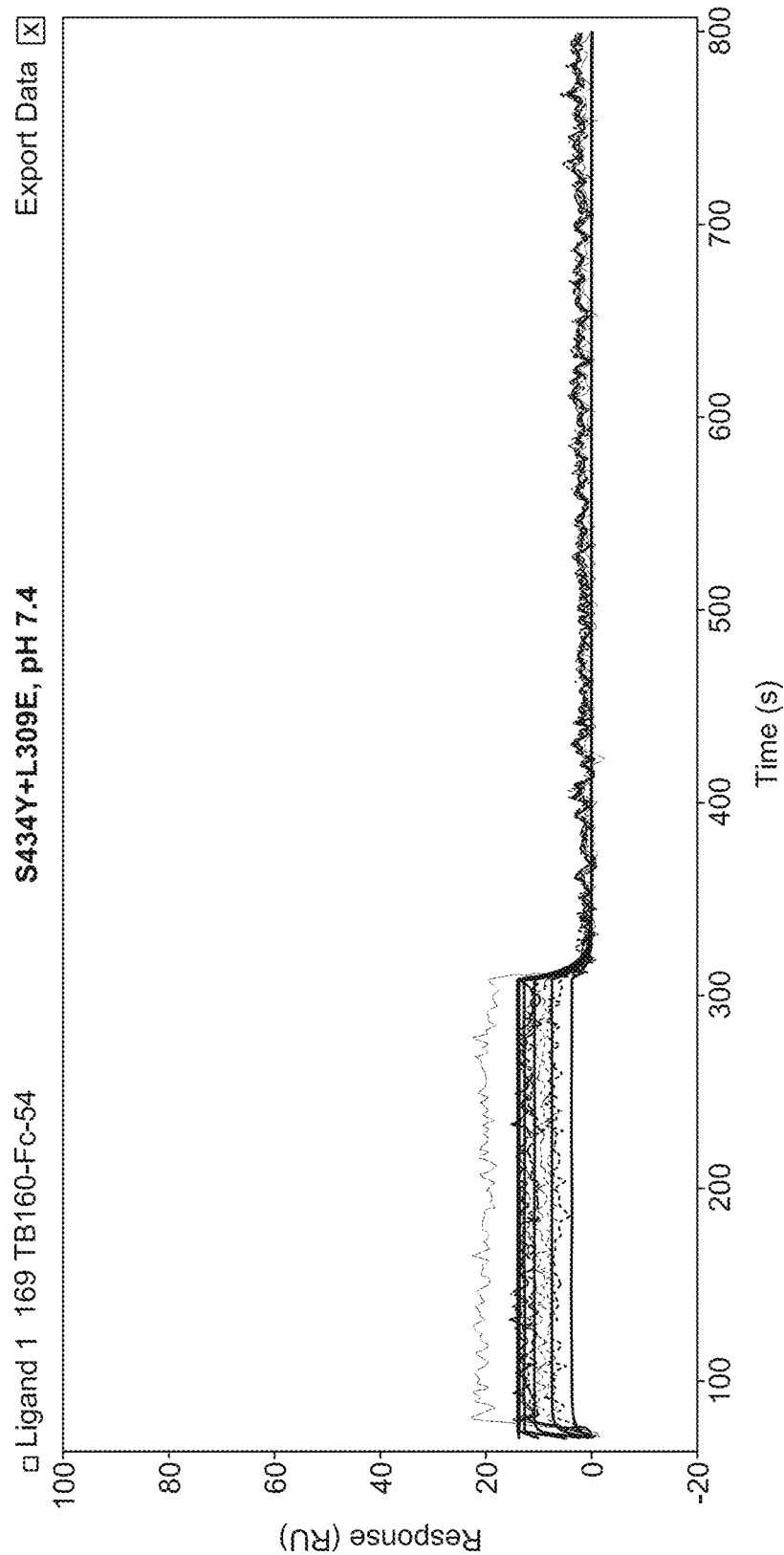
Figure 21A:
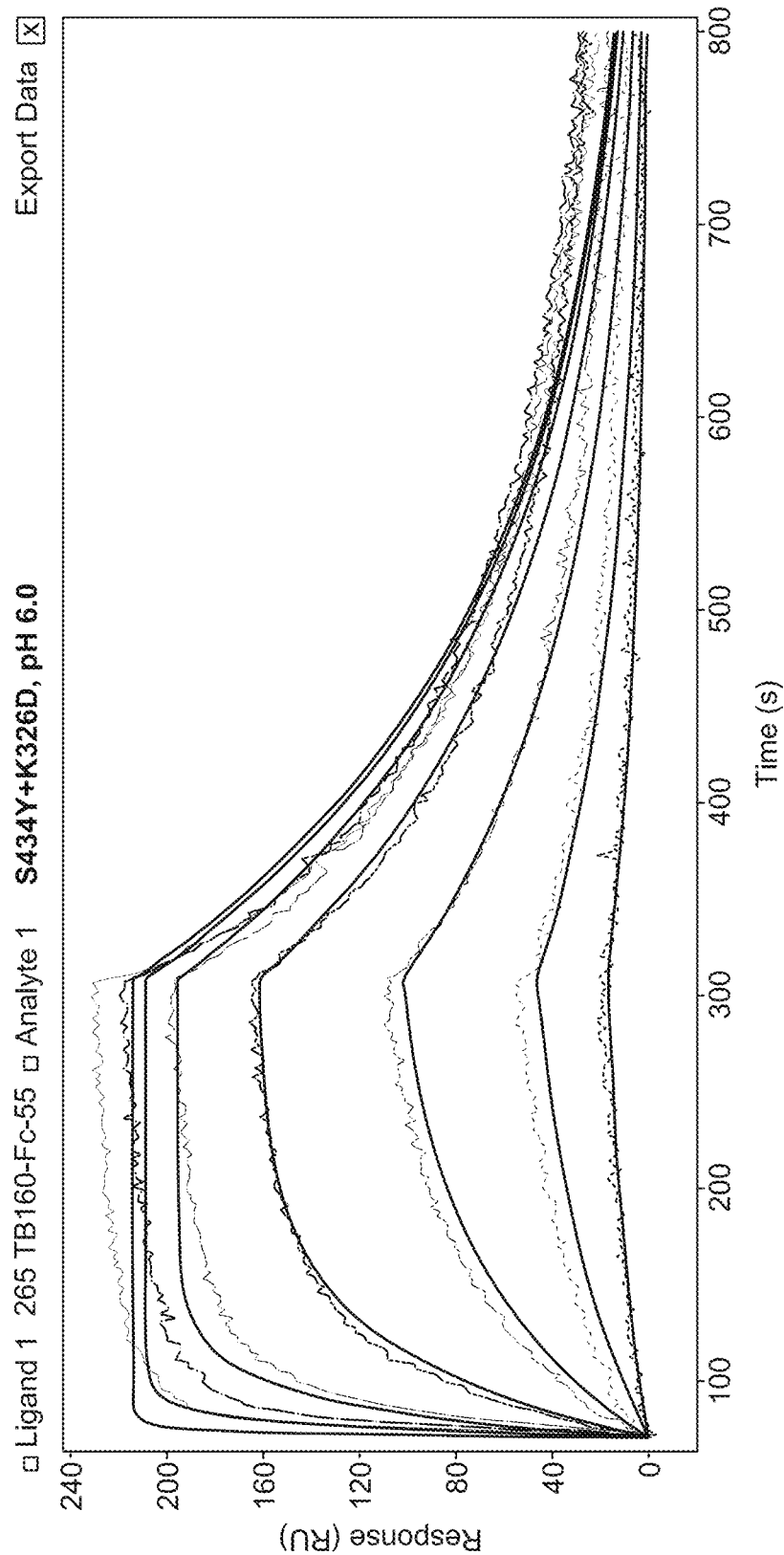
FIGS. 21A and 21B depict Carterra LSA sensorgrams for the S434Y+K326D feline IgG1a Fc variant from the phage display library and its interaction with feline FcRN at pH6.0 and pH7.4. The irregular lines represent the measured data and the smooth lines are the fitted curves using a 1:1 interaction model. Y-axis: Resonance Units (RU); X-axis: time (seconds).
Figure 21B:
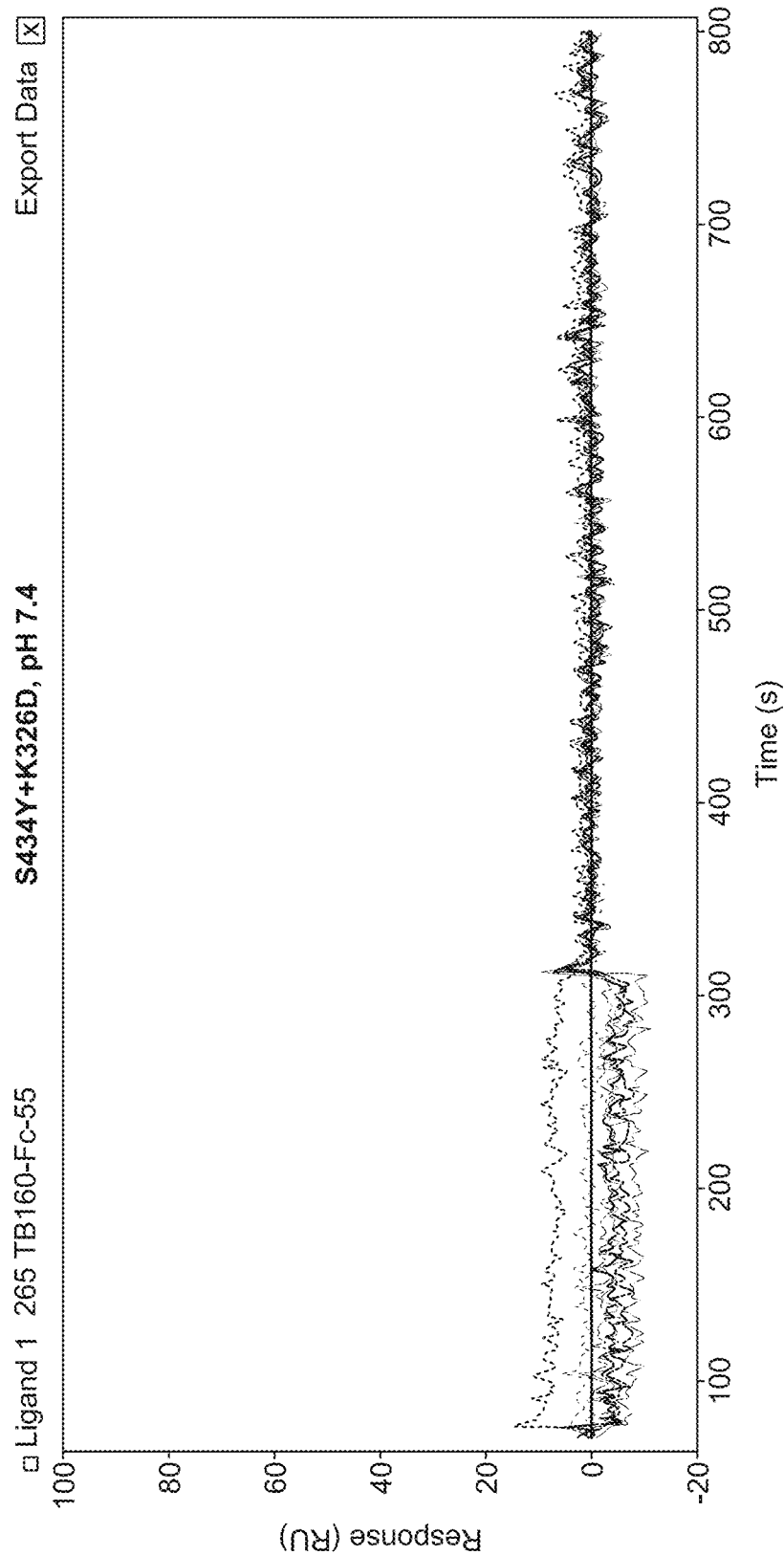
Figure 22A:
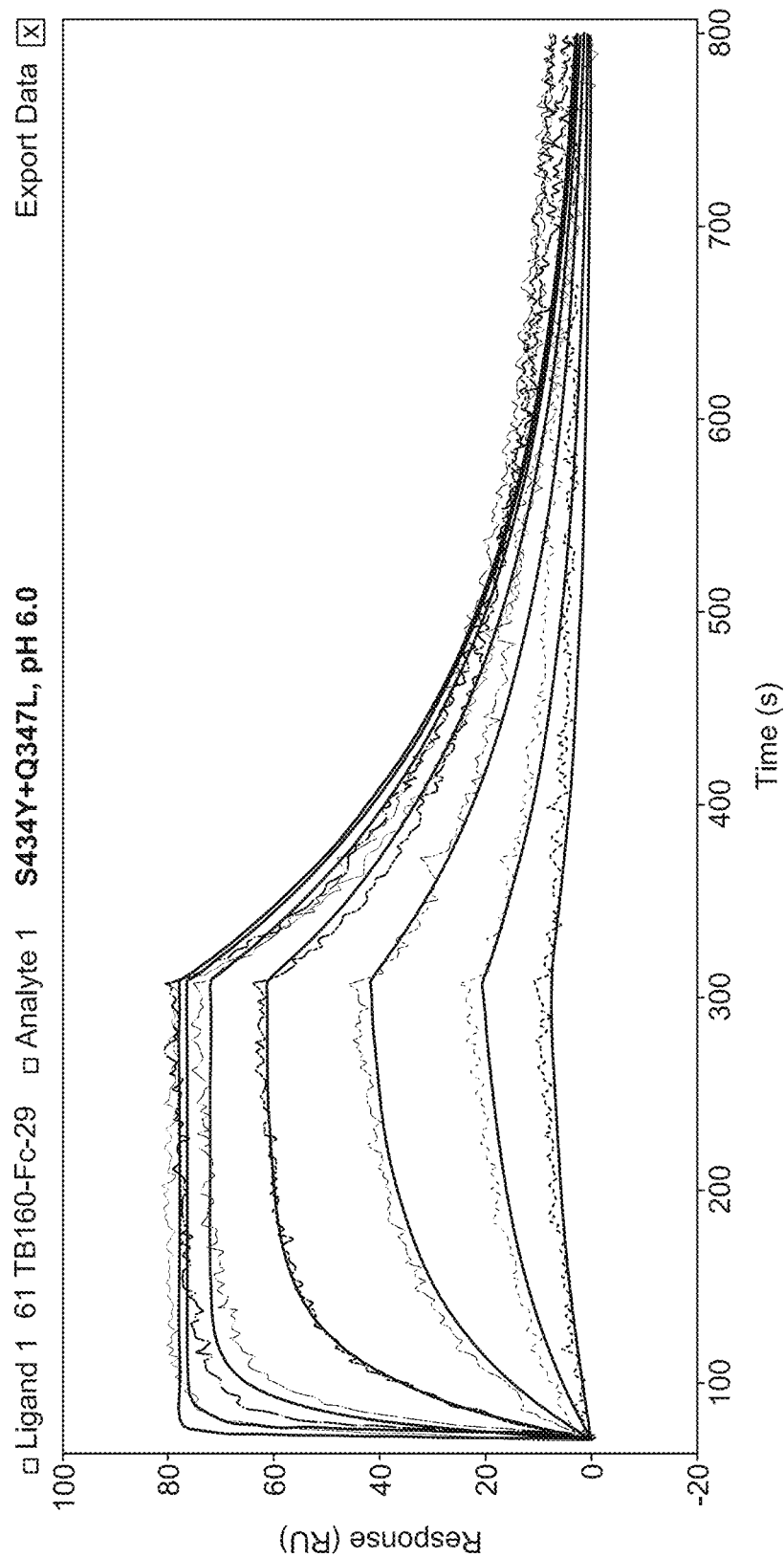
FIGS. 22A and 22B depict Carterra LSA sensorgrams for the S434Y+Q347L feline IgG1a Fc variant from the phage display library and its interaction with feline FcRN at pH6.0 and pH7.4. The irregular lines represent the measured data and the smooth lines are the fitted curves using a 1:1 interaction model. Y-axis: Resonance Units (RU); X-axis: time (seconds).
Figure 22B:
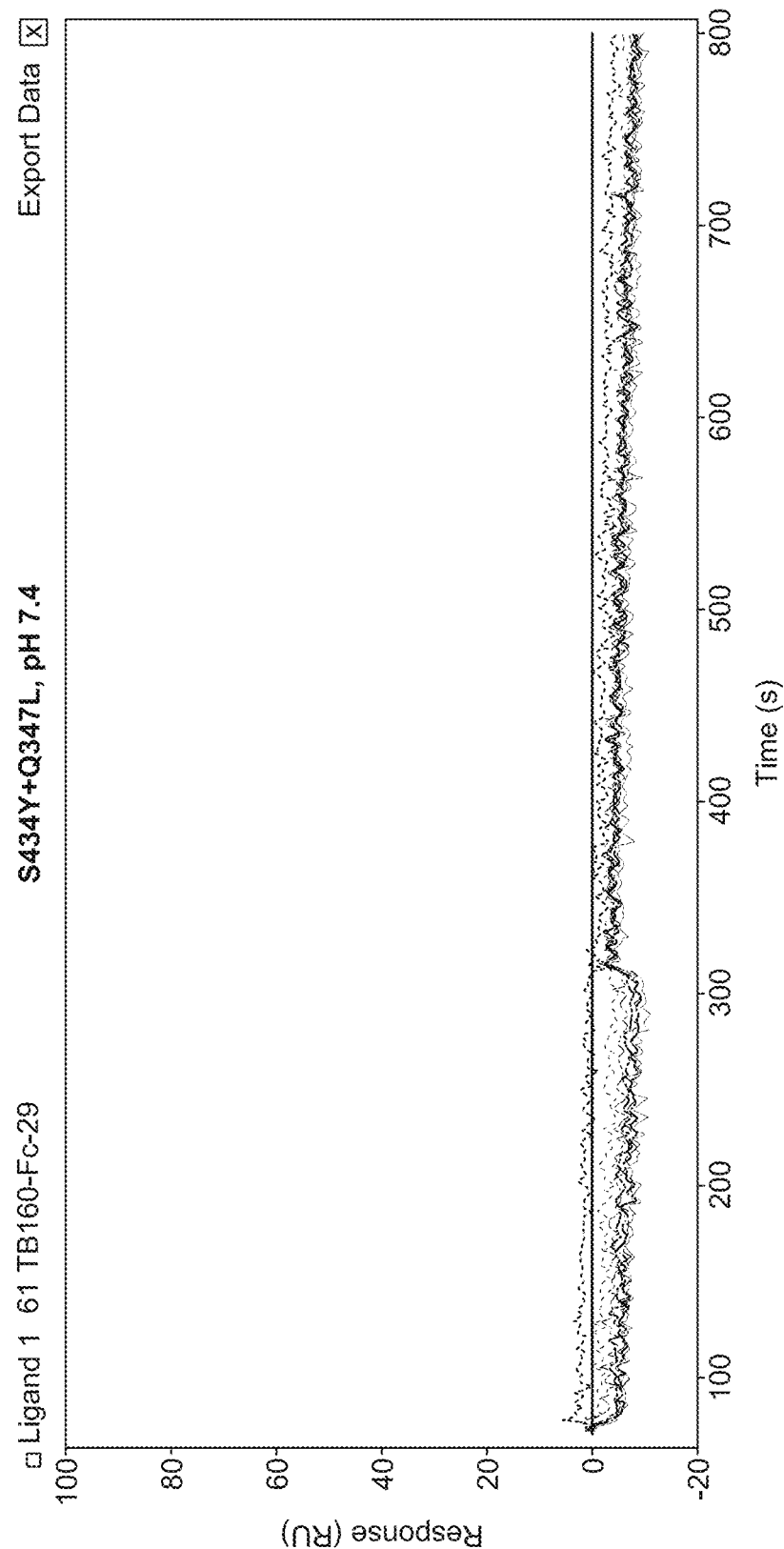
Figure 23A:
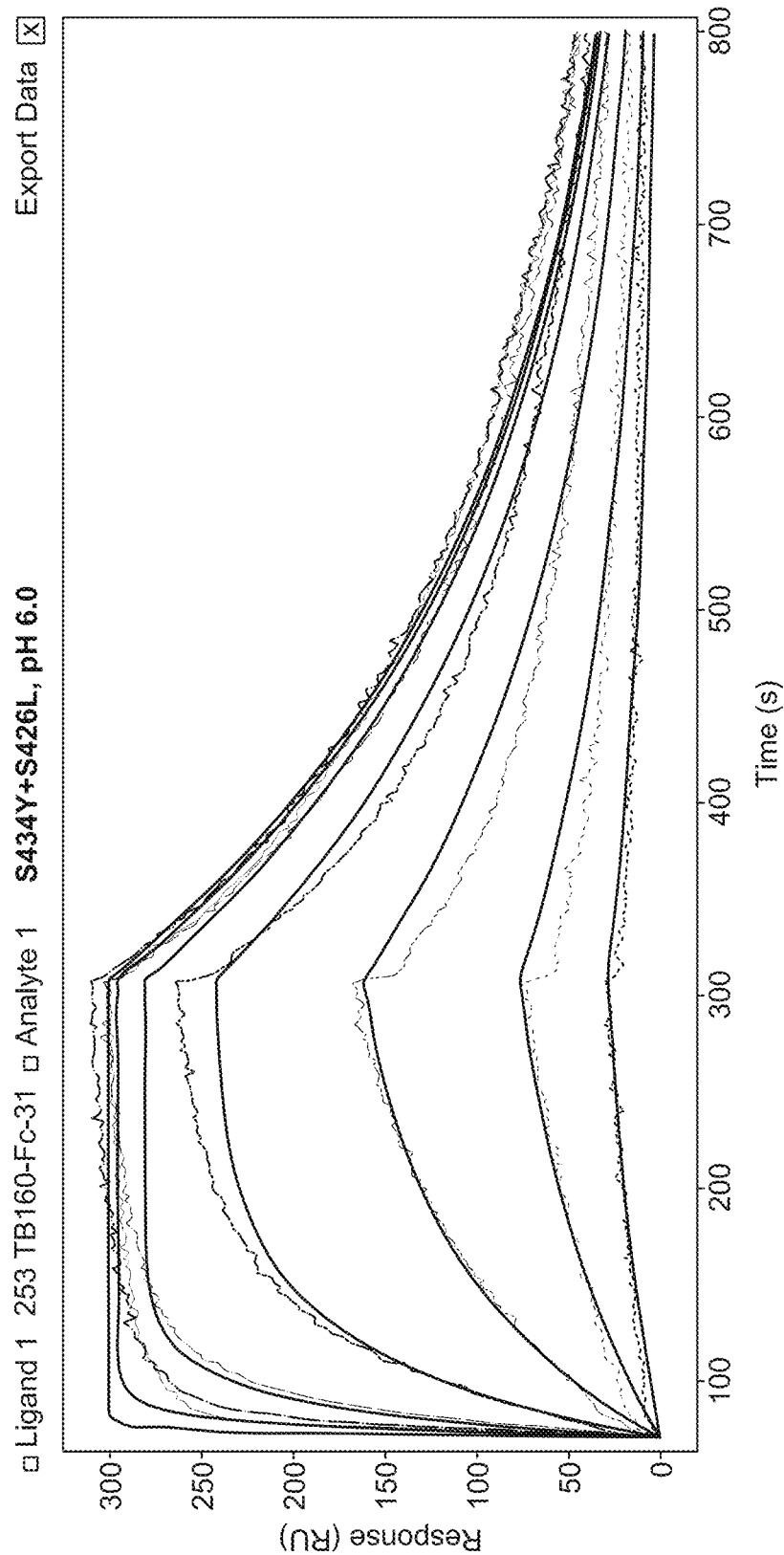
FIGS. 23A and 23B depict Carterra LSA sensorgrams for the S434Y+S426L feline IgG1a Fc variant from the phage display library and its interaction with feline FcRN at pH6.0 and pH7.4. The irregular lines represent the measured data and the smooth lines are the fitted curves using a 1:1 interaction model. Y-axis: Resonance Units (RU); X-axis: time (seconds).
Figure 23B:
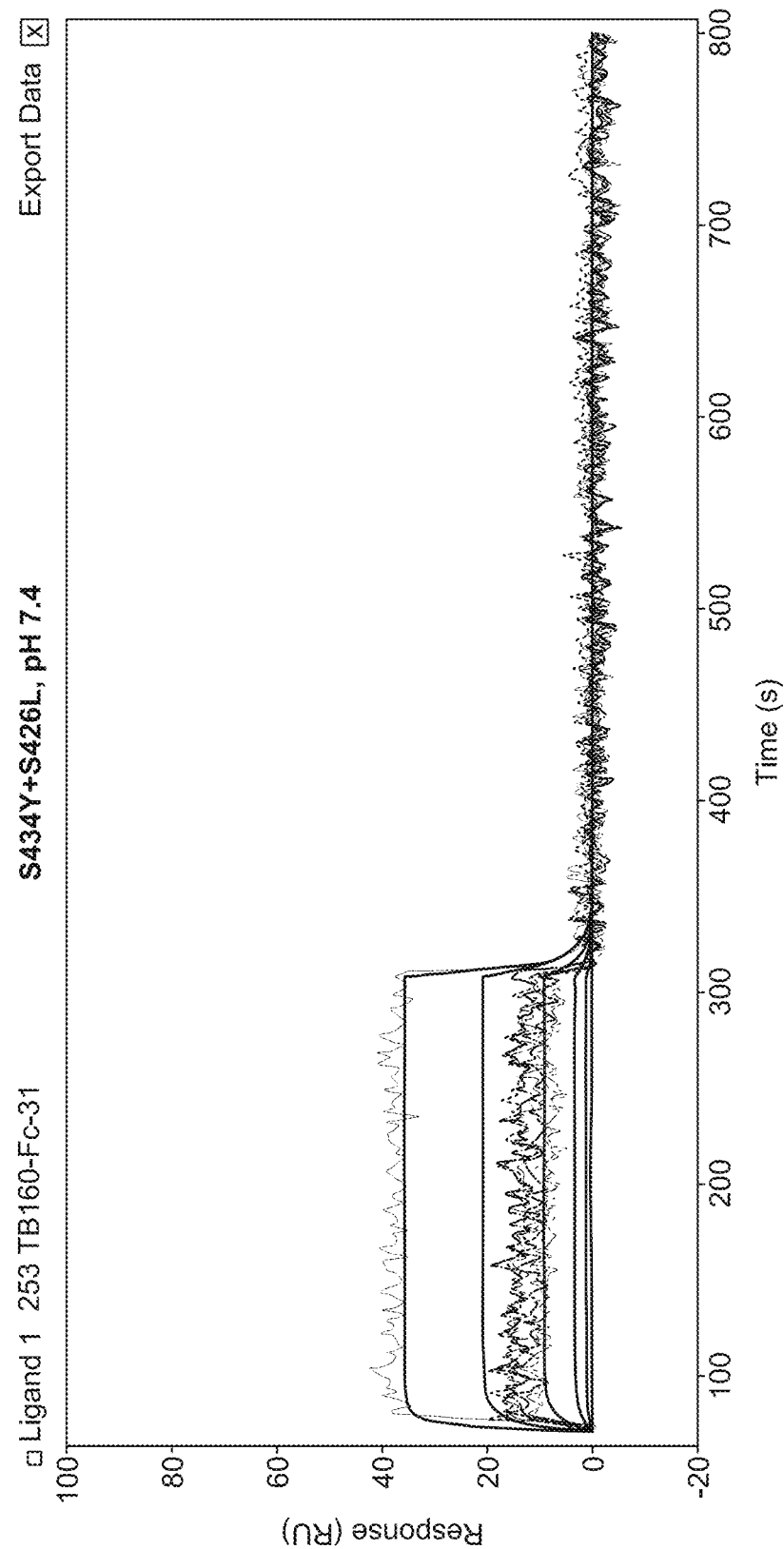
Figure 24A:
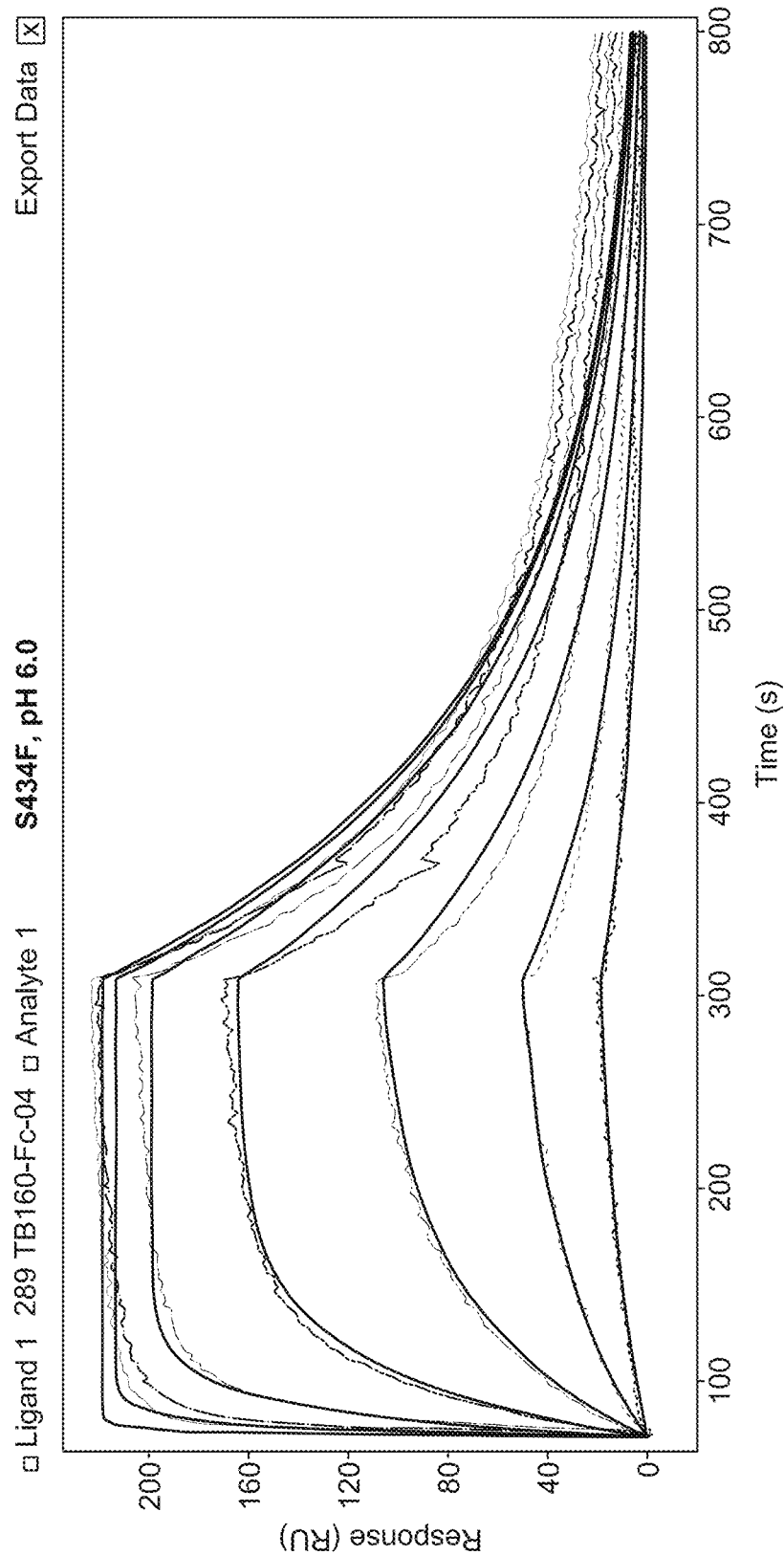
FIGS. 24A and 24B depict Carterra LSA sensorgrams for the S434F feline IgG1a Fc variant from the phage display library and its interaction with feline FcRN at pH6.0 and pH7.4. The irregular lines represent the measured data and the smooth lines are the fitted curves using a 1:1 interaction model. Y-axis: Resonance Units (RU); X-axis: time (seconds).
Figure 24B:
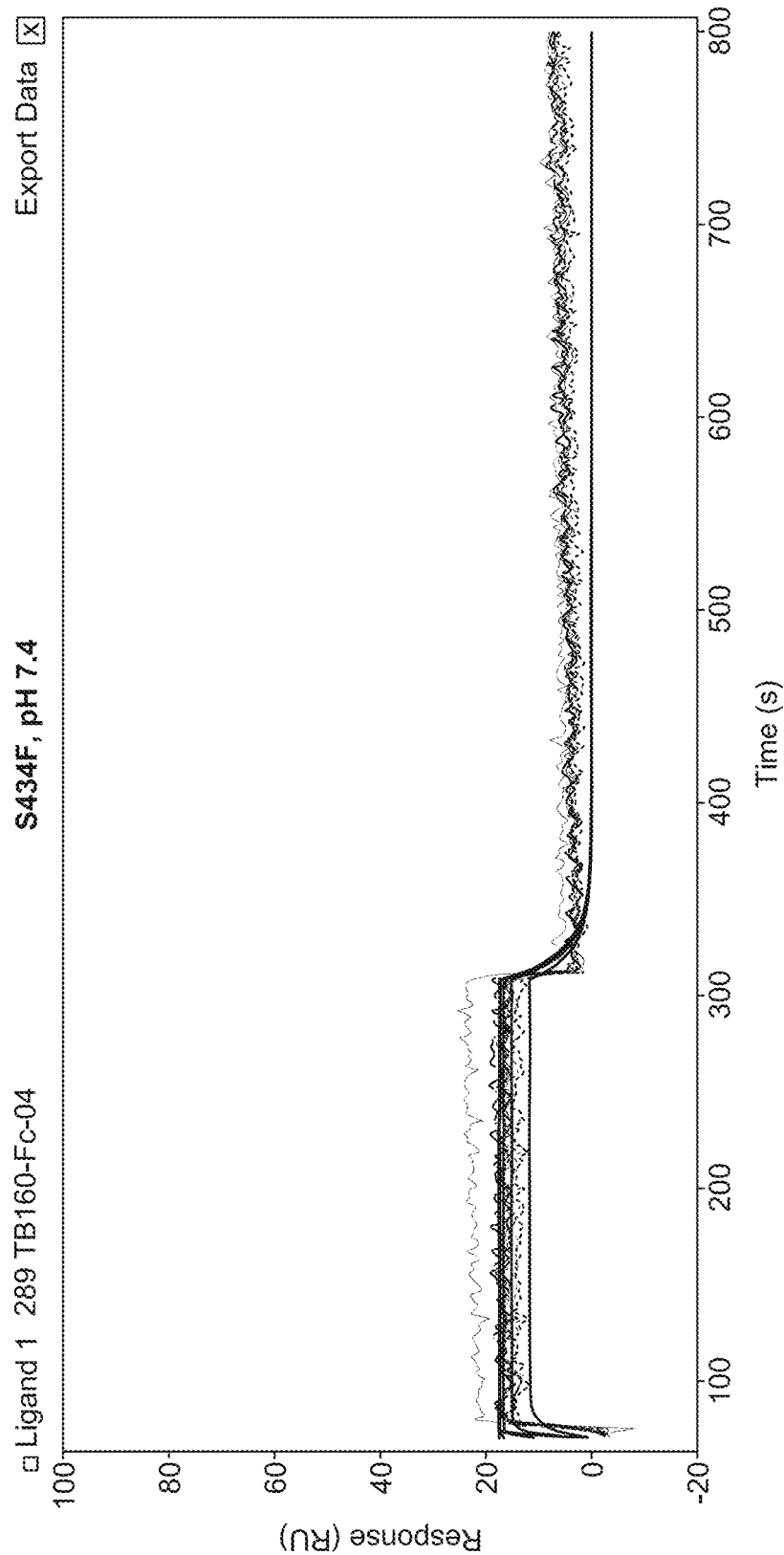
Figure 25A:
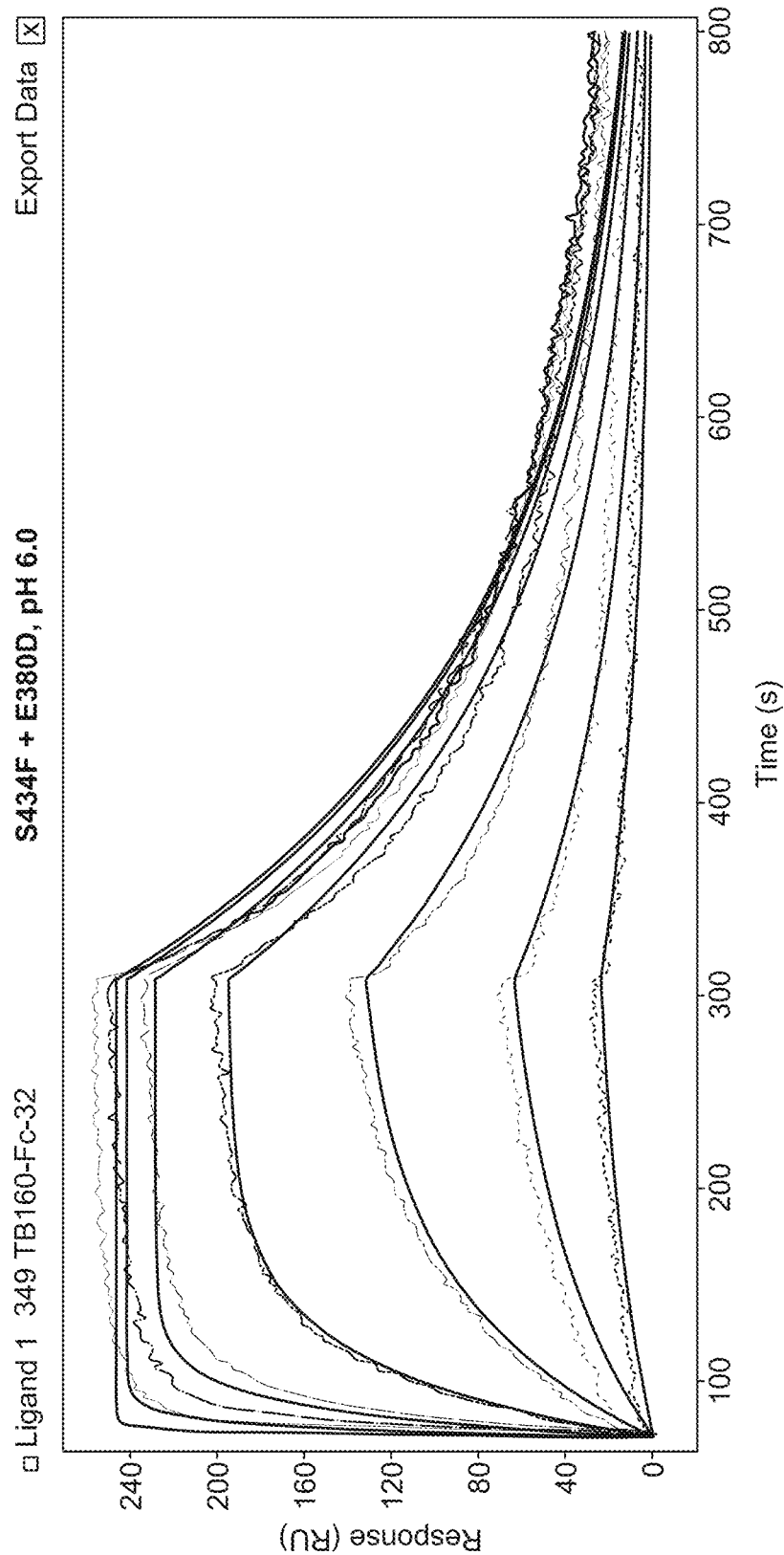
FIGS. 25A and 25B depict Carterra LSA sensorgrams for the S434F+E380D feline IgG1a Fc variant from the phage display library and its interaction with feline FcRN at pH6.0 and pH7.4. The irregular lines represent the measured data and the smooth lines are the fitted curves using a 1:1 interaction model. Y-axis: Resonance Units (RU); X-axis: time (seconds).
Figure 25B:
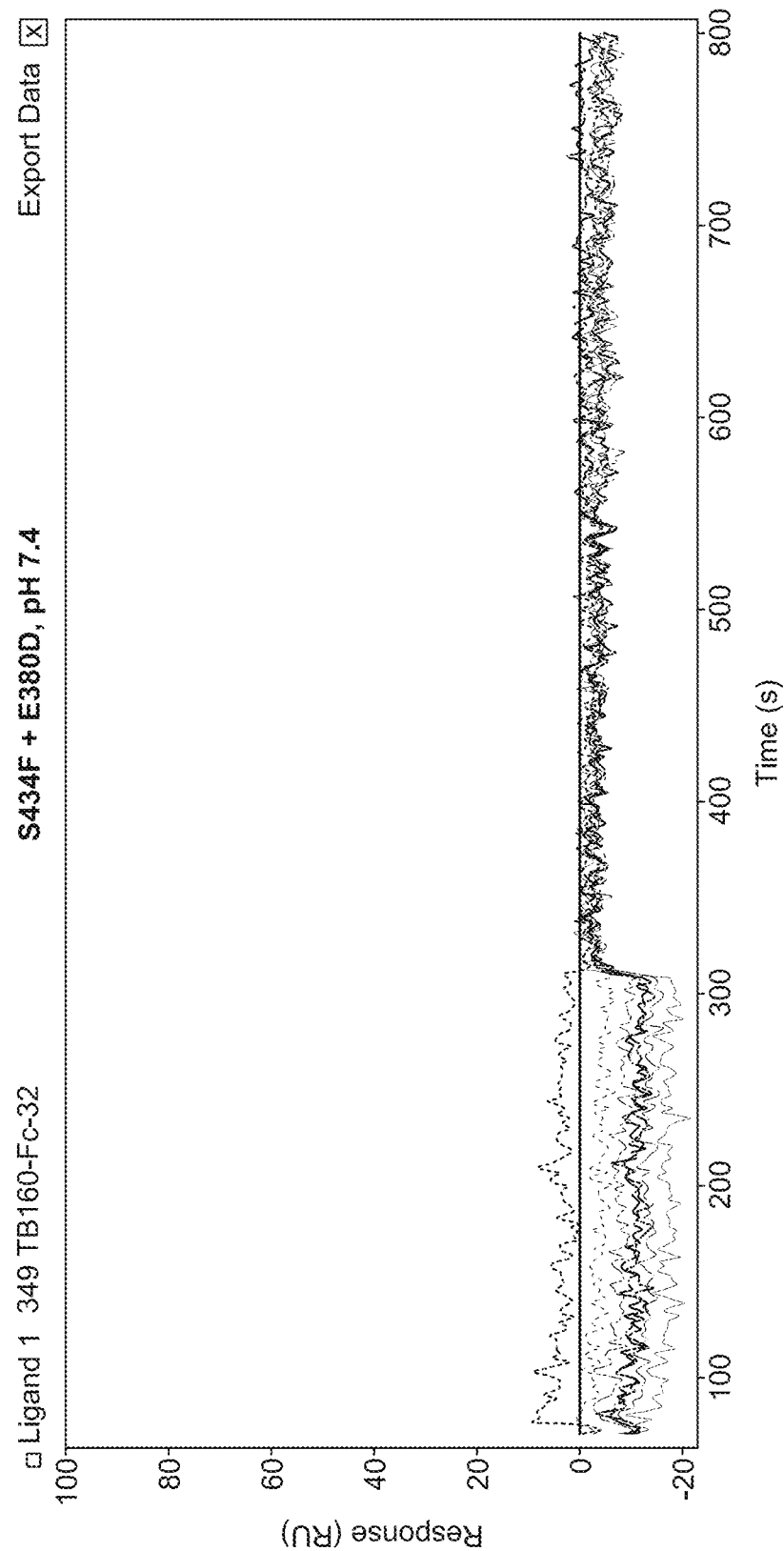
Figure 26A:
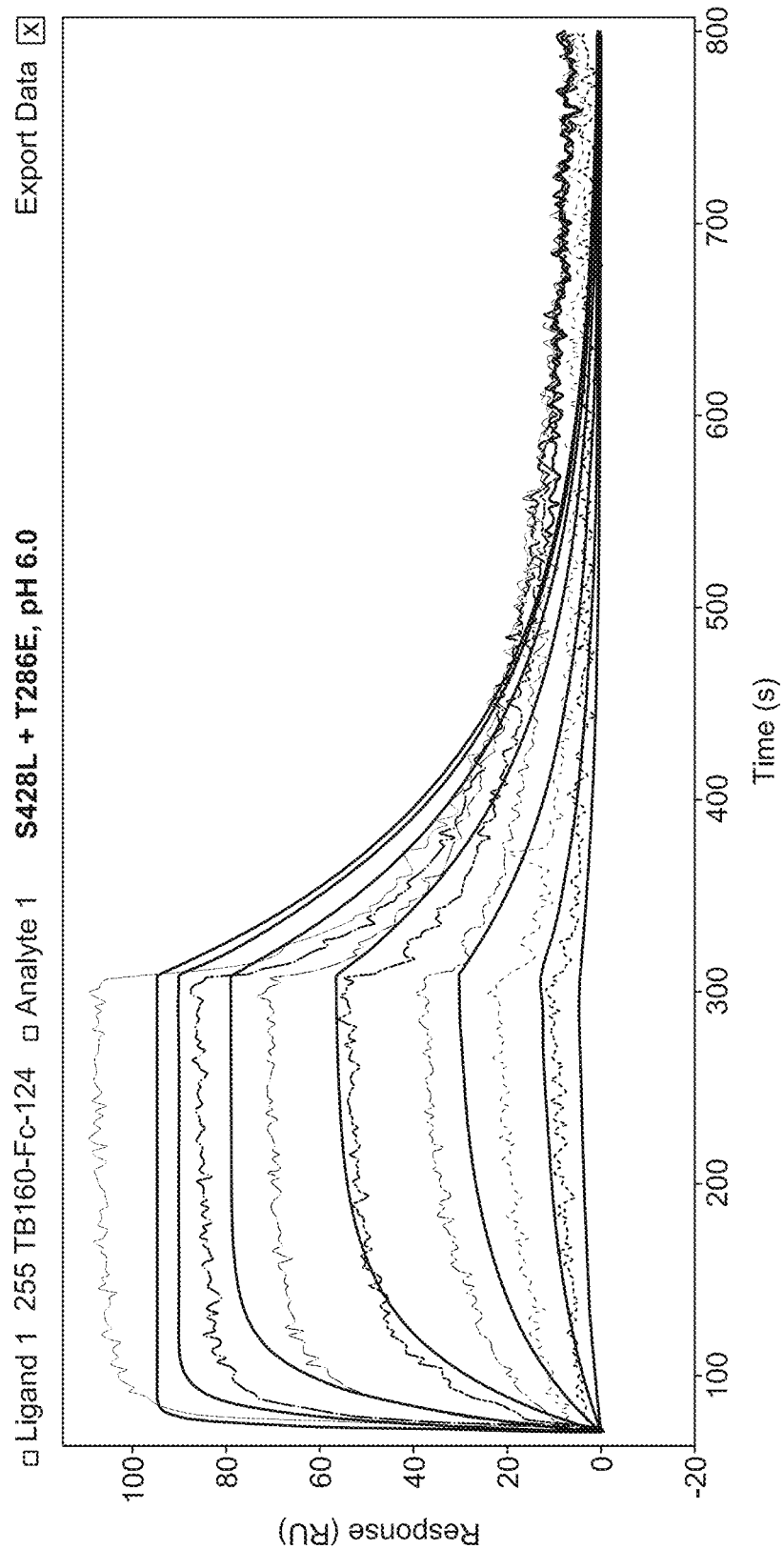
FIGS. 26A and 26B depict Carterra LSA sensorgrams for the S428L+T286E feline IgG1a Fc variant from the phage display library and its interaction with feline FcRN at pH6.0 and pH7.4. The irregular lines represent the measured data and the smooth lines are the fitted curves using a 1:1 interaction model. Y-axis: Resonance Units (RU); X-axis: time (seconds).
Figure 26B:
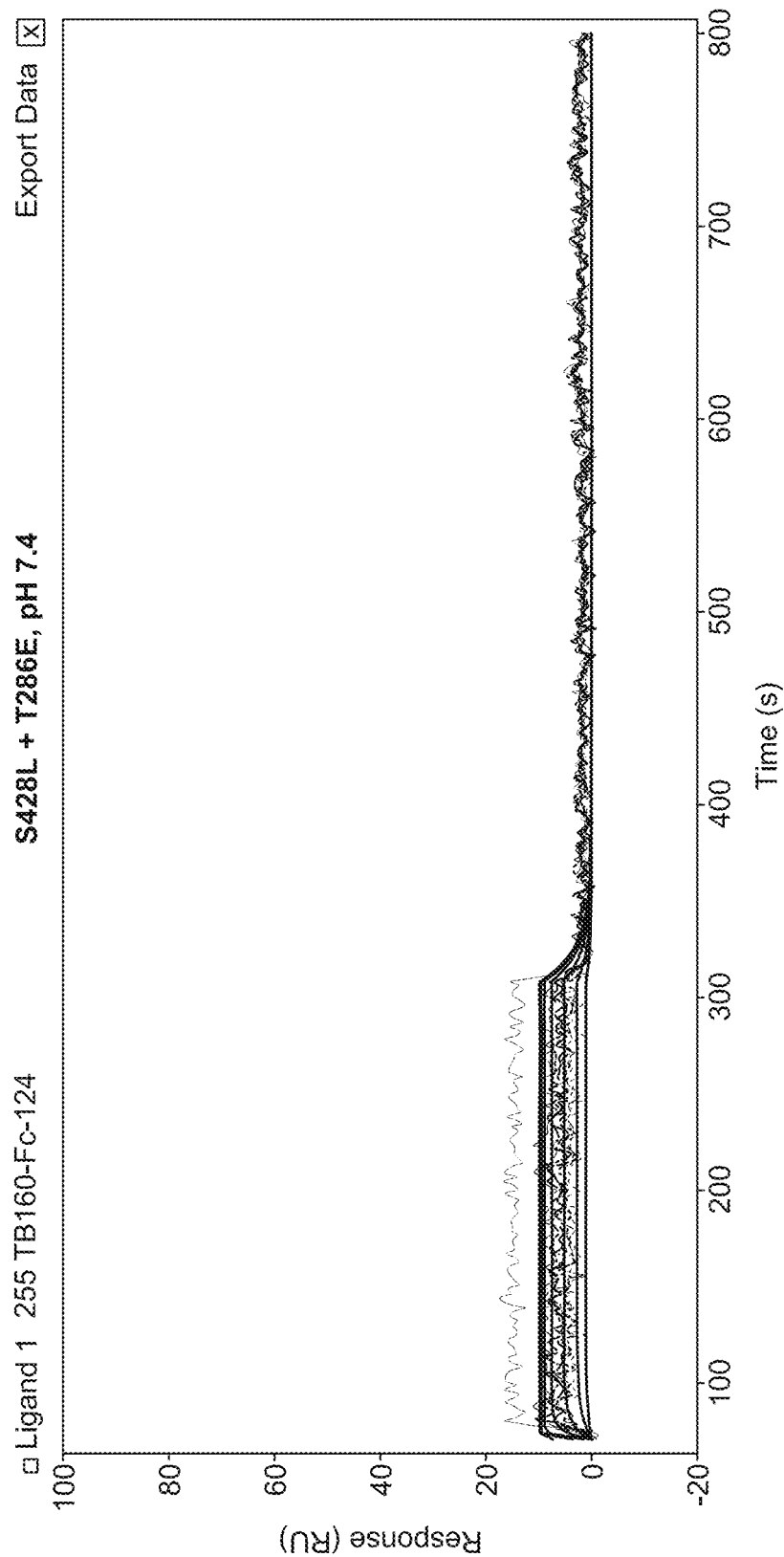
Figure 27A:
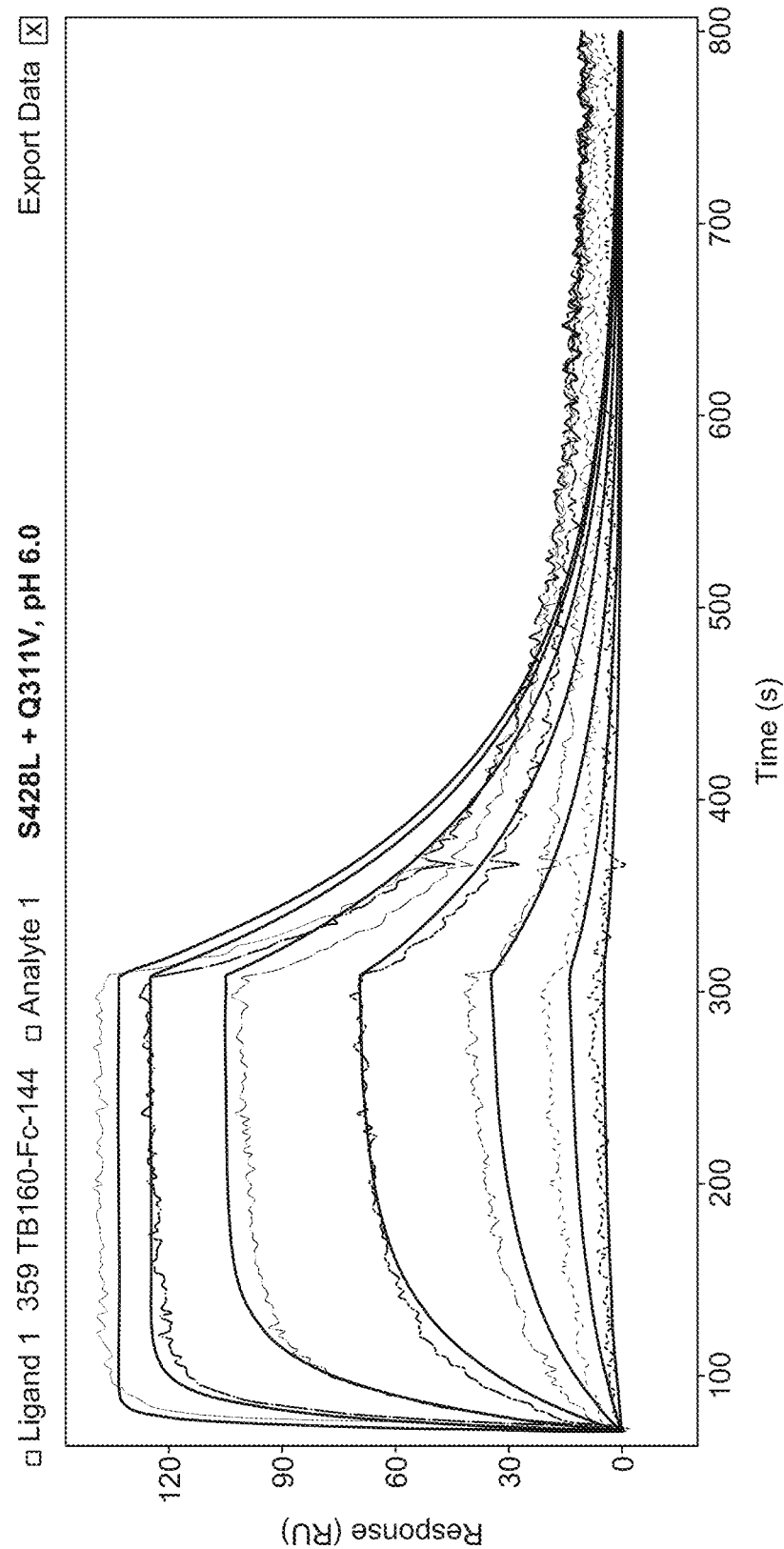
FIGS. 27A and 27B depict Carterra LSA sensorgrams for the S428L+Q311V feline IgG1a Fc variant from the phage display library and its interaction with feline FcRN at pH6.0 and pH7.4. The irregular lines represent the measured data and the smooth lines are the fitted curves using a 1:1 interaction model. Y-axis: Resonance Units (RU); X-axis: time (seconds).
Figure 27B:
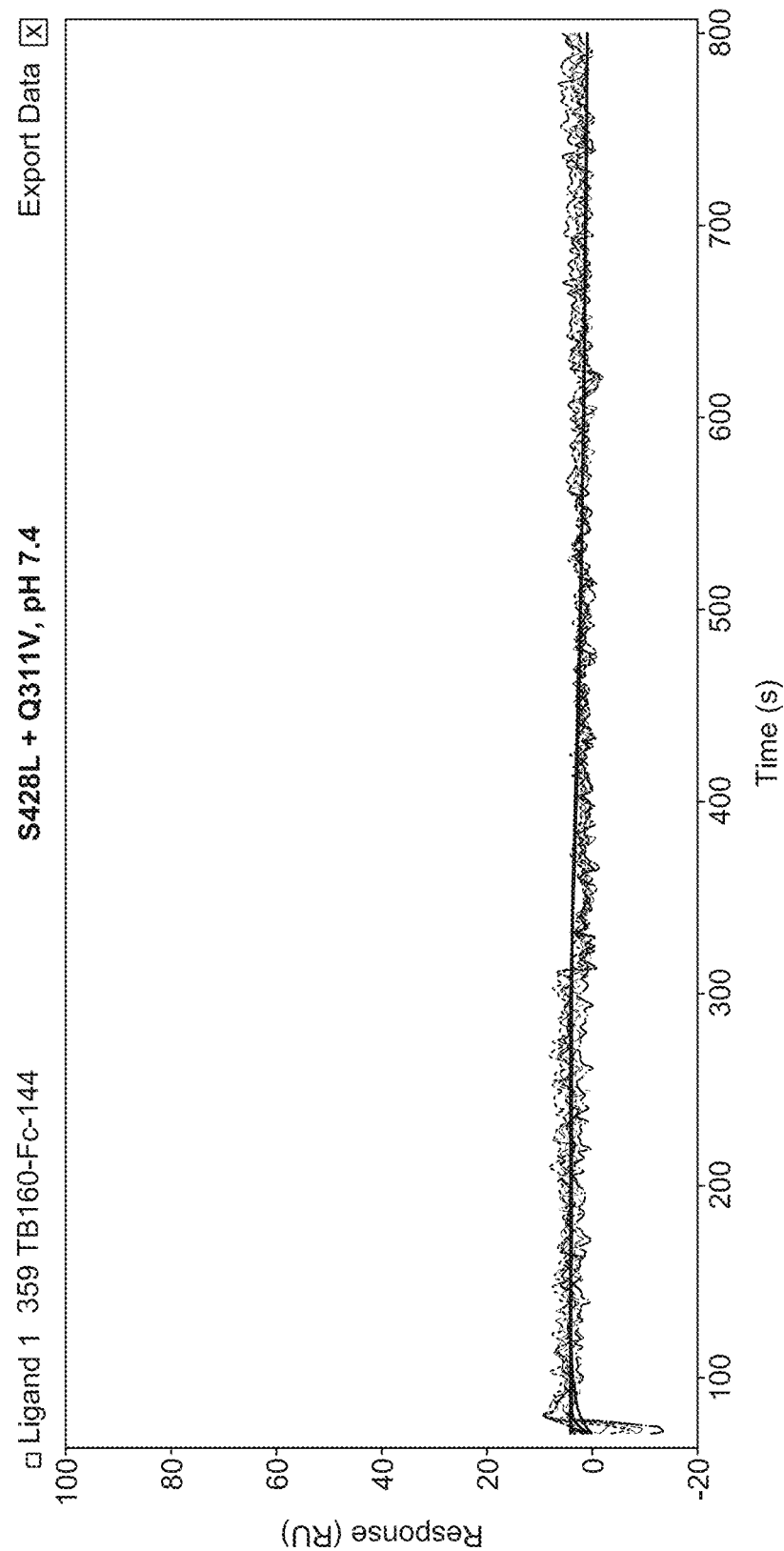
Figure 28A:
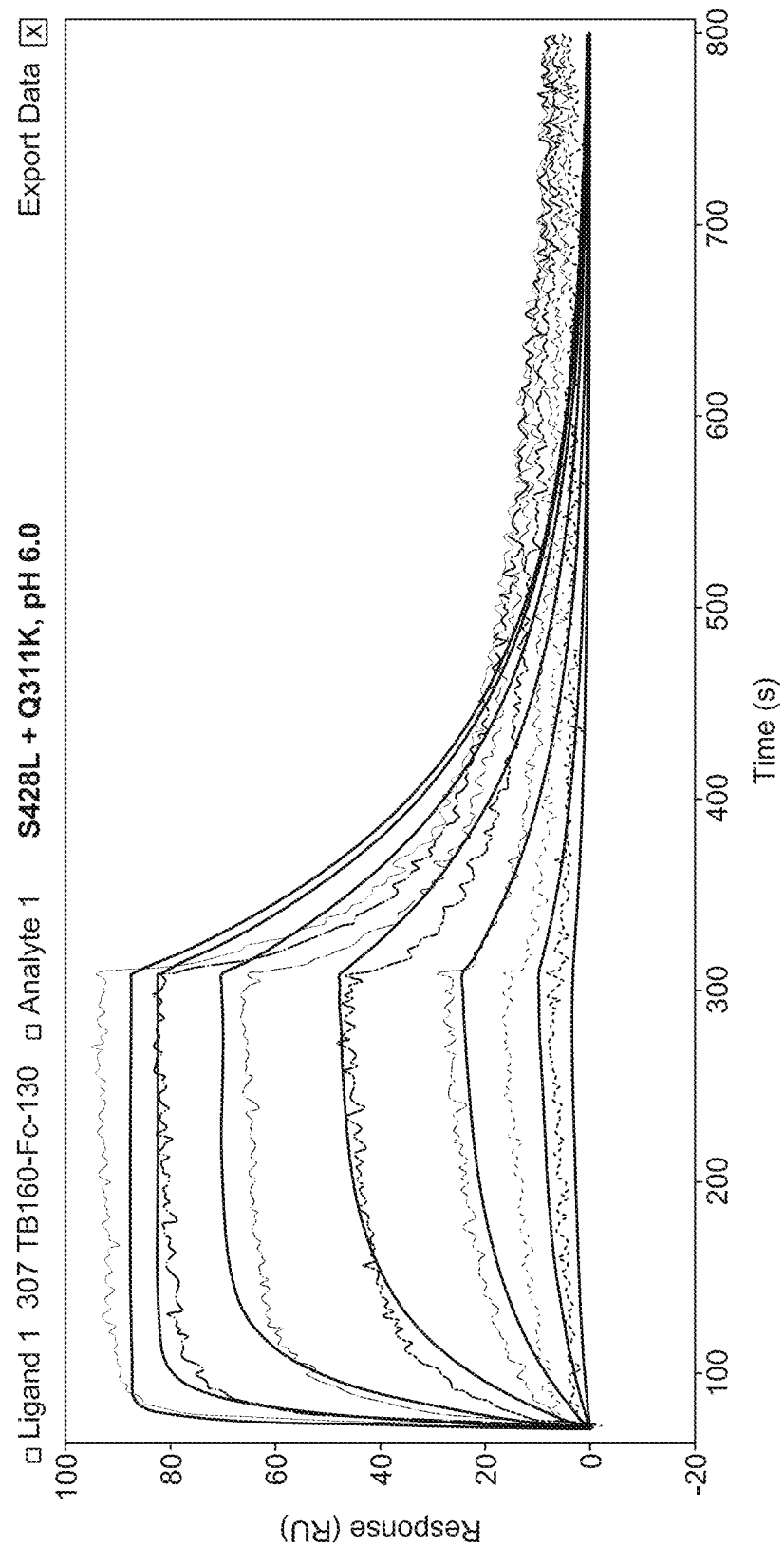
FIGS. 28A and 28B depict Carterra LSA sensorgrams for the S428L+Q311K feline IgG1a Fc variant from the phage display library and its interaction with feline FcRN at pH6.0 and pH7.4. The irregular lines represent the measured data and the smooth lines are the fitted curves using a 1:1 interaction model. Y-axis: Resonance Units (RU); X-axis: time (seconds).
Figure 28B:
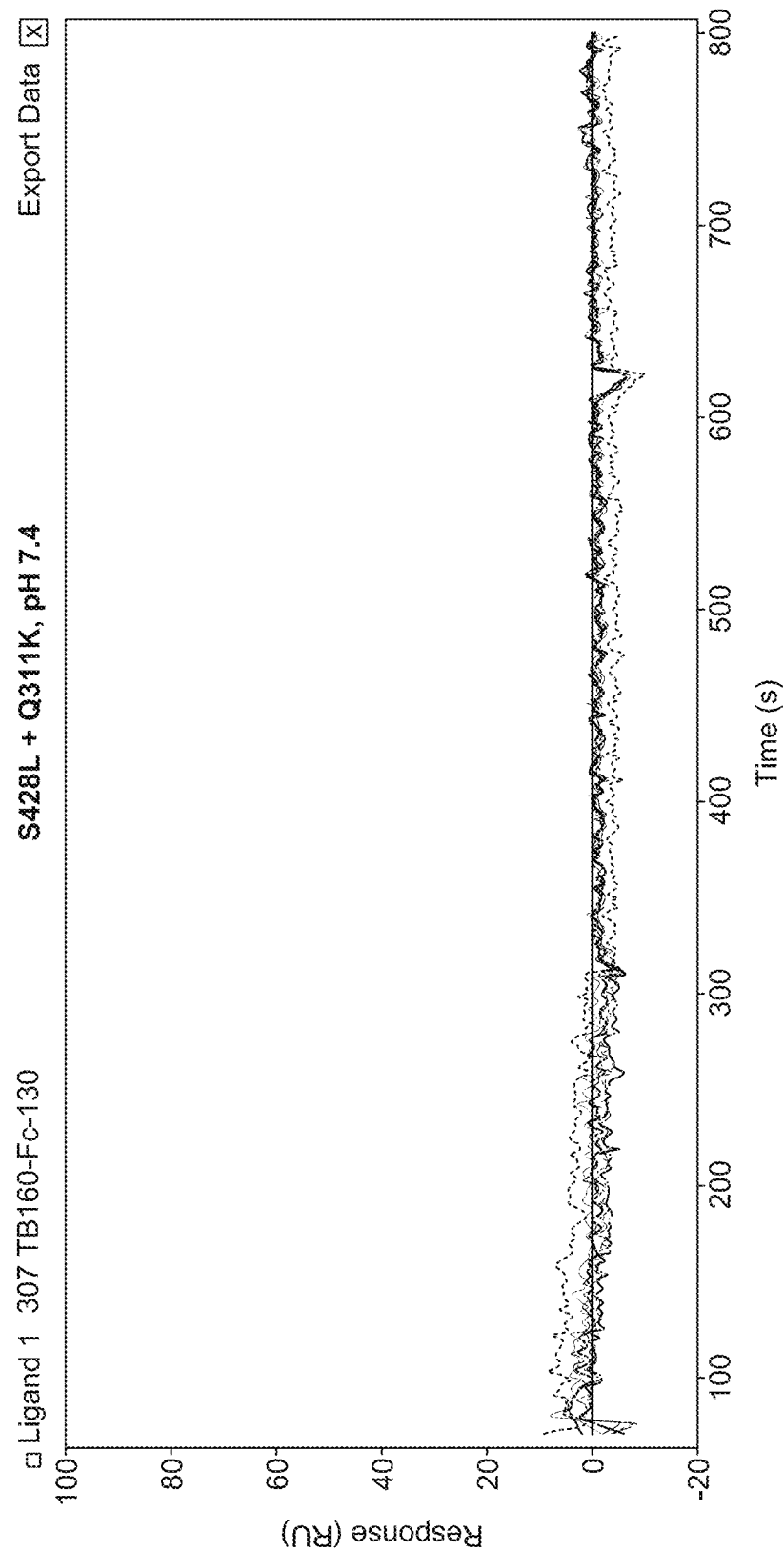
Figure 29A:
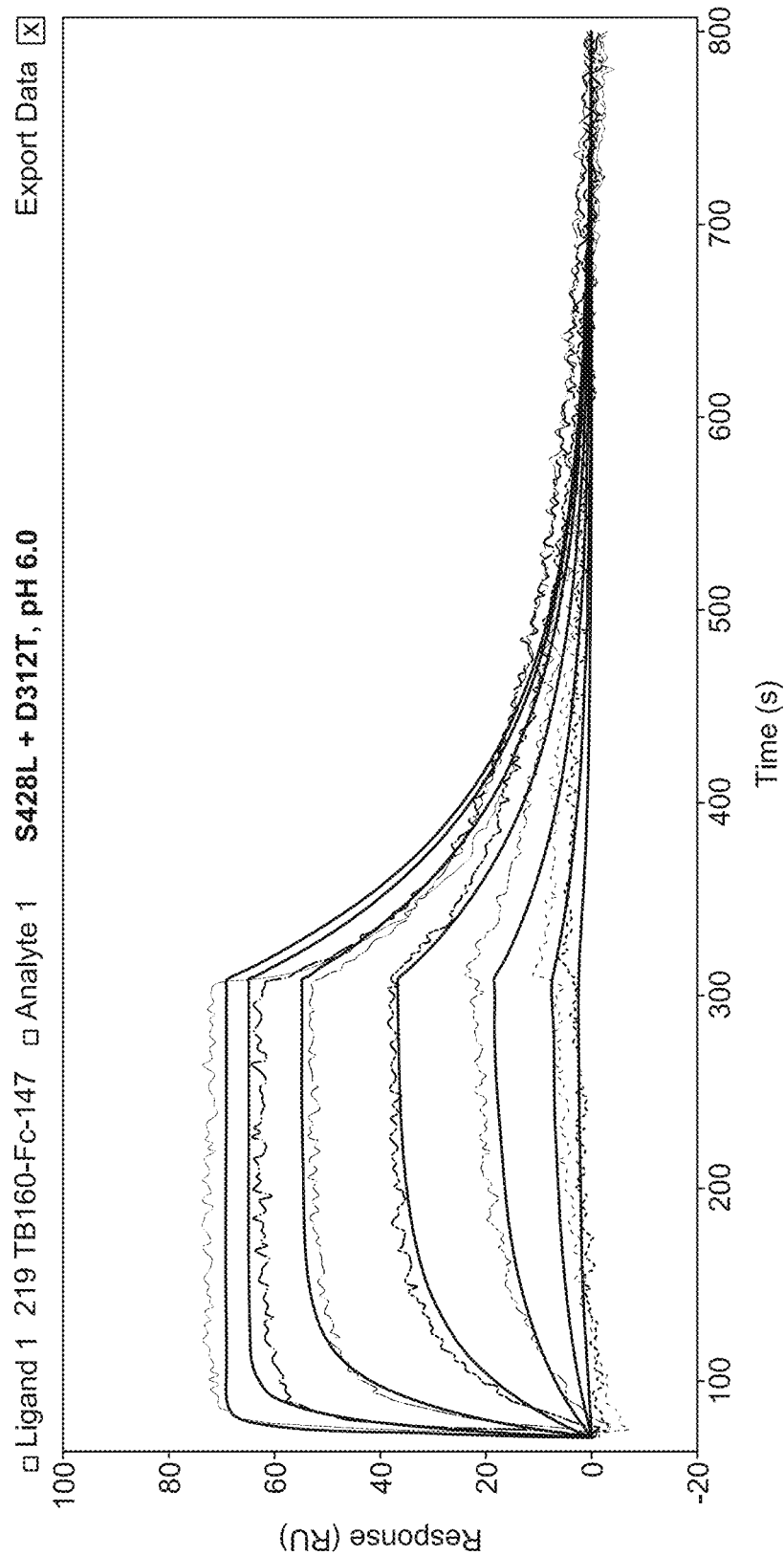
FIGS. 29A and 29B depict Carterra LSA sensorgrams for the S428L+D312T feline IgG1a Fc variant from the phage display library and its interaction with feline FcRN at pH6.0 and pH7.4. The irregular lines represent the measured data and the smooth lines are the fitted curves using a 1:1 interaction model. Y-axis: Resonance Units (RU); X-axis: time (seconds).
Figure 29B:
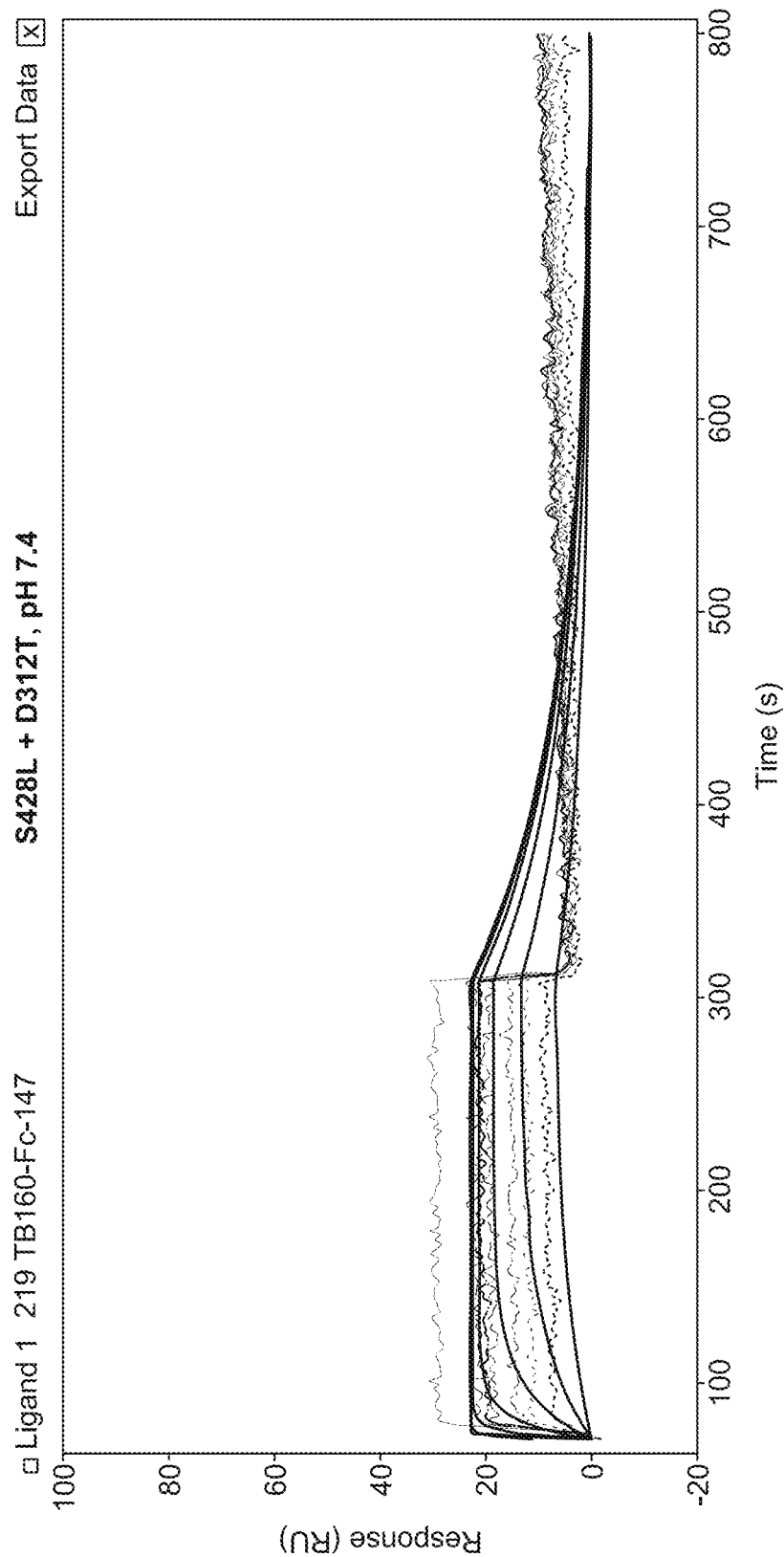
Figure 30A:
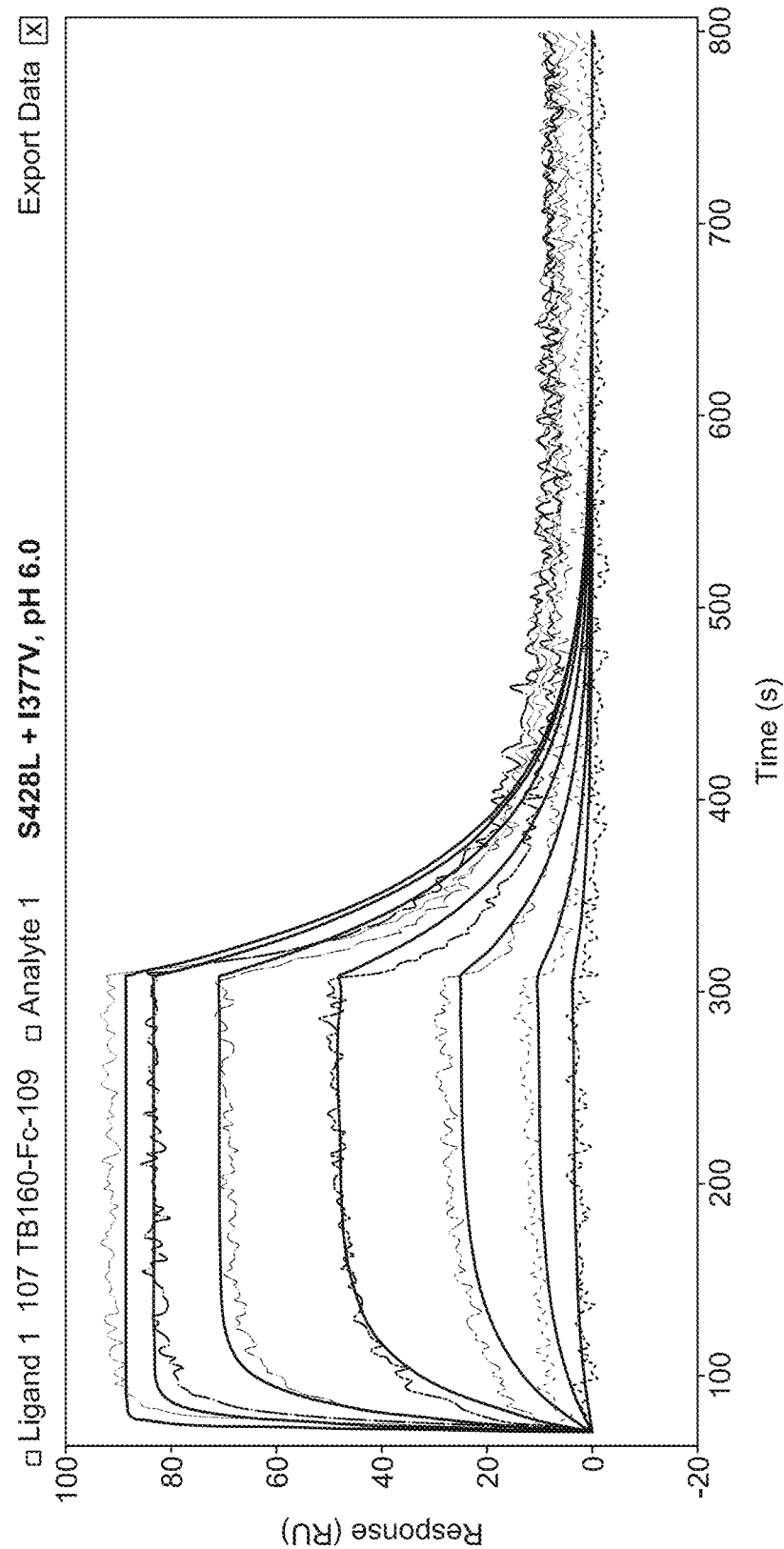
FIGS. 30A and 30B depict Carterra LSA sensorgrams for the S428L+I377V feline IgG1a Fc variant from the phage display library and its interaction with feline FcRN at pH6.0 and pH7.4. The irregular lines represent the measured data and the smooth lines are the fitted curves using a 1:1 interaction model. Y-axis: Resonance Units (RU); X-axis: time (seconds).
Figure 30B:
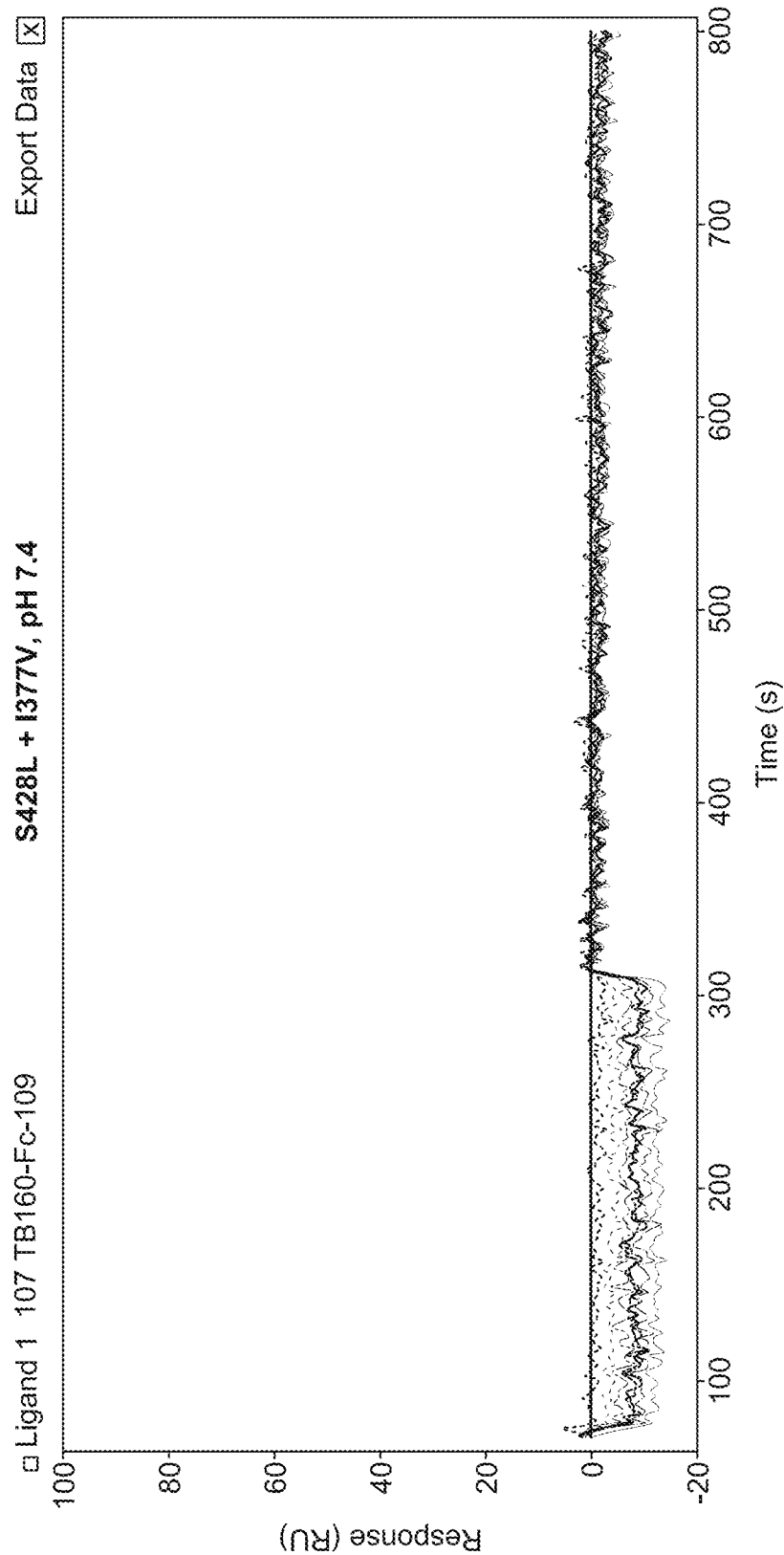
Figure 31A:
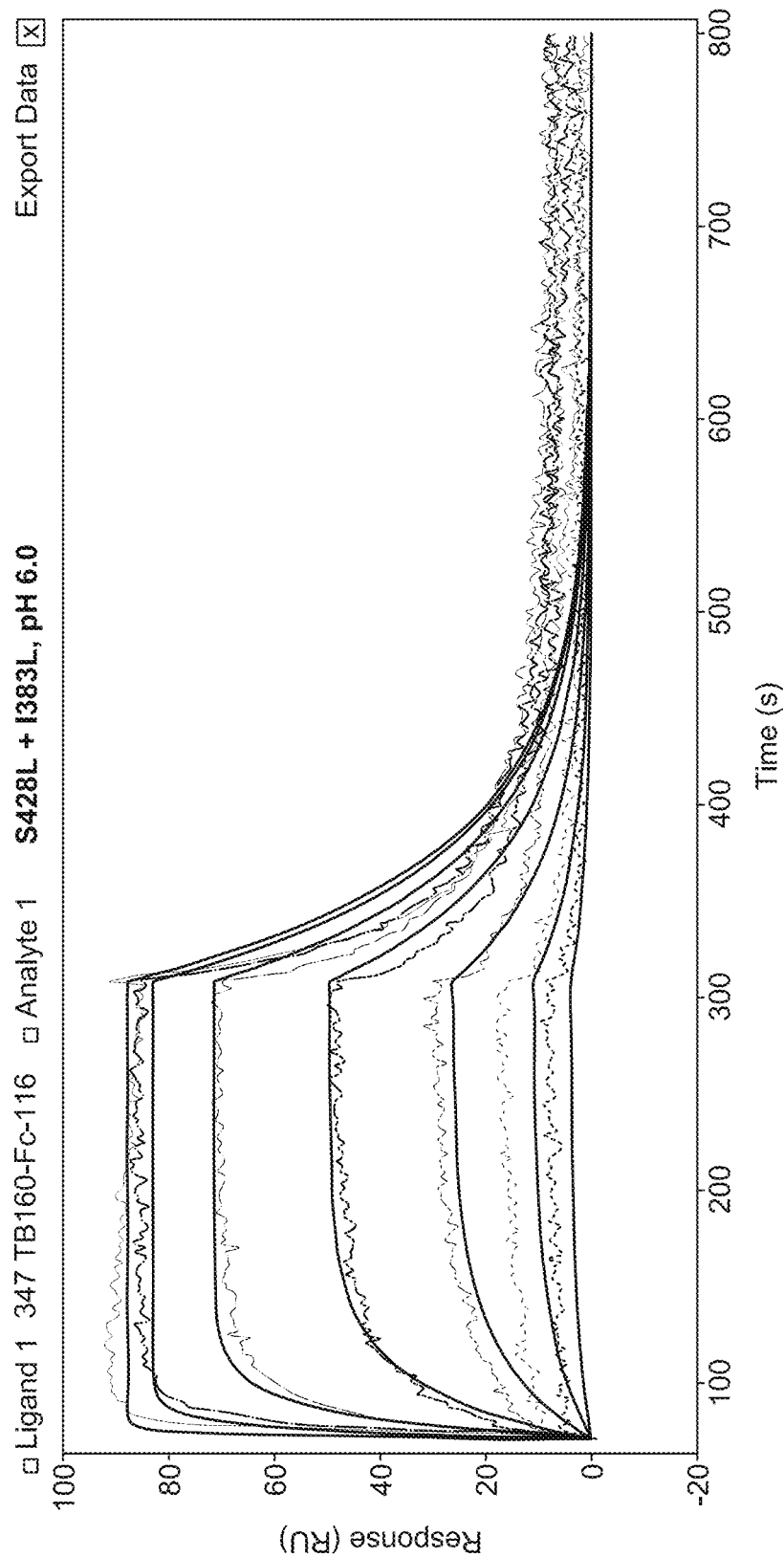
FIGS. 31A and 31B depict Carterra LSA sensorgrams for the S428L+I383L feline IgG1a Fc variant from the phage display library and its interaction with feline FcRN at pH6.0 and pH7.4. The irregular lines represent the measured data and the smooth lines are the fitted curves using a 1:1 interaction model. Y-axis: Resonance Units (RU); X-axis: time (seconds).
Figure 31B:
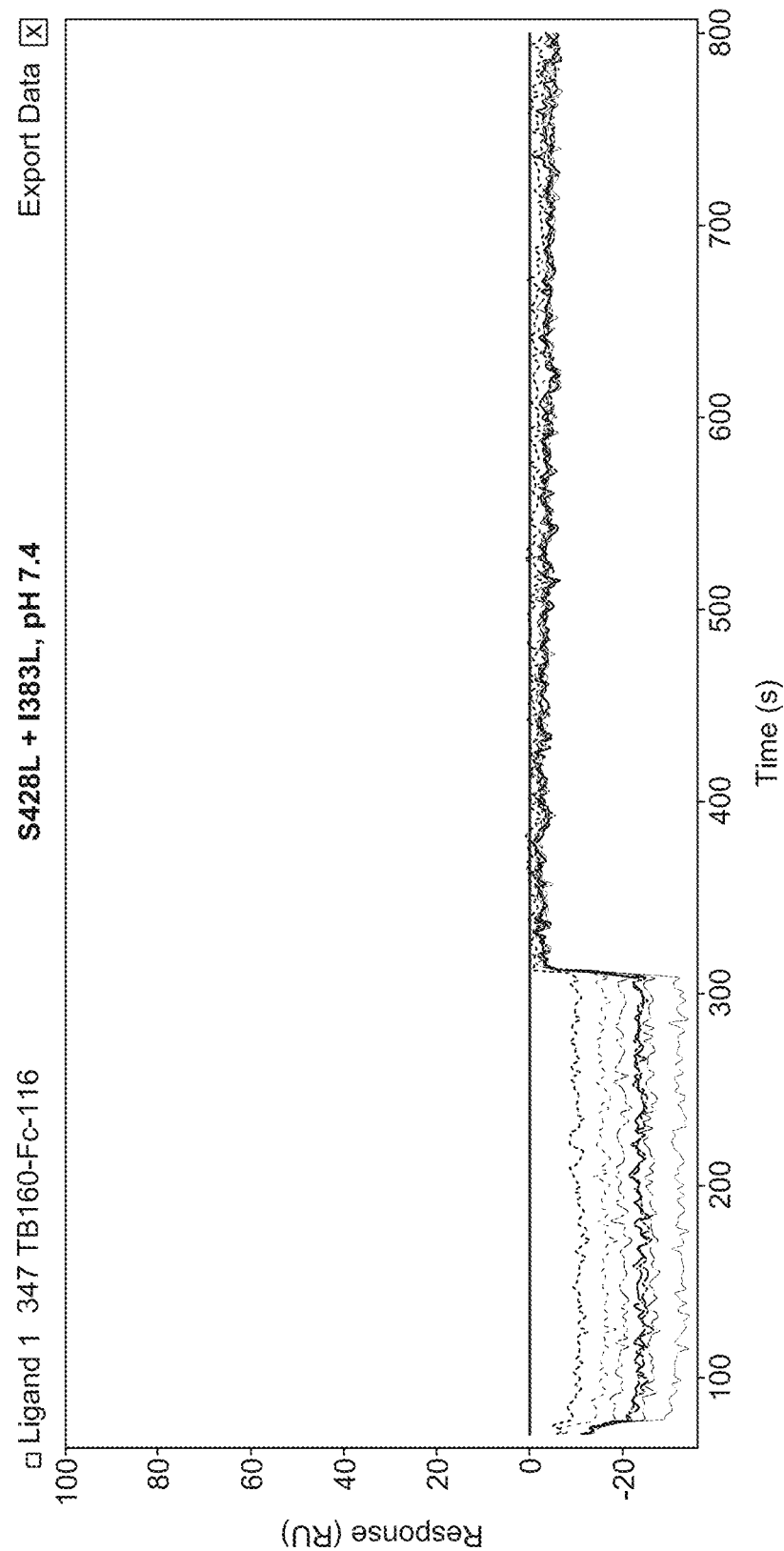
Figure 32A:
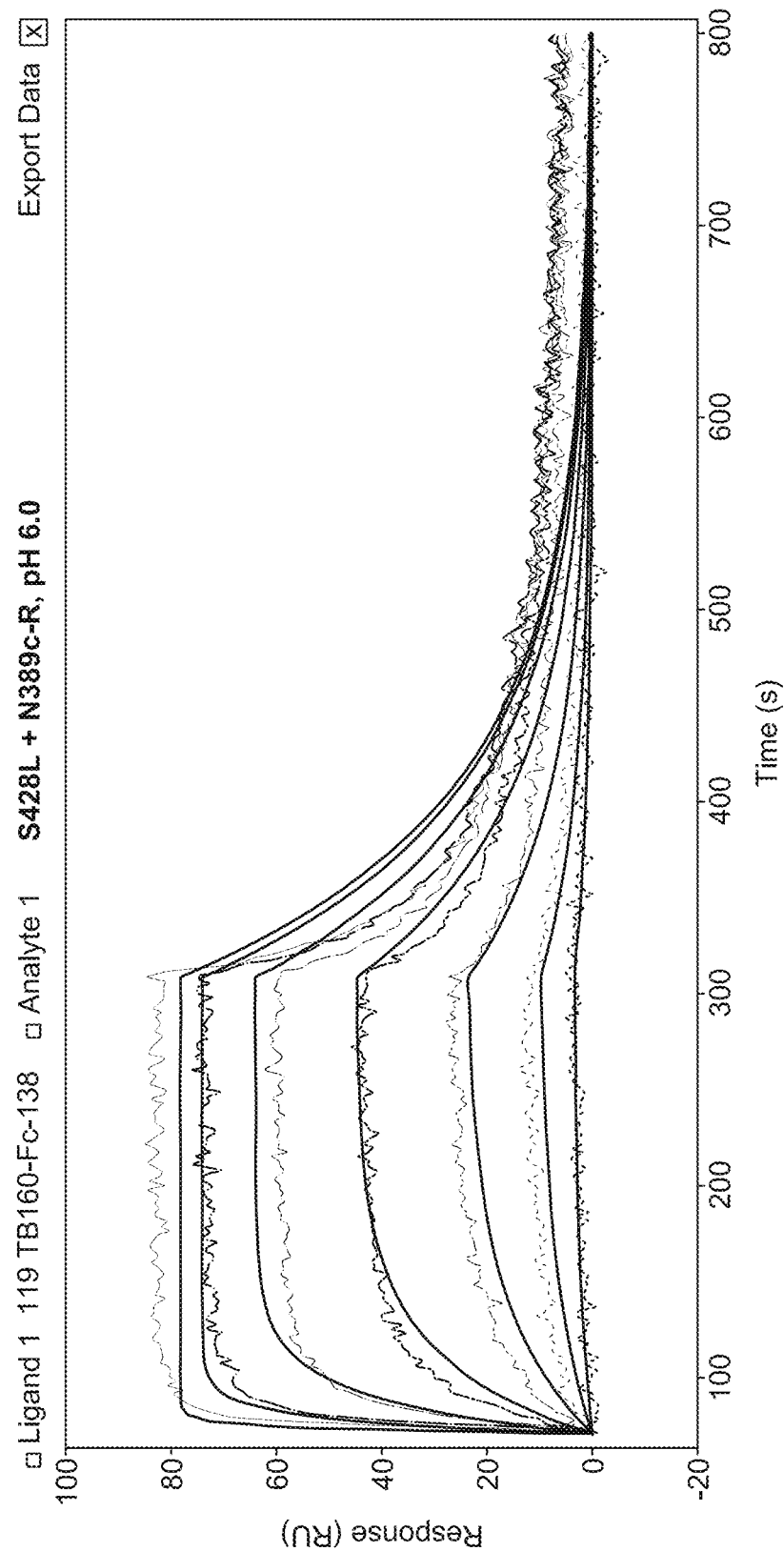
FIGS. 32A and 32B depict Carterra LSA sensorgrams for the S428L+N389cR feline IgG1a Fc variant from the phage display library and its interaction with feline FcRN at pH6.0 and pH7.4. The irregular lines represent the measured data and the smooth lines are the fitted curves using a 1:1 interaction model. Y-axis: Resonance Units (RU); X-axis: time (seconds).
Figure 32B:
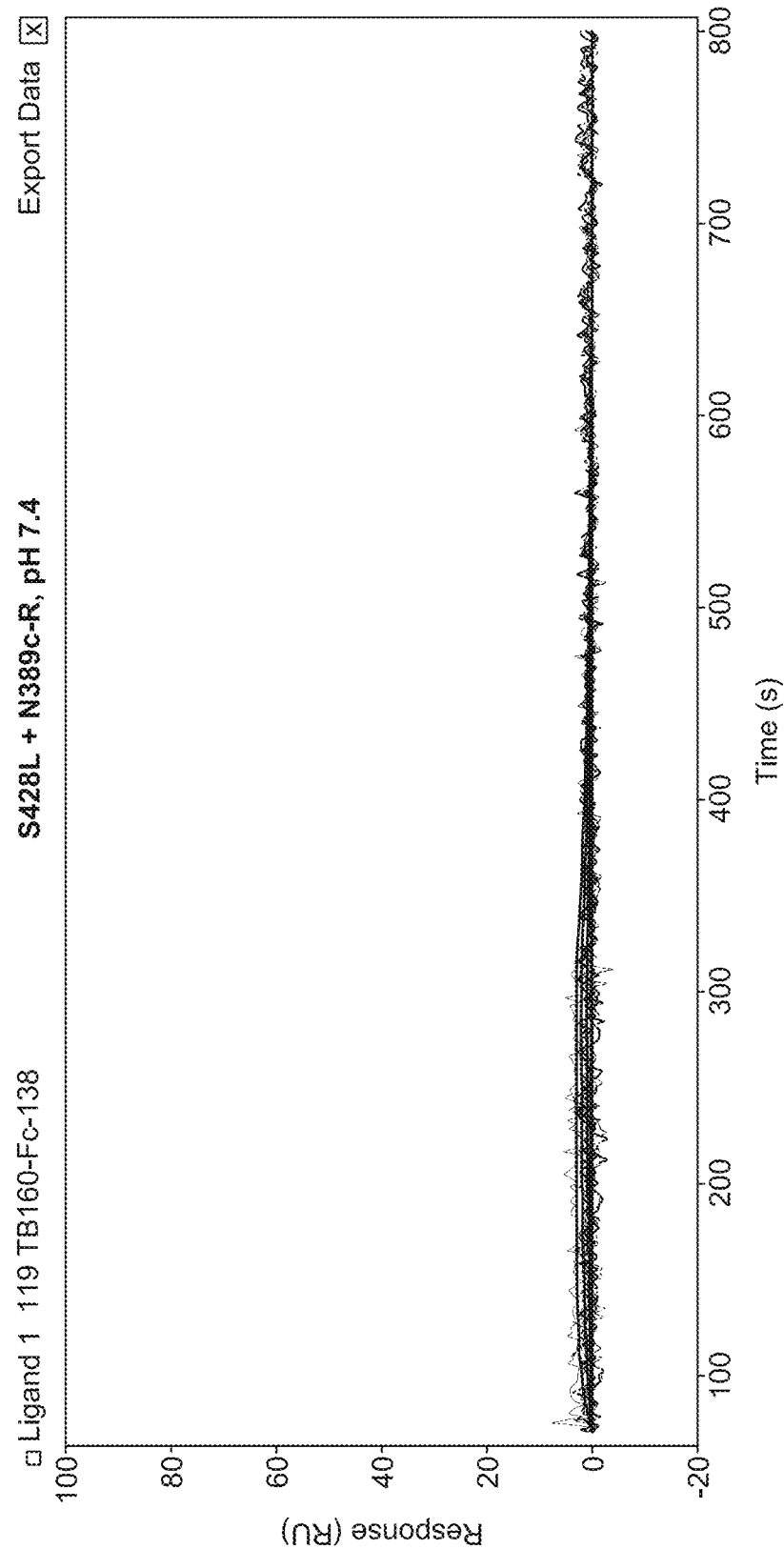
Figure 33A:
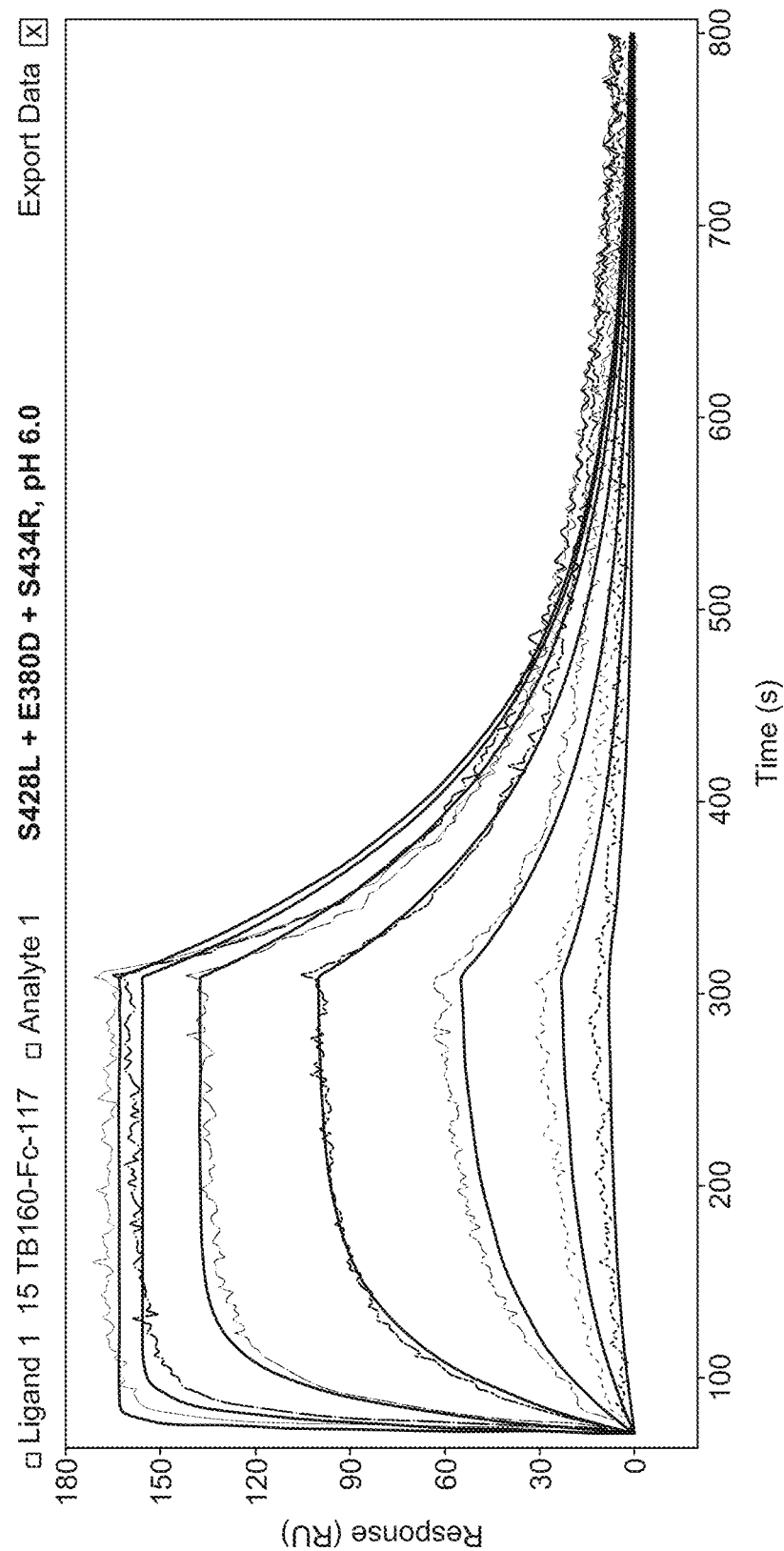
FIGS. 33A and 33B depict Carterra LSA sensorgrams for the S428L+E380D+S434R feline IgG1a Fc variant from the phage display library and its interaction with feline FcRN at pH6.0 and pH7.4. The irregular lines represent the measured data and the smooth lines are the fitted curves using a 1:1 interaction model. Y-axis: Resonance Units (RU); X-axis: time (seconds).
Figure 33B:
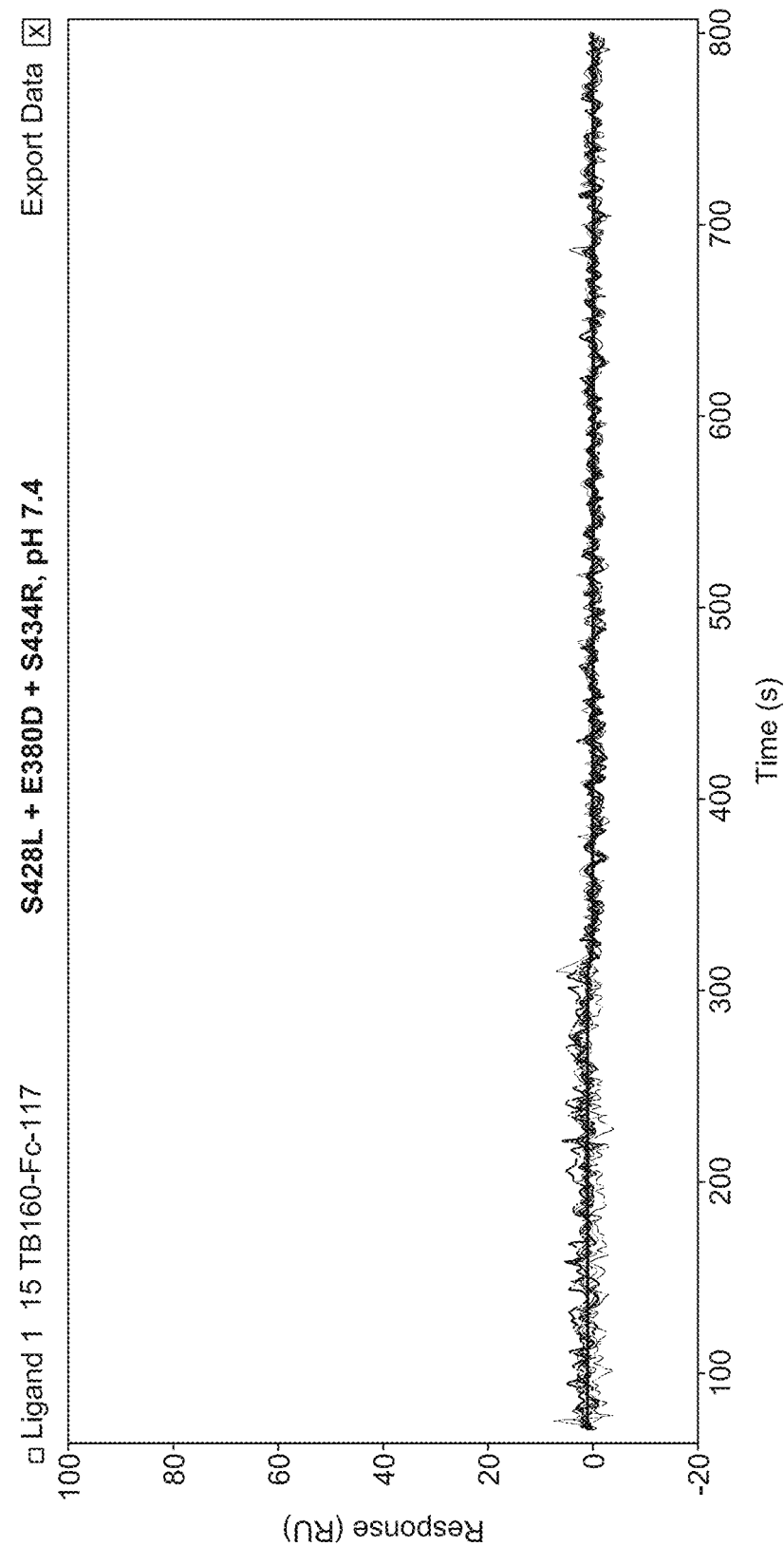
Figure 34A:
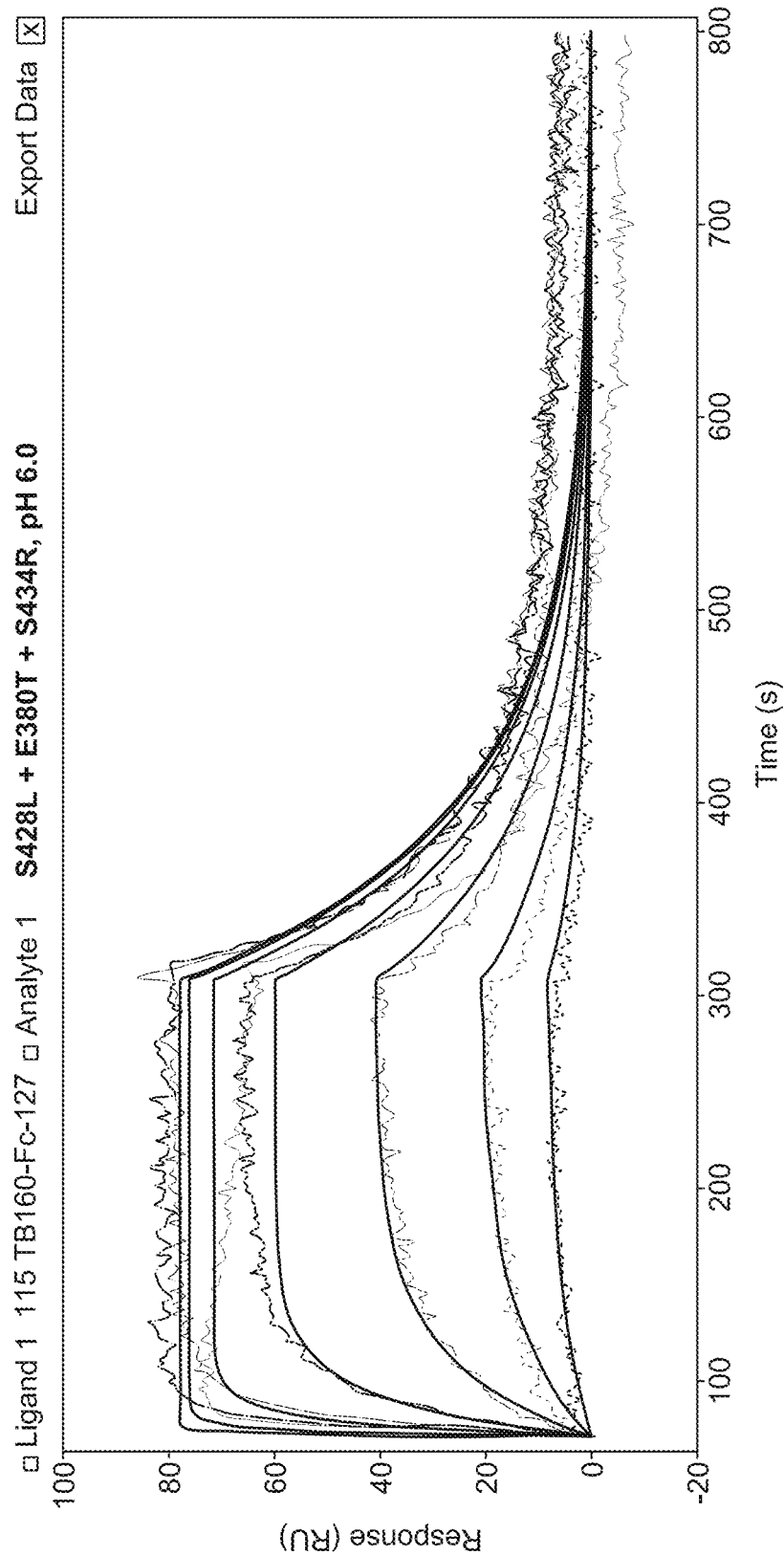
FIGS. 34A and 34B depict Carterra LSA sensorgrams for the S428L+E380T+S434R feline IgG1a Fc variant from the phage display library and its interaction with feline FcRN at pH6.0 and pH7.4. The irregular lines represent the measured data and the smooth lines are the fitted curves using a 1:1 interaction model. Y-axis: Resonance Units (RU); X-axis: time (seconds).
Figure 34B:
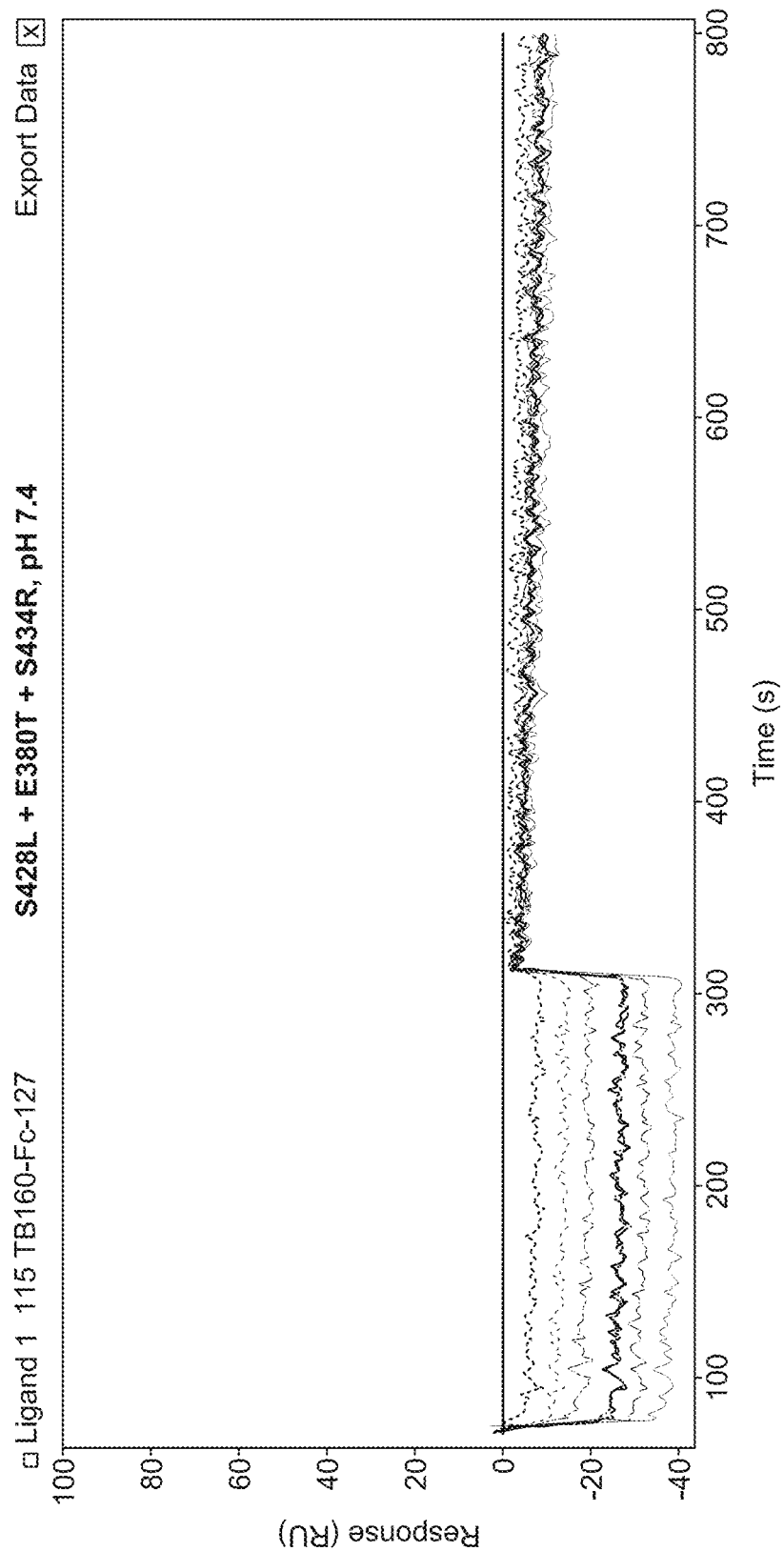
Figure 35A:
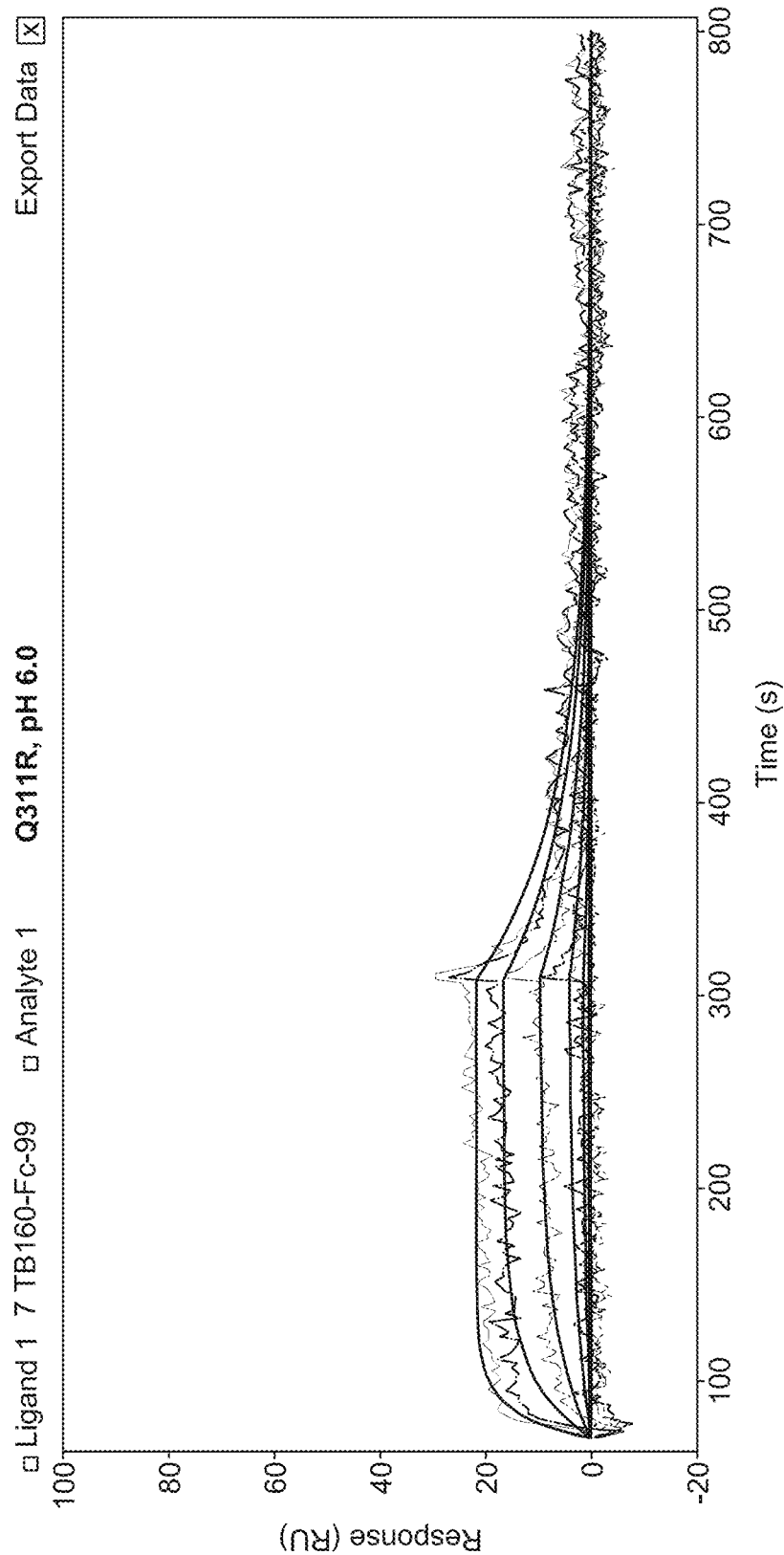
FIGS. 35A and 35B depict Carterra LSA sensorgrams for the Q311R feline IgG1a Fc variant from the phage display library and its interaction with feline FcRN at pH6.0 and pH7.4. The irregular lines represent the measured data and the smooth lines are the fitted curves using a 1:1 interaction model. Y-axis: Resonance Units (RU); X-axis: time (seconds).
Figure 35B:
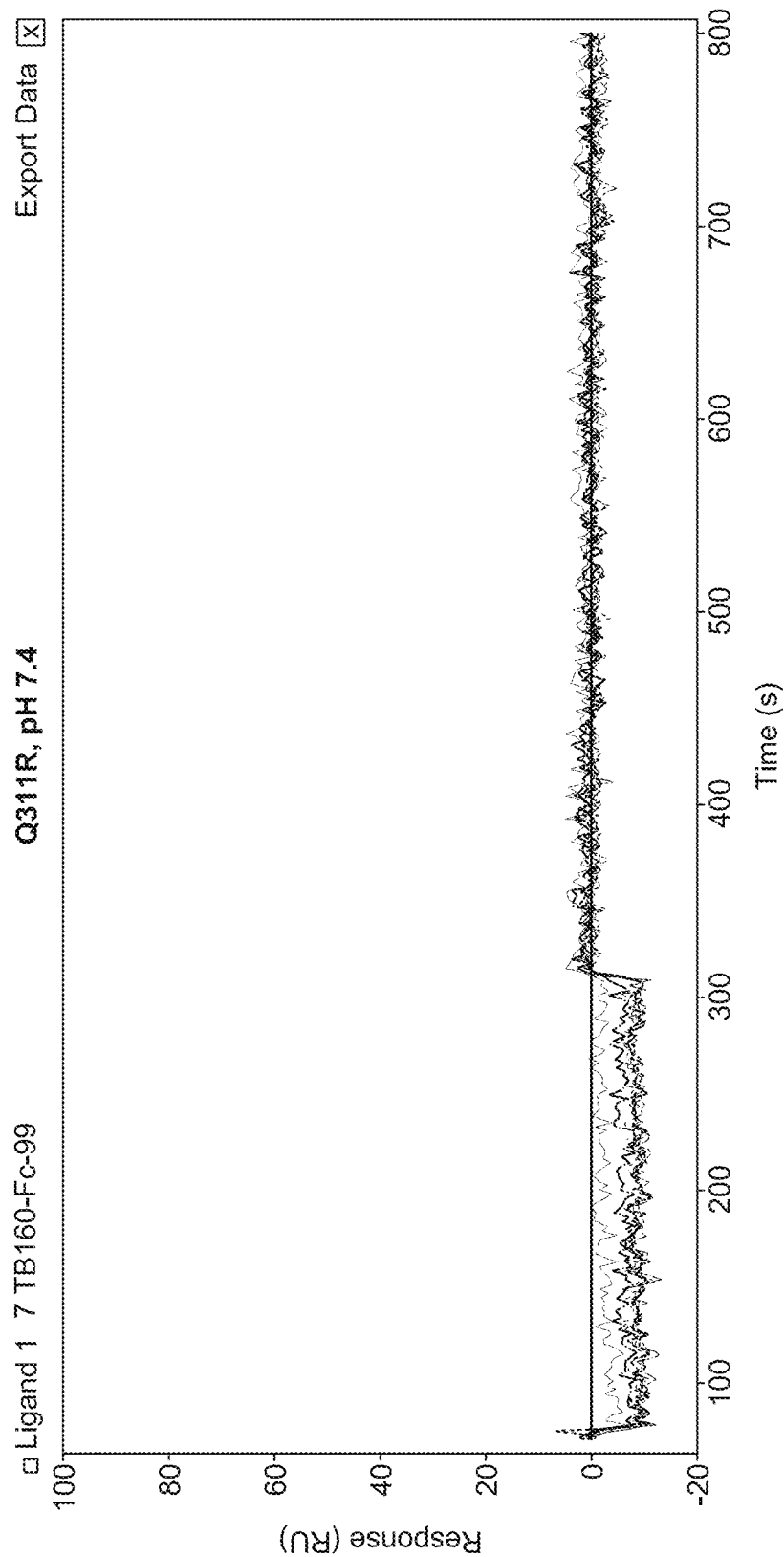
Figure 36A:
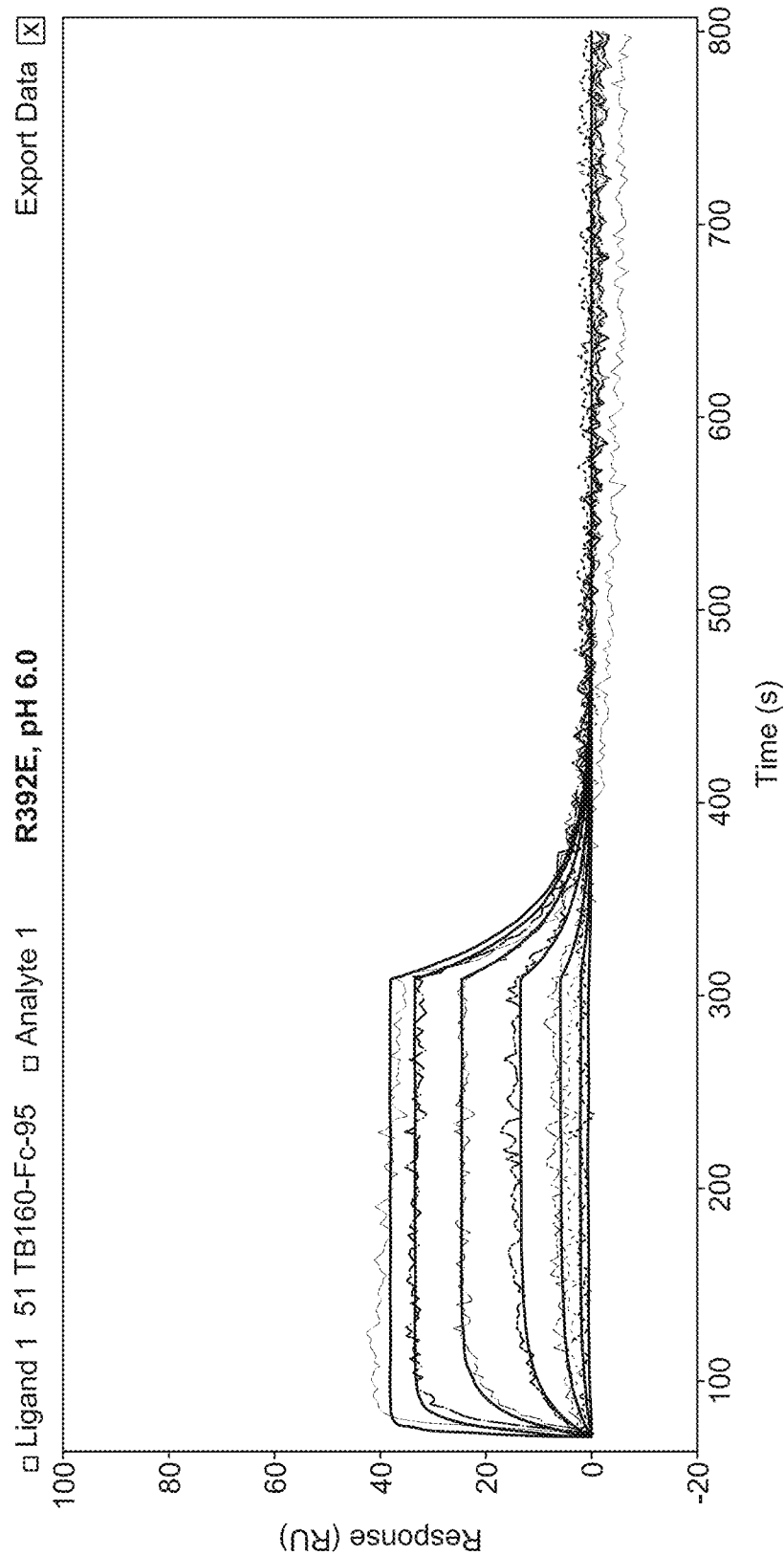
FIGS. 36A and 36B depict Carterra LSA sensorgrams for the R392E feline IgG1a Fc variant from the phage display library and its interaction with feline FcRN at pH6.0 and pH7.4. The irregular lines represent the measured data and the smooth lines are the fitted curves using a 1:1 interaction model. Y-axis: Resonance Units (RU); X-axis: time (seconds).
Figure 36B:
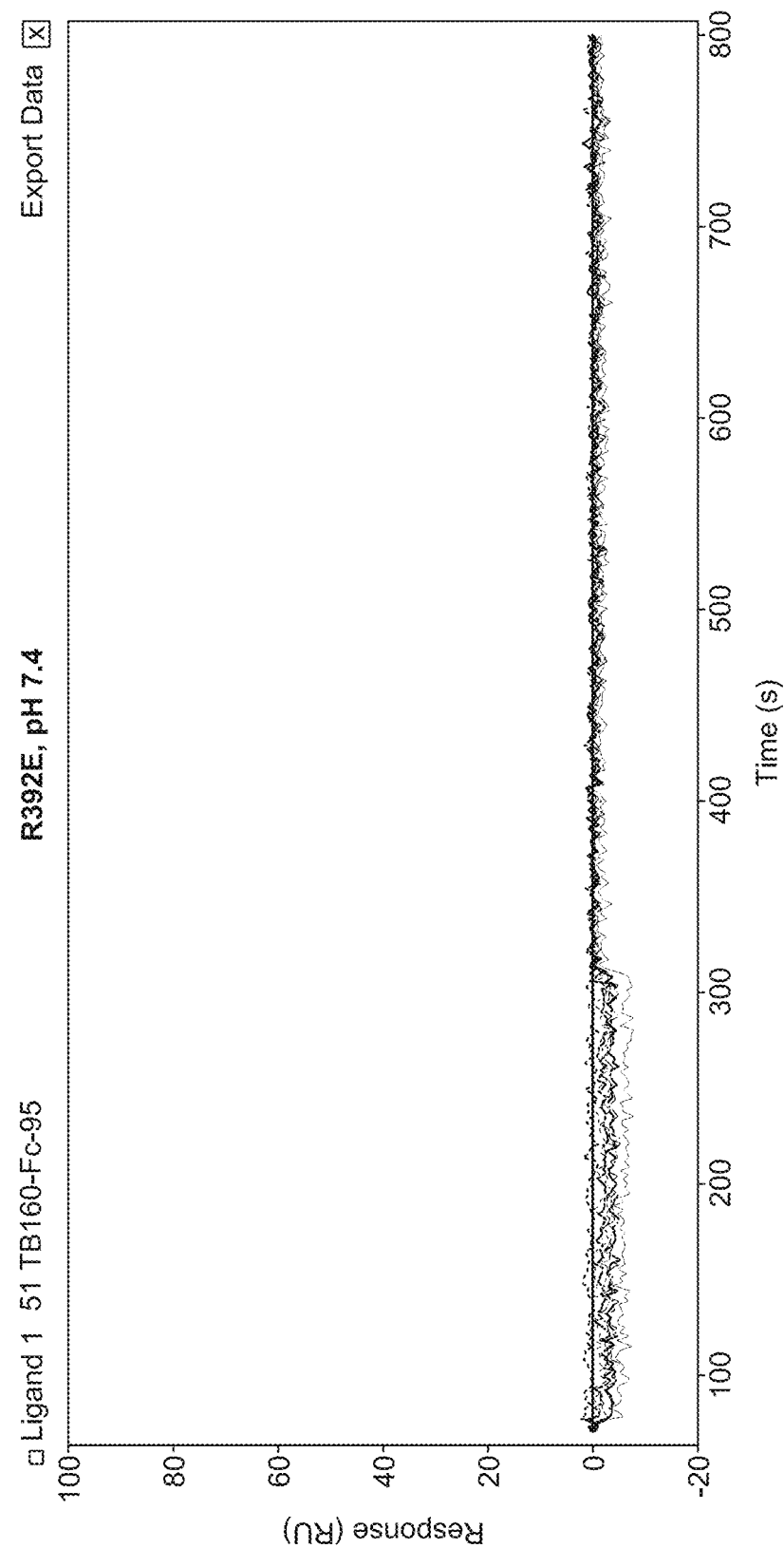
Figure 37A:
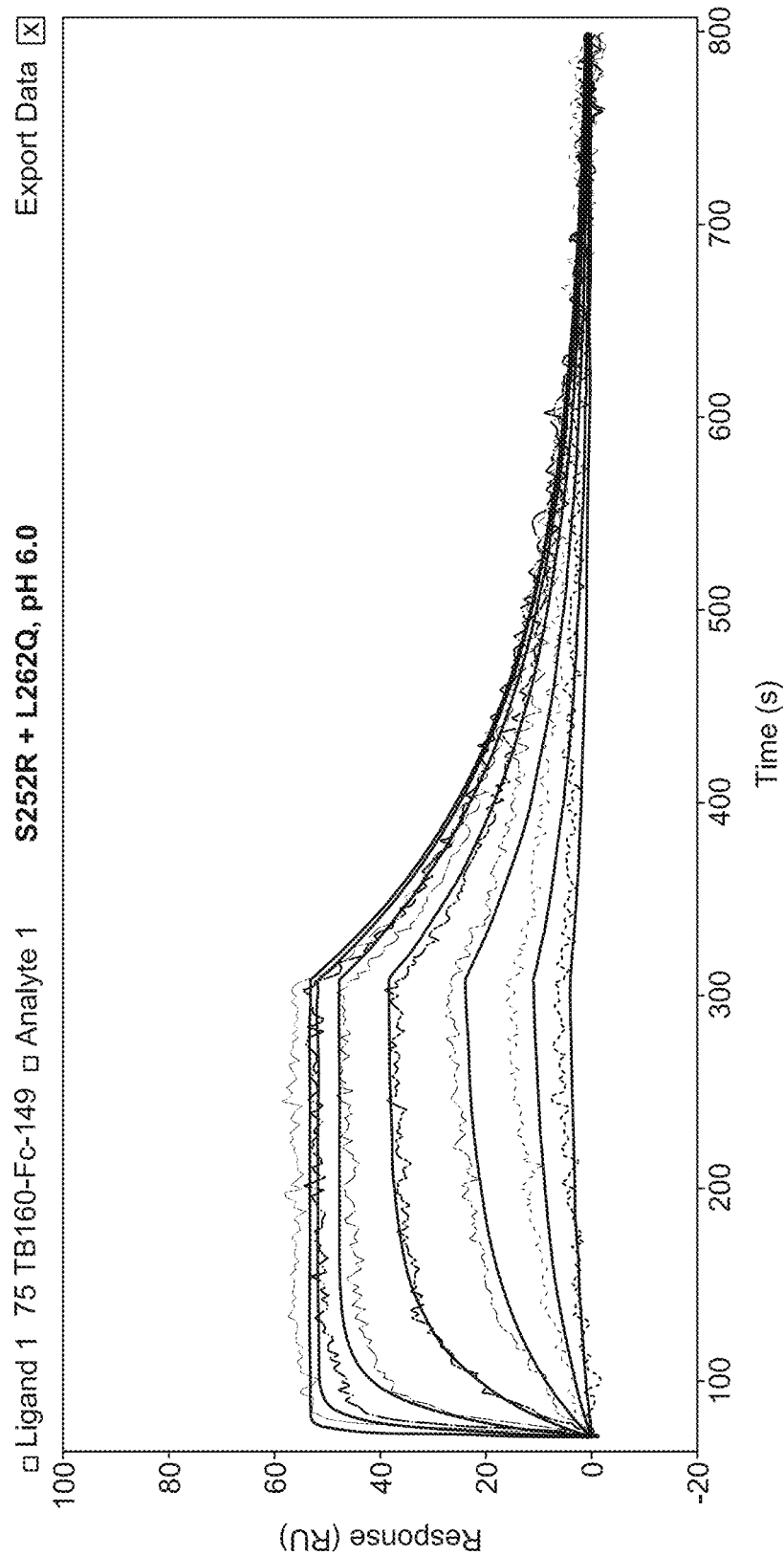
FIGS. 37A and 37B depict Carterra LSA sensorgrams for the S252R+L262Q feline IgG1a Fc variant from the phage display library and its interaction with feline FcRN at pH6.0 and pH7.4. The irregular lines represent the measured data and the smooth lines are the fitted curves using a 1:1 interaction model. Y-axis: Resonance Units (RU); X-axis: time (seconds).
Figure 37B:
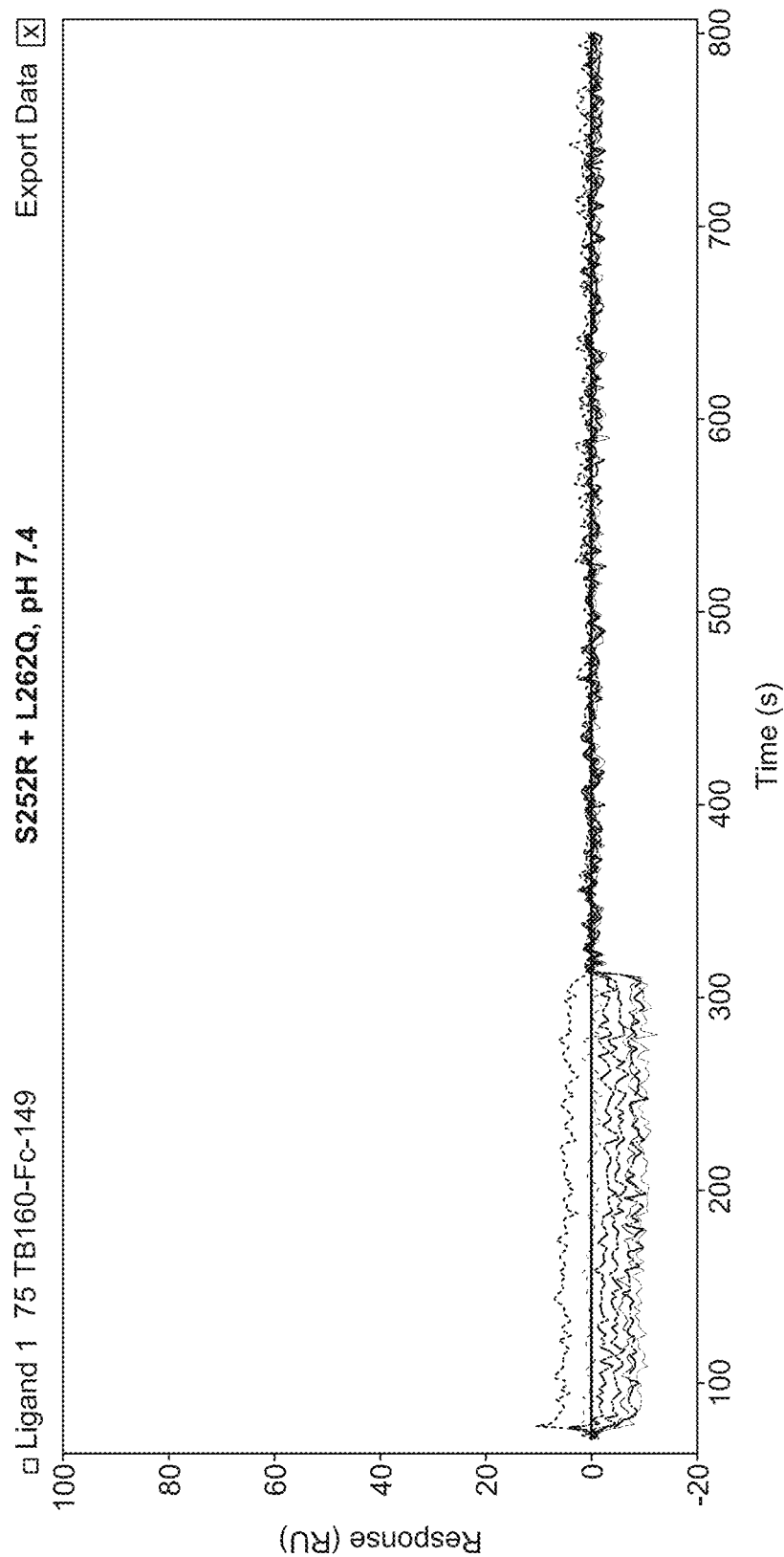
Figure 38A:
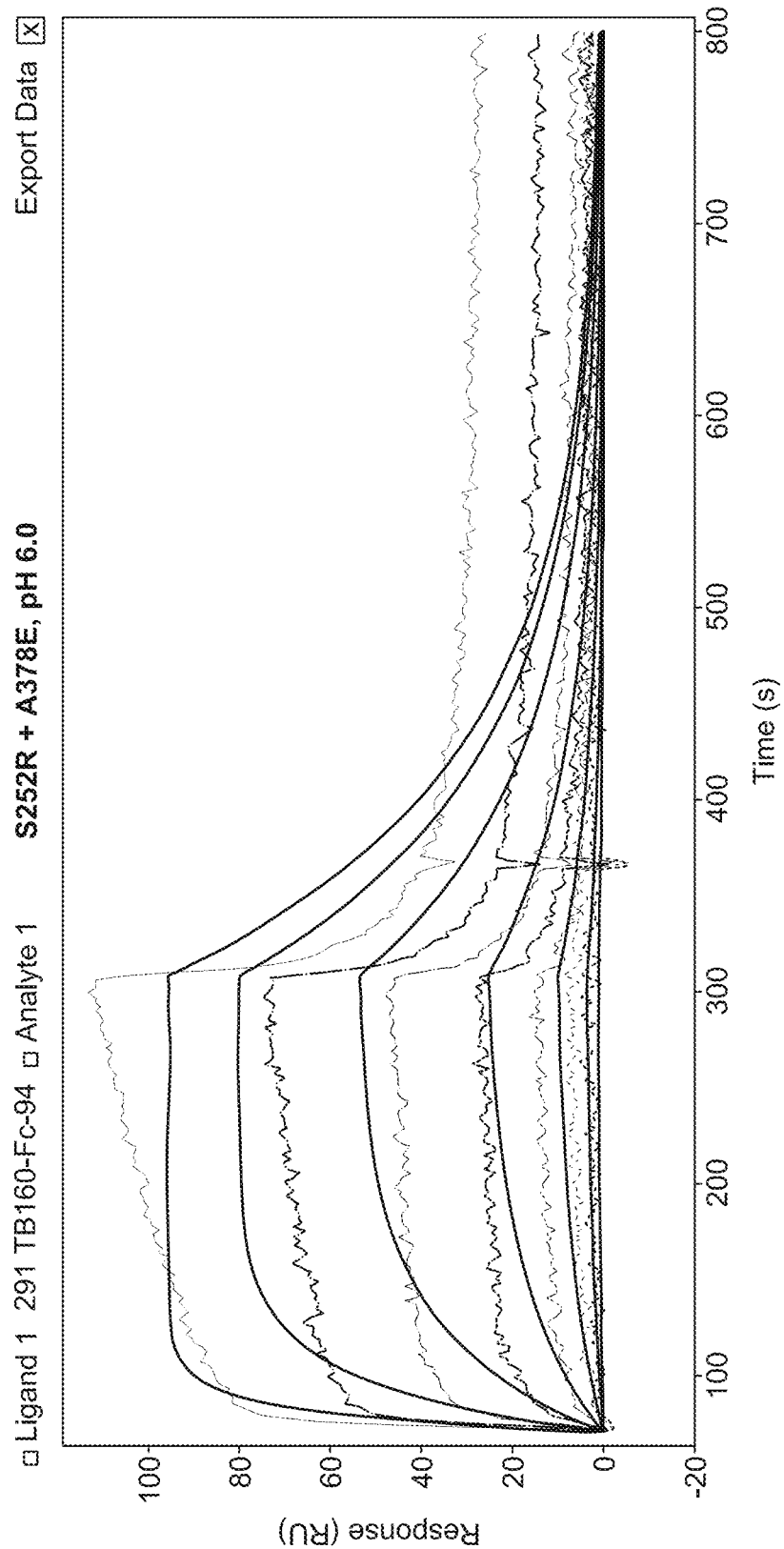
FIGS. 38A and 38B depict Carterra LSA sensorgrams for the S252R+A378E feline IgG1a Fc variant from the phage display library and its interaction with feline FcRN at pH6.0 and pH7.4. The irregular lines represent the measured data and the smooth lines are the fitted curves using a 1:1 interaction model. Y-axis: Resonance Units (RU); X-axis: time (seconds).
Figure 38B:
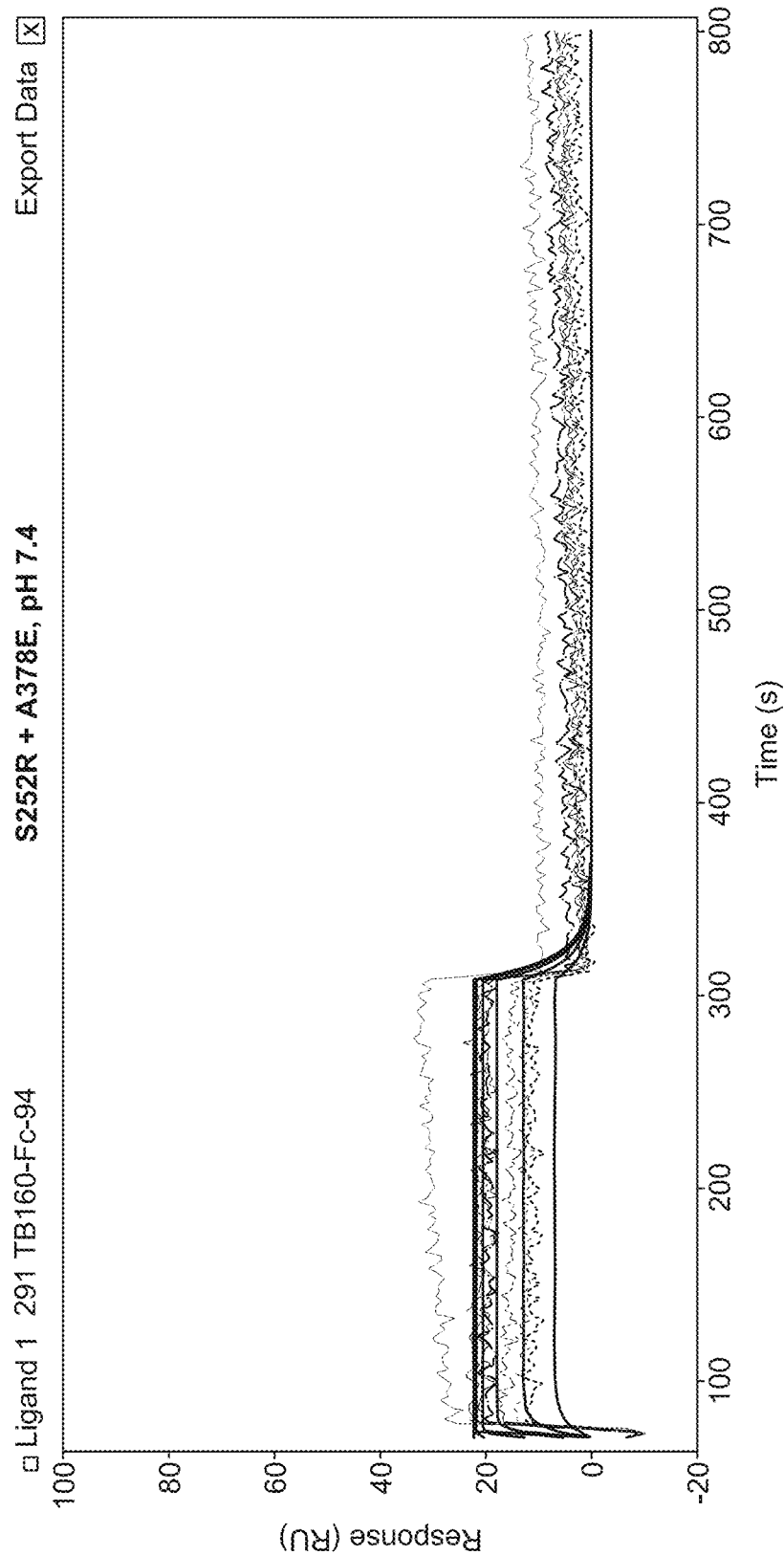
Figure 39A:
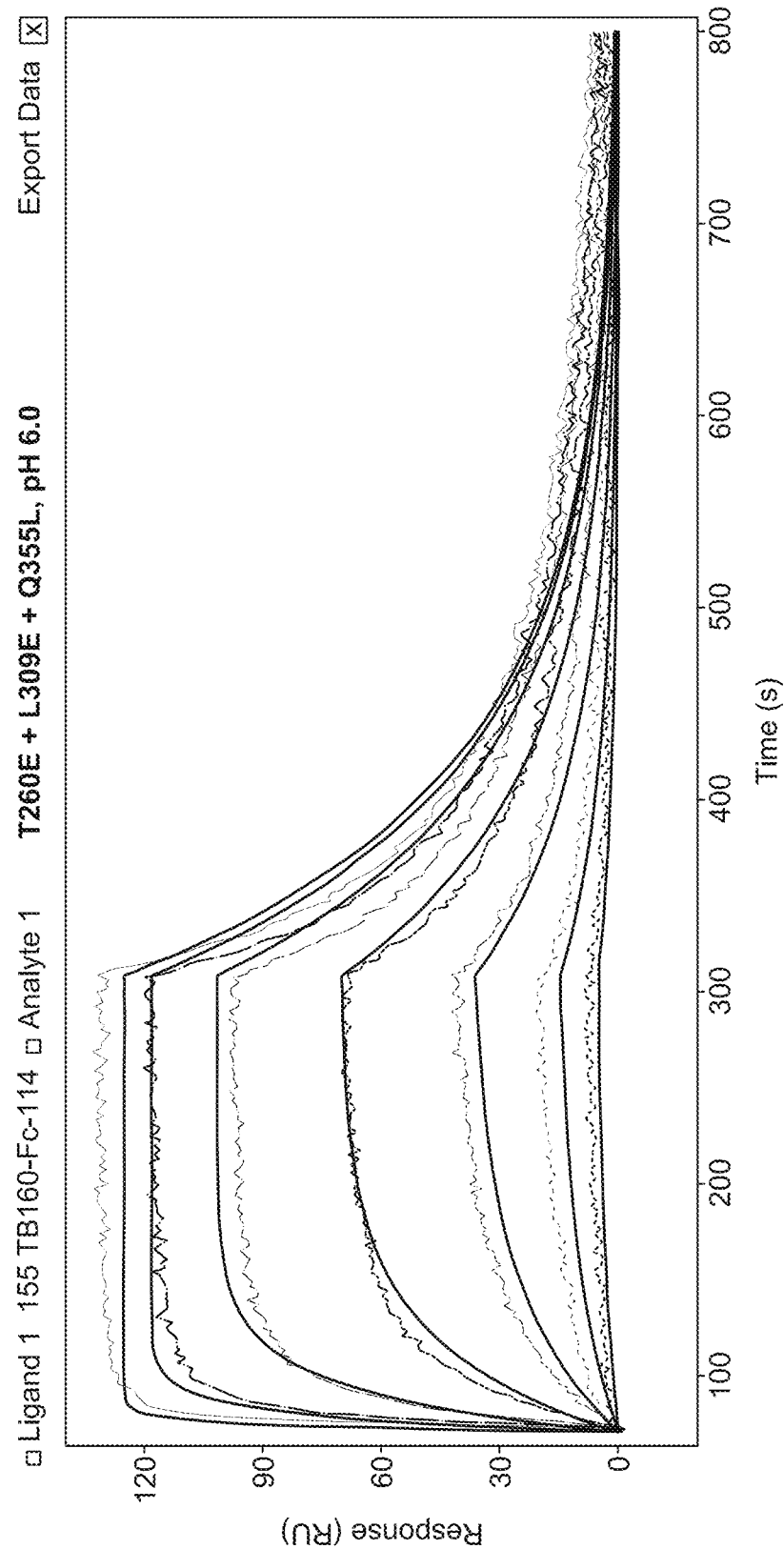
FIGS. 39A and 39B depict Carterra LSA sensorgrams for the T260E+L309E+Q355L feline IgG1a Fc variant from the phage display library and its interaction with feline FcRN at pH6.0 and pH7.4. The irregular lines represent the measured data and the smooth lines are the fitted curves using a 1:1 interaction model. Y-axis: Resonance Units (RU); X-axis: time (seconds).
Figure 39B:
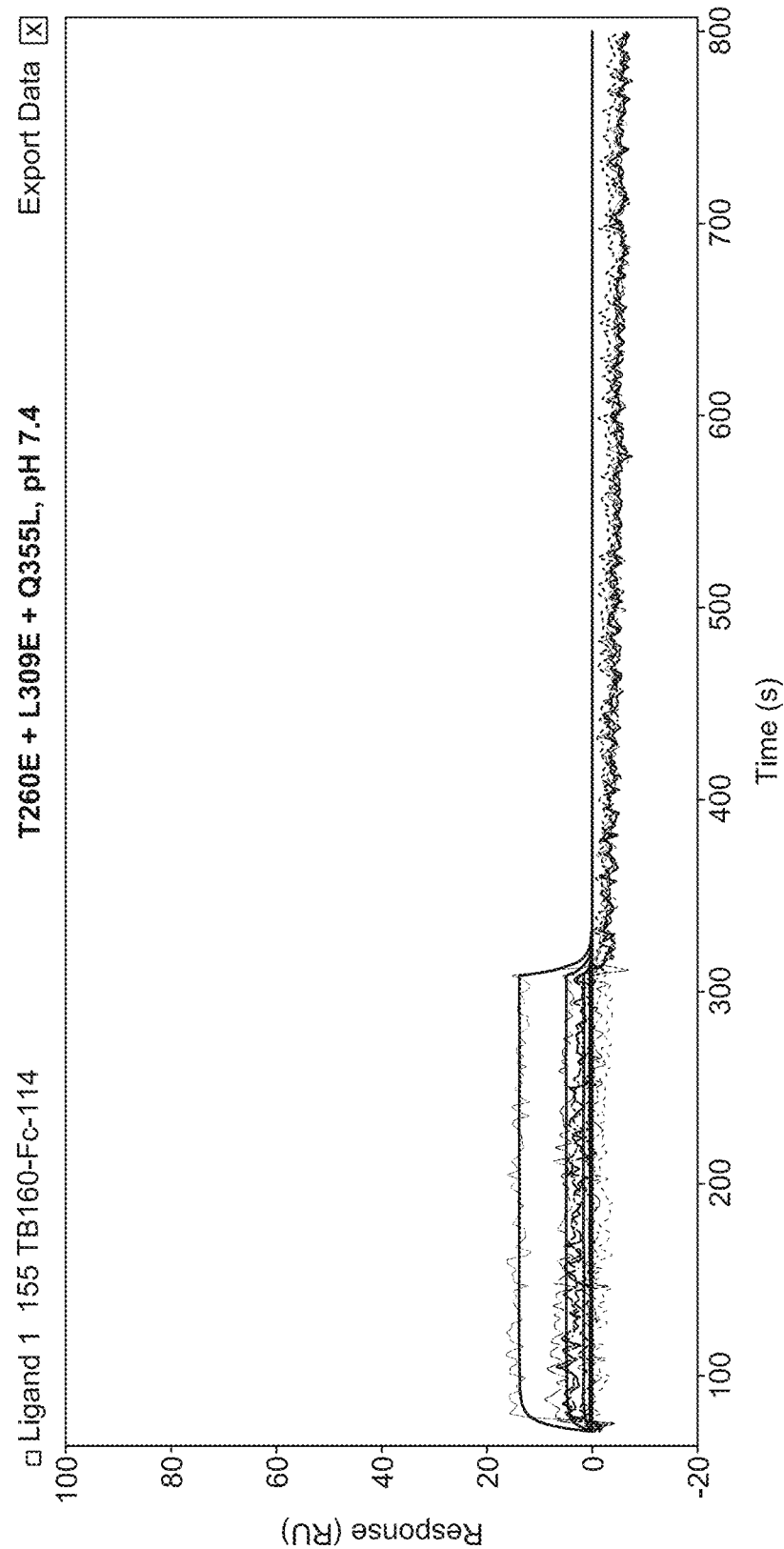
Figure 40A:
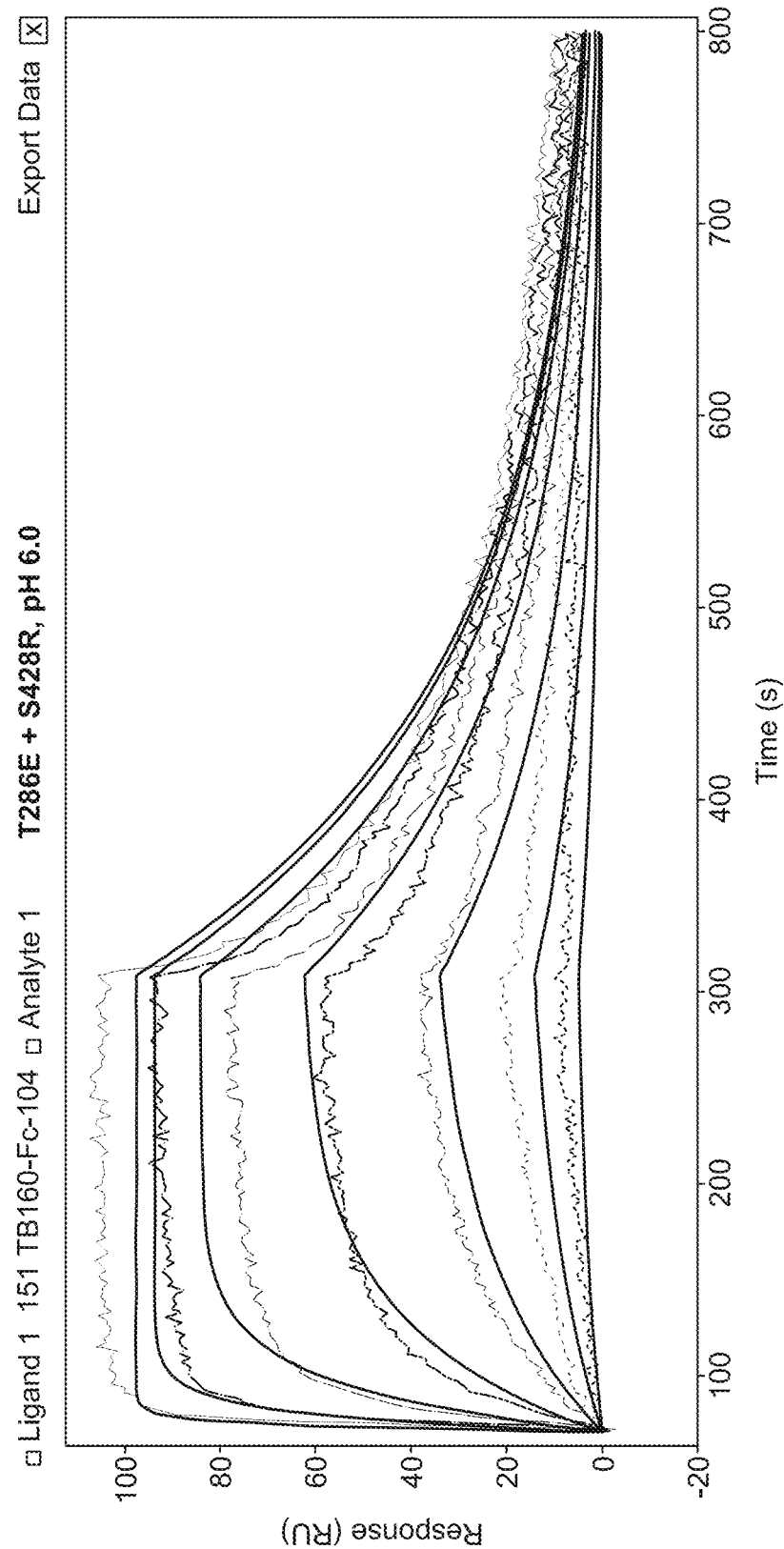
FIGS. 40A and 40B depict Carterra LSA sensorgrams for the T286E+S428R feline IgG1a Fc variant from the phage display library and its interaction with feline FcRN at pH6.0 and pH7.4. The irregular lines represent the measured data and the smooth lines are the fitted curves using a 1:1 interaction model. Y-axis: Resonance Units (RU); X-axis: time (seconds).
Figure 40B:
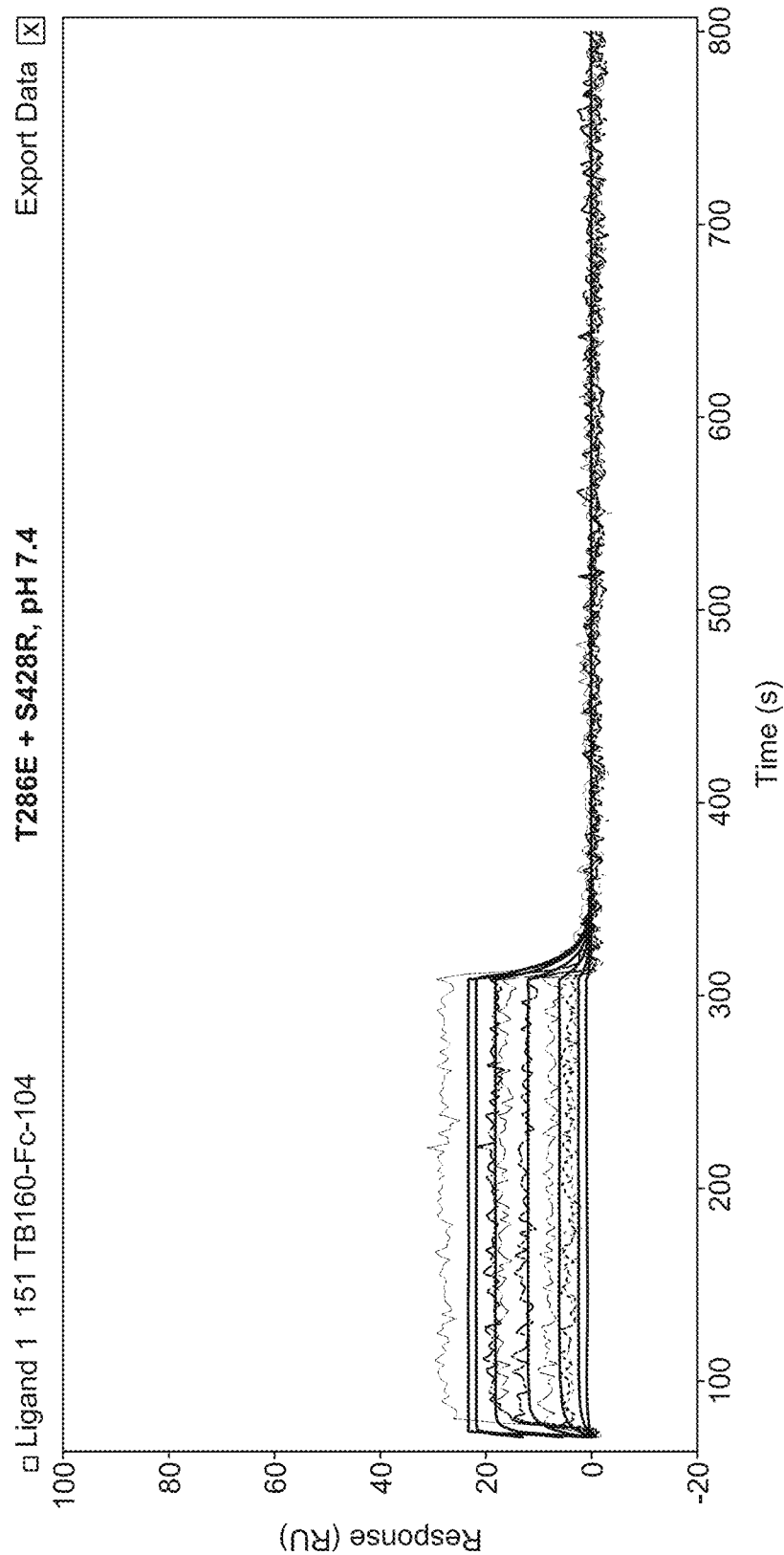
Figure 41A:
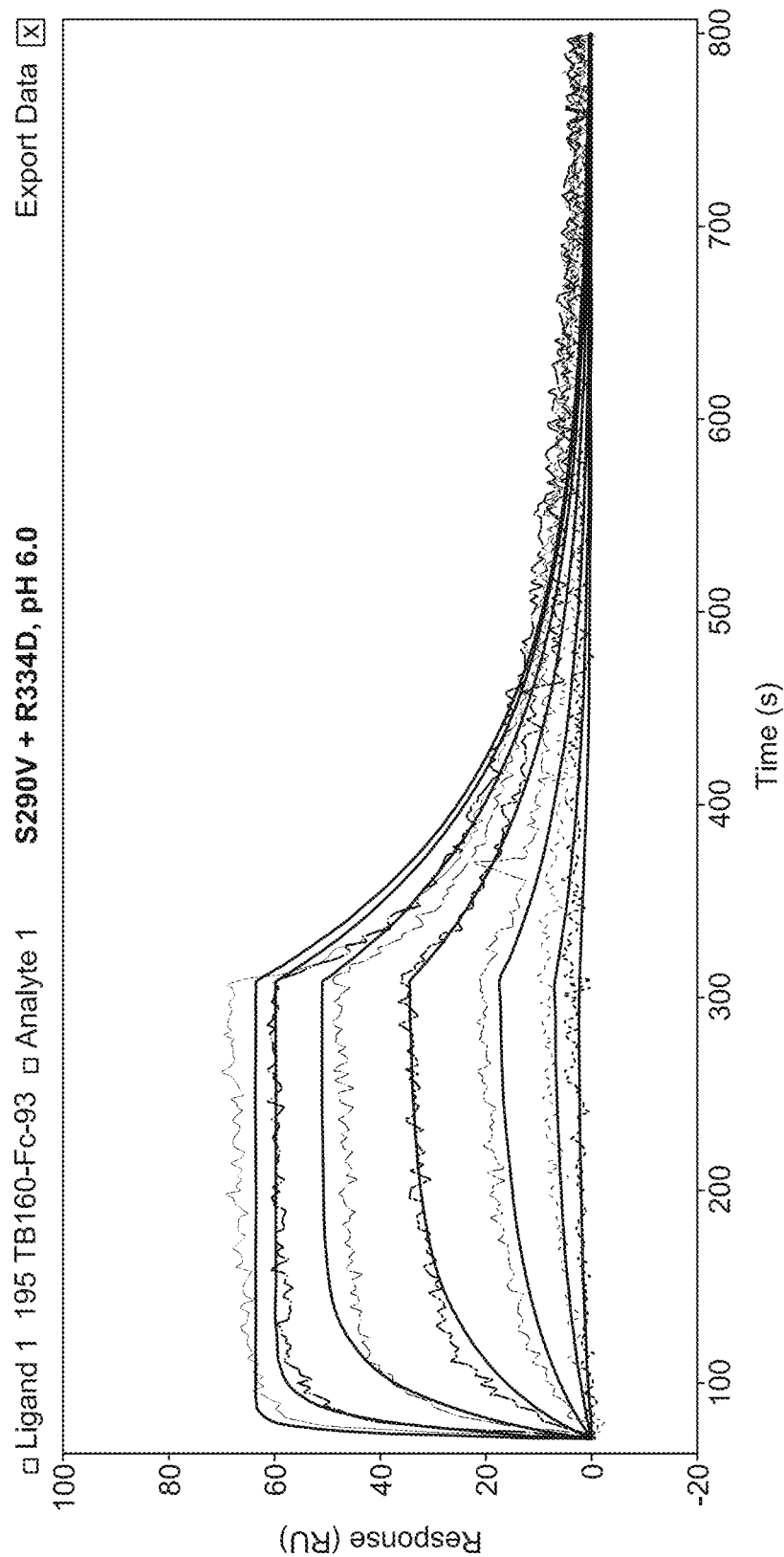
FIGS. 41A and 41B depict Carterra LSA sensorgrams for the S290V+R334D feline IgG1a Fc variant from the phage display library and its interaction with feline FcRN at pH6.0 and pH7.4. The irregular lines represent the measured data and the smooth lines are the fitted curves using a 1:1 interaction model. Y-axis: Resonance Units (RU); X-axis: time (seconds).
Figure 41B:
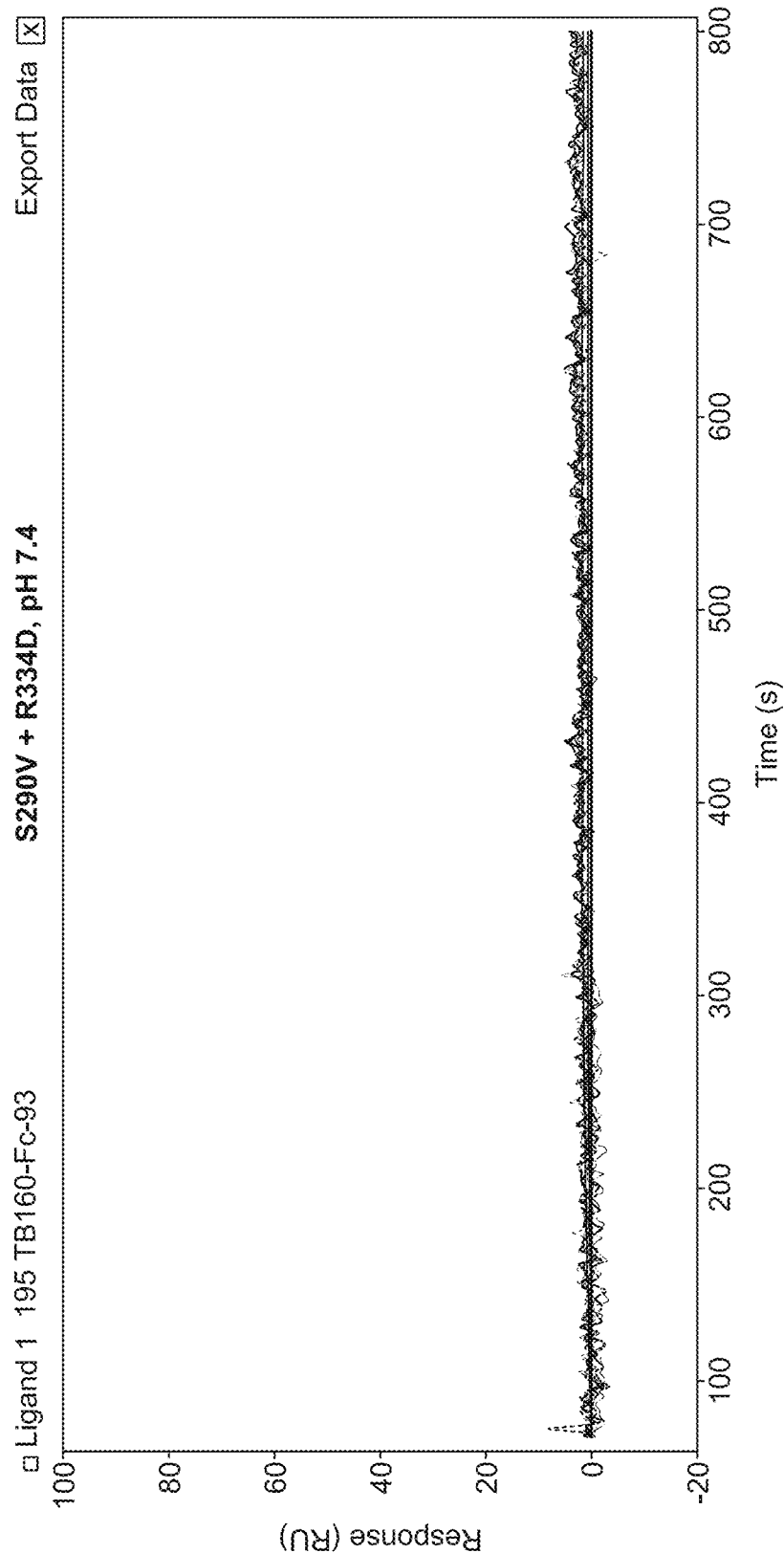
Figure 42A:
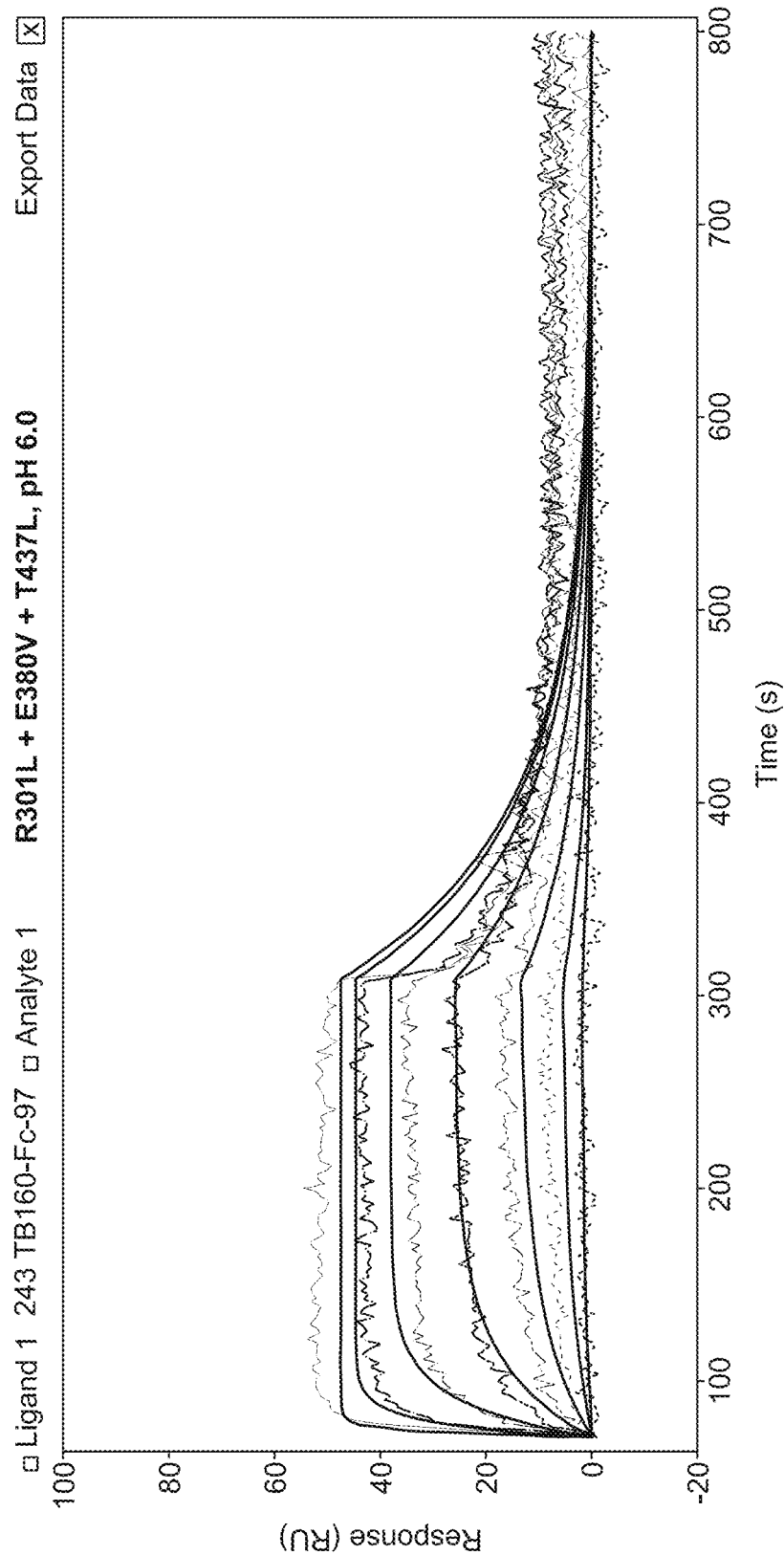
FIGS. 42A and 42B depict Carterra LSA sensorgrams for the R301L+E380V+T437L feline IgG1a Fc variant from the phage display library and its interaction with feline FcRN at pH6.0 and pH7.4. The irregular lines represent the measured data and the smooth lines are the fitted curves using a 1:1 interaction model. Y-axis: Resonance Units (RU); X-axis: time (seconds).
Figure 42B:
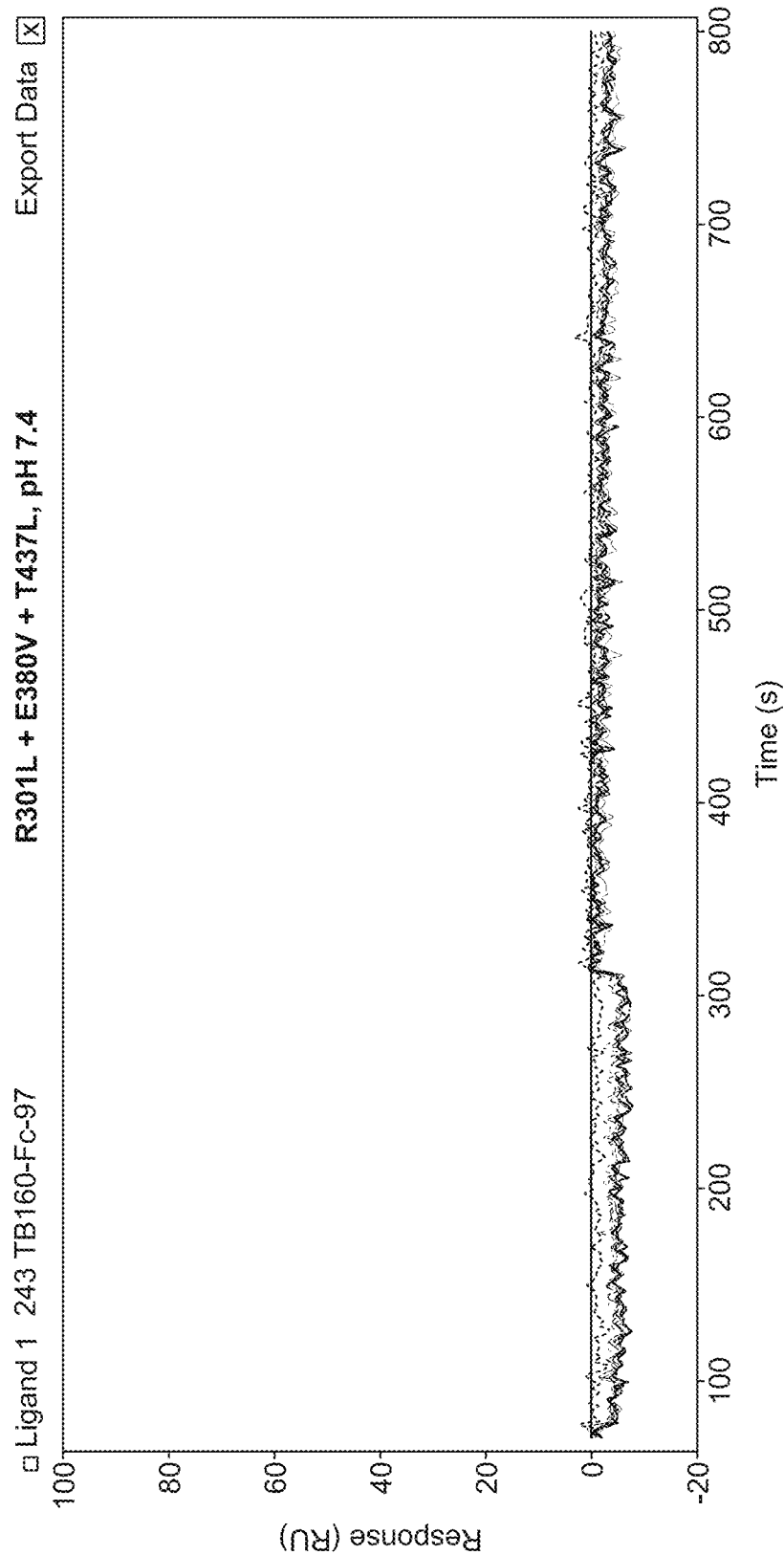
Figure 43A:
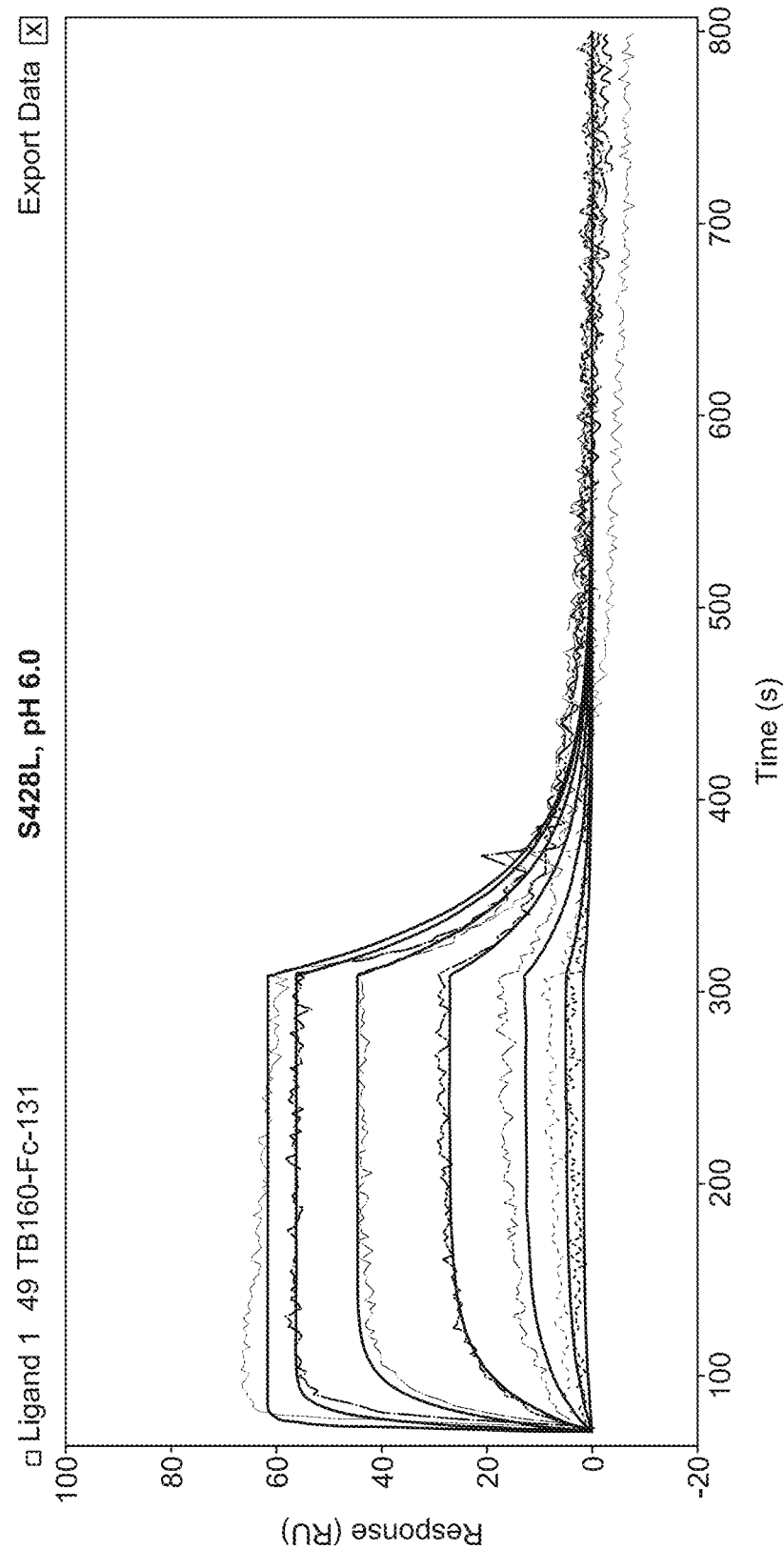
FIGS. 43A and 43B depict Carterra LSA sensorgrams for the S428L feline IgG1a Fc variant from the phage display library and its interaction with feline FcRN at pH6.0 and pH7.4. The irregular lines represent the measured data and the smooth lines are the fitted curves using a 1:1 interaction model. Y-axis: Resonance Units (RU); X-axis: time (seconds).
Figure 43B:
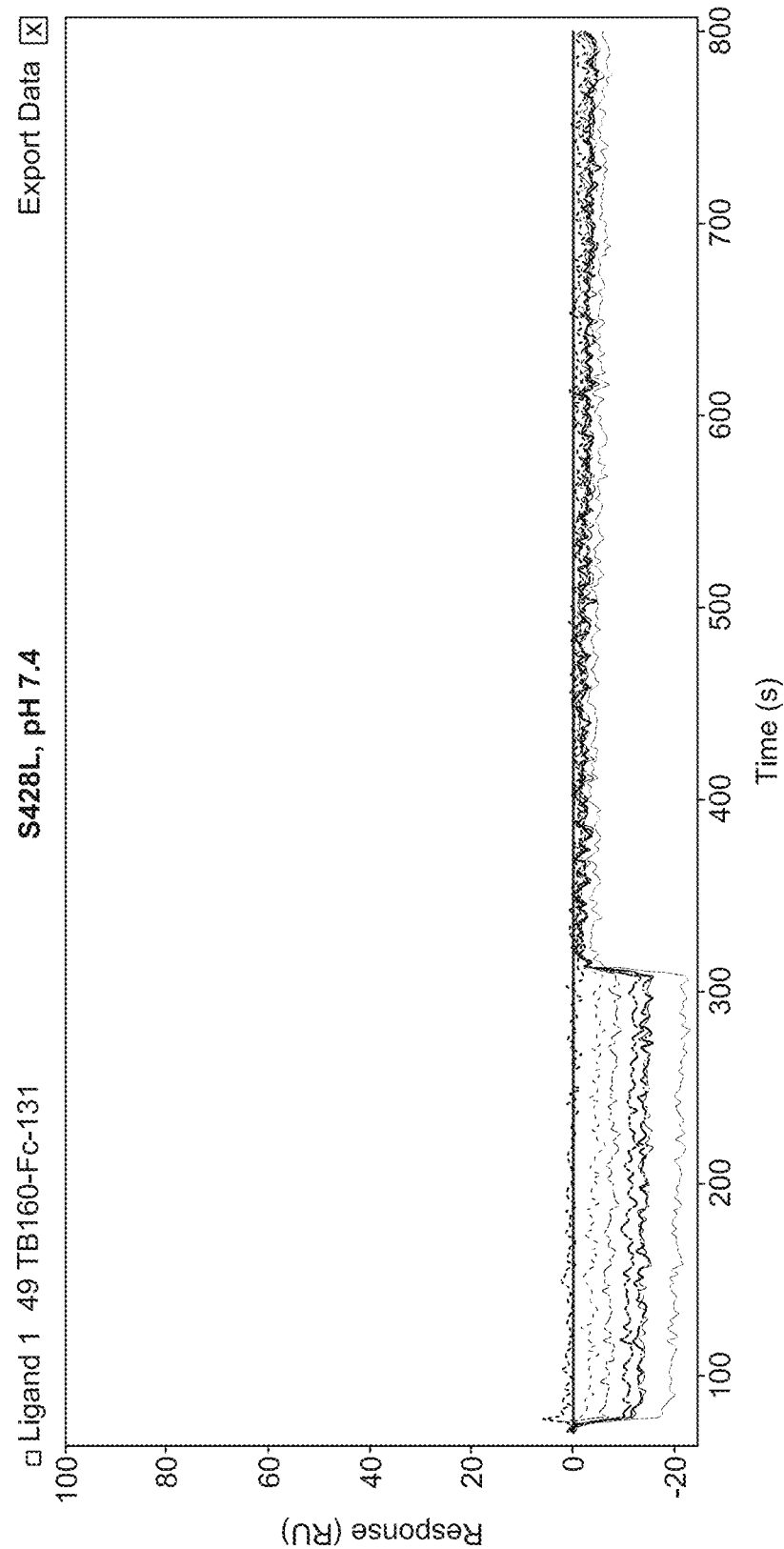
Figure 44A:
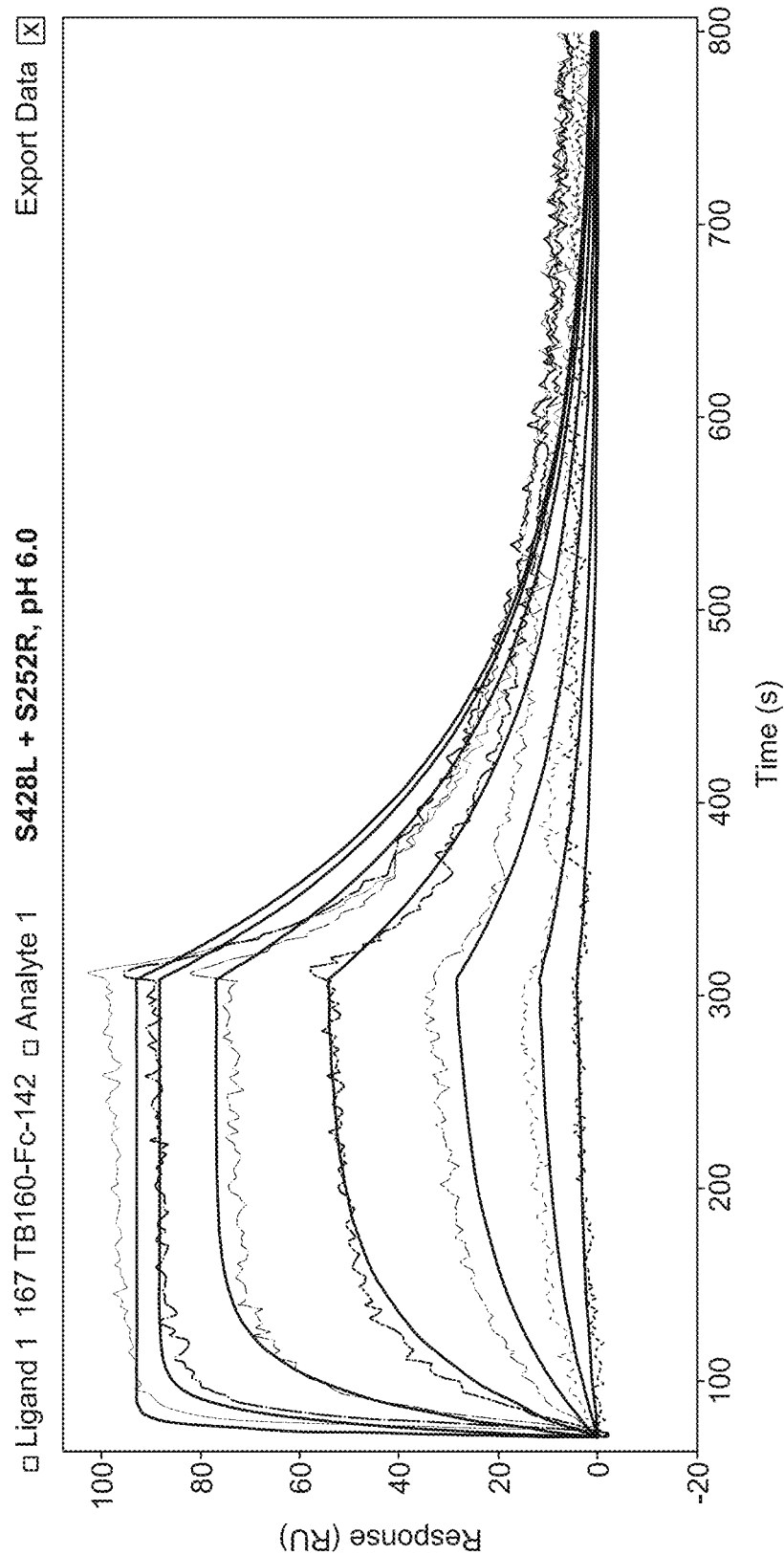
FIGS. 44A and 44B depict Carterra LSA sensorgrams for the S428L+S252R feline IgG1a Fc variant from the phage display library and its interaction with feline FcRN at pH6.0 and pH7.4. The irregular lines represent the measured data and the smooth lines are the fitted curves using a 1:1 interaction model. Y-axis: Resonance Units (RU); X-axis: time (seconds).
Figure 44B:
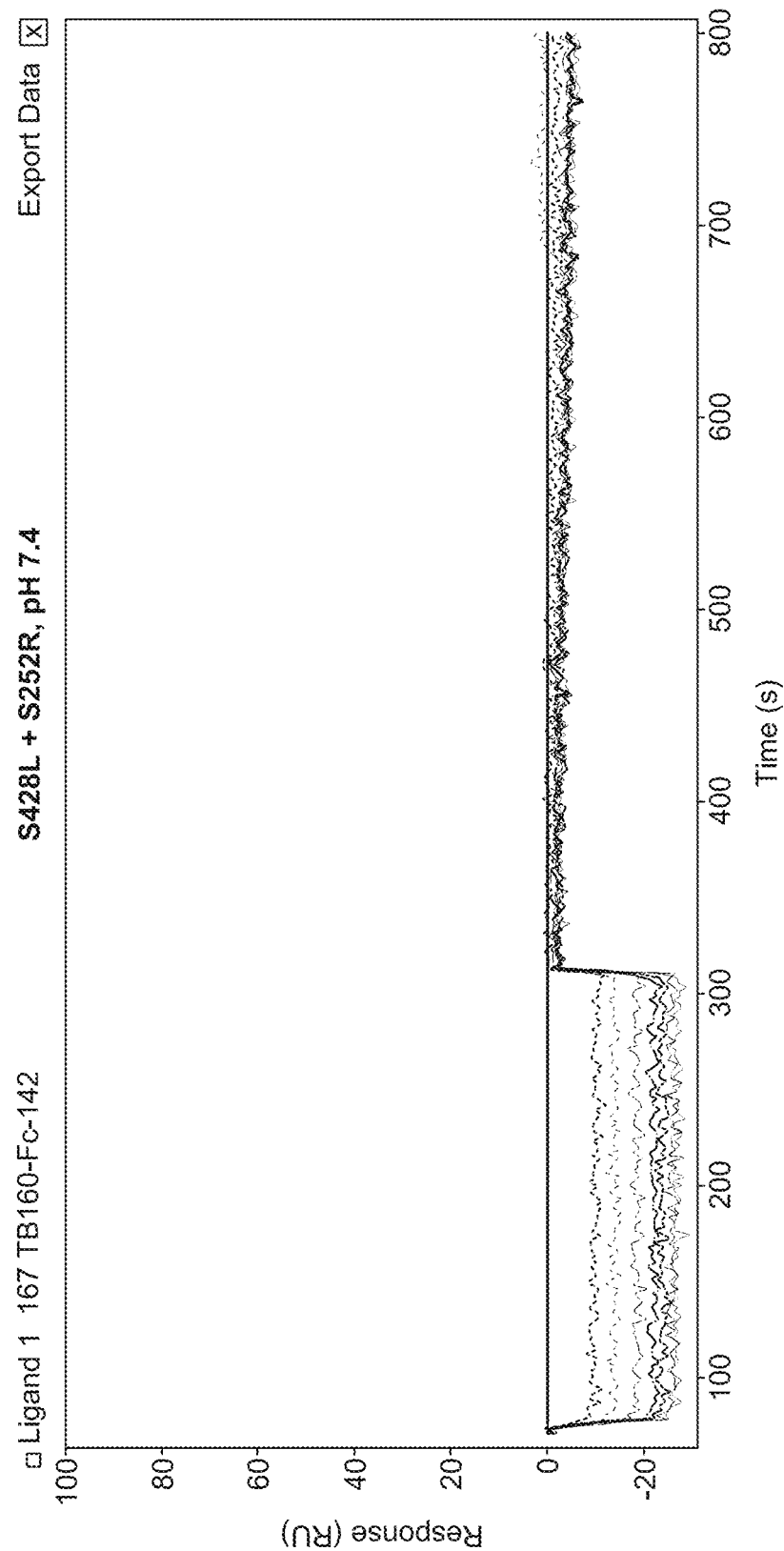
Figure 45A:
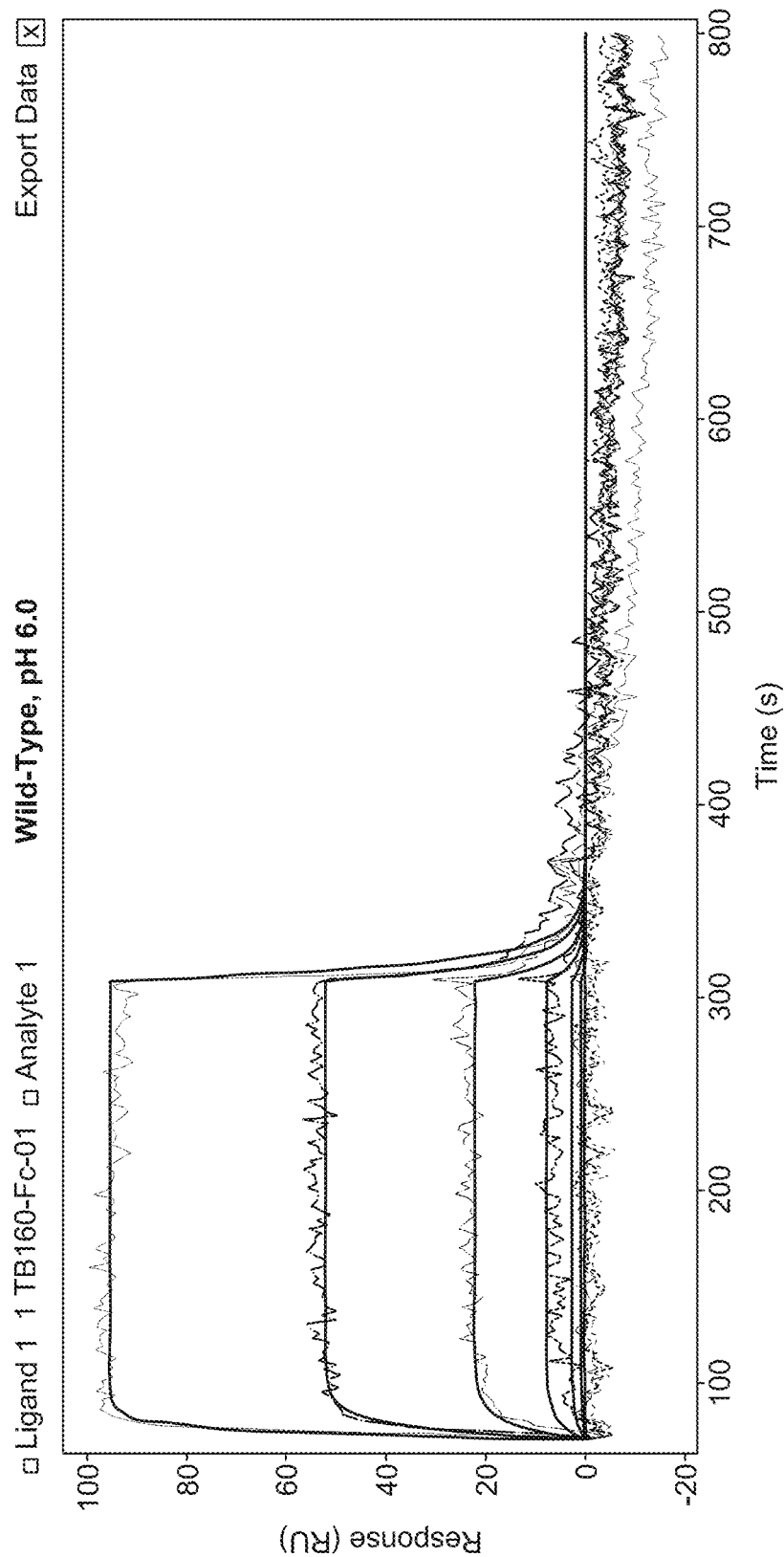
FIGS. 45A and 45B depict Carterra LSA sensorgrams for the wild-type feline IgG1a Fc variant (SEQ ID NO:1) and its interaction with feline FcRN at pH6.0 and pH7.4. The irregular lines represent the measured data and the smooth lines are the fitted curves using a 1:1 interaction model. Y-axis: Resonance Units (RU); X-axis: time (seconds).
Figure 45B:
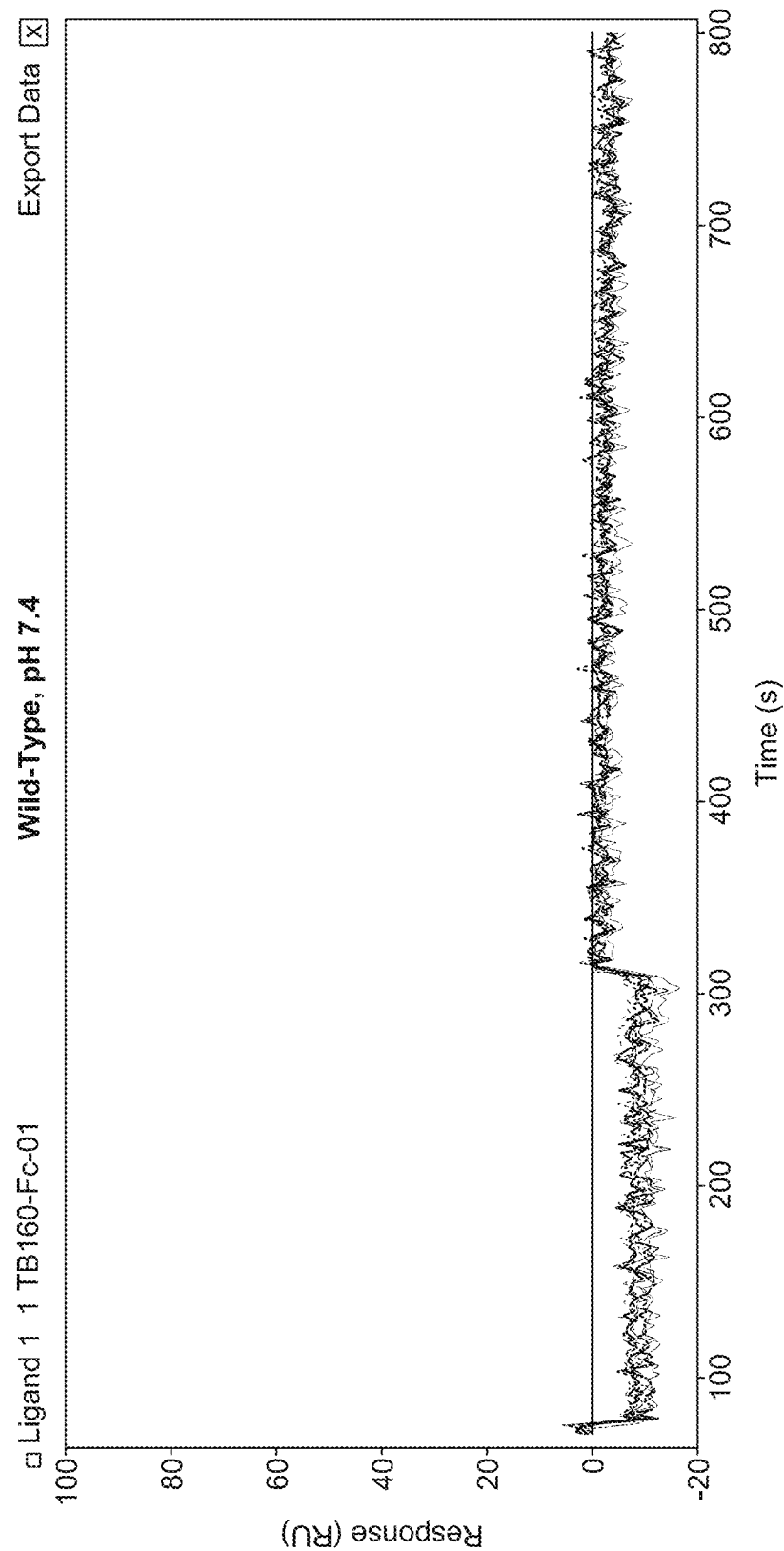

For the SPR analyses using the Biacore 8K, bovine serum albumin (BSA) was immobilized to CM5 sensor chip. The sensor chip surface of flow cells 1 and 2 were activated by freshly mixed 50 mmol/L N-Hydroxysuccinimide and 200 mmol/L 1-ethyl-3-(3-dimethylaminopropyl) carbodiimide hydrochloride for 420s (10 µL/min). Afterwards, BSA diluted in 10 mM sodium acetate (pH 4.5) was injected into the flow cell 2 to achieve conjugation, while flow cell 1 was set as blank. After the amine coupling reaction, the remaining active coupling sites on chip surface were blocked with 420 s injection of 1 mM ethanolamine hydrochloride. The running buffer for the binding experiment was HBS-EP (10 mM HEPES, 500 mM NaCl, 3 mM EDTA, 0.05% Tween 20, pH 5.5) and it was run at 25° C. Supernatants from the variants were injected over chip surface and captured via the SASA tag onto the immobilized BSA for 60 sec. Feline FcRn at 200 nM was injected for 120 sec and the dissociation was complete with running buffer for 120 sec. The flow rate for the immobilization phase of BSA was 10 µl/min and the flow rate for the association and dissociation phase was 30 µl/min. All of the data was processed using the Biacore 8K evaluation software version 1.1. See FIGS. 1 and 2 for the Biacore sensorgrams.

The variants tested showed increased binding affinity for feline FcRn at pH 6.0 when compared to wild type feline IgG1a Fc (SEQ ID NO: 1).

NNK mutagenesis at amino acid positions 252, 428 and 434 were found to yield mutants which increased binding to FcRn at pH 6.0. Sequencing of all 90 clones generated at these 3 positions indicated that the following 6 clones had not been generated, namely S252H, S428E, S428C, S428F, S428W and S434Y. All other amino acid substitutions at these positions yielded no benefit on testing. The results are summarized in Table 3 below.

TABLE 3

IgG variants and FcRn binding kinetics.

| Variant | ka (1/Ms) | kd (1/s) | KD (M) |
| --- | --- | --- | --- |
| S252W | 2.28E+05 | 5.38E−03 | 2.35E−08 |
| S252W | 2.34E+05 | 5.45E−03 | 2.33E−08 |

TABLE 3-continued

IgG variants and FcRn binding kinetics.

| Variant | ka (1/Ms) | kd (1/s) | KD (M) |
| --- | --- | --- | --- |
| S252Y | 2.58E+05 | 2.63E−02 | 1.02E−07 |
| S252Y | 2.57E+05 | 2.65E−02 | 1.03E−07 |
| S252F | 2.03E+05 | 9.57E−02 | 4.70E−07 |
| S252F | 2.05E+05 | 1.01E−01 | 4.92E−07 |
| S428L | 1.62E+05 | 7.88E−02 | 4.85E−07 |
| S428L | 1.05E+05 | 8.03E−02 | 7.63E−07 |
| S428M | 1.66E+05 | 1.00E−01 | 6.03E−07 |
| S428Y | 1.95E+05 | 1.038−01 | 5.28E−07 |
| S428Y | 1.87E+05 | 1.05E−01 | 5.65E−07 |
| S434F | 3.78E+05 | 1.58E−02 | 4.17E−08 |
| S434F | 3.71E+05 | 1.61E−02 | 4.33E−08 |
| S434W | 3.14E+05 | 1.75E−02 | 5.56E−08 |
| S434W | 4.02E+05 | 2.02E−02 | 5.02E−08 |
| S434H | 2.41E+05 | 7.61E−02 | 3.16E−07 |
| S434H | 2.00E+05 | 8.88E−02 | 4.44E−07 |
| Wild-type | 3.14E+05 | 3.74E−01 | 1.19E−06 |
| Wild-type | 1.19E+05 | 1.95E−01 | 1.64E−06 |

Example 2: Scanning Mutagenesis of Feline IgG1a Fc

A phage display library approach was used to identify feline IgG1a Fc variants that increase the affinity to feline FcRn at pH 6.0. The feline IgG1a Fc (Kanai et al., 2000. Vet. Immunol. Immunopathol. 73:53) was synthesized by Twist Bioscience to have variants at 55 different positions (FIG. 4). At each of the mutated positions, eight possible amino acids were substituted. These amino acids were arginine and lysine (positively charged side chain), aspartic acid and glutamic acid (negatively charged side chain), threonine and glutamine (polar uncharged side chain), and leucine and valine (hydrophobic side chain). The Fc DNA library was designed to have an average of two variants per Fc molecule. The complexity of this library was 95,040 combinations using the formula: $nCr=n!/r!*(n-r)!$, where n represents the number of sites, and r represents the number of variants per molecule. The Fc variants with the desired site-specific mutations were printed as mutagenic oligonucleotides on Twist's silicon-based platform.

The oligonucleotides were then assembled to create a full-length Fc gene fragment pool using assembly PCR. The assembled Fc gene fragment pool was then cloned into the pADL-22c phagemid vector from Antibody Design Labs into the Sfi cut-sites. The cloned DNA library was transformed into electrocompetent TG1 E. coli cells to create an experimental diversity of $8\times10^{10}$ variants. The phagemid transformed E. coli cells were then co-transfected with M13K07 helper phage to generate a phage pool that was used for protein-based panning. The library was resuspended into 20 mM MES buffer, pH 6.0, 0.05% tween 20 and 3% milk.

The quality of the library was determined by picking 96 random phage clones and sequenced by the Sanger method. The number of mutants per phage are shown in Table 4, below.

TABLE 4

Number of mutants per phage.

| Number of mutations | Number of clones |
| --- | --- |
| 0 | 5 |
| 1 | 19 |

TABLE 4-continued

Number of mutants per phage.

| Number of mutations | Number of clones |
|---|---|
| 2 | 44 |
| 3 | 19 |
| 4 | 5 |
| 5 | 1 |
| 6 | 2 |

For the first phage selection, a Protein A capture step was used to eliminate any Fc variants that have lost Protein A binding. For this selection, the phage library was captured onto Protein A beads and washed with PBS, pH 7.4. The phage were eluted with 0.1M glycine, pH 2.7 and the pH was immediately neutralized with 1 M Tris-HCl, pH 7.5. The neutralized phage was precipitated with polyethylene glycol/NaCl and centrifuged. The pelleted phage were resuspended in 20 mM MES, pH 6.0, 0.05% tween 20, 3% milk.

The next phage selections were based on the protocol described by Borrok et al., 2015, *J Biol. Chem.*, 290:4282. Briefly, Nunc 96 multi-well plates were coated with Neutravidin and then blocked with 5% bovine serum albumin, PBS, pH 7.4. Biotinylated feline FcRn (FCN-F82W3, Acrobiosystems) was immobilized in the well at a concentration of 0.31 µg/ml in PBS, pH 6.0. The phage library in PBS, pH 6.0 was incubated with the immobilized feline FcRn and then washed with PBS, pH 6.0, 0.05% tween 20, 0.3 M NaCl. The phage was eluted with PBS, pH 7.4 by incubating at 37° C. for 30 minutes. The eluted phage were depleted with 0.31 µg/ml of feline FcRn at pH 7.4. The unbound phage was amplified in TG1 cells. The exact conditions and results for each round are shown in Table 5, below.

TABLE 5

Wash conditions and number of depletions for phage selections.

| Round | 1 | 2 | 3 | 4 |
|---|---|---|---|---|
| Number of wells coated with FcRn (0.3125 ug/mL) | 8 | 6 | 4 | 4 |
| Wash Number | 10 | 15 | 15 | 10 + 2 × 30 min |
| Number of depletions with FcRn (0.3125 ug/mL) at pH 7.4 | 1 | 2 | 3 | 3 |
| Input Titer (phages per mL) | $5.0 \times 10^{11}$ | $7.0 \times 10^{12}$ | $1.8 \times 10^{12}$ | $6.4 \times 10^{12}$ |
| Output Titer (cfu per total volume) | $8.4 \times 10^{6}$ | $6.6 \times 10^{5}$ | $1.87 \times 10^{9}$ | $1.54\ 10^{9}$ |

A total of 768 phage clones were isolated from the output of the third round of selection and 768 phage clones from the fourth round of selection. The clones were sequenced by next generation sequencing using the Illumina MiSeq.

The sequencing results revealed a large number of clones (see Table below) containing a substituted tyrosine at position 252, a substituted tyrosine or phenylalanine at position 434 indicating that some of the substitutions contained residues other than the intended eight amino acid substitutions. Unique variants were reformatted into IgG using variable domains previously described by Gearing et al. (2016, *J Vet Intern Med*, 30:1129). The mini-prep plasmid DNA was transfected into Expi293 cells with Expi-Fectamine 293 transfection reagent. The IgG variants were purified from the conditioned medium with Protein A chromatography and formulated into 43 mM sodium citrate, 130 mM sodium bicarbonate, pH 6.0.

For determining the affinities of the IgG variants to feline FcRn, a Carterra instrument was used to determine the binding kinetics. The antibodies (~5 µg/ml) were amine-coupled to the HC30M sensor chip by EDC/NHS activation, followed by ethanolamine HCl quenching.

Concentrations (333 nM, 111 nM, 37 nM, 12.3 nM, 4.1 nM, 1.37 nM, 0.45 nM) of feline FcRn (FCN-F82W3, Acrobiosystems) was flowed over the sensor chip in HBSTE (10 mM HEPES, 150 mM NaCl, 3 mM EDTA, 0.05% Tween-20), 0.5% bovine serum albumin, pH 6.0 to determine the kinetics at pH 6.0. This same strategy was used to determine the binding kinetics to feline FcRn at pH 7.4 except the pH of the HBSTE buffer was adjusted to 7.4.

The feline FcRn binding kinetics of the IgG variants are shown in Table 6, below.

TABLE 6

IgG Fc variants and FcRn binding kinetics.

| | pH 6.0 | | | pH 7.4 | | |
|---|---|---|---|---|---|---|
| Variant | $k_a$ (M-1 s-1) | $k_d$ (s-1) | $K_D$ (nM) | $k_a$ (M-1 s-1) | $k_d$ (s-1) | $K_D$ (nM) |
| Wild-Type | 4.72E+05 | 1.10E−01 | 232.8 | No Binding | | |
| S252Y | 9.74E+05 | 9.50E−03 | 9.8 | Weak Binding | | |
| S252Y, Q311R | 9.26E+05 | 6.40E−03 | 6.9 | Weak Binding | | |
| S252Y, Q311K | 1.39E+06 | 7.79E−03 | 5.6 | 2.39E+06 | 1.12E−01 | 46.9 |
| S252Y, Q311V | 1.06E+06 | 4.05E−03 | 3.8 | 1.73E+05 | 5.28E−02 | 306.0 |
| S252Y, Q311L | 7.40E+05 | 5.16E−03 | 7.0 | Weak Binding | | |
| S434Y | 1.22E+06 | 6.29E−03 | 5.2 | No Binding | | |
| S434Y, S254R | 2.75E+06 | 5.68E−03 | 2.1 | No Binding | | |
| S434Y, S254K | 1.61E+06 | 5.04E−03 | 3.1 | Weak Binding | | |
| S434Y, L262E | 1.51E+06 | 4.98E−03 | 3.3 | Weak Binding | | |
| S434Y, T286D | 1.28E+06 | 3.71E−03 | 2.9 | No Binding | | |
| S434Y, T286E | 9.65E+05 | 3.45E−03 | 3.6 | No Binding | | |
| S434Y, T289K | 1.53E+06 | 5.59E−03 | 3.6 | Weak Binding | | |
| S434Y, E293D | 1.57E+06 | 5.34E−03 | 3.4 | No Binding | | |
| S434Y, E293K | 1.22E+06 | 5.01E−03 | 4.1 | Weak Binding | | |

TABLE 6-continued

IgG Fc variants and FcRn binding kinetics.

| Variant | pH 6.0 | | | pH 7.4 | | |
|---|---|---|---|---|---|---|
| | $k_a$ (M-1 s-1) | $k_d$ (s-1) | $K_D$ (nM) | $k_a$ (M-1 s-1) | $k_d$ (s-1) | $K_D$ (nM) |
| S434Y, L309V | 2.21E+06 | 4.00E−03 | 1.8 | Weak Binding | | |
| S434Y, L309E | 1.13E+06 | 4.58E−03 | 4.1 | Weak Binding | | |
| S434Y, K326D | 1.38E+06 | 5.49E−03 | 4.0 | No Binding | | |
| S434Y, Q347L | 1.98E+06 | 6.67E−03 | 3.4 | No Binding | | |
| S434Y, S426L | 1.48E+06 | 4.40E−03 | 3.0 | 6.36E+05 | 1.18E−01 | 184.9 |
| S434F | 1.73E+06 | 7.18E−03 | 4.2 | Weak Binding | | |
| S434F, E380D | 1.77E+06 | 5.83E−03 | 3.3 | No Binding | | |
| S428L | 1.45E+06 | 2.41E−02 | 16.7 | No Binding | | |
| S428L, S252R | 9.74E+05 | 8.73E−03 | 9.0 | No Binding | | |
| S428L, T286E | 1.15E+06 | 9.87E−03 | 8.6 | No Binding | | |
| S428L, Q311V | 9.16E+05 | 1.07E−02 | 11.7 | No Binding | | |
| S428L, Q311K | 9.58E+05 | 1.01E−02 | 10.5 | No Binding | | |
| S428L, D312T | 1.01E+06 | 1.13E−02 | 11.2 | Weak Binding | | |
| S428L, I377V | 1.69E+06 | 1.83E−02 | 10.8 | No Binding | | |
| S428L, I383L | 1.63E+06 | 1.62E−02 | 9.9 | No Binding | | |
| S428L, N389c-R | 1.14E+06 | 1.09E−02 | 9.6 | No Binding | | |
| S428L, E380D, S434R | 1.22E+06 | 9.73E−03 | 8.0 | No Binding | | |
| S428L, E380T, S434R | 3.17E+06 | 1.20E−02 | 3.8 | No Binding | | |
| Q311R | 1.96E+05 | 1.16E−02 | 59.2 | No Binding | | |
| R392E | 1.33E+06 | 3.24E−02 | 24.5 | No Binding | | |
| S252R, L262Q | 1.63E+06 | 7.95E−03 | 4.9 | No Binding | | |
| S252R, A378E | 2.62E+05 | 9.27E−03 | 35.3 | Weak Binding | | |
| T260E, L309E, Q355L | 9.83E+05 | 9.77E−03 | 9.9 | No Binding | | |
| T286E, S428R | 9.39E+05 | 6.48E−03 | 6.9 | 9.17E+06 | 1.13E−01 | 12.3 |
| S290V, R334D | 9.31E+05 | 9.97E−03 | 10.7 | No Binding | | |
| R301L, E380V, T437L | 1.15E+06 | 1.23E−02 | 10.7 | No Binding | | |

Example 3: Scanning Mutagenesis of Feline IgG1a Fc

A set of further anti-nerve growth factor (NGF) feline IgG1a antibody variants were synthesized by Twist Bioscience using the variable domains previously described by Gearing et al. (2016, *J Vet Intern Med*, 30:1129). The modifications to the Fc region of these antibodies are set out in Tables 8 and 9, below, as compared to the reference sequence of the wild-type feline IgG1a Fc domain that is described by Kanai et al. (2000, *Vet. Immunol. Immunopathol.* 73:53). The feline IgG1a constructs were subcloned into a mammalian expression vector and transfected into Expi293 cells with ExpiFectamine 293 transfection reagent. The IgG1a Fc variants were purified from the conditioned medium with Protein A chromatography and formulated in 43 mM sodium citrate, 130 mM sodium bicarbonate, pH 6.0. A Carterra instrument was then used to determine the binding affinity of the IgG Fc variants to feline FcRn. The antibody variants (~5 μg/ml) were amine-coupled to the HC30M sensor chip by EDC/NHS activation, followed by ethanolamine HCl quenching. Feline FcRn (FCN-F82W3, Acrobiosystems) at 333 nM, 111 nM, 37 nM, 12.3 nM, 4.1 nM, 1.37 nM or 0.45 nM was flowed over the sensor chip in HBSTE (10 mM HEPES, 150 mM NaCl, 3 mM EDTA, 0.05% Tween-20), 0.5% bovine serum albumin at pH 6.0 to determine the kinetics at pH 6.0. This same strategy was employed to determine the binding affinity of the Fc variants to feline FcRn at pH 7.4, where the pH of the HBSTE buffer was adjusted to 7.4.

The feline FcRn binding kinetics of the IgG variants are shown in Table 7, below.

TABLE 7

IgG Fc variants and FcRn binding kinetics - II

| Variant | pH 6.0 | | | pH 7.4 | | |
|---|---|---|---|---|---|---|
| | $k_a$ (M-1 s-1) | $k_d$ (s-1) | $K_D$ (nM) | $k_a$ (M-1 s-1) | $k_d$ (s-1) | $K_D$ (nM) |
| Wild-Type | 4.72E+05 | 1.10E−01 | 232.8 | No Binding | | |
| S254K | 5.21E+05 | 5.57E−02 | 107.1 | No Binding | | |
| T286D | 4.00E+05 | 3.89E−02 | 97.4 | Weak Binding | | |
| T286E | 4.89E+05 | 4.57E−02 | 93.4 | No Binding | | |
| S290Y | 6.61E+05 | 8.49E−02 | 128.4 | No Binding | | |
| E293H | 4.55E+05 | 6.65E−02 | 146.0 | No Binding | | |
| R301L | 4.57E+05 | 4.35E−02 | 95.2 | Weak Binding | | |
| L309V | 3.53E+05 | 4.50E−02 | 127.4 | No Binding | | |
| L309E | 4.06E+05 | 4.15E−02 | 102.1 | No Binding | | |
| L309Y | 6.00E+05 | 1.18E−01 | 196.4 | No Binding | | |
| Q311V | 6.29E+05 | 5.05E−02 | 80.4 | No Binding | | |
| Q311L | 5.65E+05 | 4.99E−02 | 88.2 | No Binding | | |
| K326D | 4.28E+05 | 5.84E−02 | 136.4 | Weak Binding | | |
| R334D | 4.23E+05 | 5.61E−02 | 132.7 | Weak Binding | | |
| Q347L | 5.44E+05 | 8.53E−02 | 156.8 | No Binding | | |
| I377Y | 8.37E+05 | 5.14E−02 | 61.4 | No Binding | | |
| E380T | 5.33E+05 | 6.20E−02 | 116.2 | Weak Binding | | |
| N389c-R | 5.02E+05 | 9.44E−02 | 188.1 | No Binding | | |
| S426H | 3.52E+05 | 6.02E−02 | 171.2 | No Binding | | |
| S428H | 3.89E+05 | 6.18E−02 | 159.0 | Weak Binding | | |
| S428Y | 7.18E+05 | 1.84E−02 | 25.6 | Weak Binding | | |
| T286E, S428H | 5.98E+05 | 2.83E−02 | 47.3 | No Binding | | |
| R334D, S428R | 6.03E+05 | 4.93E−02 | 81.7 | No Binding | | |
| R334D, T437L | 4.57E+05 | 4.37E−02 | 95.7 | Weak Binding | | |
| R334D, R301L | 4.60E+05 | 4.17E−02 | 90.7 | No Binding | | |
| S426L, T289H | 5.42E+05 | 6.22E−02 | 114.8 | No Binding | | |
| S426L, S428H | 4.45E+05 | 4.45E−02 | 100.0 | No Binding | | |
| S428Y, Q311V | 8.93E+05 | 9.77E−03 | 10.9 | Weak Binding | | |
| S428Y, S254R | 5.52E+05 | 2.65E−02 | 48.1 | No Binding | | |
| S428Y, L309V | 8.47E+05 | 1.12E−02 | 13.2 | Weak Binding | | |
| S428H, T289H | 3.52E+05 | 5.26E−02 | 149.3 | No Binding | | |

A list of the amino acid substitutions that were identified as increasing the binding of the feline IgG1a Fc variant to feline FcRN is provided in Table 8, below:

TABLE 8

Summary of the amino acid substitutions for feline IgG1a Fc variants that showed increased binding affinity to feline FcRn

| Position by EU numbering | Wild-type feline IgG1a Fc | Feline IgG1a Fc variant amino acid substitutions that enhance binding of the variant to feline FcRN (compared to wild-type) |
|---|---|---|
| 252 | S | FYWR |
| 254 | S | RK |
| 262 | L | QE |
| 286 | T | ED |
| 289 | T | KH |
| 290 | S | VY |
| 293 | E | DKH |
| 301 | R | L |
| 309 | L | VEY |
| 311 | Q | RVKL |
| 312 | D | T |
| 326 | K | D |
| 334 | R | D |
| 347 | Q | L |
| 355 | Q | L |
| 377 | I | VY |
| 380 | E | DVT |
| 383 | I | L |
| 389c | N | R |
| 392 | R | E |
| 426 | S | LH |
| 428 | S | RLMYH |
| 434 | S | RYFWH |
| 437 | T | L |

Example 4: Pharmacokinetic Study of Feline IgG1a Fc Variants with Increased FcRn Binding and Wild-Type Feline IgG1a A pharmacokinetic (PK) study was undertaken with twelve male and female cats. Feline IgG1a Fc variants, including the antibody carrying a wild-type feline IgG1a Fc domain, were prepared using the anti-NGF variable domain as previously described by Gearing et al. (2016, *J Vet Intern Med*, 30:1129).

Figure 46:
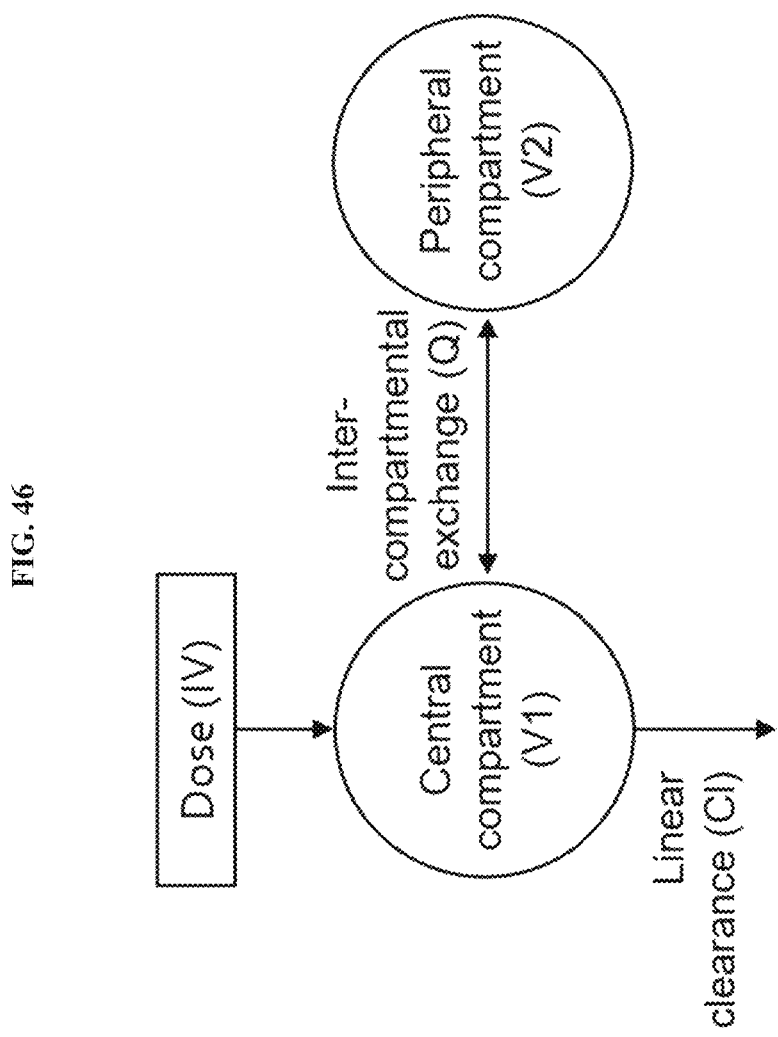
FIG. 46 depicts a flow diagram of the two-compartmental pharmacokinetic (PK) model with linear clearance using non-linear mixed effects (NLME) modelling that was used to describe serum concentrations of anti-NGF monoclonal antibody (mAb) variants.

The animals were randomized into six groups with a male and female in each group. Each animal was administered with single intravenous dose of 2 mg/kg of antibody. Approximately 0.5 ml of whole blood was collected at the following time points: 0 (pre-dose), 4 hours, and 1, 2, 4, 6, 10, 14, 18, 22, 30, 34 38, 42 days post injection. Serum was separated from whole blood and assayed for the presence of the antibody by an ELISA that is specific for anti-NGF antibodies. Serum concentrations of six anti-NGF monoclonal antibody (mAb) variants were described with a two-compartmental pharmacokinetic (PK) model with linear clearance using non-linear mixed effects (NLME) modelling (FIG. 46). Population parameters were estimated using the stochastic approximation of expectation-maximization (SAEM) algorithm implemented in Monolix Suite 2019R1 (Monolix version 2019R1. Antony, France: Lixoft SAS, 2019). Individual parameters were modeled as random variables with log-normal distributions. PK parameters depended on body weight (BW) using mAb-typical coefficients ($\beta_{BW,Cl}=0.75$, $\beta_{BW,V1}=\beta_{BW,V2}=1$, $\beta_{BW,Q}=2/3$). The equation (Dong et al. 2011. *Clin Pharmacokinet*, 50:131) for an individual parameter $\varphi_i$ was:

$$\varphi_i = \varphi_{pop}\left(\frac{BW_i}{BW_{ref}}\right)^\beta e^\eta$$

where $\varphi_{pop}$ was the population typical parameter, $\eta$ was a random variable with mean 0 and standard deviation $\omega$, $BW_i$ was the body weight of animal i, and $BW_{ref}$ was the reference body weight of 2 kg.

Antibody variants were discriminated by using a categorial covariate on clearance, inter-compartmental exchange coefficient, and peripheral volume according to the equation:

$$\varphi_i = \varphi_{pop} e^{(\beta \Omega_i)} e^\eta$$

where $\Omega_i=1$ if the individual variant covariate was in the category and $\Omega_i=0$ otherwise. The wild-type (WT) mAb variant was used as a reference.

Figure 47:
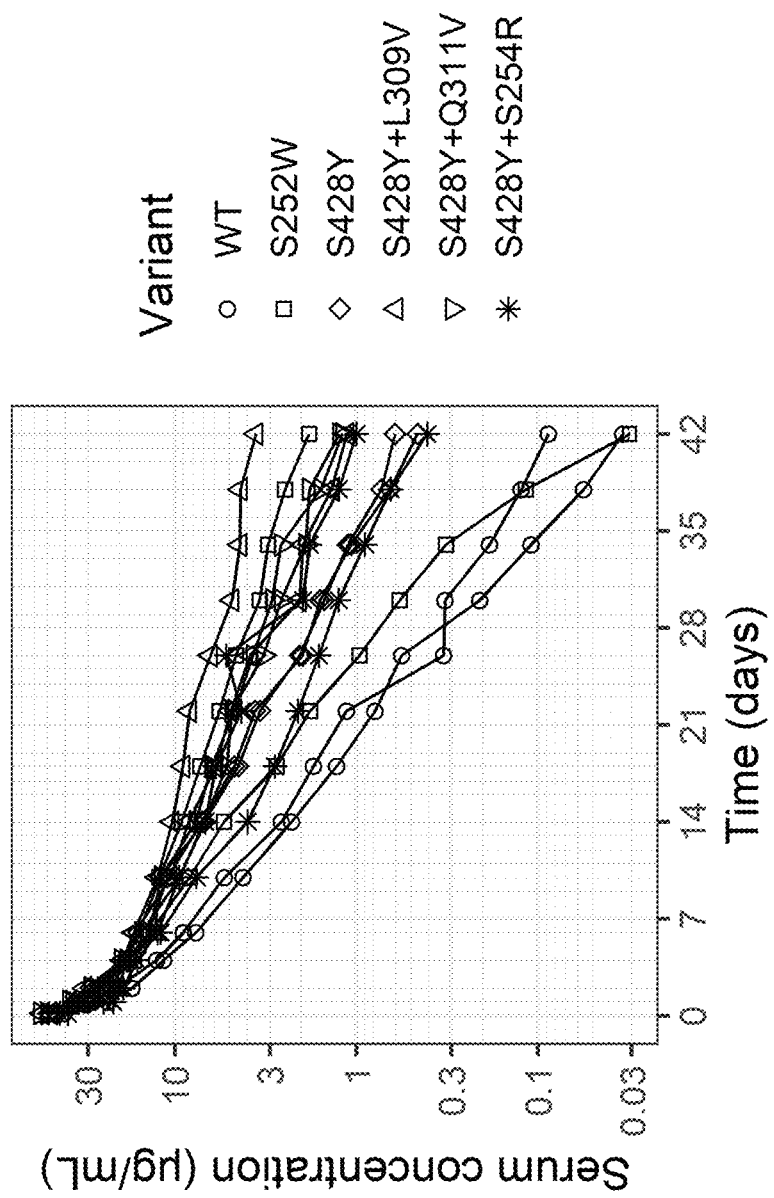
FIG. 47 depicts the individual observed serum concentrations of the wild-type (WT) antibody and antibody variants S252W, S428Y, S428Y+L309V, S428Y+Q311V, and S428Y+S254R (results from two animals per antibody/variant).

The individual observed serum concentrations of variants WT, S252W, S428Y, S428Y+L309V, S428Y+Q311V, and S428Y+S254R with two animals per variant are shown in FIG. 47.

Figure 48:
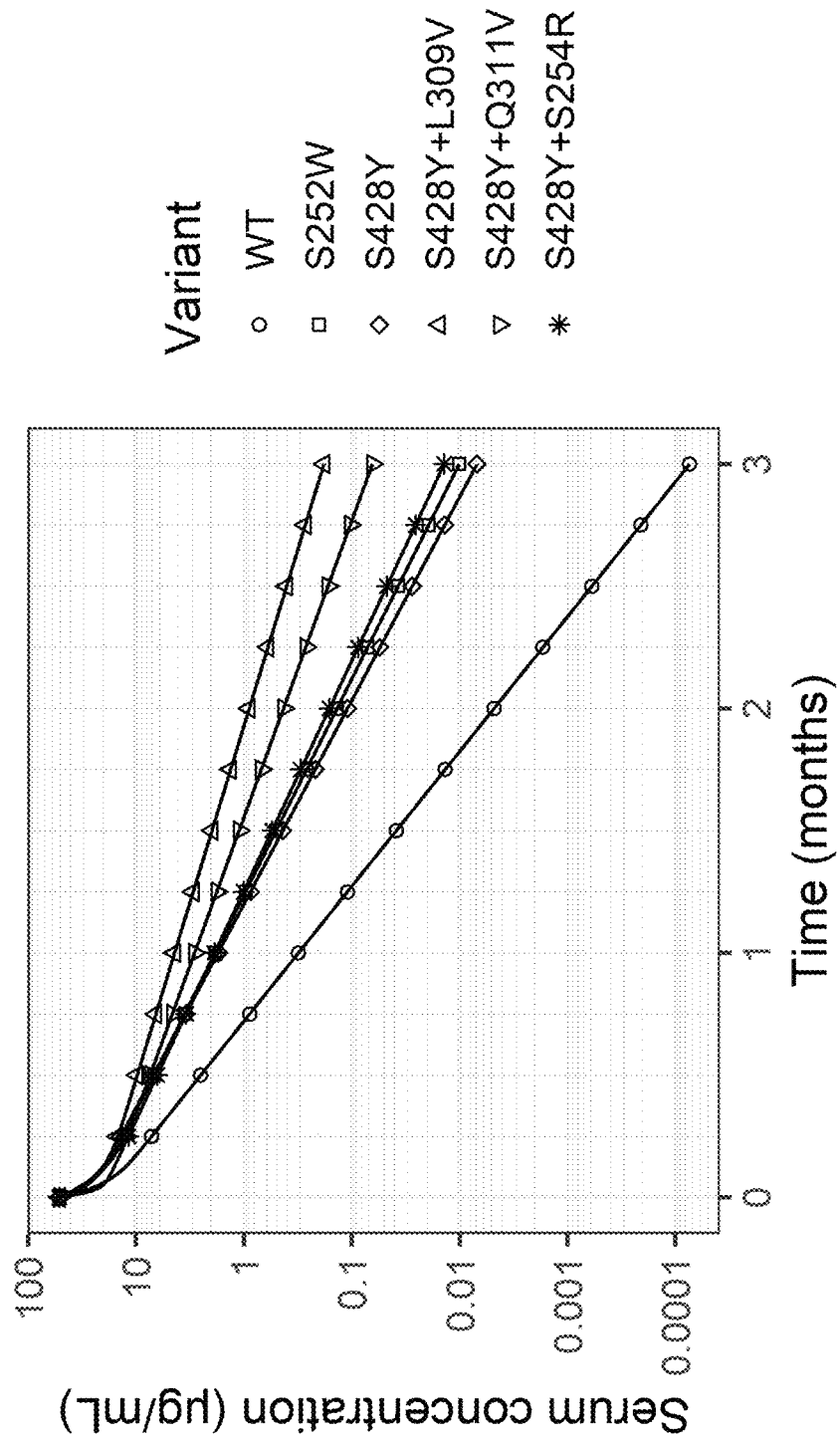
FIG. 48 depicts the predicted serum concentration profiles of the wild-type (WT) antibody and antibody variants S252W, S428Y, S428Y+L309V, S428Y+Q311V, and S428Y+S254R for a typical 2 kg cat receiving a single IV dose of 2 mg/kg antibody/variant.
Figure 49A:
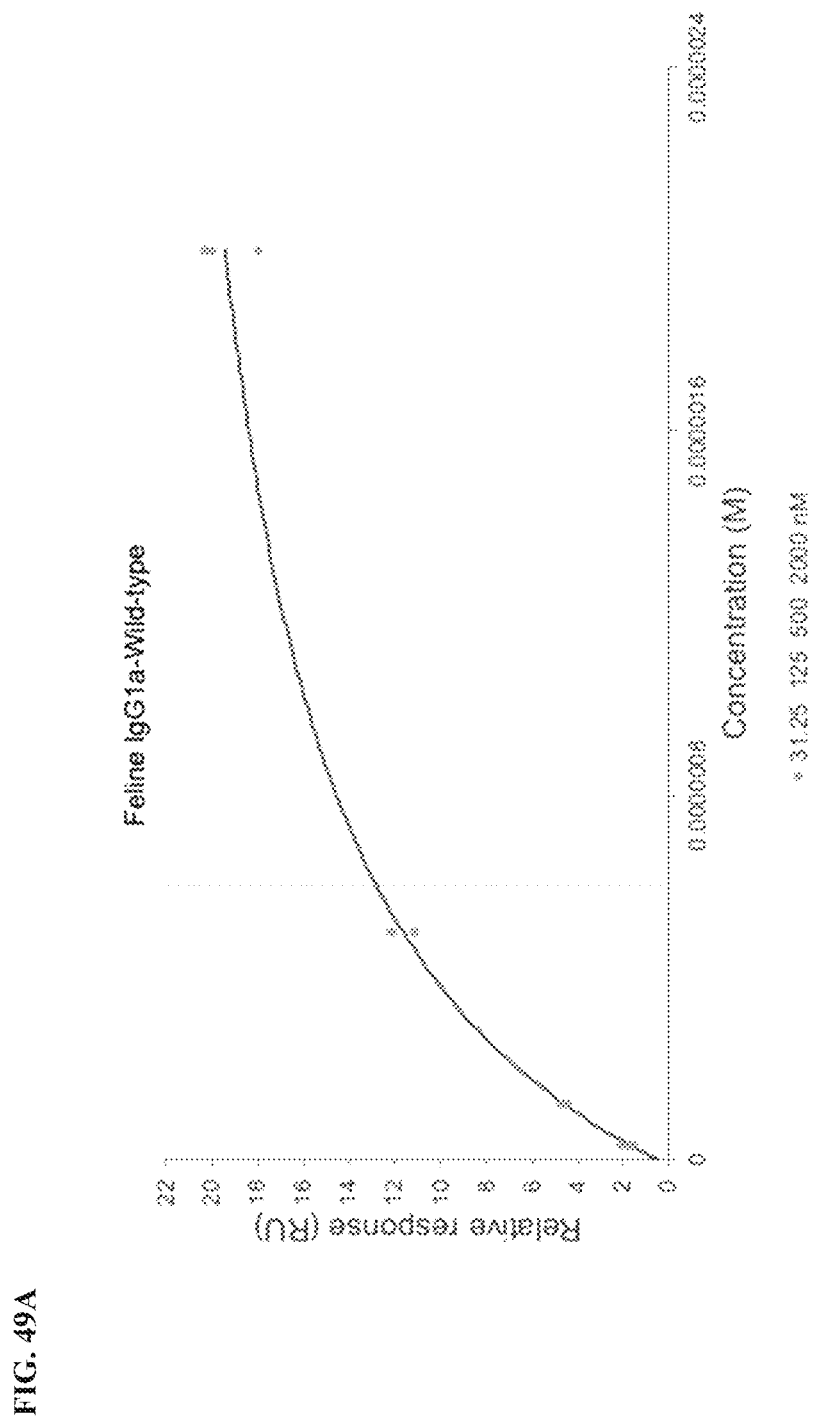
Figure 49B:
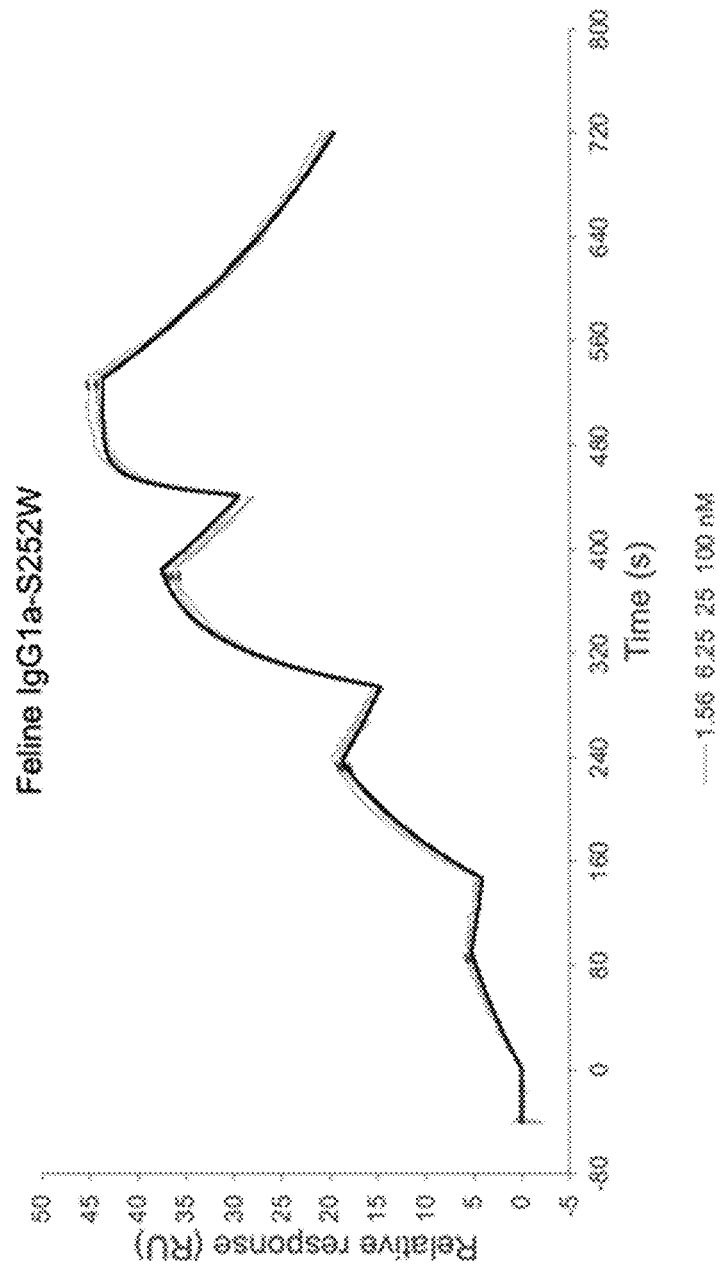
Figure 49C:
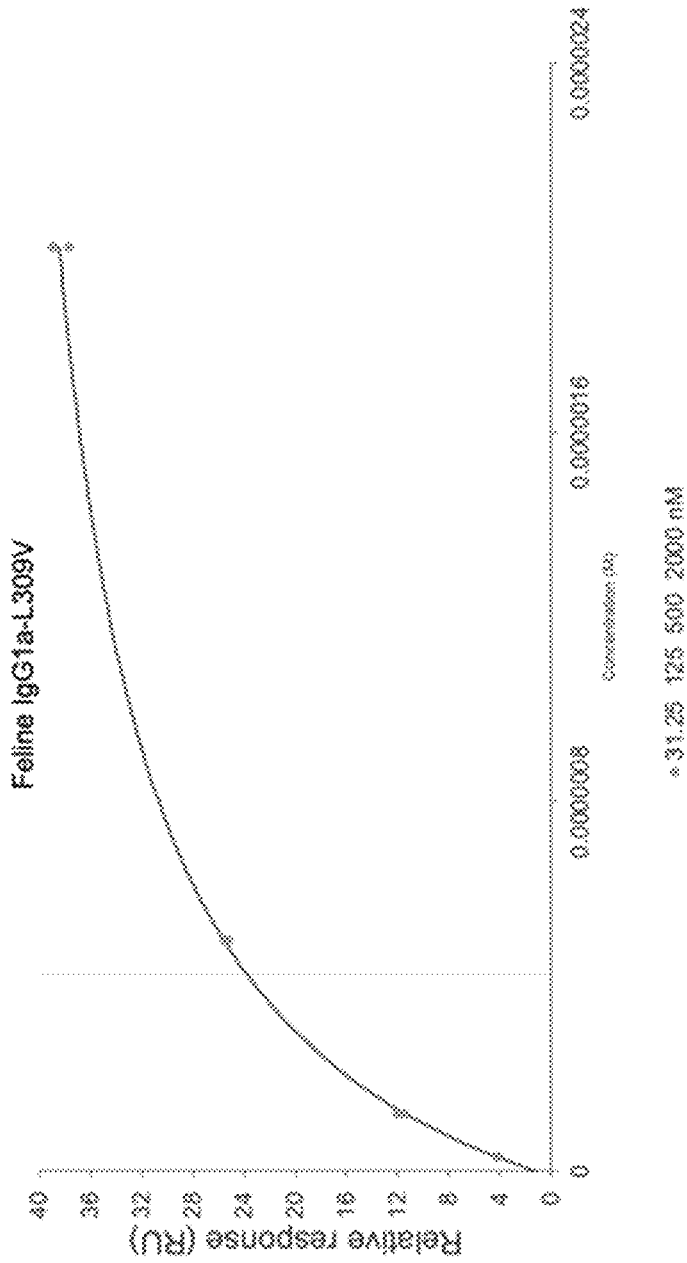
Figure 49D:
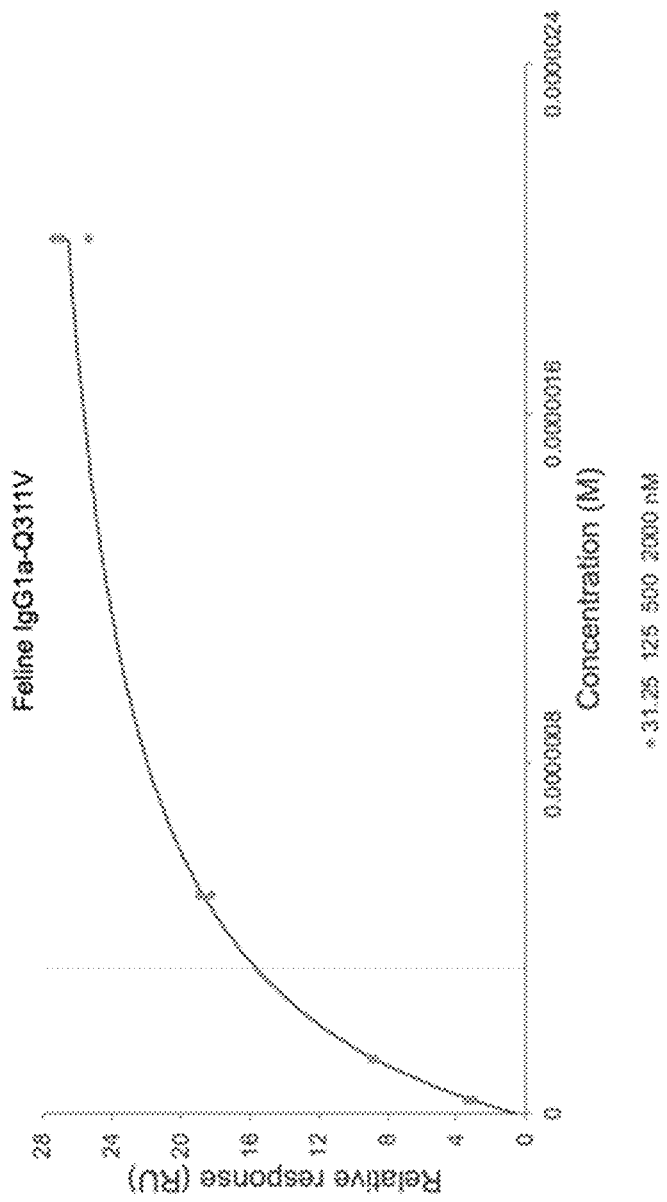
Figure 49E:
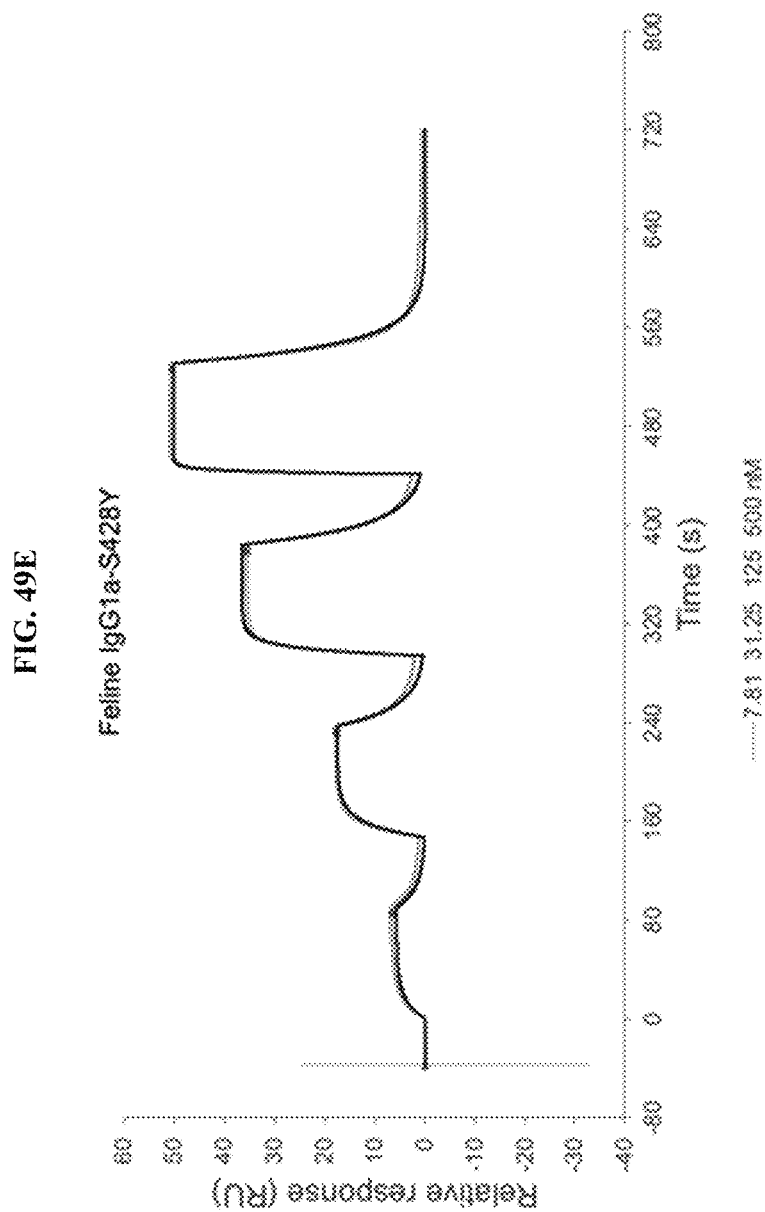
Figure 49H:
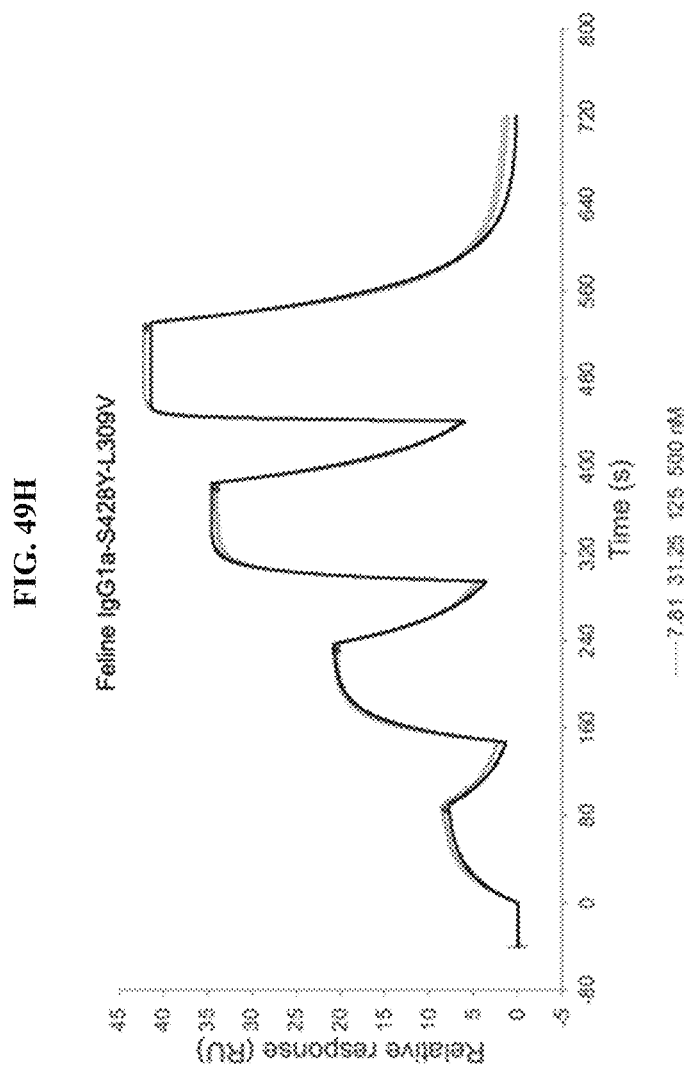
Figure 49I:
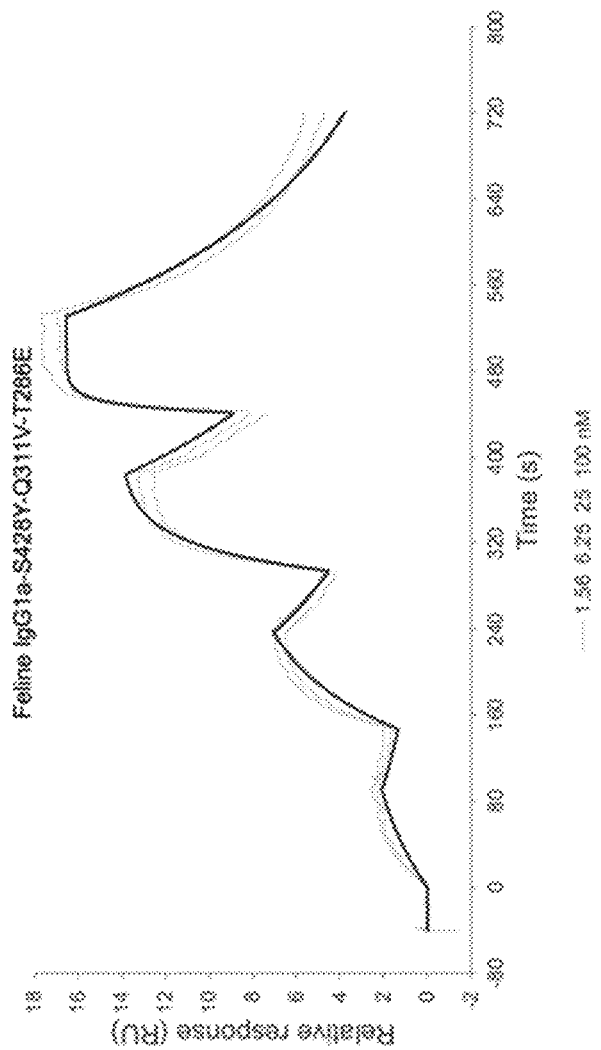
Figure 49J:
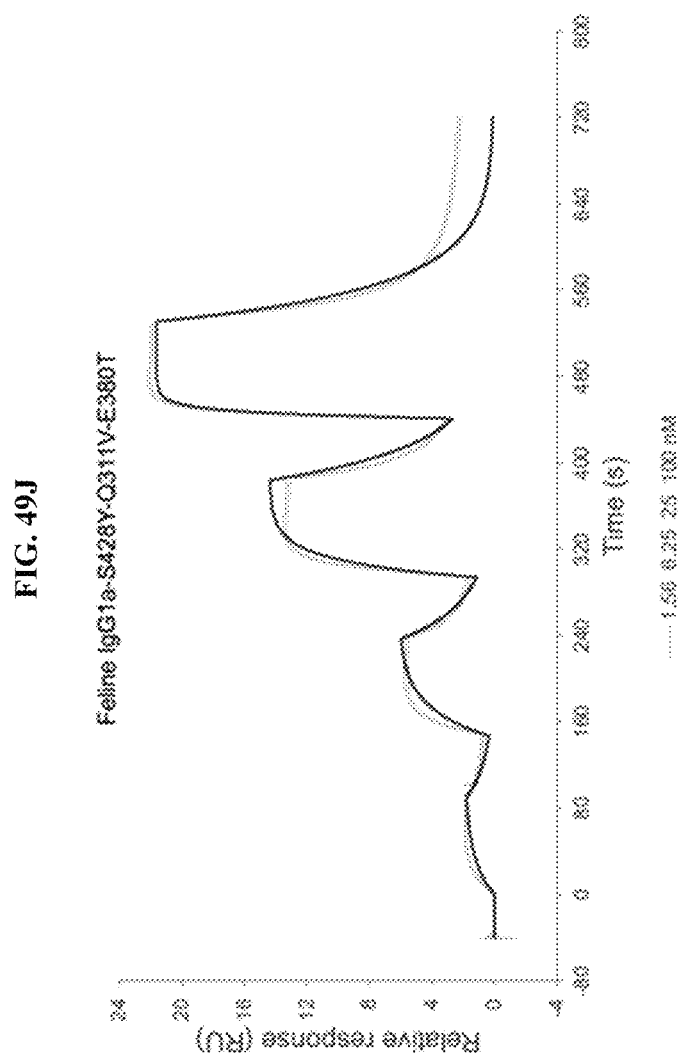
Figure 49K:
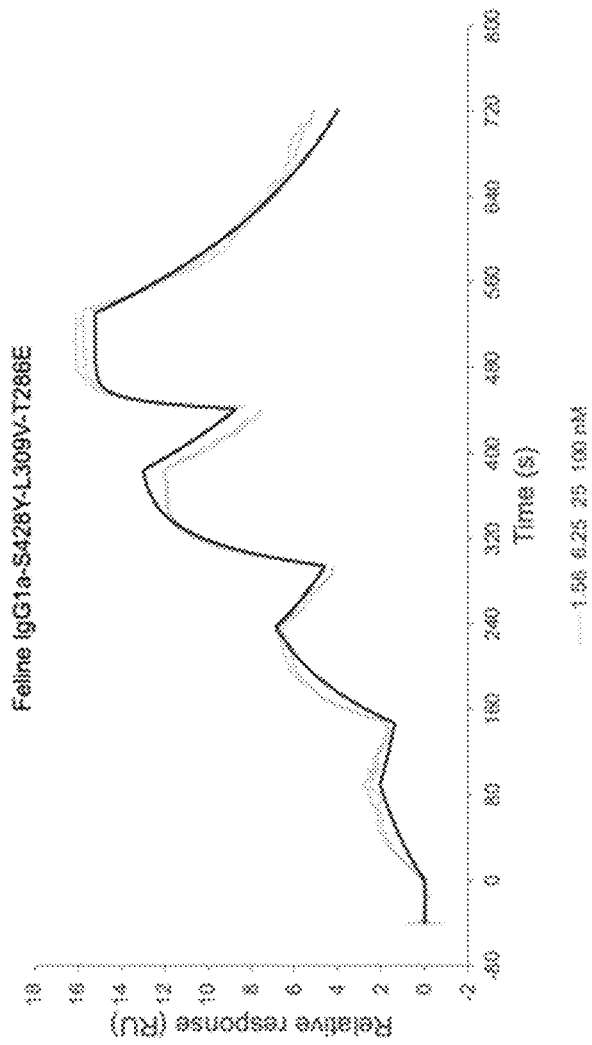
Figure 49L:
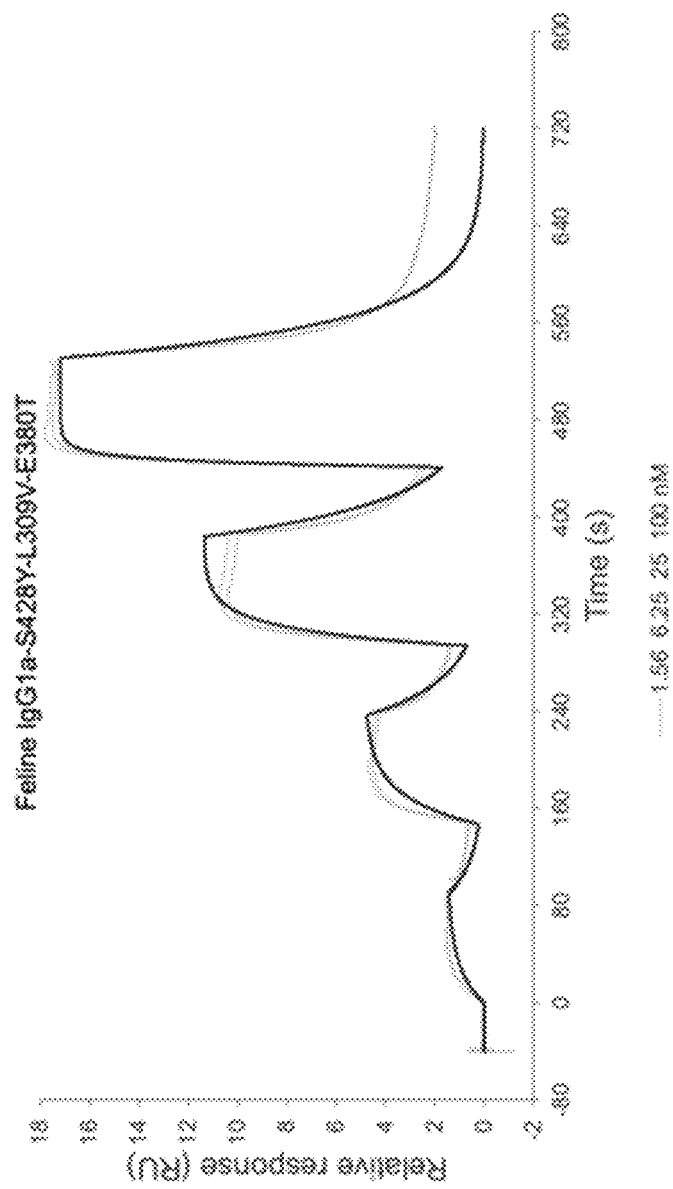

The estimated PK parameters are given in Table 9, below. The predicted serum concentration profiles of the monoclonal antibodies carrying the wild-type (WT) IgG1a Fc or the IgG1a Fc variants S252W, S428Y, S428Y+L309V, S428Y+Q311V, and S428Y+S254R for a typical 2 kg cat receiving a single IV dose of 2 mg/kg are shown in FIG. 48. These pharmacokinetic studies not only confirm the benefits of substitutions at two or more amino acid positions but, more importantly, show that amino acid modifications to feline IgG Fc domains that confer enhanced FcRn binding in vitro are also sufficient to extend the half-life of these IgG Fc variants in vivo.

TABLE 9

PK parameter estimates for a cat of 2 kg body weight.

| Variant | Cl (mL/day) | V1 (mL) | Q (mL/day) | V2 (mL) | α-$T_{1/2}$ (hour) | β-$T_{1/2}$ (day) |
|---|---|---|---|---|---|---|
| WT | 24.61 | 77.88 | 35.49 | 63.79 | 14.11 | 4.648 |
| S428Y + L309V | 9.423 | 77.88 | 23.32 | 72.65 | 24.30 | 12.22 |
| S428Y + Q311V | 11.86 | 77.88 | 18.16 | 71.21 | 29.05 | 10.22 |
| S428Y + S254R | 15.38 | 77.88 | 90.85 | 89.62 | 7.263 | 7.929 |
| S252W | 13.37 | 77.88 | 25.01 | 52.75 | 19.04 | 7.440 |
| S428Y | 13.37 | 77.88 | 32.44 | 48.70 | 14.40 | 7.002 |

Example 5: Binding Kinetics of Feline IgG1a Variants to Feline FcRn Using C1 Biosensors Several feline IgG1a variants (S252W, L309V, Q311V, S428Y, S428Y+Q311V, S428Y+254R, S428Y+L309V, S428Y+Q311V+T286E, S428Y+Q311V+E380T, S428Y+L309V+T286E, and S428Y+L309V+E380T) were evaluated for binding kinetics to feline FcRn (GenBank KF773786 [feline FcRn large subunit p51] and European Nucleotide Archive AY829266.1 [feline beta-2-microglulin]) at pH 5.9. EU numbering was used to identify the positions (FIG. 4). In this study, the feline Fc variants carrying single amino acid substitutions or a combination of amino acid substitutions were synthesized into the feline IgG1a (Kanai et al., 2000, *Vet. Immunol. Immunopathol.* 73:53) using the variable domain described by Gearing D P et al. (2016, *J Vet Intern Med*, 30:1129). The synthesized feline IgGa variant DNAs were subcloned into a mammalian expression vector and transiently transfected into CHO cells. The conditioned media were purified using protein A chromatography.

For the feline FcRn binding experiments, all assays were completed on a Biacore 8K+ system at 25° C. In this set of experiments, antibodies were immobilized using standard amine coupling reagents to Series S C1 sensor chips. A mixture of 200 mmol/L 1-ethyl-3-(3-dimethylaminopropyl) carbodiimide hydrochloride (EDC) and 50 mmol/L N-Hydroxysuccinimide (NHS) was injected for 420 seconds to activate the surface. Then, antibodies were injected at a concentration of 0.5 to 2 µg/ml in 10 mM sodium acetate pH 5.0 for 120 seconds. Finally, 1 M ethanolamine was injected for 420 seconds. The running buffer was 1×PBS-P+(Cytiva, Cat #28995084) adjusted to pH 5.9.

To evaluate the binding affinity of the feline IgG1a variants to feline FcRn at pH 5.9, a range of concentrations from 1.56-2000 nM of feline FcRn were chosen and injected in single cycle mode. The concentrations of feline FcRn tested for each variant are shown below in Table 10.

TABLE 10

Concentrations of feline FcRn used for each feline IgG1a variant

| Variant | Concentrations of FcRn [nM] |
|---|---|
| Wild-type | 31.25, 125, 500, 2000 |
| FelineIgG1a-S252W | 1.56, 6.25, 25, 100 |
| FelineIgG1a-L309V | 31.25, 125, 500, 2000 |
| FelineIgG1a-Q311V | 31.25, 125, 500, 2000 |
| FelineIgG1a-S428Y | 7.81, 31.25, 125, 500 |
| FelineIgG1a-S428Y-Q311V | 7.81, 31.25, 125, 500 |
| FelineIgG1a-S428Y-S254R | 7.81, 31.25, 125, 500 |
| FelineIgG1a-S428Y-L309V | 7.81, 31.25, 125, 500 |
| FelineIgG1a-S428Y-Q311V-T286E | 1.56, 6.25, 25, 100 |
| FelineIgG1a-S428Y-Q311V-E380T | 1.56, 6.25, 25, 100 |
| FelineIgG1a-S428Y-L309V-T286E | 1.56, 6.25, 25, 100 |
| FelineIgG1a-S428Y-E308W-E380T | 1.56, 6.25, 25, 100 |

Four concentrations per antibody were injected at 5 µl/min for 90 seconds, followed by 180 seconds dissociation. Each concentration series was injected three times in this format, with at least three buffer-only cycles for proper reference subtraction. The surface was regenerated with two injections of 1×PBS-P+, pH 7.4 for 30 seconds, followed by a 60 second wait command. Three startup cycles were included to stabilize the surface prior to analysis.

Data were evaluated using Insight Evaluation Software by fitting to a 1:1 kinetic interaction model, or by fitting to steady state affinity. Quality metrics including the U-value and T-value were used to select the accepted parameters. A U-value of less than 15 was considered acceptable for kinetic rate constants, while a T-value of greater than 100 was considered acceptable for kinetic rate constants. Where these values are outside the range, the steady state affinity parameters are considered acceptable.

The kinetic data for the feline IgG1a variants are shown below in Table 11 and the sensorgrams are shown in FIGS. 49A-49L.

TABLE 11

Feline IgG1a variants and feline FcRn binding kinetics

| Variant | $k_a$ | $k_d$ | $K_D$ | Method for fitting data |
|---|---|---|---|---|
| Wild-type | | | 1.06E−06 | Steady state affinity |
| FelineIgG1a-S252W | 1.06E+06 | 4.24E−03 | 4.01E−09 | 1.1 kinetic interaction model |
| FelineIgG1a-L309V | | | 4.27E−07 | Steady state affinity |
| FelineIgG1a-Q311V | | | 3.34E−07 | Steady state affinity |
| FelineIgG1a-S428Y | 9.02E+05 | 6.42E−02 | 7.18E−08 | 1:1 kinetic interaction model |
| FelineIgG1a-S428Y-Q311V | 8.27E+05 | 2.66E−02 | 3.22E−08 | 1:1 kinetic interaction model |
| FelineIgG1a-S428Y-S254R | 1.15E+06 | 9.31E−02 | 8.12E−08 | 1:1 kinetic interaction model |
| FelineIgG1a-S428Y-L309V | 8.80E+05 | 3.10E−02 | 3.53E−08 | 1:1 kinetic interaction model |
| FelineIgG1a-S428Y-Q311V-T285E | 1.27E+06 | 7.78E−03 | 6.11E−09 | 1:1 kinetic interaction model |
| FelineIgG1a-S428Y-Q311V-E380T | 1.60E+06 | 3.22E−02 | 2.01E−08 | 1:1 kinetic interaction model |

TABLE 11-continued

Feline IgG1a variants and feline FcRn binding kinetics

| Variant | $k_a$ | $k_d$ | $K_D$ | Method for fitting data |
|---|---|---|---|---|
| FelineIgG1a-S428Y-L309V-T286E | 1.34E+06 | 7.02E−03 | 5.26E−09 | 1:1 kinetic interaction model |
| FelineIgG1a-S428Y-L309V-E380T | 1.63E+06 | 3.34E−02 | 2.06E−08 | 1:1 kinetic interaction model |

Example 6: Pharmacokinetic Study of Feline IgG1a Fc Variants with Two or Three Fc Substitutions and Wild-Type Feline IgG1a A pharmacokinetic (PK) study was undertaken with fourteen male and female cats. Feline IgG1a Fc variants, including the antibody carrying a wild-type feline IgG1a Fc domain, were prepared using the anti-NGF variable domain as previously described by Gearing et al. (2016, *J Vet Intern Med*, 30:1129). The feline IgG1a variants tested in this study included: S428Y+L309V, S428Y+Q311V, S428Y+Q311V+T286E, S428Y+L309V+E380T, S428Y+Q311V+E380T, S428Y+L309V+T286E, wild-type.

The animals were randomized into seven groups with a male and female in each group. Each animal was administered with a single intravenous dose of 2 mg/kg of antibody. Approximately 0.5 ml of whole blood was collected at the following time points: 0 (pre-dose), 4 hours, and 1, 2, 4, 6, 10, 14, 18, 22, 30, 34 38, 42 days post injection. Serum was separated from whole blood and assayed for the presence of the antibody by an ELISA that is specific for feline anti-NGF antibodies. Serum concentrations of the seven anti-NGF monoclonal antibody (mAb) variants were described with a two-compartmental pharmacokinetic (PK) model with linear clearance using non-linear mixed effects (NLME) modelling (Population parameters were estimated using the stochastic approximation of expectation-maximization (SAEM) algorithm implemented in Monolix Suite 2019R1 (Monolix version 2019R1. Antony, France: Lixoft SAS, 2019). Serum concentrations of S428Y+Q311V, S428Y+L309V and wild-type from the PK study described in Example 4 were modeled as above and included in these calculations. Individual parameters were modeled as random variables with log-normal distributions. PK parameters depended on body weight (BW) using mAb-typical coefficients ($\beta_{BW,Cl}$=0.75, $\beta_{BW,V1}$=$\beta_{BW,V2}$=1, $\beta_{BW,Q}$=2/3). The equation (Dong et al. 2011. *Clin Pharmacokinet*, 50:131) for an individual parameter $\varphi_i$ was:

$$\varphi_i = \varphi_{pop}\left(\frac{BW_i}{BW_{ref}}\right)^\beta e^\eta$$

where $\varphi_{pop}$ was the population typical parameter, $\eta$ was a random variable with mean 0 and standard deviation $\omega$, $BW_i$ was the body weight of animal i, and $BW_{ref}$ was the reference body weight of 2 kg.

Antibody variants were discriminated by using a categorial covariate on clearance, inter-compartmental exchange coefficient, and peripheral volume according to the equation:

$$\varphi_i = \varphi_{pop} e^{(\beta\Omega_i)} e^\eta$$

where $\Omega_i$=1 if the individual variant covariate was in the category and $\Omega_i$=0 otherwise. The wild-type (WT) mAb was used as a reference.

The estimated PK parameters are given in Table 12, below.

TABLE 12

PK parameter estimates for a cat of 2 kg body weight.

| Variant | Cl (mL/day) | V1 (mL) | Q (mL/day) | V2 (mL) | α $T_{1/2}$ (hour) | β $T_{1/2}$ (day) |
|---|---|---|---|---|---|---|
| Wild-type | 22.85 | 76.46 | 31.85 | 55.4 | 14.6 | 4.597 |
| S428Y + Q311V + T286E | 9.383 | 76.46 | 31.85 | 55.4 | 15.89 | 10.28 |
| S428Y + L309V + E380T | 10.69 | 76.46 | 31.85 | 55.4 | 15.77 | 9.102 |
| S428Y + L309V | 10.79 | 76.46 | 31.85 | 55.4 | 15.76 | 9.017 |
| S428Y + Q311V | 11.46 | 76.46 | 31.85 | 55.4 | 15.69 | 8.527 |
| S428Y + Q311V + E380T | 11.58 | 76.46 | 31.85 | 55.4 | 15.68 | 8.448 |
| S428Y + L309V + T286E | 13.32 | 76.46 | 31.85 | 55.4 | 15.51 | 7.423 |

Figure 50:
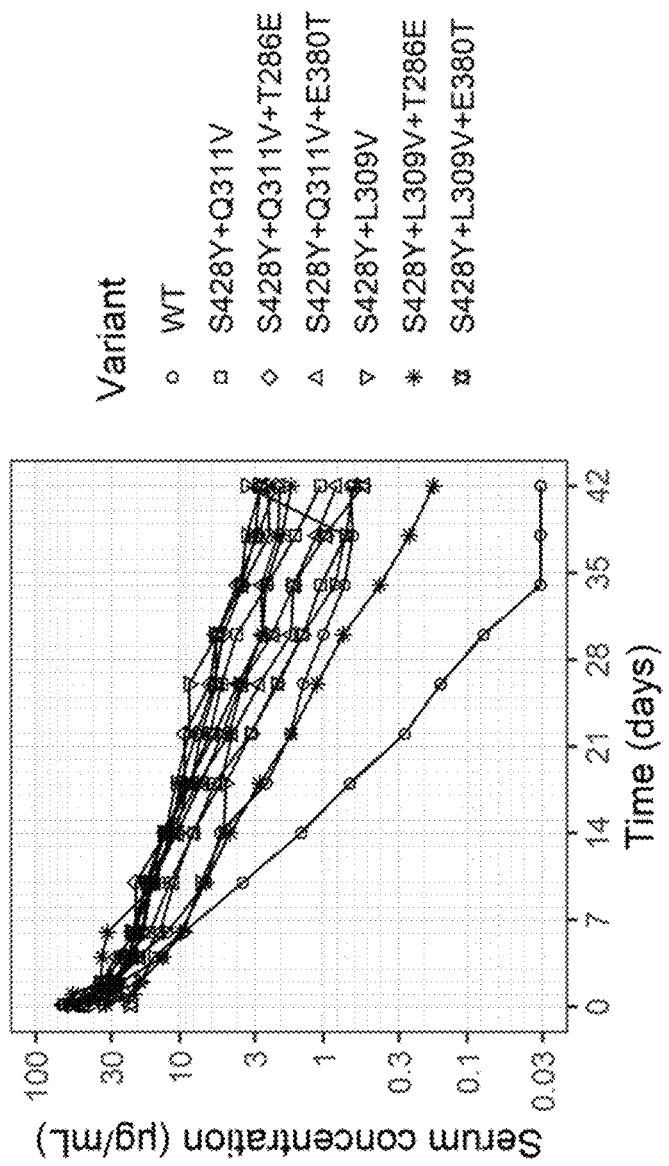
FIG. 50 depicts individual observed serum concentrations of wild-type and Fc variants with two animals per variant.

The individual observed serum concentrations of wild-type and Fc variants S428Y+Q311V, S428Y+Q311V+T286E, S428Y+Q311V+E380T, S428Y+L309V, S428Y+L309V+T286E, and S428Y+L309V+E380T with two animals per variant are shown in FIG. 50.

Figure 51:
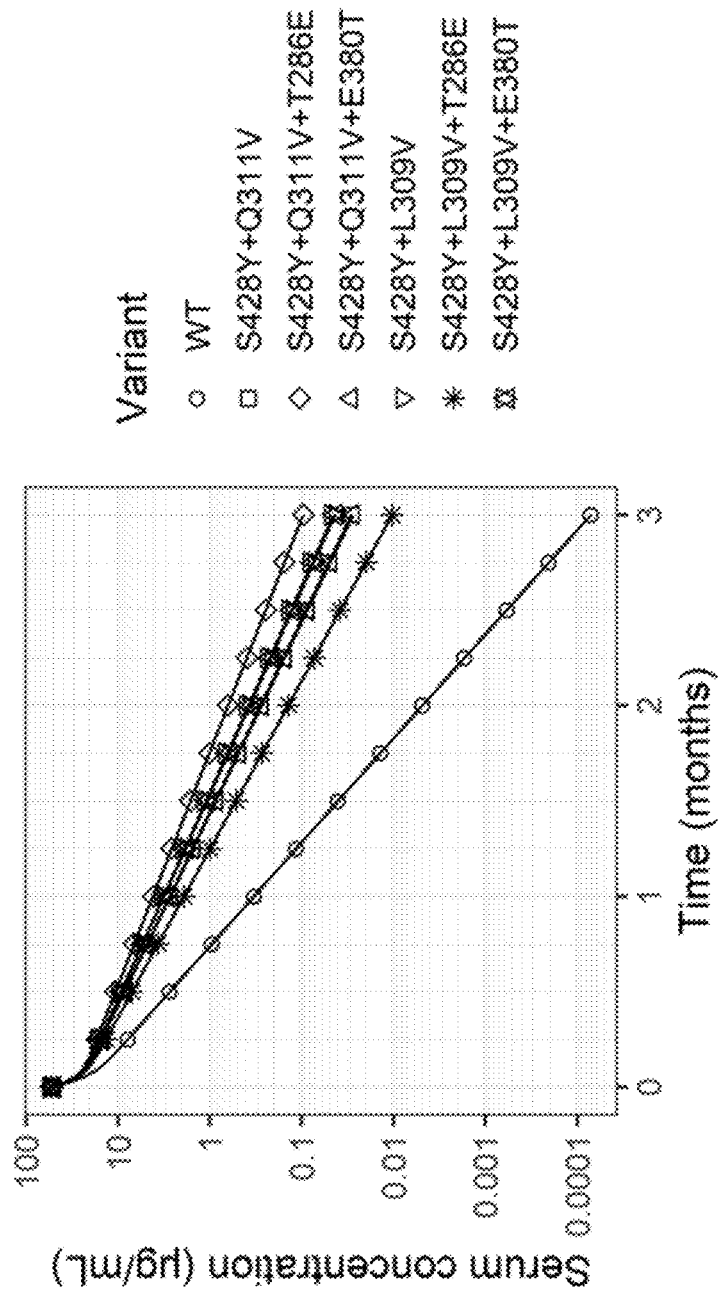
FIG. 51 depicts predicted serum concentration profiles of the monoclonal antibodies carrying the wild-type (WT) IgG1a Fc or the IgG1a Fc variants.

The predicted serum concentration profiles of the monoclonal antibodies carrying the wild-type (WT) IgG1a Fc or the IgG1a Fc variants S428Y+Q311V, S428Y+Q311V+T286E, S428Y+Q311V+E380T, S428Y+L309V, S428Y+L309V+T286E, and S428Y+L309V+E380T for a typical 2 kg cat receiving a single IV dose of 2 mg/kg are shown in FIG. 51. These pharmacokinetic studies not only confirm the benefits of substitutions at two or more amino acid positions but, more importantly, show that amino acid modifications to feline IgG Fc domains that confer enhanced FcRn binding in vitro are also sufficient to extend the half-life of these IgG Fc variants in vivo.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A polypeptide comprising a feline IgG Fc region variant, wherein the polypeptide comprises an amino acid substitution at at least one position selected from the group consisting of:
    (i) a position that corresponds to amino acid position 286 of a wild type feline IgG, wherein the amino acid substitution is T286E;
    (ii) a position that corresponds to amino acid position 311 of a wild type feline IgG, wherein the amino acid substitution is Q311V; and
    (iii) a position that corresponds to amino acid position 428 of a wild type feline IgG, wherein the amino acid substitution is S428Y;
    wherein the amino acid positions are based on EU numbering, wherein the polypeptide comprises an amino acid sequence that is at least 95% identical to an amino acid sequence selected from the group consisting of SEQ ID NOs: 1 to 3, wherein the polypeptide has increased binding affinity to feline FcRn when compared to an Fc domain of the wild type feline IgG, and wherein the polypeptide binds to feline FcRn at a higher level at pH 6.0 than at pH 7.4.

2. The polypeptide of claim 1, wherein the wild type feline IgG is a feline IgG1a comprising an Fc domain having an amino acid sequence of SEQ ID NO: 1.

3. The polypeptide of claim 1, wherein the wild type feline IgG is a feline IgG1b comprising an Fc domain having an amino acid sequence of SEQ ID NO: 2.

4. The polypeptide of claim 1, wherein the wild type feline IgG is a feline IgG2 comprising an Fc domain having an amino acid sequence of SEQ ID NO: 3.

5. The polypeptide of claim 1, further comprising a polypeptide protein selected from the group consisting of EPO, CTLA4, LFA3, VEGFR1/VEGFR3, IL-IR, IL-4R, GLP-1 receptor agonist, and Thrombopoietin binding peptide.

6. A pharmaceutical composition comprising (i) the polypeptide of claim 1, and (ii) a pharmaceutically acceptable excipient.

7. A nucleic acid or nucleic acids encoding the polypeptide of claim 1.

8. An expression vector or expression vectors comprising the nucleic acid or nucleic acids of claim 7.

9. A host cell comprising the nucleic acid or nucleic acids of claim 7 or an expression vector or expression vectors comprising the nucleic acid or nucleic acids.

10. A method of making a polypeptide, the method comprising:
    (a) providing a nucleic acid or nucleic acids of claim 7;
    (b) expressing the nucleic acid or nucleic acids in a host cell culture, thereby producing the polypeptide; and
    (c) collecting the polypeptide produced in (b) from the host cell culture.

11. The polypeptide of claim 1, wherein the polypeptide comprises an amino acid substitution at a position that corresponds to amino acid position 311 of a wild type feline IgG, wherein the amino acid substitution is Q311V.

12. The polypeptide of claim 1, wherein the polypeptide comprises an amino acid substitution at a position that corresponds to amino acid position 428 of a wild type feline IgG, wherein the amino acid substitution is S428Y.

13. The polypeptide of claim 1, wherein the polypeptide comprises an amino acid substitution at a position that corresponds to amino acid position 286 of a wild type feline IgG, wherein the amino acid substitution is T286E.

14. The polypeptide of claim 1, further comprising a binding domain, wherein the binding domain comprises a ligand binding domain of a feline receptor protein.

15. The polypeptide of claim 1, further comprising a binding domain, wherein the binding domain comprises a nanobody.

16. The polypeptide of claim 1, further comprising a binding domain, wherein the binding domain comprises an extracellular domain of a feline receptor protein.

17. A polypeptide comprising a feline IgG Fc region variant, wherein the polypeptide comprises two or more amino acid substitutions, wherein the two or more amino acid substitutions are selected from the group consisting of:
  (i) an amino acid substitution at a position that corresponds to amino acid position 286 of a wild type feline IgG, wherein the amino acid substitution is T286E;
  (ii) an amino acid substitution at a position that corresponds to amino acid position 311 of a wild type feline IgG, wherein the amino acid substitution is Q311V;
  (iii) an amino acid substitution at a position that corresponds to amino acid position 428 of a wild type feline IgG, wherein the amino acid substitution is S428Y;
  wherein the amino acid positions are based on EU numbering, wherein the polypeptide comprises an amino acid sequence that is at least 95% identical to an amino acid sequence selected from the group consisting of SEQ ID NOs: 1 to 3, wherein the two or more amino acid substitutions are at different positions, wherein the polypeptide has increased binding affinity to feline FcRn when compared to (a) an Fc domain of the wild type feline IgG, and (b) a polypeptide comprising only one of the two or more amino acid substitutions, and wherein the polypeptide binds to feline FcRn at a higher level at pH 6.0 than at pH 7.4.

18. The polypeptide of claim 17, wherein the two or more amino acid substitutions comprise an amino acid substitution at a position that corresponds to amino acid position 286 of a wild type feline IgG, wherein the amino acid substitution is T286E.

19. The polypeptide of claim 17, wherein the two or more amino acid substitutions comprise an amino acid substitution at a position that corresponds to amino acid position 311 of a wild type feline IgG, wherein the amino acid substitution is Q311V.

20. The polypeptide of claim 17, wherein the two or more amino acid substitutions comprise an amino acid substitution at a position that corresponds to amino acid position 428 of a wild type feline IgG, wherein the amino acid substitution is S428Y.

21. The polypeptide of claim 17, wherein the polypeptide comprises:
  (i) an amino acid substitution at a position that corresponds to amino acid position 286 of a wild type feline IgG, wherein the amino acid substitution is T286E;
  (ii) an amino acid substitution at a position that corresponds to amino acid position 311 of a wild type feline IgG, wherein the amino acid substitution is Q311V; and
  (iii) an amino acid substitution at a position that corresponds to amino acid position 428 of a wild type feline IgG, wherein the amino acid substitution is S428Y.

* * * * *

UNITED STATES PATENT AND TRADEMARK OFFICE
CERTIFICATE OF CORRECTION

PATENT NO. : 11,498,953 B2
APPLICATION NO. : 17/355839
DATED : November 15, 2022
INVENTOR(S) : William Brondyk et al.

It is certified that error appears in the above-identified patent and that said Letters Patent is hereby corrected as shown below:

In the Claims

Column 62, Line 38, in Claim 5, replace "polypeptide protcin selected" with --polypeptide selected--.

Column 63, Line 23, in Claim 17, replace "Q311V;" with --Q311V; and--.

Signed and Sealed this
Fourteenth Day of February, 2023

Katherine Kelly Vidal
*Director of the United States Patent and Trademark Office*

SEQUENCE LISTING

<160> NUMBER OF SEQ ID NOS: 17

<210> SEQ ID NO 1
<211> LENGTH: 219
<212> TYPE: PRT
<213> ORGANISM: Felis catus

<400> SEQUENCE: 1

Pro Pro Glu Met Leu Gly Gly Pro Ser Ile Phe Ile Phe Pro Pro Lys
1               5                   10                  15

Pro Lys Asp Thr Leu Ser Ile Ser Arg Thr Pro Glu Val Thr Cys Leu
            20                  25                  30

Val Val Asp Leu Gly Pro Asp Asp Ser Asp Val Gln Ile Thr Trp Phe
        35                  40                  45

Val Asp Asn Thr Gln Val Tyr Thr Ala Lys Thr Ser Pro Arg Glu Glu
    50                  55                  60

Gln Phe Asn Ser Thr Tyr Arg Val Val Ser Val Leu Pro Ile Leu His
65                  70                  75                  80

Gln Asp Trp Leu Lys Gly Lys Glu Phe Lys Cys Lys Val Asn Ser Lys
                85                  90                  95

Ser Leu Pro Ser Pro Ile Glu Arg Thr Ile Ser Lys Ala Lys Gly Gln
            100                 105                 110

Pro His Glu Pro Gln Val Tyr Val Leu Pro Pro Ala Gln Glu Glu Leu
        115                 120                 125

Ser Arg Asn Lys Val Ser Val Thr Cys Leu Ile Lys Ser Phe His Pro
    130                 135                 140

Pro Asp Ile Ala Val Glu Trp Glu Ile Thr Gly Gln Pro Glu Pro Glu
145                 150                 155                 160

Asn Asn Tyr Arg Thr Thr Pro Pro Gln Leu Asp Ser Asp Gly Thr Tyr
                165                 170                 175

Phe Val Tyr Ser Lys Leu Ser Val Asp Arg Ser His Trp Gln Arg Gly
            180                 185                 190

Asn Thr Tyr Thr Cys Ser Val Ser His Glu Ala Leu His Ser His His
        195                 200                 205

Thr Gln Lys Ser Leu Thr Gln Ser Pro Gly Lys
    210                 215

<210> SEQ ID NO 2
<211> LENGTH: 219
<212> TYPE: PRT
<213> ORGANISM: Felis catus

<400> SEQUENCE: 2

Pro Pro Glu Met Leu Gly Gly Pro Ser Ile Phe Ile Phe Pro Pro Lys
1               5                   10                  15

Pro Lys Asp Thr Leu Ser Ile Ser Arg Thr Pro Glu Val Thr Cys Leu
            20                  25                  30

Val Val Asp Leu Gly Pro Asp Asp Ser Asp Val Gln Ile Thr Trp Phe
        35                  40                  45

Val Asp Asn Thr Gln Val Tyr Thr Ala Lys Thr Ser Pro Arg Glu Glu
    50                  55                  60

Gln Phe Asn Ser Thr Tyr Arg Val Val Ser Val Leu Pro Ile Leu His
65                  70                  75                  80

Gln Asp Trp Leu Lys Gly Lys Glu Phe Lys Cys Lys Val Asn Ser Lys
                85                  90                  95

Ser Leu Pro Ser Pro Ile Glu Arg Thr Ile Ser Lys Asp Lys Gly Gln

```
                    100                 105                 110
Pro His Glu Pro Gln Val Tyr Val Leu Pro Pro Ala Gln Glu Leu
            115                 120                 125

Ser Arg Asn Lys Val Ser Val Thr Cys Leu Ile Glu Gly Phe Tyr Pro
130                 135                 140

Ser Asp Ile Ala Val Glu Trp Glu Ile Thr Gly Gln Pro Glu Pro Glu
145                 150                 155                 160

Asn Asn Tyr Arg Thr Thr Pro Pro Gln Leu Asp Ser Asp Gly Thr Tyr
                165                 170                 175

Phe Leu Tyr Ser Arg Leu Ser Val Asp Arg Ser Arg Trp Gln Arg Gly
            180                 185                 190

Asn Thr Tyr Thr Cys Ser Val Ser His Glu Ala Leu His Ser His His
            195                 200                 205

Thr Gln Lys Ser Leu Thr Gln Ser Pro Gly Lys
    210                 215

<210> SEQ ID NO 3
<211> LENGTH: 219
<212> TYPE: PRT
<213> ORGANISM: Felis catus

<400> SEQUENCE: 3

Val Pro Glu Ile Pro Gly Ala Pro Ser Val Phe Ile Phe Pro Pro Lys
1               5                   10                  15

Pro Lys Asp Thr Leu Ser Ile Ser Arg Thr Pro Glu Val Thr Cys Leu
            20                  25                  30

Val Val Asp Leu Gly Pro Asp Asp Ser Asn Val Gln Ile Thr Trp Phe
        35                  40                  45

Val Asp Asn Thr Glu Met His Thr Ala Lys Thr Arg Pro Arg Glu Glu
50                  55                  60

Gln Phe Asn Ser Thr Tyr Arg Val Val Ser Val Leu Pro Ile Leu His
65                  70                  75                  80

Gln Asp Trp Leu Lys Gly Lys Glu Phe Lys Cys Lys Val Asn Ser Lys
                85                  90                  95

Ser Leu Pro Ser Ala Met Glu Arg Thr Ile Ser Lys Ala Lys Gly Gln
            100                 105                 110

Pro His Glu Pro Gln Val Tyr Val Leu Pro Pro Thr Gln Glu Glu Leu
        115                 120                 125

Ser Glu Asn Lys Val Ser Val Thr Cys Leu Ile Lys Gly Phe His Pro
130                 135                 140

Pro Asp Ile Ala Val Glu Trp Glu Ile Thr Gly Gln Pro Glu Pro Glu
145                 150                 155                 160

Asn Asn Tyr Gln Thr Thr Pro Pro Gln Leu Asp Ser Asp Gly Thr Tyr
                165                 170                 175

Phe Leu Tyr Ser Arg Leu Ser Val Asp Arg Ser His Trp Gln Arg Gly
            180                 185                 190

Asn Thr Tyr Thr Cys Ser Val Ser His Glu Ala Leu His Ser His His
            195                 200                 205

Thr Gln Lys Ser Leu Thr Gln Ser Pro Gly Lys
    210                 215

<210> SEQ ID NO 4
<211> LENGTH: 110
<212> TYPE: PRT
<213> ORGANISM: Felis catus
```

```
<400> SEQUENCE: 4

Pro Pro Glu Met Leu Gly Gly Pro Ser Ile Phe Ile Phe Pro Pro Lys
1               5                   10                  15

Pro Lys Asp Thr Leu Ser Ile Ser Arg Thr Pro Glu Val Thr Cys Leu
            20                  25                  30

Val Val Asp Leu Gly Pro Asp Asp Ser Asp Val Gln Ile Thr Trp Phe
        35                  40                  45

Val Asp Asn Thr Gln Val Tyr Thr Ala Lys Thr Ser Pro Arg Glu Glu
    50                  55                  60

Gln Phe Asn Ser Thr Tyr Arg Val Val Ser Val Leu Pro Ile Leu His
65                  70                  75                  80

Gln Asp Trp Leu Lys Gly Lys Glu Phe Lys Cys Lys Val Asn Ser Lys
                85                  90                  95

Ser Leu Pro Ser Pro Ile Glu Arg Thr Ile Ser Lys Ala Lys
                100                 105                 110

<210> SEQ ID NO 5
<211> LENGTH: 110
<212> TYPE: PRT
<213> ORGANISM: Felis catus

<400> SEQUENCE: 5

Pro Pro Glu Met Leu Gly Gly Pro Ser Ile Phe Ile Phe Pro Pro Lys
1               5                   10                  15

Pro Lys Asp Thr Leu Ser Ile Ser Arg Thr Pro Glu Val Thr Cys Leu
            20                  25                  30

Val Val Asp Leu Gly Pro Asp Asp Ser Asp Val Gln Ile Thr Trp Phe
        35                  40                  45

Val Asp Asn Thr Gln Val Tyr Thr Ala Lys Thr Ser Pro Arg Glu Glu
    50                  55                  60

Gln Phe Asn Ser Thr Tyr Arg Val Val Ser Val Leu Pro Ile Leu His
65                  70                  75                  80

Gln Asp Trp Leu Lys Gly Lys Glu Phe Lys Cys Lys Val Asn Ser Lys
                85                  90                  95

Ser Leu Pro Ser Pro Ile Glu Arg Thr Ile Ser Lys Asp Lys
                100                 105                 110

<210> SEQ ID NO 6
<211> LENGTH: 110
<212> TYPE: PRT
<213> ORGANISM: Felis catus

<400> SEQUENCE: 6

Val Pro Glu Ile Pro Gly Ala Pro Ser Val Phe Ile Phe Pro Pro Lys
1               5                   10                  15

Pro Lys Asp Thr Leu Ser Ile Ser Arg Thr Pro Glu Val Thr Cys Leu
            20                  25                  30

Val Val Asp Leu Gly Pro Asp Asp Ser Asn Val Gln Ile Thr Trp Phe
        35                  40                  45

Val Asp Asn Thr Glu Met His Thr Ala Lys Thr Arg Pro Arg Glu Glu
    50                  55                  60

Gln Phe Asn Ser Thr Tyr Arg Val Val Ser Val Leu Pro Ile Leu His
65                  70                  75                  80

Gln Asp Trp Leu Lys Gly Lys Glu Phe Lys Cys Lys Val Asn Ser Lys
                85                  90                  95

Ser Leu Pro Ser Ala Met Glu Arg Thr Ile Ser Lys Ala Lys
```

<210> SEQ ID NO 7
<211> LENGTH: 109
<212> TYPE: PRT
<213> ORGANISM: Felis catus

<400> SEQUENCE: 7

Gly Gln Pro His Glu Pro Gln Val Tyr Val Leu Pro Pro Ala Gln Glu
1               5                   10                  15

Glu Leu Ser Arg Asn Lys Val Ser Val Thr Cys Leu Ile Lys Ser Phe
            20                  25                  30

His Pro Pro Asp Ile Ala Val Glu Trp Glu Ile Thr Gly Gln Pro Glu
        35                  40                  45

Pro Glu Asn Asn Tyr Arg Thr Thr Pro Pro Gln Leu Asp Ser Asp Gly
    50                  55                  60

Thr Tyr Phe Val Tyr Ser Lys Leu Ser Val Asp Arg Ser His Trp Gln
65                  70                  75                  80

Arg Gly Asn Thr Tyr Thr Cys Ser Val Ser His Glu Ala Leu His Ser
                85                  90                  95

His His Thr Gln Lys Ser Leu Thr Gln Ser Pro Gly Lys
            100                 105

<210> SEQ ID NO 8
<211> LENGTH: 109
<212> TYPE: PRT
<213> ORGANISM: Felis catus

<400> SEQUENCE: 8

Gly Gln Pro His Glu Pro Gln Val Tyr Val Leu Pro Pro Ala Gln Glu
1               5                   10                  15

Glu Leu Ser Arg Asn Lys Val Ser Val Thr Cys Leu Ile Glu Gly Phe
            20                  25                  30

Tyr Pro Ser Asp Ile Ala Val Glu Trp Glu Ile Thr Gly Gln Pro Glu
        35                  40                  45

Pro Glu Asn Asn Tyr Arg Thr Thr Pro Pro Gln Leu Asp Ser Asp Gly
    50                  55                  60

Thr Tyr Phe Leu Tyr Ser Arg Leu Ser Val Asp Arg Ser Arg Trp Gln
65                  70                  75                  80

Arg Gly Asn Thr Tyr Thr Cys Ser Val Ser His Glu Ala Leu His Ser
                85                  90                  95

His His Thr Gln Lys Ser Leu Thr Gln Ser Pro Gly Lys
            100                 105

<210> SEQ ID NO 9
<211> LENGTH: 109
<212> TYPE: PRT
<213> ORGANISM: Felis catus

<400> SEQUENCE: 9

Gly Gln Pro His Glu Pro Gln Val Tyr Val Leu Pro Pro Thr Gln Glu
1               5                   10                  15

Glu Leu Ser Glu Asn Lys Val Ser Val Thr Cys Leu Ile Lys Gly Phe
            20                  25                  30

His Pro Pro Asp Ile Ala Val Glu Trp Glu Ile Thr Gly Gln Pro Glu
        35                  40                  45

Pro Glu Asn Asn Tyr Gln Thr Thr Pro Pro Gln Leu Asp Ser Asp Gly
    50                  55                  60

Thr Tyr Phe Leu Tyr Ser Arg Leu Ser Val Asp Arg Ser His Trp Gln
65                  70                  75                  80

Arg Gly Asn Thr Tyr Thr Cys Ser Val Ser His Glu Ala Leu His Ser
                85                  90                  95

His His Thr Gln Lys Ser Leu Thr Gln Ser Pro Gly Lys
            100                 105

<210> SEQ ID NO 10
<211> LENGTH: 17
<212> TYPE: PRT
<213> ORGANISM: Felis catus

<400> SEQUENCE: 10

Lys Thr Asp His Pro Pro Gly Pro Lys Pro Cys Asp Cys Pro Lys Cys
1               5                   10                  15

Pro

<210> SEQ ID NO 11
<211> LENGTH: 17
<212> TYPE: PRT
<213> ORGANISM: Felis catus

<400> SEQUENCE: 11

Lys Thr Asp His Pro Pro Gly Pro Lys Pro Cys Asp Cys Pro Lys Cys
1               5                   10                  15

Pro

<210> SEQ ID NO 12
<211> LENGTH: 17
<212> TYPE: PRT
<213> ORGANISM: Felis catus

<400> SEQUENCE: 12

Lys Thr Ala Ser Thr Ile Glu Ser Lys Thr Gly Glu Gly Pro Lys Cys
1               5                   10                  15

Pro

<210> SEQ ID NO 13
<211> LENGTH: 335
<212> TYPE: PRT
<213> ORGANISM: Felis catus

<400> SEQUENCE: 13

Ala Ser Thr Thr Ala Pro Ser Val Phe Pro Leu Ala Pro Ser Cys Gly
1               5                   10                  15

Thr Thr Ser Gly Ala Thr Val Ala Leu Ala Cys Leu Val Leu Gly Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ala Ser Gly Leu Tyr Ser
    50                  55                  60

Leu Ser Ser Met Val Thr Val Pro Ser Ser Arg Trp Leu Ser Asp Thr
65                  70                  75                  80

Phe Thr Cys Asn Val Ala His Pro Pro Ser Asn Thr Lys Val Asp Lys
                85                  90                  95

Thr Val Arg Lys Thr Asp His Pro Pro Gly Pro Lys Pro Cys Asp Cys
            100                 105                 110

Pro Lys Cys Pro Pro Pro Glu Met Leu Gly Gly Pro Ser Ile Phe Ile

```
            115                 120                 125
Phe Pro Pro Lys Pro Lys Asp Thr Leu Ser Ile Ser Arg Thr Pro Glu
130                 135                 140

Val Thr Cys Leu Val Val Asp Leu Gly Pro Asp Asp Ser Asp Val Gln
145                 150                 155                 160

Ile Thr Trp Phe Val Asp Asn Thr Gln Val Tyr Thr Ala Lys Thr Ser
                    165                 170                 175

Pro Arg Glu Glu Gln Phe Asn Ser Thr Tyr Arg Val Val Ser Val Leu
                180                 185                 190

Pro Ile Leu His Gln Asp Trp Leu Lys Gly Lys Glu Phe Lys Cys Lys
                195                 200                 205

Val Asn Ser Lys Ser Leu Pro Ser Pro Ile Glu Arg Thr Ile Ser Lys
210                 215                 220

Ala Lys Gly Gln Pro His Glu Pro Gln Val Tyr Val Leu Pro Pro Ala
225                 230                 235                 240

Gln Glu Glu Leu Ser Arg Asn Lys Val Ser Val Thr Cys Leu Ile Lys
                245                 250                 255

Ser Phe His Pro Pro Asp Ile Ala Val Glu Trp Glu Ile Thr Gly Gln
                260                 265                 270

Pro Glu Pro Glu Asn Asn Tyr Arg Thr Thr Pro Pro Gln Leu Asp Ser
                275                 280                 285

Asp Gly Thr Tyr Phe Val Tyr Ser Lys Leu Ser Val Asp Arg Ser His
                290                 295                 300

Trp Gln Arg Gly Asn Thr Tyr Thr Cys Ser Val Ser His Glu Ala Leu
305                 310                 315                 320

His Ser His His Thr Gln Lys Ser Leu Thr Gln Ser Pro Gly Lys
                    325                 330                 335

<210> SEQ ID NO 14
<211> LENGTH: 335
<212> TYPE: PRT
<213> ORGANISM: Felis catus

<400> SEQUENCE: 14

Ala Ser Thr Thr Ala Pro Ser Val Phe Pro Leu Ala Pro Ser Cys Gly
1               5                   10                  15

Thr Thr Ser Gly Ala Thr Val Ala Leu Ala Cys Leu Val Leu Gly Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ala Ser Gly Leu Tyr Ser
50                  55                  60

Leu Ser Ser Met Val Thr Val Pro Ser Ser Arg Trp Leu Ser Asp Thr
65                  70                  75                  80

Phe Thr Cys Asn Val Ala His Pro Pro Ser Asn Thr Lys Val Asp Lys
                85                  90                  95

Thr Val Arg Lys Thr Asp His Pro Pro Gly Pro Lys Pro Cys Asp Cys
                100                 105                 110

Pro Lys Cys Pro Pro Pro Glu Met Leu Gly Gly Pro Ser Ile Phe Ile
                115                 120                 125

Phe Pro Pro Lys Pro Lys Asp Thr Leu Ser Ile Ser Arg Thr Pro Glu
                130                 135                 140

Val Thr Cys Leu Val Val Asp Leu Gly Pro Asp Asp Ser Asp Val Gln
145                 150                 155                 160
```

```
Ile Thr Trp Phe Val Asp Asn Thr Gln Val Tyr Thr Ala Lys Thr Ser
            165                 170                 175

Pro Arg Glu Glu Gln Phe Asn Ser Thr Tyr Arg Val Val Ser Val Leu
        180                 185                 190

Pro Ile Leu His Gln Asp Trp Leu Lys Gly Lys Glu Phe Lys Cys Lys
    195                 200                 205

Val Asn Ser Lys Ser Leu Pro Ser Pro Ile Glu Arg Thr Ile Ser Lys
210                 215                 220

Asp Lys Gly Gln Pro His Glu Pro Gln Val Tyr Val Leu Pro Pro Ala
225                 230                 235                 240

Gln Glu Glu Leu Ser Arg Asn Lys Val Ser Val Thr Cys Leu Ile Glu
                245                 250                 255

Gly Phe Tyr Pro Ser Asp Ile Ala Val Glu Trp Glu Ile Thr Gly Gln
            260                 265                 270

Pro Glu Pro Glu Asn Asn Tyr Arg Thr Thr Pro Pro Gln Leu Asp Ser
        275                 280                 285

Asp Gly Thr Tyr Phe Leu Tyr Ser Arg Leu Ser Val Asp Arg Ser Arg
    290                 295                 300

Trp Gln Arg Gly Asn Thr Tyr Thr Cys Ser Val Ser His Glu Ala Leu
305                 310                 315                 320

His Ser His His Thr Gln Lys Ser Leu Thr Gln Ser Pro Gly Lys
                325                 330                 335

<210> SEQ ID NO 15
<211> LENGTH: 335
<212> TYPE: PRT
<213> ORGANISM: Felis catus

<400> SEQUENCE: 15

Ala Ser Thr Thr Ala Ser Ser Val Phe Pro Leu Ala Pro Ser Cys Gly
1               5                   10                  15

Thr Thr Ser Gly Ala Thr Val Ala Leu Ala Cys Leu Val Leu Gly Tyr
            20                  25                  30

Phe Pro Glu Pro Val Thr Val Ser Trp Asn Ser Gly Ala Leu Thr Ser
        35                  40                  45

Gly Val His Thr Phe Pro Ser Val Leu Gln Ala Ser Gly Leu Tyr Ser
    50                  55                  60

Leu Ser Ser Met Val Thr Val Pro Ser Ser Arg Trp Leu Ser Asp Thr
65                  70                  75                  80

Phe Thr Cys Asn Val Ala His Arg Pro Ser Ser Thr Lys Val Asp Lys
                85                  90                  95

Thr Val Pro Lys Thr Ala Ser Thr Ile Glu Ser Lys Thr Gly Glu Gly
            100                 105                 110

Pro Lys Cys Pro Val Pro Glu Ile Pro Gly Ala Pro Ser Val Phe Ile
        115                 120                 125

Phe Pro Pro Lys Pro Lys Asp Thr Leu Ser Ile Ser Arg Thr Pro Glu
    130                 135                 140

Val Thr Cys Leu Val Val Asp Leu Gly Pro Asp Asp Ser Asn Val Gln
145                 150                 155                 160

Ile Thr Trp Phe Val Asp Asn Thr Glu Met His Thr Ala Lys Thr Arg
                165                 170                 175

Pro Arg Glu Glu Gln Phe Asn Ser Thr Tyr Arg Val Val Ser Val Leu
            180                 185                 190

Pro Ile Leu His Gln Asp Trp Leu Lys Gly Lys Glu Phe Lys Cys Lys
        195                 200                 205
```

```
Val Asn Ser Lys Ser Leu Pro Ser Ala Met Glu Arg Thr Ile Ser Lys
    210                 215                 220
Ala Lys Gly Gln Pro His Glu Pro Gln Val Tyr Val Leu Pro Pro Thr
225                 230                 235                 240
Gln Glu Glu Leu Ser Glu Asn Lys Val Ser Val Thr Cys Leu Ile Lys
                245                 250                 255
Gly Phe His Pro Pro Asp Ile Ala Val Glu Trp Glu Ile Thr Gly Gln
            260                 265                 270
Pro Glu Pro Glu Asn Asn Tyr Gln Thr Thr Pro Pro Gln Leu Asp Ser
        275                 280                 285
Asp Gly Thr Tyr Phe Leu Tyr Ser Arg Leu Ser Val Asp Arg Ser His
    290                 295                 300
Trp Gln Arg Gly Asn Thr Tyr Thr Cys Ser Val Ser His Glu Ala Leu
305                 310                 315                 320
His Ser His His Thr Gln Lys Ser Leu Thr Gln Ser Pro Gly Lys
                325                 330                 335

<210> SEQ ID NO 16
<211> LENGTH: 200
<212> TYPE: PRT
<213> ORGANISM: Felis catus

<400> SEQUENCE: 16

Ile Phe Ile Phe Pro Pro Lys Pro Lys Asp Thr Leu Ser Ile Ser Arg
1               5                   10                  15
Thr Pro Glu Val Thr Cys Leu Val Val Asp Leu Gly Pro Asp Asp Ser
            20                  25                  30
Asp Val Gln Ile Thr Trp Phe Val Asp Asn Thr Gln Val Tyr Thr Ala
        35                  40                  45
Lys Thr Ser Pro Arg Glu Glu Gln Phe Asn Ser Thr Tyr Arg Val Val
    50                  55                  60
Ser Val Leu Pro Ile Leu His Gln Asp Trp Leu Lys Gly Lys Glu Phe
65                  70                  75                  80
Lys Cys Lys Val Asn Ser Lys Ser Leu Pro Ser Pro Ile Glu Arg Thr
                85                  90                  95
Ile Ser Lys Ala Lys Gly Gln Pro His Glu Pro Gln Val Tyr Val Leu
            100                 105                 110
Pro Pro Ala Gln Glu Glu Leu Ser Arg Asn Lys Val Ser Val Thr Cys
        115                 120                 125
Leu Ile Lys Ser Phe His Pro Pro Asp Ile Ala Val Glu Trp Glu Ile
    130                 135                 140
Thr Gly Gln Pro Glu Pro Glu Asn Asn Tyr Arg Thr Thr Pro Pro Gln
145                 150                 155                 160
Leu Asp Ser Asp Gly Thr Tyr Phe Val Tyr Ser Lys Leu Ser Val Asp
                165                 170                 175
Arg Ser His Trp Gln Arg Gly Asn Thr Tyr Thr Cys Ser Val Ser His
            180                 185                 190
Glu Ala Leu His Ser His His Thr
        195                 200

<210> SEQ ID NO 17
<211> LENGTH: 198
<212> TYPE: PRT
<213> ORGANISM: Homo sapiens

<400> SEQUENCE: 17
```

-continued

```
Val Phe Leu Phe Pro Pro Lys Pro Lys Asp Thr Leu Met Ile Ser Arg
1               5                   10                  15

Thr Pro Glu Val Thr Cys Val Val Val Asp Val Ser His Glu Asp Pro
            20              25                  30

Glu Val Lys Phe Asn Trp Tyr Val Asp Gly Val Glu Val His Asn Ala
        35              40                  45

Lys Thr Lys Pro Arg Glu Glu Gln Tyr Asn Ser Thr Tyr Arg Val Val
    50              55                  60

Ser Val Leu Thr Val Leu His Gln Asp Trp Leu Asn Gly Lys Glu Tyr
65              70                  75                  80

Lys Cys Lys Val Ser Asn Lys Ala Leu Pro Ala Pro Ile Glu Lys Thr
                85                  90                  95

Ile Ser Lys Ala Lys Gly Gln Pro Arg Glu Pro Gln Val Tyr Thr Leu
            100                 105                 110

Pro Pro Ser Arg Glu Glu Met Thr Lys Asn Gln Val Ser Leu Thr Cys
            115                 120                 125

Leu Val Lys Gly Phe Tyr Pro Ser Asp Ile Ala Val Glu Trp Glu Ser
    130                 135                 140

Asn Gly Gln Pro Glu Asn Asn Tyr Lys Thr Thr Pro Pro Val Leu Asp
145                 150                 155                 160

Ser Asp Gly Ser Phe Phe Leu Tyr Ser Lys Leu Thr Val Asp Lys Ser
                165                 170                 175

Arg Trp Gln Gln Gly Asn Val Phe Ser Cys Ser Val Met His Glu Ala
                180                 185                 190

Leu His Asn His Tyr Thr
            195
```